US012491241B2

(12) United States Patent
Smith et al.

(10) Patent No.: US 12,491,241 B2

(45) Date of Patent: Dec. 9, 2025

(54) CORONAVIRUS VACCINE FORMULATIONS

(71) Applicant: Novavax, Inc., Gaithersburg, MD (US)

(72) Inventors: Gale Smith, Germantown, MD (US); Michael J. Massare, Mt. Airy, MD (US); Jing-Hui Tian, Germantown, MD (US)

(*) Notice: Subject to any disclaimer, the term of this patent is extended or adjusted under 35 U.S.C. 154(b) by 0 days.

(21) Appl. No.: 18/526,015

(22) Filed: Dec. 1, 2023

(65) Prior Publication Data

US 2024/0165221 A1 May 23, 2024

Related U.S. Application Data

(60) Division of application No. 17/572,182, filed on Jan. 10, 2022, now Pat. No. 11,896,664, which is a continuation of application No. 17/205,990, filed on Mar. 18, 2021, now Pat. No. 11,253,586, which is a continuation of application No. 16/997,001, filed on Aug. 19, 2020, now Pat. No. 10,953,089.

(60) Provisional application No. 63/054,182, filed on Jul. 20, 2020, provisional application No. 63/051,706, filed on Jul. 14, 2020, provisional application No. 63/048,945, filed on Jul. 7, 2020, provisional application No. 62/983,180, filed on Feb. 28, 2020, provisional application No. 62/976,858, filed on Feb.

(Continued)

(51) Int. Cl.

| | |
|---|---|
| ***C12N 7/00*** | (2006.01) |
| ***A61K 39/215*** | (2006.01) |
| ***A61P 31/14*** | (2006.01) |
| *A61K 39/00* | (2006.01) |

(52) U.S. Cl.

CPC ............ *A61K 39/215* (2013.01); *A61P 31/14* (2018.01); *A61K 2039/545* (2013.01); *A61K 2039/55577* (2013.01); *C12N 2770/20034* (2013.01)

(58) Field of Classification Search

None

See application file for complete search history.

(56) References Cited

U.S. PATENT DOCUMENTS

| | | | |
|---|---|---|---|
| 4,900,549 | A | 2/1990 | De Vries et al. |
| 4,911,928 | A | 3/1990 | Wallach |

(Continued)

FOREIGN PATENT DOCUMENTS

| | | | |
|---|---|---|---|
| AU | 2003245220 | B2 | 4/2009 |
| CA | 2491457 | C | 9/2012 |

(Continued)

OTHER PUBLICATIONS

Frauenfeld et al., "A novel lipoprotein nanoparticle system for membrane proteins," Nat Methods 13(4): 345-351 (Year: 2016).*

(Continued)

*Primary Examiner* — M Franco G Salvoza

(74) *Attorney, Agent, or Firm* — Carlson, Caspers, Vandenburgh & Lindquist, P.A.

(57) ABSTRACT

Disclosed herein are coronavirus Spike (S) proteins and nanoparticles comprising the same, which are suitable for use in vaccines. The nanoparticles present antigens from pathogens surrounded to and associated with a detergent core resulting in enhanced stability and good immunogenicity. Dosages, formulations, and methods for preparing the vaccines and nanoparticles are also disclosed.

11 Claims, 83 Drawing Sheets

(74 of 83 Drawing Sheet(s) Filed in Color)

Specification includes a Sequence Listing.

Related U.S. Application Data 14, 2020, provisional application No. 62/966,271, filed on Jan. 27, 2020.

(56) References Cited

U.S. PATENT DOCUMENTS

| | | | |
|---|---|---|---|
| 5,057,540 | A | 10/1991 | Kensil et al. |
| 5,620,690 | A | 4/1997 | Kersten et al. |
| 5,629,021 | A | 5/1997 | Wright |
| 6,231,859 | B1 | 5/2001 | Kensil |
| 6,352,697 | B1 | 3/2002 | Cox et al. |
| 6,387,373 | B1 | 5/2002 | Wright et al. |
| 6,428,807 | B1 | 8/2002 | MacFarlan et al. |
| 6,524,584 | B2 | 2/2003 | Kensil |
| 6,558,670 | B1 | 5/2003 | Friede et al. |
| 6,846,489 | B1 | 1/2005 | Garcon et al. |
| 7,776,343 | B1 | 8/2010 | Cox et al. |
| 8,173,141 | B2 | 5/2012 | Cox et al. |
| 8,541,003 | B2 | 9/2013 | Anderson et al. |
| 8,821,881 | B2 | 9/2014 | Morein et al. |
| 10,022,437 | B2 | 7/2018 | Pushko et al. |
| 10,426,829 | B2 | 10/2019 | Smith et al. |
| 10,485,863 | B2 | 11/2019 | Osterhaus et al. |
| 10,729,764 | B2 | 8/2020 | Morein et al. |
| 10,906,944 | B2 | 2/2021 | He et al. |
| 10,953,089 | B1 | 3/2021 | Smith et al. |
| 11,149,286 | B1 | 10/2021 | Barry |
| 11,253,586 | B2 | 2/2022 | Smith et al. |
| 11,541,112 | B2 | 1/2023 | Smith et al. |
| 11,896,664 | B2 | 2/2024 | Smith et al. |
| 2006/0121065 | A1 | 6/2006 | Morein et al. |
| 2006/0239963 | A1 | 10/2006 | Morein et al. |
| 2010/0017904 | A1 | 1/2010 | Abad et al. |
| 2012/0107353 | A1 | 5/2012 | Morein et al. |
| 2013/0129770 | A1 | 5/2013 | Osterhaus et al. |
| 2014/0335049 | A1 | 11/2014 | Morein et al. |
| 2015/0209425 | A1 | 7/2015 | Morein et al. |
| 2015/0265698 | A1 | 9/2015 | Pushko et al. |
| 2016/0008451 | A1 | 1/2016 | Stary et al. |
| 2016/0046675 | A1 | 2/2016 | Kwong et al. |
| 2016/0184427 | A1 | 6/2016 | Morein et al. |
| 2016/0206729 | A1 | 7/2016 | Smith et al. |
| 2018/0346521 | A1 | 12/2018 | Langedijk |
| 2018/0369368 | A1 | 12/2018 | Morein et al. |
| 2020/0061185 | A1 | 2/2020 | Graham et al. |
| 2020/0215189 | A1 | 7/2020 | Morein et al. |
| 2020/0345840 | A1 | 11/2020 | Morein et al. |
| 2020/0407402 | A1 | 12/2020 | He et al. |
| 2021/0139543 | A1 | 5/2021 | He et al. |
| 2021/0228708 | A1 | 7/2021 | Smith et al. |
| 2021/0228709 | A1 | 7/2021 | Smith et al. |
| 2021/0246170 | A1 | 8/2021 | Langedijk et al. |
| 2022/0125914 | A1 | 4/2022 | Smith et al. |
| 2022/0332765 | A1 | 10/2022 | Smith et al. |
| 2022/0354944 | A1 | 11/2022 | Patel et al. |
| 2023/0070886 | A1 | 3/2023 | Smith et al. |
| 2023/0330216 | A1 | 10/2023 | Smith et al. |

FOREIGN PATENT DOCUMENTS

| | | | |
|---|---|---|---|
| CN | 1472332 | A | 2/2004 |
| EP | 0109942 | A2 | 5/1984 |
| EP | 0242380 | B1 | 4/1991 |
| EP | 0180564 | B1 | 7/1991 |
| EP | 0436620 | B1 | 8/1994 |
| EP | 0362279 | B1 | 1/1995 |
| EP | 0889736 | B1 | 12/2003 |
| EP | 1539231 | B1 | 6/2009 |
| JP | 2018532703 | A | 11/2018 |
| RU | 2403063 | C1 | 11/2010 |
| RU | 2639559 | C2 | 12/2017 |
| WO | WO-8809336 | A1 | 12/1988 |
| WO | WO-9003184 | A1 | 4/1990 |
| WO | WO-9611711 | A1 | 4/1996 |
| WO | WO-9730728 | A1 | 8/1997 |
| WO | WO-9836772 | A1 | 8/1998 |
| WO | WO-2004004762 | A1 | 1/2004 |
| WO | WO-2004085633 | A1 | 10/2004 |
| WO | WO-2005002620 | A1 | 1/2005 |
| WO | WO-2009081285 | A2 | 7/2009 |
| WO | WO-2013049342 | A1 | 4/2013 |
| WO | WO-2014153087 | A1 | 9/2014 |
| WO | WO-2015042373 | A1 | 3/2015 |
| WO | WO-2015080973 | A1 | 6/2015 |
| WO | WO-2017041100 | A2 | 3/2017 |
| WO | WO-2017161151 | A1 | 9/2017 |
| WO | WO-2018081318 | A1 | 5/2018 |
| WO | WO-2018170347 | A1 | 9/2018 |
| WO | WO-2021147025 | A1 | 7/2021 |
| WO | WO-2021154763 | A1 | 8/2021 |
| WO | WO-2021155323 | A1 | 8/2021 |
| WO | WO-2022046634 | A1 | 3/2022 |

OTHER PUBLICATIONS

Dorr et al., "Detergent-free isolation, characterization, and functional reconstitution of a tetrameric K+ channel: The power or native nanodiscs," PNAS, vol. 111, No. 52: 18607-18612 (Year: 2014).*

Thermoscientific, "Tech Tip #19: Remove detergent from protein samples," TR00192 (Year: 2010).*

United Arab Emirates Ministry of Economy, "Office Action Summary", App. No. P6001416/2022, Dec. 16, 2024, 7 pgs.

United Arab Emirates Ministry of Economy, "Search Report", App. No. P6001416/2022, Dec. 16, 2024, 4 pgs.

Federal Institute for Intellectual Property Rights (Rospatent), Office Action and Information Search Report, App. No. 2022122879, Jun. 6, 2024, 11 pgs. (w/English Translation).

"Safety Evaluation of Certain Food Additives and Contaminants Quillaia Extracts," WHO Food Additives Series:48, 14 pages (1996).

Ahlberg et al., Global transcriptional response to ISCOM-Matrix adjuvant at the site of administration and in the draining lymph node early after intramuscular injection in pigs, Developmental and Comparative Immunology, vol. 38, pp. 17-26 (2012), Elsevier Ltd.

Anonymous, "Novavax to Present at the 2013 Stifel Nicolaus Healthcare Conference," Reuters, 1 page http://in.reuters.com/article/2013/09/05/idUSnGNX7PTmrq+1d8+GNW20130905 (2013).

Anonymous, "Stifel 2013 Healthcare Conference," pp. 1-35, http://www.novavax.com/download/file/2013_09_12%20Novavax_Stifel_presentation.pdf (2013).

Barr et al., "ISCOMs and other saponin based adjuvants," Advanced Drug Delivery Reviews, (1998), 32: 247-271.

Behboudi et al., "Quillaja Saponin Formulations that Stimulate Proinflammatory Cytokines Elicit a Potent Acquired Cell-Mediated Immunity," Scand. J. Immunol. 50:371-377 (1999).

Bengtsson et al., "ISCOM technology-based Matrix™ adjuvant: success in future vaccines relies on formulation," Expert. Rev. Vaccines 10(4):401-403 (2011).

Bengtsson et al., Matrix-M adjuvant increases immunogenicity of seasonal influenza vaccine for the elderly, manuscript in preparation, pp. 1-27 (2014).

Boulter, et al., Evaluation of recombinant sporozoite antigen SPAG-1 as a vaccine candidate against Theileria annulata by the use of different delivery systems, Tropical Medicine and International Health, vol. 4, pages A71-A77 (1999), Blackwell Science, Ltd.

Chan et al., "Functional Characterization of Heptad Repeat 1 and 2 Mutants of theSpike Protein of Severe Acute Respiratory Syndrome Coronavirus," Journal of Virology 3225-3237 (2006).

Chatterjee et al., "The 2019 novel coronavirus disease (COVID-19) pandemic: A review of the current evidence," Indian J Med Res 151(2-3):147-159 (Year: 2020).

Chen et al., "RNA based mNGS approach identifies a novel human coronavirus from two individual pneumonia cases in 2019 Wuhan outbreak," Emerging Microbes & Infections 9(1):313-319 (2019).

Chen, Y. et al., "Emerging coronaviruses: Genome structure, replication, and pathogenesis"; Journal of Medical Virology; (Jan. 22, 2020); vol. 92; issue 4, pp. 418-423.

(56) References Cited

OTHER PUBLICATIONS

Cheng et al., "Use of convalescent plasma therapy in SARS patients in Hong Kong," Eur. J. Clin. Microbiol. Infect. Dis. 24(1):44-46 (2005).
Coleman et al., "Purified coronavirus spike protein nanoparticles induce coronavirus neutralizing antibodies in mice," Vaccine 32(26):3169-3174 (2014).
"Committee for Veterinary Medicinal Products, Quillaia Saponins, Summary Report", The European Agency for the rgJ Evaluation of Medicinal Products, EMEA/MRL/055/95-FINAL, Feb. 1996, pp. 1-2.
Copland et al., "Hydration of lipid films with an aqueous solution of Quil A: a simple method for the preparation of immune-stimulating complexes," International Journal of Pharmaceutics 196:135-139 (2000).
Coulter, et al., Studies on experimental adjuvanted influenza vaccines: comparison of immune stimulating complexes(Iscoms) and oil-in-water vaccines; Vaccine, vol. 16, No. 11/12, pp. 1243-1253 (1998), Elsevier Science Ltd., Great Britain.
Cox, et al., Development of an Influenza-ISCOM Vaccine, in Vaccine Design (eds. G. Gregoriadis et al.), Springer Science+ Business Media, New York (1997), pp. 33-49.
Cox, et al., Evaluation of a virosomal H5N1 vaccine formulated with Maxtrix M adjuvant in phase I clinical trial, Elsevier Ltd, Vaccine, 29, pp. 8049-8059, Aug. 22, 2011.
Cox, et al., Prospects for the Development of New Vaccine Adjuvants, BioDrugs, vol. 12(6), pp. 439-453 (1999), Ad is International Limited.
Danaei et al., "Impact of particle Size and Polydispersity Index on the Clinical Applications of Lipidic nanocarrier Systems", Pharmaceutics, 2018, pp. 1-17, vol. 10.
Database UniProt [Online], "SubName: Full=S Protein {ECO:0000313|EMBL:AGN70973.1}," EBI accesion No. UNIPROT:R9UQ53, Database accession No. R9UQ53 (2013), 2 pages.
Delmas and Laude, "Assembly of Coronavirus Spike Protein into Trimers and its Role in Epitope Expression," Journal of Virology 64(11):5367-5375 (1990).
Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).
Demana et al., "Pseudo-ternary phase diagrams of aqueous mixtures of Quil A, cholesterol and phospholipid prepared by the lipid-film hydration method," International Journal of Pharmaceutics 270:229-239 (2004).
Drane et al., "ISCOMATRIX adjuvant for prophylactic and therapeutic vaccines", Expert Review Vaccines, 2007, vol. 6, No. 6, pp. 761-772.
Du et al., "The spike protein of SRS-CpV—a target for vaccine and therapeutic development," Nat. Rev. Microbiol. 7(3):226-236 (2009).
Du, L., et al., "Identification of a Receptor-Binding Domain in the S Protein of the Novel Human Coronavirus Middle East Respiratory Syndrome Coronavirus as an Essential Target for Vaccine Development," J. Virol. 87(17):9939-9942 (2013).
Duan, et al., An overview of the novel coronavirus MERS-CoV, Chin J Viral Dis, 3(4):245-249 (2013).
Eckert et al., "Mechanisms of Viral Membrane Fusion and Its Inhibition," Annual Review of Biochemistry 70:770-810 (2001).
Ekstrom et al., "Iscom and iscom-matrix enhance by intranasal route the IgA responses to OVA and rCTB in local and remote mucosal secretions," Vaccine 17:2690-2701 (1999).
Ennis et al., "Augmentation of Human Influenza A Virus-Specific Cytotoxic T Lymphocyte Memory by Influenza Vaccine and Adjuvanted Carriers (ISCOMS)," Virology 25:256-261 (1999).
Extended European Search Report for European Application No. EP21747453.5 dated Jan. 12, 2024, 18 pages.
Eyles et al., "Immunodominant Francisella tularensis antigens identified using proteome microarray," Proteomics 7:2172-2183 (2007).
Follis et al., "Furin cleavage of the SARS coronavirus spike glycoprotein enhances cell-cell fusion but does not affect virion entry," Virology 350(2):358-369 (2006).
Fossum et al., Early inflammatory response to the saponin adjuvant Matrix-M in the pig, Veterinary Immunology and Immunopathology, http://dx.doi.org/10.1016/j.vetimm.2013.07.007 (2013), pp. 1-9, Elsevier B.V.
Genocea Biosciences, Genocea Reports Positive Initial Phase 1/2A Results for GEN-003, it's Pioneering Therapeutic Vaccine Candidate for the Treatment of Herpes Simplex Virus-2 (HSV-2), at ICAAC 2013, press release, Cambridge MA, Sep. 12, 2013, pp. 1-3.
Gillim-Ross et al., "Emerging Respiratory Viruses: Challenges and Vaccine Strategies," Clin. Microbiol. Rev. 19(4):614-636 (2006).
Gonzalez-Reyes et al., "Cleavage of the human respiratory syncytial virus fusion protein at two distinct sites is required for activation of membrane fusion," Proc. Natl. Acad. Sci. USA 98(17):9859-9864 (2001).
Gretebeck et al., "Animal models for SARS and MERS coronaviruses," Virology, 13:123-129 (Year: 2015).
Gruenke et al., "New Insights into the Spring-Loaded Conformational Change of Influenza Virus Hemagglutinin," Journal of Virology, May 2002, 76:(9) 4456-4466 (2002).
Hilgenfeld et al., "From SARS to MERS: 10 years of research on highly pathogenic human coronaviruses," Antiviral Res. 100(1):286-295 (2013).
Hoffman, M. et al., "Priming Time: How Cellular Proteases Arm Coronavirus Spike Proteins"; Coronavirus Spike Protein: Springer International Publishing AG; (2018); pp. 71-98; DOI: 10.1007/978-3-319-75474-1_4.
International Search Report and Written Opinion issued by the International Searching Authority for Application No. PCT/US21/15220, dated Jun. 30, 2021, 14 pages.
Jackson et al., "An mRNA Vaccine against SARS-CoV-2 Preliminary Report," The New England Journal of Medicine, pp. 1-12 (2020).
Jiang et al., "A predicted receptor-binding and critical neutralizing domain in S protein of the novel human coronavirus HCoV-EMC", Journal of Infection (66):464-466 (2013).
Johansson et al., "Iscoms with different quillaja saponin components differ in their immunomodulating activities," Vaccine 17:2894-2900 (1999).
Kam et al., "Antibodies against trimeric S glycoprotein protect hamsters against SARS-CoV challenge despite their capacity to mediate FcgammaRII-dependent entry into B cells in vitro," Vaccine 25(4):729-740 (2007).
Kensil, "Saponins as Vaccine Adjuvants," Critical Reviews in Therapeutic Drug Carrier Systems, vol. 13(1&2), pp. 1-55 (1996), Begell House, Inc.
Kersten et al., On the structure of immune-stimulating saponin-lipid complexes (iscoms) Biochimica et Biophysica Acta, 1062:165-171 (1991).
Kirchdoerfer et al., "Stabilized coronavirus spikes are resistant to conformational changes induced by receptor recognition or proteolysis.," Scientific Reports, (2018); 8(1):15701.
Kleine-Weber et al., Functional analysis of potential cleavage sites in the MERS coronavirus spike protein, Scientific Reports vol. 8, No. 1, article 16597, pp. 1-11 (2018).
Korber et al., "Tracking Changes in SARS-CoV-2 Spike: Evidence that D614G Increases Infectivity of the COVID-19 Virus," Cell 182:1-16 (2020).
Kuroiwa, Y., et al., "Antigen-specific human polyclonal antibodies from hyperimmunized cattle," Nat. Biotechnol. 27(2):173-181 (2009).
Lavelle et al., "Cholera Toxin Promotes the Induction of Regulatory T Cells Specific for Bystander Antigens by Modulating Dendritic Cell Activation," Journal of Immunology 171:2384-2392 (2003).
Li et al., "Immunogenicity and Protection Efficacy of Monomeric and Trimeric Recombinant SARS Coronavirus Spike Protein Subunit Vaccine Candidates," Viral Immunology 26(2):126-132 (2013).
Liu et al., "Chimeric severe acute respiratory syndrome coronavirus (SARS-CoV) S glycoprotein and influenza matrix 1 efficiently form virus-like particles (VLPs) that protect mice against challenge with SARS-CoV," Vaccine 29(38):6606-6613 (2011).

(56) References Cited

OTHER PUBLICATIONS

Lovgren et al., The Requirement of Lipids for the Formation of Immunostimulating Complexes (Iscoms), Biotechnol. Appl. Biochem. 10:161-172 (1988).
Lovgren-Bengtsson, 6 Preparation and Use of Adjuvants; Methods in Microbiology, vol. 25, pp. 471-502 (1998), Academic Press Ltd.
Lovgren-Bengtsson et al., "4.5 Preparation and Use of Adjuvants," Methods in Microbiology 32:551-588 (2002).
Lu et al., "Immune responses against severe acute respiratory syndrome coronavirus induced by virus-like particles in mice," Immunol. 122:496-502 (2007).
Lucy et al., "Structure and Assembly of Macromolecular Lipid Complexes Composed of Globular Micelles," Journal of Molecular Biology, (1964), 8: 727-748.
Magnusson et al., Immune enhancing properties of the novel Matrix-M adjuvant leads to potentiated immune responses to an influenza vaccine in mice, Vaccine, http://dx.doi.org/10.1 016/j.vaccine.2013.01.039 (2013), pp. 1-9, Elsevier Ltd.
Magnusson et al., Matrix-M adjuvanted envelope protein vaccine protects against lethal lineage 1 and 2 West Nile virus infection in mice, Vaccine vol. 32, pp. 800-808 (2014), Elsevier Ltd.
Matsushita et al., "Triple immunoglobulin gene knockout transchromosomic cattle: bovine lambda cluster deletion and its effect on fully human polyclonal antibody production," PLOS One 9(3):1-14 (2014).
McKenzie et al., ISCOMATRIX vaccines: Safety in human clinical studies, Human Vaccines, vol. 6, No. 3, pp. 237-246 (2010), Landes BioScience.
Morein et al., "Current status and potential application of ISCOMs in veterinary medicine," Advanced Drug Delivery Reviews 56:1367-1382 (2004).
NCT01669512, Adjuvanting Viral Vectored Malaria Vaccines with Matrix M, dated Mar. 9, 2014, pp. 1-4.
NCT04368988, Evaluation of the Safety and Immunogenicity of a SARS-CoV-2 rS Nanoparticle Vaccine With/Without Matrix-M Adjuvant, dated Apr. 30, 2020, 21 pages.
NCT04533399, A Study Looking at the Effectiveness and Safety of a COVID-19 Vaccine in South African Adults, dated Aug. 31, 2020, 18 pages.
NCT04583995, A Study Looking at the Effectiveness, Immune Response, and Safety of a COVID-19 Vaccine in Adults in the United Kingdom, dated Oct. 12, 2020, 11 pages.
NCT04611802, A Study to Evaluate the Efficacy, Immune Response, and Safety of a COVID-19 Vaccine in Adults â‰¥ 18 Years With a Pediatric Expansion in Adolescents (12 to 18 Years) at Risk for SARS-CoV-2, dated Nov. 2, 2020,18 pages.
NCT04834869, COVID-19 Vaccines Safety Tracking (CoVaST), dated Apr. 8, 2021, 11 pages.
NCT04889209, Delayed Heterologous SARS-CoV-2 Vaccine Dosing (Boost) After Receipt of EUA Vaccines, dated May 17, 2021, 16 pages.
NCT04961541, Evaluation of the Safety and Immunogenicity of Influenza and COVID-19 Combination Vaccine, dated Jul. 14, 2021, 14 pages.
NCT05029856, Evaluation of the Safety and Immunogenicity of SII Vaccine Constructs Based on the SARS-CoV-2 (COVID-19) Variant in Adults, dated Sep. 1, 2021, 13 pages.
NCT05112848, a study to evaluate safety and immunogenicity of a covid-19 vaccine in people living with HIV at Risk for SARS-CoV-2 (COVID-19), dated Nov. 9, 2021, 16 pages.
NCT05236491, Covid-19 Vaccine Booster in Immunocompromised Rheumatic Diseases, Dated Feb. 11, 2022, 9 pages.
NCT05249816, Phase 3 Study to Evaluate a Single Booster of the NVX-CoV2373 COVID19 Vaccine in Adults, dated Feb. 22, 2022, 11 pages.
NCT05372588, Phase 3 Booster Study for the SARS-CoV-2 rS Vaccines, dated May 12, 2022, 12 pages.
Nord, "Novel acetylated triterpenoid saponins in a chromatographic fraction from Quilaja saponinaria Molina," Carb. Res. 329:817-829 (2000).
Ozel et al., "Quaternary Structure of the Immunostimulating Complex (Iscom), "Journal of Ultrastructure and Molecular Structure Research 102:240-248 (1989).
Pallesen et al., Immunogenicity and structures of a rationally designed prefusion MERS-CoV spike antigen. Proc Natl Acad Sci US A. Aug. 29, 2017;114(35):E7348-E7357. doi: 10.1073/pnas.1707304114. Epub Aug. 14, 2017.
Parrish, "Novavax creates MERS-COV vaccine candidate," http://vaccinenewsdaily.com/vaccine_development/325407-novavax-creates-mers- cov-vaccine-candidate/ (2013), 2 pages.
Pedersen et al., Matrix-M adjuvanted virosomal H5N1 vaccine confers protection against lethal viral challenge in a murine model, Influenza and Other Respiratory Viruses. DOI: 1 0.1111/j.1750-2659.2011.00256.x (2011 ), pp. 1-12, Blackwell Publishing Ltd.
Pedersen, et al.; T-Helper 1 Cells Elicited by H5N1 Vaccination Predict Seroprotection, Journal of Infectious Disease, 206, pp. 158-166, Jul. 15, 2016.
Poulsen et al., "Limits for Antibody Affinity Maturation and Repetoire Diversification in Hyper vaccinated Humans," J. Immunol. 187(8):4429-4235 (2011).
Ranade et al., "Rapid, high throughput protein estimation method for saponin and alhydrogel adjuvanted R21 VLP Malaria vaccine based on intrinsic fluorescence," Vaccine 40:600-601 (2022).
Rey, F. A. et al., "Common Features of Enveloped Viruses and Implications for Immunogen Design for Next-Generation Vaccines"; Cell; (Mar. 8, 2018); vol. 172; issue 6, pp. 1319-1334.
Rimmelzwaan. et al., A randomized, double blind study in young healthy adults comparing cell mediated and 1 humoral immune responses induced by influenza ISCOM vaccines and conventional vaccines; Vaccine, 2001, vol. 19, pp. 1180-1187, Elsevier Science Limited.
Ronnberg et al., "Adjuvant activity of non-toxic Quillaja saponaria Molina components for use in ISCOM matrix," Vaccine, vol. 13, No. 14, pp. 1375-1382 (1995).
Safety and Immunogenicity Study of Therapeutic HSV-2 Vaccine, Identifier NCT01667341, ClinicalTrials.gov, U.S. National Institutes of Health; available at http://clinicaltrials.gov/ct2/show/NCT01667341 ?term=matrix+m&rank=3, Mar. 9, 2014, pp. 1-4.
Sekimukai et al., "Gold nanoparticle-adjuvanted S protein induces a strong antigen-specific IgG response against severe acute respiratory syndrome-related coronavirus infection, but fails to induce protective antibodies and limit eosinophilic infiltration in lungs, "Microbiology and Immunology, 64:33-51 (Year: 2020).
Shen, X. et al., "Neutralization of SARS-CoV-2 Variants B.1.429 and B.1.351," N Engl J Med. (Apr. 7, 2021), pp. 1-3.
Shimizu, "Chapter 32. Routes of Administration," in The Laboratory Mouse, Hans Hedrich and Gillian Bullock, Eds., Elsevier Academic Press, 15 pages (2004).
Sjolander et al., "ISCOMs: an adjuvant with multiple functions", J Leukoc Biol. Dec. 1998; 64(6): 713-23.
Sjolander, et al., Uptake and adjuvant activity of orally delivered saponin and ISCOM vaccines, Advanced Drug Delivery Reviews, vol. 34, pp. 321-338 (1998), Elsevier Science B.V.
Skoberne et al., An adjuvanted herpes simplex virus 2 subunit vaccine elicits a T cell response in mice and is an effective therapeutic vaccine in Guinea pigs, J. Virol. 87:3930-3942 (2013).
Song, F., et al., "Middle East Respiratory Syndrome Coronavirus Spike Protein Delivered by Modified Vaccinia Virus Ankara Efficiently Induces Virus-Neutralizing Antibodies," J. Virol. 87(21):11950-11954 (2013).
Sun et al., "Advances in saponin-based adjuvants", Vaccine. Mar. 13, 2009; 27(12):1787-96. Epub Feb. 7, 2009.
Sun et al., "ISCOMs and ISOMATRIX," Vaccine 27:4388-4401 (2009).
Third Party Observation: Additional Comments in Respect of WO2021154812, Document #11 issued for International Application No. PCT/US2021/015220 on May 27, 2022, 2 pages.
Third Party Observation issued for International Application No. PCT/US2021/015220 on May 27, 2022, 11 pages.
Tian et al., "SARS-CoV-2 spike glycoprotein vaccine candidate NVX-CoV2373 elicits immunogenicity in baboons and protection in mice," Jun. 30, 2020, 50 pages.

(56) References Cited

OTHER PUBLICATIONS

Tian et al., "SARS-CoV-2 spike glycoprotein vaccine candidate NVX-CoV2373 immunogenicity in baboons and protection in mice", Nature Communications, Jan. 2021, vol. 12, No. 1, article 372, pp. 1-14.
Van Boheemen et al., "Genomic Characterization of a Newly Discovered Coronavirus Associated with Acute Respiratory Distress Syndrome in Humans," mBio 3(6):e00473-12, 9 pages (2012).
Van Doremalen N. et al. ChAdOx1 nCoV-19 vaccination prevents SARS-CoV-2 pneumonia in rhesus macaques. bioRxiv, 23 pages (2020).
Wald, "A Novel Therapeutic Vaccine (GEN003) for Genital Herpes Reduces HSV-2 Shedding: Initial Results of Clinical Trial GEN003-001," Presented at Interscience Conference on Antimicrobial Agents and Chemotherapy (ICAAC 2013), Denver, CO, Sep. 12, 2013, pp. 1-21.
Wald et al., Novel Therapeutic Vaccine for Genital Herpes Reduces Genital HSV-2 Shedding, in ICAAC 2013, Denver, CO, Sep. 2013, cover page and p. 279, Abstract 183(G).
Walls et al., "Functional Characterization of Heptad Repeat 1 and 2 Mutants of the Spike Protein of Severe Acute Respiratory Syndrome Coronavirus," Nature 531, 17 pages (2016).
Wang et al., "Subunit Vaccines Against Emerging Pathogenic Human Coronaviruses," Frontiers in Microbiology, 11:298, 19 pages (Year: 2020).
Wrapp et al., "Cryo EM Structure of the 2019 nCoV spike in the Prefusion Conformation," bioRxiv, posted Feb. 15, 2020 online at https://doi.org/10.1101/2020.02.11.944462, 30 pages.
Wrapp et al., Cryo EM Structure of the 2019 nCoV spike in the Prefusion Conformation Science 10.1126/science.abb2507 (2020), 9 pages.
Yeh, "Experience of using convalescent plasma for severe acute respiratory syndrome among healthcare workers in a Taiwan hospital," J. Antimicrob. Chemother. 56(5):919-922 (2005).
Canadian Intellectual Property Office, "First Office Action", App. No. 3,165,371, Apr. 4, 2024, 6 pgs.
Karin Lovgren Bengtsson, Bror Morein & Albert DME Osterhaus, (2011), "ISCOM technology-based Matrix M adjuvant: success in future vaccines relies on formulation," Expert Review of Vaccines, 10:4, 401-403, DOI: 10.1586/erv.11.25.
Federal Institute for Intellectual Property Rights (ROSPATENT), Office Action, App. No. 2022122879, Jan. 16, 2025, 6 pgs. (with English translation).
GenBank: "Wuhan seafood market pneumonia virus isolate Wuhan-Hu-1, Complete Genome," Accession No. MN908947.1; GenBank, Jan. 12, 2020, 11 pages.
Japanese Patent Office, "Office Action," App. No. 2022-545141, Dec. 6, 2024, 8 pgs. (w/English translation).
Taiwan Intellectual Property Office, "First Office Action", App. No. TW 110103013, Jan. 3, 2025, 11 pgs. (w/English Translation).
United States Patent and Trademark Office, "Final Office Action", U.S. Appl. No. 18/061,831, Jan. 28, 2025, 8 pgs.
Liener, "The Lectins: Properties, Functions, and Applications in Biology and Medicine," Elsevier, 2012.
Sharon, N. and Lis, H. (1990), Legume lectins—a large family of homologous proteins. The FASEB Journal, 4: 3198-3208.
Van Doremalen N. et al. A single dose of ChAdOx1 MERS provides protective immunity in rhesus macaques. Science Advances, 2020.
Taiwan Intellectual Property Office, "Final Office Action", App. No. TW 110103013, Jun. 25, 2025, 7 pgs. (w/English Translation).

* cited by examiner

Fig. 1

MFVFLVLLPLVSSQCVNLTTRTQLPPAYTNSFTRGVYYPDKVFRSSVLHSTQDLFLPFFSN
VTWFHAIHVSGTNGTKRFDNPVLPFNDGVYFASTEKSNIIRGWIFGTTLDSKTQSLLIVNN
ATNVVIKVCEFQFCNDPFLGVYYHKNNKSWMESEFRVYSSANNCTFEYVSQPFLMDLEG
KQGNFKNLREFVFKNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALDPLSETKCTLK
SFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLP
DDFTGCVIAWNSNNLDSKVGGNYNYLYRLFRKSNLKPFERDISTEIYQAGSTPCNGVEGF
NCYFPLQSYGFQPTNGVGYQPYRVVVLSFELLHAPATVCGPKKSTNLVKNKCVNFNFNG
LTGTGVLTESNKKFLPFQQFGRDIADTTDAVRDPQTLEILDITPCSFGGVSVITPGTNTSNQ
VAVLYQDVNCTEVPVAIHADQLTPTWRVYSTGSNVFQTRAGCLIGAEHVNNSYECDIPIG
AGICASYQTQTNSPRRARSVASQSIIAYTMSLGAENSVAYSNNSIAIPTNFTISVTTEILPVS
MTKTSVDCTMYICGDSTECSNLLLQYGSFCTQLNRALTGIAVEQDKNTQEVFAQVKQIYK
TPPIKDFGGFNFSQILPDPSKPSKRSFIEDLLFNKVTLADAGFIKQYGDCLGDIAARDLICA
QKFNGLTVLPPLLTDEMIAQYTSALLAGTITSGWTFGAGAALQIPFAMQMAYRFNGIGVT
QNVLYENQKLIANQFNSAIGKIQDSLSSTASALGKLQDVVNQNAQALNTLVKQLSSNFGA
ISSVLNDILSRLDKVEAEVQIDRLITGRLQSLQTYVTQQLIRAAEIRASANLAATKMSECV
LGQSKRVDFCGKGYHLMSFPQSAPHGVVFLHVTYVPAQEKNFTTAPAICHDGKAHFPRE
GVFVSNGTHWFVTQRNFYEPQIITTDNTFVSGNCDVVIGIVNNTVYDPLQPELDSFKEEL
DKYFKNHTSPDVDLGDISGINASVVNIQKEIDRLNEVAKNLNESLIDLQELGKYEQYIKWP
WYIWLGFIAGLIAIVMVTIMLCCMTSCCSCLKGCCSCGSCCKFDEDDSEPVLKGVKLHYT

BV2378: 3Q-ΔFP-2P

BV2373

WTSARS-CoV-2 S
nm
Time (S)
300nM
150nM
75nM
37.5nM
18.8nM
9.4nM
4.7nM

BV2365
nm
Time (S)
300nM
150nM
75nM
37.5nM
18.8nM
9.4nM
4.7nM

BV2373
nm
Time (S)
300nM
150nM
75nM
37.5nM
18.8nM
9.4nM
4.7nM

WTSARS-CoV-2 S
hACE2
hDPP4
IC50 (ng mL-1)
hACE2: 38
hDPP4: >5000
A450nm
hACE2 or hDPP4 (μg mL-1)

BV2365
hACE2
hDPP4
IC50 (ng mL-1)
hACE2: 36
hDPP4: >5000
A450nm
hACE2 or hDPP4 (μg mL-1)

BV2373
hACE2
hDPP4
IC50 (ng mL-1)
hACE2: 18
hDPP4: >5000
A450nm
hACE2 or hDPP4 (μg mL-1)

Fig. 30

BV2384: CoV-2019/GSAS/K986P/V987P (SEQ ID NO: 109)

Isoelectric Pt (pI) 5.89

Signal peptide

MFVFLVLLPLVSSQCVNLTTRTQLPPAYTNSFTRGVYYPDKVFRSSVLHSTQDLFLPFFSNVTWFHAIHVSGT
NGTKRFDNPVLPFNDGVYFASTEKSNIIRGWIFGTTLDSKTQSLLIVNNATNVVIKVCEFQFCNDPFLGVYYH
KNNKSWMESEFRVYSSANNCTFEYVSQPFLMDLEGKQGNFKNLREFVFKNIDGYFKIYSKHTPINLVRDLPQG
FSALEPLVDLPIGINITRFQTLLALHRSYLPGDSSSGWTAGAAAYYVGYLQPRTFLLKYNENGTITDAVDCAL
DPLSETKCTLKSFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLPDDFTGCVIAWNSN
NLDSKVGGNYNYLYRLFRKSNLKPFERDISTEIYQAGSTPCNGVEGFNCYFPLQSYGFQPTNGVGYQPYRVVV
LSFELLHAPATVCGPKKSTNLVKNKCVNFNFNGLTGTGVLTESNKKFLPFQQFGRDIADTTDAVRDPQTLEIL
DITPCSFGGVSVITPGTNTSNQVAVLYQDVNCTEVPVAIHADQLTPTWRVYSTGSNVFQTRAGCLIGAEHVNN
SYECDIPIGAGICASYQTQTNSPGSASSVASQSIIAYTMSLGAENSVAYSNNSIAIPTNFTISVTTEILPVSM
TKTSVDCTMYICGDSTECSNLLLQYGSFCTQLNRALTGIAVEQDKNTQEVFAQVKQIYKTPPIKDFGGFNFSQ
ILPDPSKPSKRSFIEDLLFNKVTLADAGFIKQYGDCLGDIAARDLICAQKFNGLTVLPPLLTDEMIAQYTSAL
LAGTITSGWTFGAGAALQIPFAMQMAYRFNGIGVTQNVLYENQKLIANQFNSAIGKIQDSLSSTASALGKLQD
VVNQNAQALNTLVKQLSSNFGAISSVLNDILSRLDPPEAEVQIDRLITGRLQSLQTYVTQQLIRAAEIRASAN
LAATKMSECVLGQSKRVDFCGKGYHLMSFPQSAPHGVVFLHVTYVPAQEKNFTTAPAICHDGKAHFPREGVFV
SNGTHWFVTQRNFYEPQIITTDNTFVSGNCDVVIGIVNNTVYDPLQPELDSFKELDKYFKNHTSPDVDLGDIS
GINASVVNIQKEIDRLNEVAKNLNESLIDLQELGKYEQYIKWPWYIWLGFIAGLIAIVMVTIMLCCMTSCCSC
LKGCCSCGSCCKFDEDDSEPVLKGVKLHYT

Fig. 31

BV2373 (SEQ ID NO: 86)

CoV-2019/QQAQ/K986P/V987P

Inactive furin cleavage site

Signal peptide

MFVFLVLLPLVSSQCVNLTTRTQLPPAYTNSFTRGVYYPDKVFRSSVLHSTQDLFLPFFSNVTWFHAIHVSGT
NGTKRFDNPVLPFNDGVYFASTEKSNIIRGWIFGTTLDSKTQSLLIVNNATNVVIKVCEFQFCNDPFLGVYYH
KNNKSWMESEFRVYSSANNCTFEYVSQPFLMDLEGKQGNFKNLREFVFKNIDGYFKIYSKHTPINLVRDLPQG
FSALEPLVDLPIGINITRFQTLLALHRSYLTPGDSSSGWTAGAAAYYVGYLQPRTFLLKYNENGTITDAVDCA
LDPLSETKCTLKSFTVEKGIYQTSNFRVQPTESIVRFPNITNLCPFGEVFNATRFASVYAWNRKRISNCVADY
SVLYNSASFSTFKCYGVSPTKLNDLCFTNVYADSFVIRGDEVRQIAPGQTGKIADYNYKLPDDFTGCVIAWNS
NNLDSKVGGNYNYLYRLFRKSNLKPFERDISTEIYQAGSTPCNGVEGFNCYFPLQSYGFQPTNGVGYQPYRVV
VLSFELLHAPATVCGPKKSTNLVKNKCVNFNFNGLTGTGVLTESNKKFLPFQQFGRDIADTTDAVRDPQTLEI
LDITPCSFGGVSVITPGTNTSNQVAVLYQDVNCTEVPVAIHADQLTPTWRVYSTGSNVFQTRAGCLIGAEHVN
NSYECDIPIGAGICASYQTQTNSPQQAQSVASQSIIAYTMSLGAENSVAYSNNSIAIPTNFTISVTTEILPVS
MTKTSVDCTMYICGDSTECSNLLLQYGSFCTQLNRALTGIAVEQDKNTQEVFAQVKQIYKTPPIKDFGGFNFS
QILPDPSKPSKRSFIEDLLFNKVTLADAGFIKQYGDCLGDIAARDLICAQKFNGLTVLPPLLTDEMIAQYTSA
LLAGTITSGWTFGAGAALQIPFAMQMAYRFNGIGVTQNVLYENQKLIANQFNSAIGKIQDSLSSTASALGKLQ
DVVNQNAQALNTLVKQLSSNFGAISSVLNDILSRLDPPEAEVQIDRLITGRLQSLQTYVTQQLIRAAEIRASA
NLAATKMSECVLGQSKRVDFCGKGYHLMSFPQSAPHGVVFLHVTYVPAQEKNFTTAPAICHDGKAHFPREGVF
VSNGTHWFVTQRNFYEPQIITTDNTFVSGNCDVVIGIVNNTVYDPLQPELDSFKEELDKYFKNHTSPDVDLGD
ISGINASVVNIQKEIDRLNEVAKNLNESLIDLQELGKYEQYIKWPWYIWLGFIAGLIAIVMVTIMLCCMTSCC
SCLKGCCSCGSCCKFDEDDSEPVLKGVKLHYT

Densitometry

Purity: 38.5%

Protein concentration:

A280(0.9226) - A340(0.187) = 0.7356 /1.067 = 0.6894 mg/mL

Total Volume: 19.0mL X 0.6894 mg/mL = 13.098 mg

Yield: 13.098mg/4.8 liter = 2.728 mg/L

Densitometry

Purity: 94.8%

Protein concentration:

A280(0.8368) - A340(0.0248) = 0.8142 /1.067 = 0.761 mg/mL

Total Volume: 42.47mL X 0.761 mg/mL = 42.32 mg

Yield: 42.32mg/5 liter = 6.4 mg/L

SARS-CoV-2 Neutralizing Titers by PRNT (EC90 titers)

Fig. 41

| Procedure | Screening | Day | | | | | | | | |
|---|---|---|---|---|---|---|---|---|---|---|
| | | 0 | 7 | 21 | 28 | 35 | 49 | 105 | 189 | 386 |
| Vaccination | | X | | X | | | | | | |
| Blood sample: safety | X | | X | X | X | | | | | |
| Blood sample: immunogenicity | | X | X | X | X | X | X | X | X | |
| Nasal swab | X | | | | | X | | | | |
| Reactogenicity | | ← | → | ← | → | | | | | |
| Unsolicited AE | | ← | — | — | — | — | → | | | |
| MAAE: All/Related | | ← | — | — | — | — | — | → | — | — |
| SAE or AESI | | ← | — | — | — | — | — | — | — | → |

CORONAVIRUS VACCINE FORMULATIONS

CROSS REFERENCE TO RELATED APPLICATIONS

This application is a divisional of U.S. application Ser. No. 17/572,182, filed Jan. 10, 2022, which is a continuation of U.S. application Ser. No. 17/205,990, filed Mar. 18, 2021, now U.S. Pat. No. 11,253,586, which is a continuation of U.S. application Ser. No. 16/997,001, filed Aug. 19, 2020, now U.S. Pat. No. 10,953,089, which claims priority to the following applications: U.S. Provisional Application No. 62/966,271, filed Jan. 27, 2020; U.S. Provisional Application No. 62/976,858, filed Feb. 14, 2020; U.S. Provisional Application No. 62/983,180, filed Feb. 28, 2020; U.S. Provisional Application No. 63/048,945, filed Jul. 7, 2020; U.S. Provisional Application No. 63/051,706, filed Jul. 14, 2020; and U.S. Provisional Application No. 63/054,182, filed Jul. 20, 2020. Each of the aforementioned applications is incorporated by reference herein in its entirety.

REFERENCE TO AN ELECTRONIC SEQUENCE LISTING

The contents of the electronic sequence listing (NOVV_088_13US_SeqList_ST26.xml; Size: 231,723 bytes; and Date of Creation: Nov. 29, 2023) are herein incorporated by reference in its entirety.

FIELD

The present disclosure is generally related to non-naturally occurring coronavirus (CoV) Spike (S) polypeptides and nanoparticles and vaccines comprising the same, which are useful for stimulating immune responses. The nanoparticles provide antigens, for example, glycoprotein antigens, optionally associated with a detergent core and are typically produced using recombinant approaches. The nanoparticles have improved stability and enhanced epitope presentation. The disclosure also provides compositions containing the nanoparticles, methods for producing them, and methods of stimulating immune responses.

BACKGROUND OF THE INVENTION

Infectious diseases remain a problem throughout the world. While progress has been made on developing vaccines against some pathogens, many remain a threat to human health. The outbreak of sudden acute respiratory syndrome coronavirus 2 (SARS-CoV-2) (also called Wuhan coronavirus and SARS-CoV-2) has infected more than 2000 people in China and killed at least 17 people Recently, the SARS-CoV-2coronavirus has spread to the United States, Thailand, South Korea, Taiwan, and Japan. The SARS-CoV-2coronavirus belongs to the same family of viruses as severe acute respiratory syndrome coronavirus (SARS-CoV) and Middle East respiratory syndrome coronavirus (MERS-CoV), which have killed hundreds of people in the past 17 years. SARS-CoV-2 causes the disease COVID-19.

The development of vaccines that prevent or reduce the severity of life-threatening infectious diseases like the SARS-CoV-2 coronavirus is desirable. However, human vaccine development remains challenging because of the highly sophisticated evasion mechanisms of pathogens and difficulties stabilizing vaccines. Optimally, a vaccine must both induce antibodies that block or neutralize infectious agents and remain stable in various environments, including environments that do not enable refrigeration.

SUMMARY OF THE INVENTION

The present disclosure provides non-naturally occurring CoV S polypeptides suitable for inducing immune responses against SARS-CoV-2 (also called Wuhan CoV and 2019-nCOV)). The disclosure also provides nanoparticles containing the glycoproteins as well as methods of stimulating immune responses.

The present disclosure also provides CoV S polypeptides suitable for inducing immune responses against multiple coronaviruses, including SARS-CoV-2, Middle East Respiratory Syndrome (MERS), and Severe Acute Respiratory Syndrome (SARS).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a schematic of the wild-type amino acid sequence of the SARS-CoV-2 Spike (S) protein (SEQ ID NO: 1). The furin cleavage site RRAR (SEQ ID NO: 6) is highlighted in bold, and the signal peptide is underlined.

FIG. 17A shows the effect of immunization on weight loss with a single 0.01 μg, 0.1 μg, 1 μg, or 10 μg of BV2373 plus MATRIX-M™. FIG. 17B shows the effect of immunization on weight loss with two doses of BV2373 (0.01 μg, 0.1 μg, 1 μg) plus MATRIX-M™. FIG. 17C shows the effect of immunization on weight loss with two doses of BV2373 (10 μg) in the presence or absence of MATRIX-M™.

FIG. 20A shows the frequency of IFN-γ secreting CD4+ T cells. FIG. 20B shows the frequency of TNF-α secreting CD4+ T cells. FIG. 20C shows the frequency of IL-2 secreting CD4+ T cells. FIG. 20D shows the frequency of CD4+ T cells that secrete two cytokines selected from IFN-γ, TNF-α, and IL-2 FIG. 20E shows the frequency of CD4+ T cells that express IFN-γ, TNF-α, and IL-2.

FIG. 21A shows the frequency of IFN-γ secreting $CD8^+$ T cells. FIG. 21B shows the frequency of TNF-α secreting $CD8^+$ T cells. FIG. 21C shows the frequency of IL-2 secreting $CD8^+$ T cells. FIG. 20D shows the frequency of $CD8^+$ T cells that secrete two cytokines selected from IFN-γ, TNF-α, and IL-2. FIG. 21E shows the frequency of $CD8^+$ T cells that express IFN-γ, TNF-α, and IL-2.

FIG. 23A shows the frequency of IL-4 secreting cells. FIG. 23B shows the frequency of IL-5 $CD4^+$ secreting cells. FIG. 23C shows the ratio of IFN-γ secreting to IL-4 secreting $CD4^+$ T cells.

FIG. 24A shows the frequency of $CD4^+$ T follicular helper cells in spleens, and FIG. 24B shows the phenotype (e.g. $CD4^+$ $CXCR5^+$ $PD\text{-}1^+$) of the $CD4^+$ T follicular helper cells.

FIG. 25A shows the frequency of GC B cells in spleens, and FIG. 25B reveals the phenotype (e.g. $CD19^+$ $GL7^+$ $CD\text{-}95^+$) of the $CD4^+$ T follicular helper cells.

FIG. 26A shows the anti-SARS-CoV-2 S polypeptide IgG titer in baboons after immunization with BV2373. FIG. 26B shows the presence of hACE2 receptor blocking antibodies in baboons following a single immunization with 5 μg or 25 μg of BV2373 in the presence of MATRIX-M™. FIG. 26C shows the titer of virus neutralizing antibodies following a single immunization with BV2373 and MATRIX-M™.

FIG. 29A shows the frequency of IFN-γ secreting CD4+ T cells. FIG. 29B shows the frequency of IL-2 secreting CD4+ T cells. FIG. 29C shows the frequency of TNF-α secreting CD4+ T cells. FIG. 29D shows the frequency of CD4+ T cells that secrete two cytokines selected from IFN-γ, TNF-α, and IL-2. FIG. 29E shows the frequency of CD4+ T cells that express IFN-γ, TNF-α, and IL-2.

FIG. 30 shows a schematic of the coronavirus Spike (S) protein (SEQ ID NO: 109) (BV2384). The furin cleavage site GSAS (SEQ ID NO: 97) is underlined once, and the K986P and V987P mutations are underlined twice.

FIG. 31 shows a schematic of the coronavirus Spike (S) protein (SEQ ID NO: 86) (BV2373). The furin cleavage site QQAQ (SEQ ID NO: 7) is underlined once, and the K986P and V987P mutations are underlined twice.

FIG. 41 shows administration timings of a clinical trial that evaluated the safety and efficacy of a vaccine comprising BV2373 and optionally MATRIX-M™. AESI denotes an adverse event of special interest. MAEE denotes a medically attended adverse event, and SAE denotes a serious adverse event.

DETAILED DESCRIPTION OF THE INVENTION

Definitions

Figure 2:
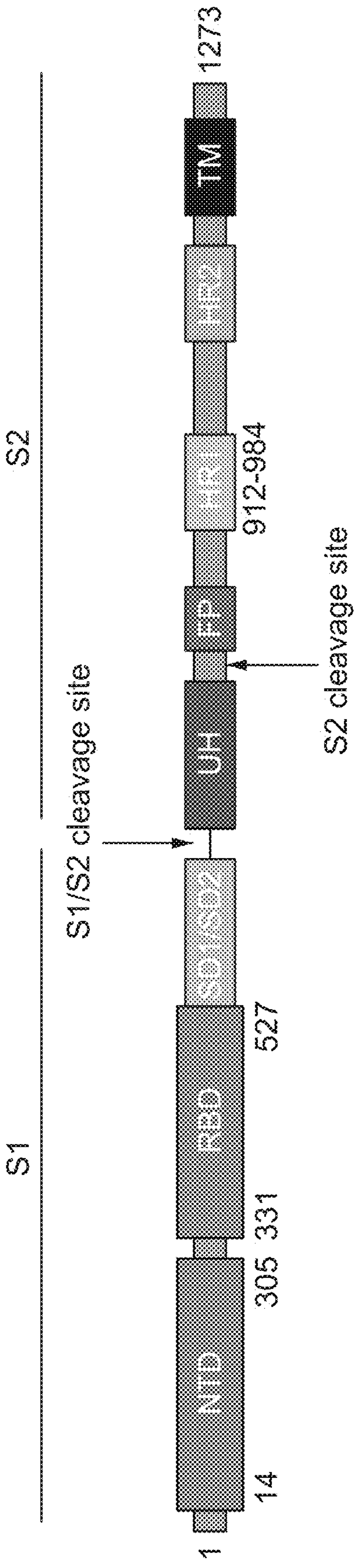
FIG. 2 shows the primary structure of the wild-type CoV S polypeptide, which has an inactive furin cleavage site, a fusion peptide deletion, and K986P and V987P mutations. The domain positions are numbered with respect to the amino acid sequence of the wild-type CoV S polypeptide from SARS-CoV-2 containing a signal peptide (SEQ ID NO. 1).

As used herein, and in the appended claims, the singular forms "a", "an", and "the" include plural referents unless the context clearly dictates otherwise. Thus, for example, reference to "a protein" can refer to one protein or to mixtures of such protein, and reference to "the method" includes reference to equivalent steps and/or methods known to those skilled in the art, and so forth.

As used herein, the term "adjuvant" refers to a compound that, when used in combination with an immunogen, augments or otherwise alters or modifies the immune response induced against the immunogen. Modification of the immune response may include intensification or broadening the specificity of either or both antibody and cellular immune responses.

As used herein, the term "about" or "approximately" when preceding a numerical value indicates the value plus or minus a range of 10%. For example, "about 100" encompasses 90 and 110.

As used herein, the terms "immunogen," "antigen," and "epitope" refer to substances such as proteins, including glycoproteins, and peptides that are capable of eliciting an immune response.

As used herein, an "immunogenic composition" is a composition that comprises an antigen where administration of the composition to a subject results in the development in the subject of a humoral and/or a cellular immune response to the antigen.

As used herein, a "subunit" composition, for example a vaccine, that includes one or more selected antigens but not all antigens from a pathogen. Such a composition is substantially free of intact virus or the lysate of such cells or particles and is typically prepared from at least partially purified, often substantially purified immunogenic polypeptides from the pathogen. The antigens in the subunit composition disclosed herein are typically prepared recombinantly, often using a baculovirus system.

As used herein, "substantially" refers to isolation of a substance (e.g. a compound, polynucleotide, or polypeptide) such that the substance forms the majority percent of the sample in which it is contained. For example, in a sample, a substantially purified component comprises 85%, preferably 85%-90%, more preferably at least 95%-99.5%, and most preferably at least 99% of the sample. If a component is substantially replaced the amount remaining in a sample is less than or equal to about 0.5% to about 10%, preferably less than about 0.5% to about 1.0%.

The terms "treat," "treatment," and "treating." as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to an immunogenic composition, such as an immunogen derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a subject to produce protective immunity.

As used herein, the term "subject" includes humans and other animals. Typically, the subject is a human. For example, the subject may be an adult, a teenager, a child (2 years to 14 years of age), an infant (birth to 2 year), or a neonate (up to 2 months). In particular aspects, the subject is up to 4 months old, or up to 6 months old. In some aspects, the adults are seniors about 65 years or older, or about 60 years or older. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

As used herein, the term "about" means plus or minus 10% of the indicated numerical value.

As used herein, the term "NVX-CoV2373" refers to a vaccine composition comprising the BV2373 Spike glycoprotein (SEQ ID NO: 87) and Fraction A and Fraction C iscom matrix (e.g., MATRIX-M™).

Vaccine Compositions Containing Coronavirus (CoV) Spike (S) Proteins

The disclosure provides non-naturally occurring coronavirus (CoV) Spike (S) polypeptides, nanoparticles containing CoV S polypeptides, and immunogenic compositions and vaccine compositions containing either non-naturally occurring CoV S polypeptides or nanoparticles containing CoV S polypeptides. In embodiments, provided herein are methods of using CoV S polypeptides, nanoparticles, immunogenic compositions, and vaccine compositions to stimulate an immune response.

Also provided herein are methods of manufacturing the nanoparticles and vaccine compositions. Advantageously, the methods provide nanoparticles that are substantially free from contamination by other proteins, such as proteins associated with recombinant expression of proteins in insect cells. In embodiments, expression occurs in baculovirus/Sf9 systems.

CoV S Polypeptide Antigens

The vaccine compositions of the disclosure contain non-naturally occurring CoV S polypeptides. CoV S polypeptides may be derived from coronaviruses, including but not limited to SARS-CoV-2, for example from SARS-CoV-2, from MERS CoV, and from SARS CoV. In contrast to the SARS-CoV S protein, the SARS-CoV-2 S protein has a four amino acid insertion in the S1/S2 cleavage site resulting in a polybasic RRAR furin-like cleavage motif. The SARS-CoV-2 S protein is synthesized as an inactive precursor (S0) that is proteolytically cleaved at the furin cleavage site into S1 and S2 subunits which remain non-covalently linked to form prefusion trimers. The S2 domain of the SARS-CoV-2

S protein comprises a fusion peptide (FP), two heptad repeats (HR1 and HR2), a transmembrane (TM) domain, and a cytoplasmic tail. The S1 domain of the SARS-CoV-2 S protein folds into four distinct domains: the N-terminal domain (NTD) and the C-terminal domain, which contains the receptor binding domain (RBD) and two subdomains SD1 and SD2. The prefusion SARS-CoV-2 S protein trimers undergo a structural rearrangement from a prefusion to a postfusion conformation upon S-protein receptor binding and cleavage.

Figure 3:
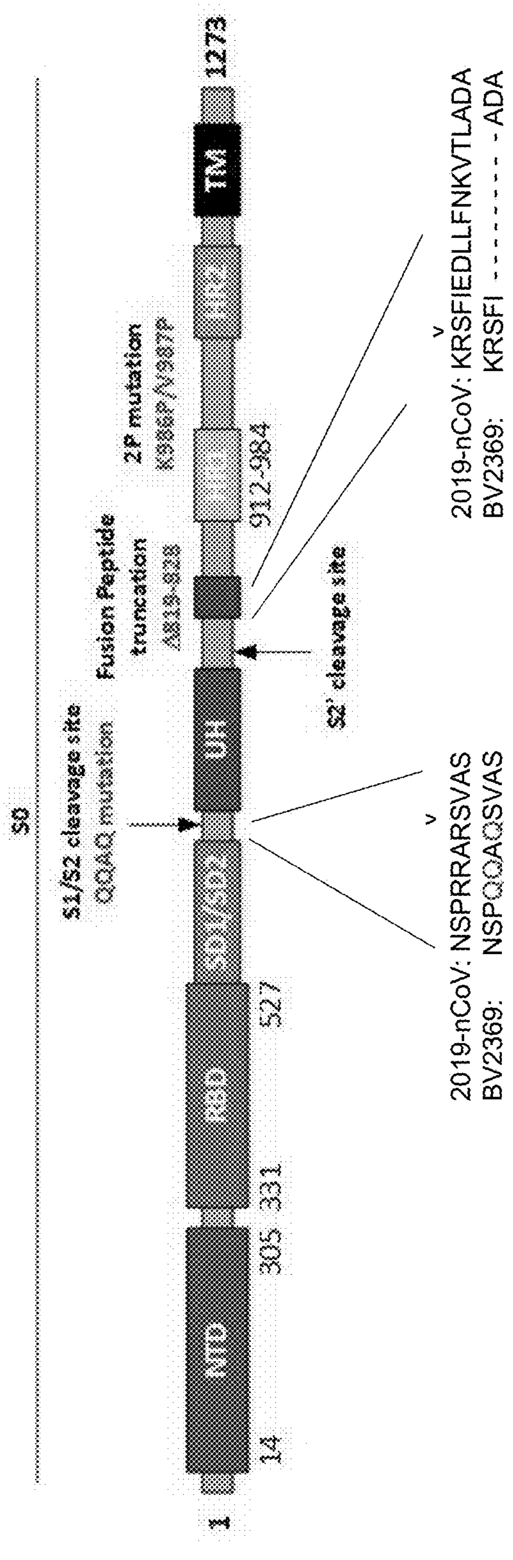
FIG. 3 shows the primary structure of the BV2378 CoV S polypeptide, which has an inactive furin cleavage site, a fusion peptide deletion, and K986P and V987P mutations. The domain positions are numbered with respect to the amino acid sequence of the wild-type CoV S polypeptide from SARS-CoV-2 containing a signal peptide (SEQ ID NO: 1).

In embodiments, the CoV S polypeptides are glycoproteins, due to post-translational glycosylation. The glycoproteins comprise one or more of an NTD, an RBD, an SD1/SD2 portion a UH domain, an intact or modified fusion protein region, an HR1 domain an HR2 domain, and a TM domain. In embodiments, the amino acids for each domain are given in FIG. 2 and FIG. 3 (shown corresponding to SEQ ID NO: 1). In embodiments, each domain may have at least 95%, at least 97% or at least 99% identity to the sequences for each domain as in SEQ ID NO: 1. Each domain may have a deletion or an insertion of about 10, about 20, or about 30 amino acids compared to those shown in SEQ ID NO: 1. Note that FIGS. 2 and 3 illustrate the 13-amino acid N-terminal signal peptide that is absent from the mature peptide. The CoV S polypeptides may be used to stimulate immune responses against the native CoV Spike (S) polypeptide.

In embodiments, the native CoV Spike (S) polypeptide (SEQ ID NO: 2) is modified resulting in non-naturally occurring CoV Spike (S) polypeptides (FIG. 1). In embodiments, the CoV Spike (S) glycoproteins comprise one or more modifications selected from the group consisting of:

(a) an inactivated mutated furin cleavage site amino acids 669-672;

(b) a deletion of one or more amino acids from amino acids 676-685;

(c) a deletion of one or more amino acids from amino acids 702-711;

(d) a deletion of one or more amino acids of the fusion peptide (amino acids 806-815);

(e) mutation of amino acid 601;

(f) mutation of amino acid 973;

(g) mutation of amino acid 974;

(h) a deletion of one or more amino acids from the N-terminal domain (NTD) (amino acids 1-318); and (i) a deletion of one or more amino acids from the transmembrane and cytoplasmic domain (TMCT) (amino acids 1201-1260), wherein the amino acids of the CoV S glycoprotein are numbered with respect to SEQ ID NO: 2. FIG. 3 shows a CoV S polypeptide called BV2378, which has an inactive furin cleavage site, deleted fusion peptide, a K986P, and a V987 mutation.

In embodiments, the CoV S polypeptides described herein exist in a prefusion conformation. In embodiments, the CoV S polypeptides described herein comprise a flexible HR2 domain. Unless otherwise mentioned, the flexibility of a domain is determined by transition electron microscopy (TEM) and 2D class averaging. A reduction in electron density corresponds to a flexible domain.

In embodiments, the CoV S polypeptides contain a furin site (RRAR), amino acids 669 to 672 of the native CoV Spike (S) polypeptide (SEQ ID NO: 2), that is inactivated by one or more mutations. Inactivation of the furin cleavage site prevents furin from cleaving the CoV S polypeptide. In embodiments, the CoV S polypeptides described herein which contain an inactivated furin cleavage site are expressed as a single chain.

In embodiments, one or more of the amino acids comprising the native furin cleavage site is mutated to any natural amino acid. In embodiments, the amino acids are L-amino acids. Non-limiting examples of amino acids include alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine.

In embodiments, one or more of the amino acids comprising the native furin cleavage site is mutated to glutamine. In embodiments, 1, 2, 3, or 4 amino acids may be mutated to glutamine. In embodiments, one of the arginines comprising the native furin cleavage site is mutated to glutamine. In embodiments, two of the arginines comprising the native furin cleavage site are mutated to glutamine. In embodiments, three of the arginines comprising the native furin cleavage site are mutated to glutamine.

In embodiments, one or more of the amino acids comprising the native furin cleavage site, is mutated to alanine. In embodiments, 1, 2, 3, or 4 amino acids may be mutated to alanine. embodiments, one of the arginines comprising the native furin cleavage site is mutated to alanine. In embodiments, two of the arginines comprising the native furin cleavage site are mutated to alanine. In embodiments, three of the arginines comprising the native furin cleavage site are mutated to alanine.

In embodiments, one or more of the amino acids comprising the native furin cleavage site is mutated to glycine. In embodiments, 1, 2, 3, or 4 amino acids may be mutated to glycine. In embodiments, one of the arginines of the native furin cleavage site is mutated to glycine. In embodiments, two of the arginines comprising the native furin cleavage site are mutated to glycine. In embodiments, three of the arginines comprising the native furin cleavage site are mutated to glycine.

In embodiments, one or more of the amino acids comprising the native furin cleavage site, is mutated to asparagine. For example 1, 2, 3, or 4 amino acids may be mutated to asparagine. In embodiments, one of the arginines comprising the native furin cleavage site is mutated to asparagine. In embodiments, two of the arginines comprising the native furin cleavage site are mutated to asparagine. In embodiments, three of the arginines comprising the native furin cleavage site are mutated to asparagine.

Non-limiting examples of the amino acid sequences of the inactivated furin sites contained within the CoV S polypeptides are found in Table 1.

TABLE 1

Inactivated Furin Cleavage Sites

| Amino Acid Sequence of Furin Cleavage Site | Active or Inactive Furin Cleavage Site |
|---|---|
| RRAR (SEQ ID NO: 6) | Active |
| QQAQ (SEQ ID NO: 7) | Inactive |
| QRAR (SEQ ID NO: 8) | Inactive |
| RQAR (SEQ ID NO: 9) | Inactive |
| RRAQ (SEQ ID NO: 10) | Inactive |
| QQAR (SEQ ID NO: 11) | Inactive |

TABLE 1-continued

Inactivated Furin Cleavage Sites

| Amino Acid Sequence of Furin Cleavage Site | Active or Inactive Furin Cleavage Site |
|---|---|
| RQAQ (SEQ ID NO: 12) | Inactive |
| QRAQ (SEQ ID NO: 13) | Inactive |
| NNAN (SEQ ID NO: 14) | Inactive |
| NRAR (SEQ ID NO: 15) | Inactive |
| RNAR (SEQ ID NO: 16) | Inactive |
| RRAN (SEQ ID NO: 17) | Inactive |
| NNAR (SEQ ID NO: 18) | Inactive |
| RNAN (SEQ ID NO: 19) | Inactive |
| NRAN (SEQ ID NO: 20) | Inactive |
| AAAA (SEQ ID NO: 21) | Inactive |
| ARAR (SEQ ID NO: 22) | Inactive |
| RAAR (SEQ ID NO: 23) | Inactive |
| RRAA (SEQ ID NO: 24) | inactive |
| AAAR (SEQ ID NO: 25) | Inactive |
| RAAA (SEQ ID NO: 26) | Inactive |
| ARAA (SEQ ID NO: 27) | Inactive |
| GGAG (SEQ ID NO: 28) | Inactive |
| GRAR (SEQ ID NO: 29) | Inactive |
| RGAR (SEQ ID NO: 30) | Inactive |
| RRAG (SEQ ID NO: 31) | Inactive |
| GGAR (SEQ ID No: 32) | Inactive |
| RGAG (SEQ ID NO: 33) | Inactive |
| GRAG (SEQ ID NO: 34) | Inactive |
| GSAS (SEQ ID NO: 97) | Inactive |
| GSGA (SEQ ID NO: 113) | Inactive |

In embodiments, in lieu of an active furin cleavage site (SEQ ID NO: 6) the CoV S polypeptides described herein contain an inactivated furin cleavage site. In embodiments, the amino acid sequence of the inactivated furin cleavage site is represented by any one of SEQ ID NO: 7-34 or SEQ ID NO: 97. In embodiments, the amino acid sequence of the inactivated furin cleavage site is QQAQ (SEQ ID NO: 7). In embodiments, the amino acid sequence of the inactivated furin cleavage site is GSAS (SEQ ID NO: 97). In embodiments, the amino acid sequence of the inactivated furin cleavage site is GSGA (SEQ ID NO: 113).

In embodiments, the CoV S polypeptides contain a deletion, corresponding to one or more deletions within amino acids 676-685 of the native CoV Spike (S) polypeptide (SEQ ID NO: 2). In embodiments, 1, 2, 3, 4, 5, 6, 7, 8, 9, or 10 amino acids of amino acids 676-685 of the native CoV Spike (S) polypeptide (SEQ ID NO:2) are deleted. In embodiments, the deletions of amino acids within amino acids 676-685 are consecutive e.g. amino acids 676 and 677 are deleted or amino acids 680 and 681 are deleted. In embodiments, the deletions of amino acids within amino acids 676-685 are non-consecutive e.g. amino acids 676 and 680 are deleted or amino acids 677 and 682 are deleted. In embodiments, CoV S polypeptides containing a deletion, corresponding to one or more deletions within amino acids 676-685, have an amino acid sequence selected from the group consisting of SEQ ID NO: 62 and SEQ ID NO: 63.

In embodiments, the CoV S polypeptides contain a deletion, corresponding to one or more deletions within amino acids 702-711 of the native CoV Spike (S) polypeptide (SEQ ID NO: 2). In embodiments, 1, 2, 3, 4, 5, 6, 7, 8, 9, or 10 amino acids of amino acids 702-711 of the native SARS-CoV-2 Spike (S) polypeptide (SEQ ID NO:2) are deleted. In embodiments, the one or more deletions of amino acids within amino acids 702-711 are consecutive e.g. amino acids 702 and 703 are deleted or amino acids 708 and 709 are deleted. In embodiments, the deletions of amino acids within amino acids 702-711 are non-consecutive e.g. amino acids 702 and 704 are deleted or amino acids 707 and 710 are deleted. In embodiments, the CoV S polypeptides containing a deletion, corresponding to one or more deletions within amino acids 702-711, have an amino acid sequence selected from the group consisting of SEQ ID NO: 64 and SEQ ID NO: 65.

In embodiments, the CoV S polypeptides contain a deletion of the fusion peptide (SEQ ID NO: 104), which corresponds to amino acids 806-815 of SEQ ID NO: 2. In embodiments, 1, 2, 3, 4, 5, 6, 7, 8, 9, or 10 amino acids of the fusion peptide of the CoV Spike (S) polypeptide (SEQ ID NO:2) are deleted. In embodiments, the deletions of amino acids within the fusion peptide are consecutive e.g. amino acids 806 and 807 are deleted or amino acids 809 and 810 are deleted. In embodiments, the deletions of amino acids within the fusion peptide are non-consecutive e.g. amino acids 806 and 808 are deleted or amino acids 810 and 813 are deleted. In embodiments, the CoV S polypeptides containing a deletion, corresponding to one or more amino acids of the fusion peptide, have an amino acid sequence selected from SEQ ID NOS: 66, 77, and 105-108.

In embodiments, the CoV S polypeptides contain a deletion of one or more amino acids from the N-terminal domain (NTD) (corresponding to amino acids 1-318 of SEQ ID NO: 2. The amino acid sequence of the NTD is represented by SEQ ID NO: 45. In embodiments, the CoV S polypeptides contain a deletion of amino acids 1-318 of the N-terminal domain (NTD) of SEQ ID NO: 2. In embodiments, deletion of the NTD enhances protein expression of the CoV Spike (S) polypeptide. In embodiments, the CoV S polypeptides which have an NTD deletion have amino acid sequences represented by SEQ ID NOS: 46, 48, 49, 51, 52, and 54. In embodiments, the CoV S polypeptides which have an NTD deletion are encoded by an isolated nucleic acid sequence selected from the group consisting of SEQ ID NO: 47, SEQ ID NO: 50, and SEQ ID NO: 53.

In embodiments, the CoV Spike (S) polypeptides contain a deletion of one or more amino acids from the transmembrane and cytoplasmic domain (TMCT) (corresponding to amino acids 1201-1260). The amino acid sequence of the TMCT is represented by SEQ ID NO: 39. In embodiments, the CoV S polypeptides which have a deletion of one or more residues of the TMCT have enhanced protein expression. In embodiments, the CoV Spike (S) polypeptides which have one or more deletions from the TMCT have an amino acid sequence selected from the group consisting of SEQ ID NO: 40, 41, 42, 52, 54, 59, 61, 88, and 89. In embodiments, the CoV S polypeptides which have one or more deletions from the TMCT are encoded by an isolated nucleic acid sequence selected from the group consisting of SEQ ID NO: 39, 43, 53, and 60.

In embodiments, the CoV S polypeptides contain a mutation at Asp-601 of the native CoV Spike (S) polypeptide (SEQ ID NO: 2). In embodiments, Asp-601 is mutated to any natural amino acid. In embodiments, Asp-601 is mutated to glycine.

In embodiments, the CoV S polypeptides contain mutations that stabilize the prefusion conformation of the CoV S polypeptide. In embodiments, the CoV S polypeptides contain proline substitutions which stabilize the prefusion conformation. This strategy has been utilized for to develop a prefusion stabilized MERS-CoV S protein as described in the following documents which are each incorporated by reference herein in their entirety: Proc Natl Acad Sci USA. 2017 Aug. 29:114(35):E7348-E7357; Sci Rep. 2018 Oct. 24;8(1):15701; U.S. Publication No. 2020/0061185; and PCT Application No. PCT/US2017/058370.

In embodiments, the CoV S polypeptides contain a mutation at Lys-973 of the native CoV Spike (S) polypeptide (SEQ ID NO: 2). In embodiments, Lys-973 is mutated to any natural amino acid. In embodiments, Lys-973 is mutated to proline. In embodiments, the CoV S polypeptides containing a mutation at amino acid 973 are selected from the group consisting of SEQ ID NO: 84-89, 105-106, and 109-110.

In embodiments, the CoV S polypeptides contain a mutation at Val-974 of the native CoV Spike (S) polypeptide (SEQ ID NO: 2). In embodiments, Val-974 is mutated to any natural amino acid. In embodiments, Val-974 is mutated to proline. In embodiments, the CoV S polypeptides containing a mutation at amino acid 974 are selected from the group consisting of SEQ ID NO: 84-89, 105-106, and 109-110.

In embodiments, the CoV S polypeptides contain a mutation at Lys-973 and Val-974 of the native CoV Spike (S) polypeptide (SEQ ID NO: 2). In embodiments, Lys-973 and Val-974 are mutated to any natural amino acid. In embodiments, Lys-973 and Val-974 are mutated to proline. In embodiments, the CoV S polypeptides containing a mutation at amino acids 973 and 974 are selected from SEQ ID NOS: 84-89, 105-106, and 109-110.

Figure 8:
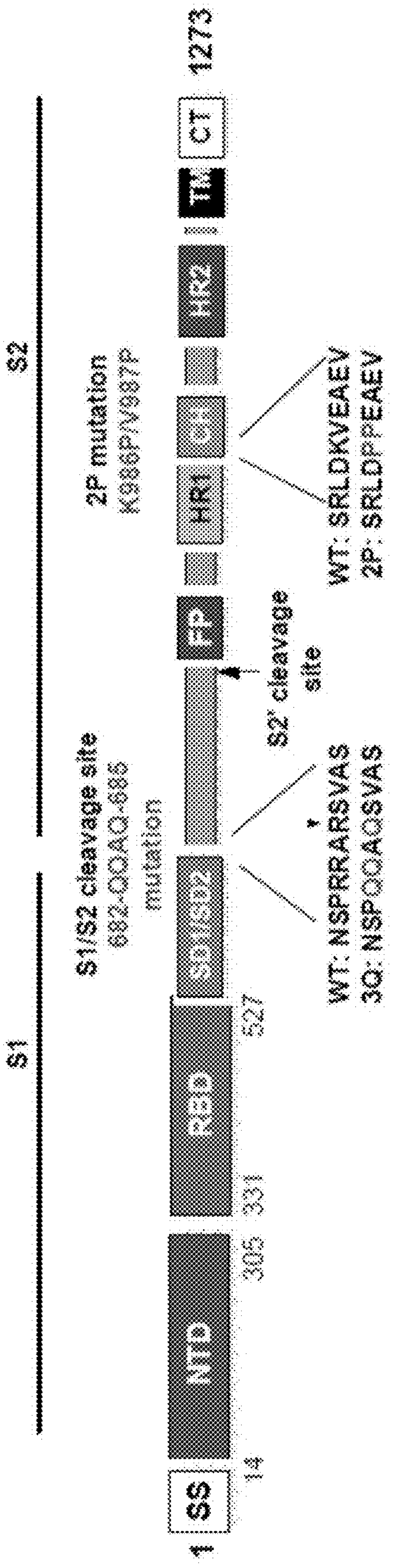
FIG. 8 shows the primary structure of the BV2373 CoV S polypeptide and modifications to the furin cleavage site, K986P, and V987P.

In embodiments, the CoV S polypeptides contain a mutation at Lys-973 and Val-974 and an inactivated furin cleavage site. In embodiments, the CoV S polypeptides contain mutations of Lys-973 and Val-974 to proline and an inactivated furin cleavage site, having the amino acid sequence of QQAQ (SEQ ID NO: 7) or GSAS (SEQ ID NO: 96). An exemplary CoV S polypeptide containing a mutation at Lys-973 and Val-974 and an inactivated furin cleavage site is depicted in FIG. 8. In embodiments, the CoV S polypeptides containing mutations of Lys-973 and Val-974 to proline and an inactivated furin cleavage site have an amino acid sequences of SEQ ID NOS: 86 or 87 and a nucleic acid sequence of SEQ ID NO: 96.

In embodiments, the CoV S polypeptides contain a mutation at Lys-973 and Val-974, an inactivated furin cleavage site, and a deletion of one or more amino acids of the fusion peptide. In embodiments, the CoV S polypeptides contain mutations of Lys-973 and Val-974 to proline, an inactivated furin cleavage site having the amino acid sequence of QQAQ (SEQ ID NO: 7) or GSAS (SEQ ID NO: 96), and deletion of one or more amino acids of the fusion peptide. In embodiments, the CoV S polypeptides containing mutations of Lys-973 and Val-974 to proline, an inactivated furin cleavage site, and deletion of one or more amino acids of the fusion peptide has an amino acid sequence of SEQ ID NO: 105 or 106.

In embodiments, the CoV Spike (S) polypeptides comprise a polypeptide linker. In embodiments, the polypeptide linker contains glycine and serine. In embodiments, the linker has about 50%, about 55%, about 60%, about 65%, about 70%, about 75%, about 80%, about 85%, about 90%, about 95%, or about 100% glycine.

In embodiments, the polypeptide linker has a repeat of $(SGGG)_n$ (SEQ ID NO: 91), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In embodiments, the polypeptide linker has an amino acid sequence corresponding to SEQ ID NO: 90.

In embodiments, the polypeptide linker has a repeat of $(GGGGS)_n$ (SEQ ID NO: 93), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50).

In embodiments, the polypeptide linker has a repeat of $(GGGS)_n$ (SEQ ID NO. 92), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50).

In some aspects, the polypeptide linker is a poly-(Gly)n linker, wherein n is 1, 2, 3, 4, 5, 6, 7, 8, 9, 10, 15, 16, 17, 18, 19, or 20. In other embodiments, the linker is selected from the group consisting of: dipeptides, tripeptides, and quadripeptides. In embodiments, the linker is a dipeptide selected from the group consisting of alanine-serine (AS), leucine-glutamic acid (LE), and serine-arginine (SR).

In embodiments, the polypeptide linker comprises between 1 to 100 contiguous amino acids of a naturally occurring CoV S polypeptide or of a CoV S polypeptide disclosed herein. In embodiments, the polypeptide linker has an amino acid sequence corresponding to SEQ ID NO: 94.

In embodiments, the CoV Spike (S) polypeptides comprise a foldon. In embodiments, the TMCT is replaced with a foldon. In embodiments, a foldon causes trimerization of the CoV Spike (S) polypeptide. In embodiments, the foldon is an amino acid sequence known in the art. In embodiments, the foldon has an amino acid sequence of SEQ ID NO: 68. In embodiments, the foldon is a T4 fibritin trimerization motif. In embodiments, the T4 fibritin trimerization domain has an amino acid sequence of SEQ ID NO: 103. In embodiments, the foldon is separated in amino acid sequence from the CoV Spike (S) polypeptide by a polypeptide linker. Non-limiting examples of polypeptide linkers are found throughout this disclosure.

In embodiments, the disclosure provides CoV S polypeptides comprising a fragment of a coronavirus S protein and nanoparticles and vaccines comprising the same. In embodiments, the fragment of the coronavirus S protein is between 10 and 1500 amino acids in length (e.g. about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 amino acids in length). In embodiments, the fragment of the coronavirus S protein is selected from the group consisting of the receptor binding domain (RBD), subdomain 1, subdomain 2, upper helix, fusion peptide, connecting region, heptad repeat 1, central helix, heptad repeat 2, NTD, and TMCT.

In embodiments, the CoV S polypeptide comprises an RBD and a subdomain 1. In embodiments, the CoV S polypeptide comprising an RBD and a subdomain 1 is amino acids 319 to 591 of SEQ ID NO: 1.

In embodiments, the CoV S polypeptide contains a fragment of a coronavirus S protein, wherein the fragment of the coronavirus S protein is the RBD. Non-limiting examples of RBDs include the RBD of SARS-CoV-2 (amino acid sequence=SEQ ID NO: 69), the RBD of SARS (amino acid sequence=SEQ ID NO: 70), and the RBD of MERS, (amino acid sequence=SEQ ID NO: 71).

In embodiments, the CoV S polypeptide contains two or more RBDs, which are connected by a polypeptide linker. In embodiments, the polypeptide linker has an amino acid sequence of SEQ ID NO: 90 or SEQ ID NO: 94.

In embodiments, the CoV S polypeptide contains 1, 2, 3, 4, 5, 6, 7, 8, 9, 10, 11, 12, 13, 14, 15, 16, 17, 18, 19, or 20 RBDs.

In some embodiments, the CoV S polypeptide contains two or more SARS-CoV-2 RBDs, which are connected by a polypeptide linker. In embodiments, the antigen containing two or more SARS-CoV-2 RBDs has an amino acid sequence corresponding to one of SEQ ID NOS: 72-75.

In embodiments, the CoV S polypeptide contains a SARS-CoV-2 RBD and a SARS RBD. In embodiments, the CoV S polypeptide comprises a SARS-CoV-2 RBD and a SARS RBD, wherein each RBD is separated by a polypeptide linker. In embodiments, the CoV S polypeptide comprising a SARS-CoV-2 RBD and a SARS RBD has an amino acid sequence selected from the group consisting of SEQ ID NOS: 76-79.

In embodiments, the CoV S polypeptide contains a SARS-CoV-2 RBD and a MERS RBD. In embodiments, the CoV S polypeptide comprises a SARS-CoV-2 RBD and a MERS RBD, wherein each RBD is separated by a polypeptide linker.

In embodiments, the CoV S polypeptide comprises a SARS RBD and a MERS RBD. In embodiments, the CoV S polypeptide comprises a SARS RBD and a MERS RBD, wherein each RBD is separated by a polypeptide linker.

In embodiments, the CoV S polypeptide contains a SARS-CoV-2 RBD, a SARS RBD, and a MERS RBD. In embodiments, the CoV S polypeptide contains a SARS-CoV-2 RBD, a SARS RBD, and a MERS RBD, wherein each RBD is separated by a polypeptide linker. In embodiments, the CoV S polypeptide comprising a SARS-CoV-2 RBD, a SARS RBD, and a MERS RBD has an amino acid sequence selected from the group consisting of SEQ ID NOS: 80-83.

In embodiments, the CoV S polypeptides described herein are expressed with an N-terminal signal peptide. In embodiments, the N-terminal signal peptide consists of an amino acid sequence of SEQ ID NO: 5 (MFVFLVLLPLVSS). In embodiments, the signal peptide may be replaced with any signal peptide that enables expression of the CoV S protein. In embodiments, one or more of the CoV S protein signal peptide amino acids may be deleted or mutated. An initiating methionine residue is maintained to initiate expression. In embodiments, the CoV S polypeptides are encoded by a nucleic acid sequence selected from the group consisting of SEQ ID NO: 35, SEQ ID NO: 37, SEQ ID NO: 95, SEQ ID NO: 43, SEQ ID NO: 47, SEQ ID NO: 50, SEQ ID NO: 53, SEQ ID NO: 55, SEQ ID NO: 57, SEQ ID NO: 96, and SEQ ID NO: 60.

Following expression of the CoV S protein in a host cell, the N-terminal signal peptide is cleaved to provide the mature CoV protein sequence (SEQ ID NOS: 2, 4, 38, 41, 44, 48, 51, 54, 58, 61, 63, 65, 67, 73, 75, 78, 79, 82, 83, 85, 87, 89, 106, and 110). In embodiments, the signal peptide is cleaved by host cell proteases. In aspects, the full-length protein may be isolated from the host cell and the signal peptide cleaved subsequently.

Following cleavage of the signal peptide from the CoV Spike (S) polypeptide with an amino acid sequence corresponding to SEQ ID NOS: 1, 3, 36, 40, 42, 46, 49, 52, 56, 59, 62, 64, 66, 72, 74, 76, 77, 80, 81, 84, 86, 87, 105, 107, 88, and 109 during expression and purification, a mature polypeptide having an amino acid sequence selected from the group consisting of SEQ ID NOS: 2, 4, 38, 41, 44, 48, 51, 54, 58, 61, 63, 65, 67, 73, 75, 78, 79, 82, 83, 85, 106, 108, 89, and 110 is obtained and used to produce a CoV S nanoparticle vaccine or CoV S nanoparticles.

Advantageously, the disclosed CoV S polypeptides may have enhanced protein expression and stability relative to the native CoV Spike (S) protein.

In embodiments, the CoV S polypeptides described herein contain further modifications from the native coronavirus S protein (SEQ ID NO: 2). In embodiments, the coronavirus S proteins described herein exhibit at least 80%, or at least 90%, or at least 95%, or at least 97%, or at least 99% identity to the native coronavirus S protein. A person of skill in the art would use known techniques to calculate the percent identity of the recombinant coronavirus S protein to the native protein. For example, percentage identity can be calculated using the tools CLUSTALW2 or Basic Local Alignment Search Tool (BLAST), which are available online. The following default parameters may be used for CLUSTALW2 Pairwise alignment: Protein Weight Matrix=Gonnet; Gap Open=10; Gap Extension=0.1.

In embodiments, the CoV S polypeptides described herein comprise about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 substitutions compared to the coronavirus S protein (SEQ ID NO: 87).

In embodiments, the coronavirus S polypeptide is extended at the N-terminus, the C-terminus, or both the N-terminus and the C-terminus. In some aspects, the extension is a tag useful for a function, such as purification or detection. In some aspects the tag contains an epitope. For example, the tag may be a polyglutamate tag, a FLAG-tag, a HA-tag, a polyHis-tag (having about 5-10 histidines) (SEQ ID NO: 101), a hexahistidine tag (SEQ ID NO: 100), an 8X-His-tag (having eight histidines) (SEQ ID NO: 102), a Myc-tag, a Glutathione-S-transferase-tag, a Green fluorescent protein-tag, Maltose binding protein-tag, a Thioredoxin-tag, or an Fc-tag. In other aspects, the extension may be an N-terminal signal peptide fused to the protein to enhance expression. While such signal peptides are often cleaved during expression in the cell, some nanoparticles may contain the antigen with an intact signal peptide. Thus, when a nanoparticle comprises an antigen, the antigen may contain an extension and thus may be a fusion protein when incorporated into nanoparticles. For the purposes of calculating identity to the sequence, extensions are not included. In embodiments, the tag is a protease cleavage site. Non-limiting examples of protease cleavage sites include the HRV3C protease cleavage site, chymotrypsin, trypsin, elastase, endopeptidase, caspase-1, caspase-2, caspase-3, caspase-4, caspase-5, caspase-6, caspase-7, caspase-8, caspase-9, caspase-10, enterokinase, factor Xa, Granzyme B, TEV protease, and thrombin. In embodiments, the protease cleavage site is an HRV3C protease cleavage site. In embodiments, the protease cleavage site comprises an amino acid sequence of SEQ ID NO: 98.

In embodiments, the CoV S glycoprotein comprises a fusion protein. In embodiments, the CoV S glycoprotein comprises an N-terminal fusion protein. In embodiments, the Cov S glycoprotein comprises a C-terminal fusion protein. In embodiments, the fusion protein encompasses a tag useful for protein expression, purification, or detection. In embodiments, the tag is a polyHis-tag (having about 5-10 histidines), a Myc-tag, a Glutathione-S-transferase-tag, a Green fluorescent protein-tag, Maltose binding protein-tag, a Thioredoxin-tag, a Strep-tag, a Twin-Strep-tag, or an Fc-tag. In embodiments, the tag is an Fc-tag. In embodiments, the Fc-tag is monomeric, dimeric, or trimeric. In embodiments, the tag is a hexahistidine tag, e.g. a polyHis-tag which contains six histidines (SEQ ID NO: 100). In embodiments, the tag is a Twin-Strep-tag with an amino acid sequence of SEQ ID NO: 99.

In embodiments, the CoV S polypeptide is a fusion protein comprising another coronavirus protein. In embodiments, the other coronavirus protein is from the same coronavirus. In embodiments, the other coronavirus protein is from a different coronavirus.

In some aspects, the CoV S protein may be truncated. For example, the N-terminus may be truncated by about 10 amino acids, about 30 amino acids, about 50 amino acids, about 75 amino acids, about 100 amino acids, or about 200 amino acids. The C-terminus may be truncated instead of or in addition to the N-terminus. For example, the C-terminus may be truncated by about 10 amino acids, about 30 amino acids, about 50 amino acids, about 75 amino acids, about 100 amino acids, or about 200 amino acids. For purposes of calculating identity to the protein having truncations, identity is measured over the remaining portion of the protein.

Nanoparticles Containing CoV Spike (S) Polypeptides

Figure 10:
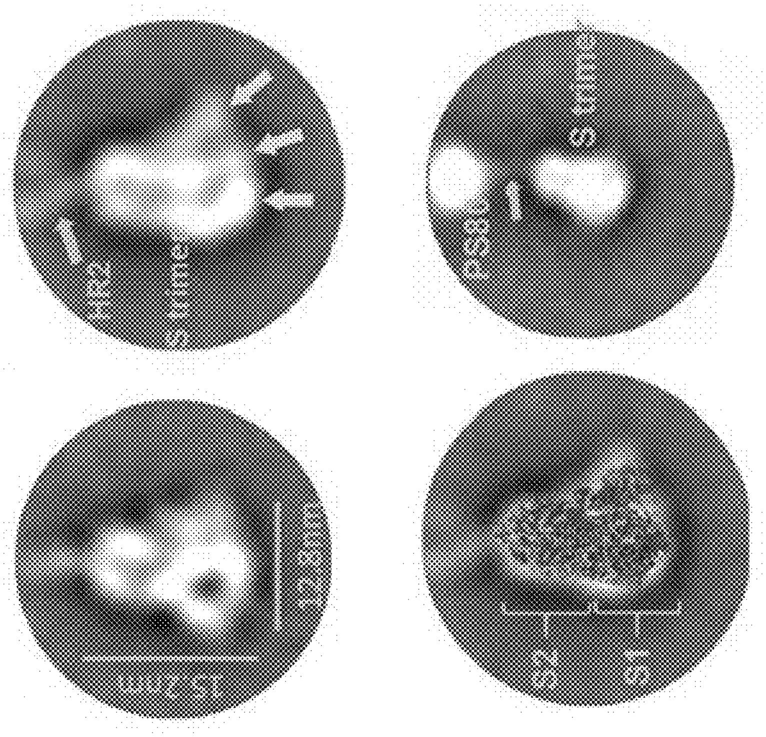
FIG. 10 shows a cryo-electron microscopy (cryoEM) structure of the BV2373 CoV S polypeptide overlaid on the cryoEM structure of the SARS-CoV-2 spike protein (EMB ID: 21374).

In embodiments, the mature CoV S polypeptide antigens are used to produce a vaccine comprising coronavirus S nanoparticles. In embodiments, nanoparticles of the present disclosure comprise the CoV S polypeptides described herein. In embodiments, the nanoparticles of the present disclosure comprise CoV S polypeptides associated with a detergent core. The presence of the detergent facilitates formation of the nanoparticles by forming a core that organizes and presents the antigens. In embodiments, the nanoparticles may contain the CoV S polypeptides assembled into multi-oligomeric glycoprotein-detergent (e.g. PS80) nanoparticles with the head regions projecting outward and hydrophobic regions and PS80 detergent forming a central core surrounded by the glycoprotein. In embodiments, the CoV S polypeptide inherently contains or is adapted to contain a transmembrane domain to promote association of the protein into a detergent core. In embodiments, the CoV S polypeptide contains a head domain. FIG. 10 shows an exemplary structure of a CoV S polypeptide of the disclosure. Primarily the transmembrane domains of a CoV S polypeptide trimer associate with detergent; however, other portions of the polypeptide may also interact. Advantageously, the nanoparticles have improved resistance to environmental stresses such that they provide enhanced stability and/or improved presentation to the immune system due to organization of multiple copies of the protein around the detergent.

In embodiments, the detergent core is a non-ionic detergent core. In embodiments, the CoV S polypeptide is associated with the non-ionic detergent core. In embodiments, the detergent is selected from the group consisting of polysorbate-20 (PS20), polysorbate-40 (PS40), polysorbate-60 (PS60), polysorbate-65 (PS65) and polysorbate-80 (PS80).

In embodiments, the detergent is PS80.

In embodiments, the CoV S polypeptide forms a trimer. In embodiments, the CoV S polypeptide nanoparticles are composed of multiple polypeptide trimers surrounding a non-ionic detergent core. In embodiments, the nanoparticles contain at least about 1 trimer or more. In embodiments, the nanoparticles contain at least about 5 trimers to about 30 trimers of the Spike protein. In embodiments, each nanoparticle may contain 1, 2, 3, 4, 5, 6, 7, 8, 9, 10, 11, 12, or 15, 20, 25, or 30 trimers, including all values and ranges in between. Compositions disclosed herein may contain nanoparticles having different numbers of trimers. For example, a composition may contain nanoparticles where the number of trimers ranges from 2-9; in embodiments, the nanoparticles in a composition may contain from 2-6 trimers. In embodiments, the compositions contain a heterogeneous population of nanoparticles having 2 to 6 trimers per nanoparticle, or 2 to 9 trimers per nanoparticle. In embodiments, the compositions may contain a substantially homogenous population of nanoparticles. For example, the population may contain about 95% nanoparticles having 5 trimers.

The nanoparticles disclosed herein range in particle size. In embodiments, the nanoparticles disclosed herein range in particle size from a Z-ave size from about 20 nm to about 60 nm, about 20 nm to about 50 nm, about 20 nm to about 45 nm, about 20 nm to about 35 nm, about 20 nm to about 30 nm, about 25 nm to about 35 nm, or about 25 nm to about 45 nm. Particle size (Z-ave) is measured by dynamic light scattering (DLS) using a Zetasizer NanoZS (Malvern, UK), unless otherwise specified.

In embodiments, the nanoparticles comprising the CoV S polypeptides disclosed herein have a reduced particle size compared to nanoparticles comprising a wild-type CoV S polypeptide. In embodiments, the CoV S polypeptides are at least about 40% smaller in particle size, for example, at least about 40%, at least about 45%, at least about 50%, at least about 55%, at least about 60%, at least about 65%, at least about 70%, at least about 75%, at least about 80%, or at least about 85% smaller in particle size.

The nanoparticles comprising CoV S polypeptides disclosed herein are more homogenous in size, shape, and mass than nanoparticles comprising a wild-type CoV S polypeptide. The polydispersity index (PDI), which is a measure of heterogeneity, is measured by dynamic light scattering using a Malvern Setasizer unless otherwise specified. In embodiments, the particles measured herein have a PDI from about 0.2 to about 0.45, for example, about 0.2, about 0.25, about 0.29, about 0.3, about 0.35, about 0.40, or about 0.45. In embodiments, the nanoparticles measured herein have a PDI that is at least about 25% smaller than the PDI of nanoparticles comprising the wild-type CoV S polypeptide, for example, at least about 25%, at least about 30%, at least about 35%, at least about 40%, at least about 45%, at least about 50%, at least about 55%, or at least about 60%, smaller.

The CoV S polypeptides and nanoparticles comprising the same have improved thermal stability as compared to the wild-type CoV S polypeptide or a nanoparticle thereof. The thermal stability of the CoV S polypeptides is measured using differential scanning calorimetry (DSC) unless otherwise specified. The enthalpy of transition (ΔHcal) is the energy required to unfold a CoV S polypeptide. In embodiments, the CoV S polypeptides have an increased ΔHcal as compared to the wild-type CoV S polypeptide. In embodiments, the ΔHcal of a CoV S polypeptide is about 2-fold, about 3-fold, about 4-fold, about 5-fold, about 6-fold, about 7-fold, about 8-fold, about 9-fold, or about 10-fold greater than the ΔHcal of a wild-type CoV S polypeptide.

Several nanoparticle types may be included in vaccine compositions disclosed herein. In some aspects, the nanoparticle type is in the form of an anisotropic rod, which may be a dimer or a monomer. In other aspects, the nanoparticle type is a spherical oligomer. In yet other aspects, the nanoparticle may be described as an intermediate nanoparticle, having sedimentation properties intermediate between the first two types. Formation of nanoparticle types may be regulated by controlling detergent and protein concentration during the production process. Nanoparticle type may be determined by measuring sedimentation co-efficient.

Production of Nanoparticles Containing CoV S Polypeptide Antigens

The nanoparticles of the present disclosure are non-naturally occurring products, the components of which do not occur together in nature. Generally, the methods disclosed herein use a detergent exchange approach wherein a first detergent is used to isolate a protein and then that first detergent is exchanged for a second detergent to form the nanoparticles.

The antigens contained in the nanoparticles are typically produced by recombinant expression in host cells. Standard recombinant techniques may be used. In embodiments, the CoV S polypeptides are expressed in insect host cells using a baculovirus system. In embodiments, the baculovirus is a cathepsin-L knock-out baculovirus, a chitinase knock-out baculovirus. Optionally, the baculovirus is a double knock-out for both cathepsin-L and chitinase. High level expression may be obtained in insect cell expression systems. Non limiting examples of insect cells are, Spodoptera frugiperda (Sf) cells, e.g. Sf9, Sf21, Trichoplusiani cells, e.g. High Five cells, and Drosophila S2 cells. In embodiments, the CoV S polypeptide described herein are produced in any suitable host cell. In embodiments, the host cell is an insect cell. In embodiments, the insect cell is an St9 cell.

Typical transfection and cell growth methods can be used to culture the cells. Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents. In one embodiment, the vector is a recombinant baculovirus.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 3500 L bags.

Extraction and Purification of Nanoparticles Containing CoV Spike (S) Protein Antigens After growth of the host cells, the protein may be harvested from the host cells using detergents and purification protocols. Once the host cells have grown for 48 to 96 hours, the cells are isolated from the media and a detergent-containing solution is added to solubilize the cell membrane, releasing the protein in a detergent extract. Triton X-100 and TERGITOL® nonylphenol ethoxylate, also known as NP-9, are each preferred detergents for extraction. The detergent may be added to a final concentration of about 0.1% to about 1.0%. For example, the concentration may be about 0.1%, about 0.2%, about 0.3%, about 0.5%, about 0.7%, about 0.8%, or about 1.0%. The range may be about 0.1% to about 0.3%. In aspects, the concentration is about 0.5%.

In other aspects, different first detergents may be used to isolate the protein from the host cell. For example, the first detergent may be Bis(polyethylene glycol bis[imidazoylcarbonyl]), nonoxynol-9, Bis(polyethylene glycol bis[imidazoyl carbonyl]), BRIJ® Polyethylene glycol dodecyl ether 35, BRIJ® Polyethylene glycol (3) cetyl ether 56, BRIJ® alcohol ethoxylate 72, BRIJ® Polyoxyl 2 stearyl ether 76, BRIJ® polyethylene glycol monoolelyl ether 92V, BRIJ® Polyoxyethylene (10) oleyl ether 97, BRIJ® Polyethylene glycol hexadecyl ether 58P, CREMOPHOR® EL Macrogolglycerol ricinoleate, Decaethyleneglycol monododecyl ether, N-Decanoyl-N-methylglucamine, n-Decyl alpha-Dglucopyranoside,Decyl beta-D-maltopyranoside, n-Dodecanoyl-N-methylglucamide, nDodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA –630, Methyl-6-0-(N-heptylcarbamoyl)-alpha-D-glucopyranoside, Nonaethylene glycol monododecyl ether, N-Nonanoyl-N-methylglucamine, N-NonanoylN-methylglucamine, Octaetbylene glycol monodecyl ether, Octaethylene glycolmonododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin from Quillaja bark, SPAN® 20 sorbitan laurate, SPAN® 40 sorbitan monopalmitate, SPAN® 60 sorbitan stearate, SPAN® 65 sorbitan tristearate, SPAN® 80 sorbitane monooleate, SPAN® 85 sorbitane trioleate, TERGITOL® secondary alcohol ethoxylate Type 15-S-12, TERGITOL® secondary alcohol ethoxylate Type 15-S-30, TERGITOL® secondary alcohol ethoxylate Type 15-S-5, TERGITOL® secondary alcohol ethoxylate Type 15-S-7, TERGITOL® secondary alcohol ethoxylate Type 15-S-9, TERGITOL® nonylphenol ethoxylate Type NP-10, TERGITOL® nonylphenol ethoxylate Type NP-4, TERGITOL® nonylphenol ethoxylate Type NP-40, TERGITOL® nonylphenol ethoxylate Type NP-7, TERGITOL® nonylphenol ethoxylate Type NP-9, TERGITOL® branched secondary alcohol ethoxylate Type TMN-10, TERGITOL® branched secondary alcohol ethoxylate Type TMN-6, TRITON™ X-100 Polyethylene glycol tert-octylphenyl ether or combinations thereof.

The nanoparticles may then be isolated from cellular debris using centrifugation. In embodiments, gradient centrifugation, such as using cesium chloride, sucrose and iodixanol, may be used. Other techniques may be used as alternatives or in addition, such as standard purification techniques including, e.g., ion exchange, affinity, and gel filtration chromatography.

For example, the first column may be an ion exchange chromatography resin, such as FRACTOGEL® EMD methacrylate based polymeric beads TMAE (EMD Millipore), the second column may be a lentil (Lens culinaris) lectin affinity resin, and the third column may be a cation exchange column such as a FRACTOGEL® EMD methacrylate based polymeric beads SO3 (EMD Millipore) resin. In other aspects, the cation exchange column may be an MMC column or a Nuvia C Prime column (Bio-Rad Laboratories, Inc). Preferably, the methods disclosed herein do not use a detergent extraction column; for example a hydrophobic interaction column. Such a column is often used to remove detergents during purification but may negatively impact the methods disclosed here.

Detergent Exchange of Nanoparticles Containing CoV S Polypeptide Antigens

To form nanoparticles, the first detergent, used to extract the protein from the host cell is substantially replaced with a second detergent to arrive at the nanoparticle structure. NP-9 is a preferred extraction detergent. Typically, the nanoparticles do not contain detectable NP-9 when measured by HPLC. The second detergent is typically selected from the group consisting of PS20, PS40, PS60, PS65, and PS80. Preferably, the second detergent is PS80.

In particular aspects, detergent exchange is performed using affinity chromatography to bind glycoproteins via their carbohydrate moiety. For example, the affinity chromatography may use a legume lectin column. Legume lectins are proteins originally identified in plants and found to interact specifically and reversibly with carbohydrate residues. See, for example, Sharon and Lis, "Legume lectins—a large family of homologous proteins," FASEB J. 1990 Nov.;4 (14):3198-208; Liener, "The Lectins: Properties, Functions, and Applications in Biology and Medicine," Elsevier, 2012. Suitable lectins include concanavalin A (con A), pea lectin, sainfoin lect, and lentil lectin. Lentil lectin is a preferred column for detergent exchange due to its binding properties. Lectin columns are commercially available; for example, Capto Lentil Lectin, is available from GE Healthcare. In certain aspects, the lentil lectin column may use a recombinant lectin. At the molecular level, it is thought that the carbohydrate moieties bind to the lentil lectin, freeing the amino acids of the protein to coalesce around the detergent resulting in the formation of a detergent core providing nanoparticles having multiple copies of the antigen, e.g., glycoprotein oligomers which can be dimers, trimers, or tetramers anchored in the detergent. In embodiments, the CoV S polypeptides form trimers. In embodiments, the CoV S polypeptide trimers are anchored in detergent. In embodiments, each CoV S polypeptide nanoparticle contains at least one trimer associated with a non-ionic core.

The detergent, when incubated with the protein to form the nanoparticles during detergent exchange, may be present at up to about 0.1% (w/v) during early purifications steps and this amount is lowered to achieve the final nanoparticles having optimum stability. For example, the non-ionic detergent (e.g., PS80) may be about 0.005% (v/v) to about 0.1% (v/v), for example, about 0.005% (v/v), about 0.006% (v/v), about 0.007% (v/v), about 0.008% (v/v), about 0.009% (v/v), about 0.01% (v/v), about 0.015% (v/v), about 0.02% (v/v), about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), or about 0.1% (v/v) PS80. In embodiments, the nanoparticle contains about 0.03% to about 0.05% PS80. In embodiments, the nanoparticle contains about 0.01% (v/v) PS80.

In embodiments, purified CoV S polypeptides are dialyzed. In embodiments, dialysis occurs after purification. In embodiments, the CoV S polypeptides are dialyzed in a solution comprising sodium phosphate, NaCl, and PS80. In embodiments, the dialysis solution comprising sodium phosphate contains between about 5 mM and about 100 mM of sodium phosphate, for example, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM sodium phosphate. In embodiments, the pH of the solution comprising sodium phosphate is about 6.5, about 6.6, about 6.7, about 6.8, about 6.9, about 7.0, about 7.1, about 7.2, about 7.3, about 7.4, or about 7.5. In embodiments, the dialysis solution comprising sodium chloride comprises about 50 mM NaCl to about 500 mM NaCl, for example, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM, or about 500 mM NaCl. In embodiments, the dialysis solution comprising PS80 comprises about 0.005% (v/v), about 0.006% (v/v), about 0.007% (v/v), about 0.008% (v/v), about 0.009% (v/v), about 0.01% (v/v), about 0.015% (v/v), about 0.02% (v/v), about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), or about 0.1% (v/v) PS80. In embodiments, the dialysis solution comprises about 25 mM sodium phosphate (pH 7.2), about 300 mM NaCl, and about 0.01% (v/v) PS80.

Detergent exchange may be performed with proteins purified as discussed above and purified, frozen for storage, and then thawed for detergent exchange.

Figure 12A:
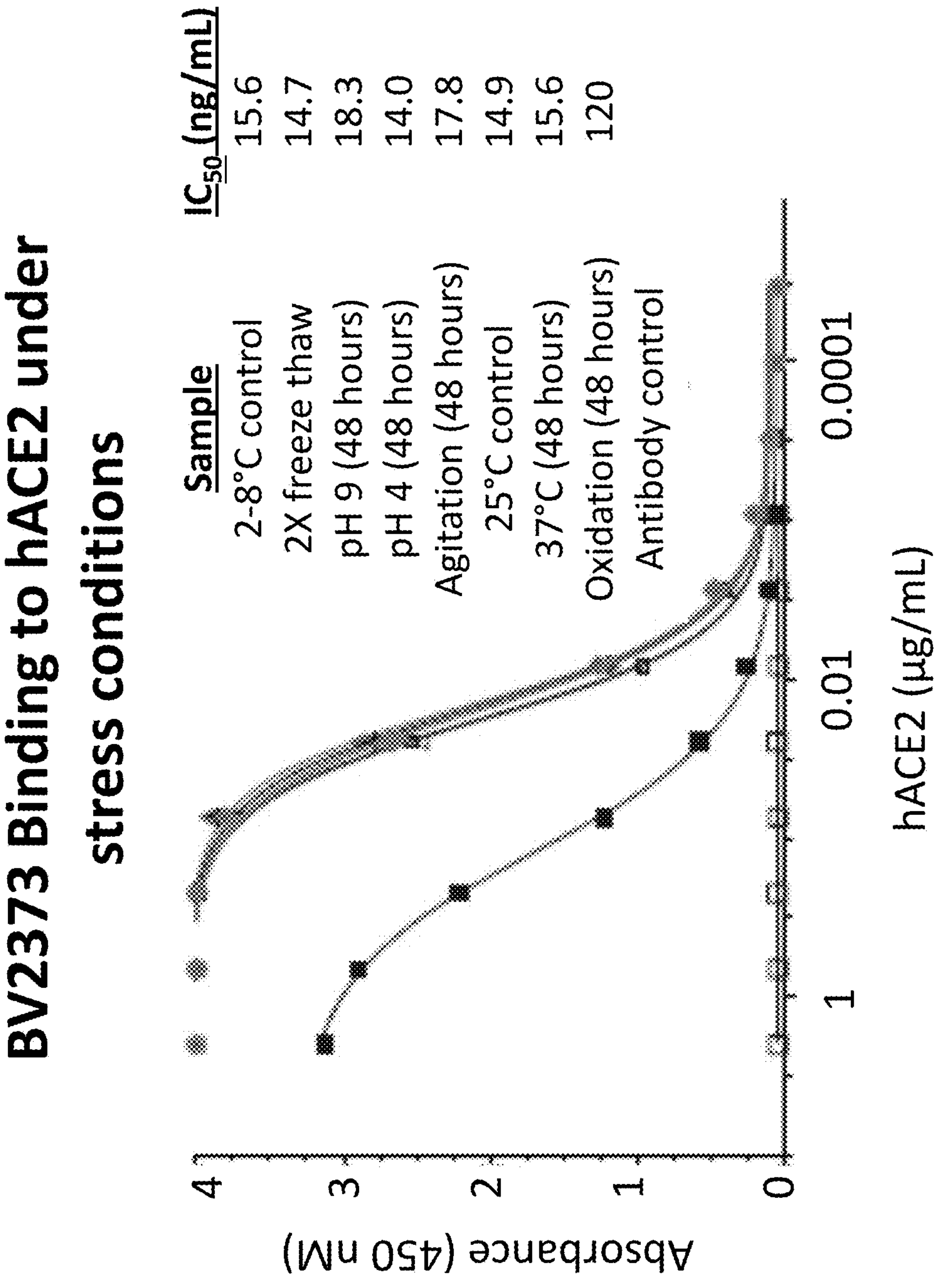
FIGS. 12A-B show the effect of stress conditions, such as temperature, two freeze/thaw cycles, oxidation, agitation, and pH extremes on binding of the CoV S polypeptides BV2373 (FIG. 12A) and BV2365 (FIG. 12B) to hACE2.
Figure 12B:
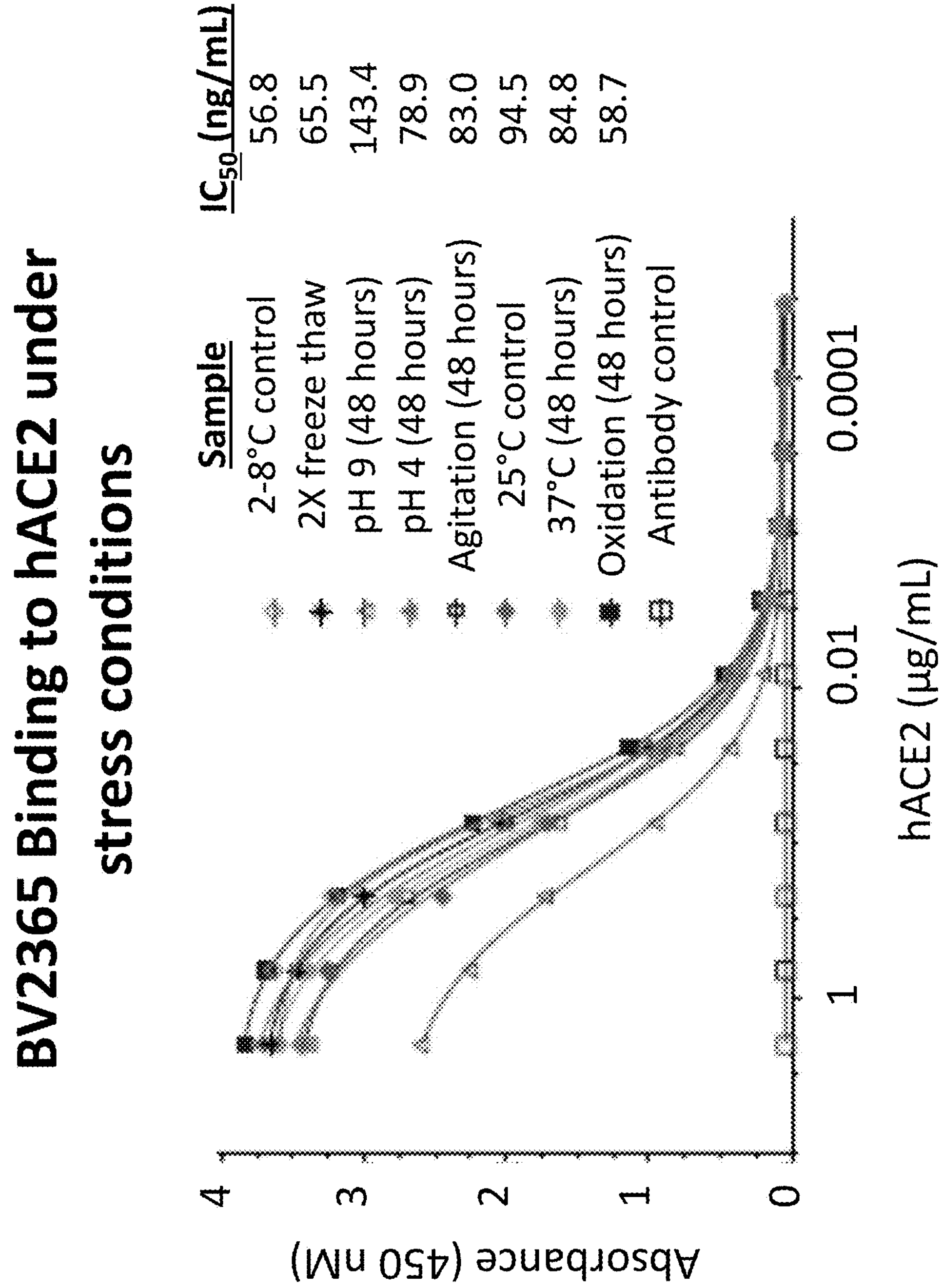
Figure 33:
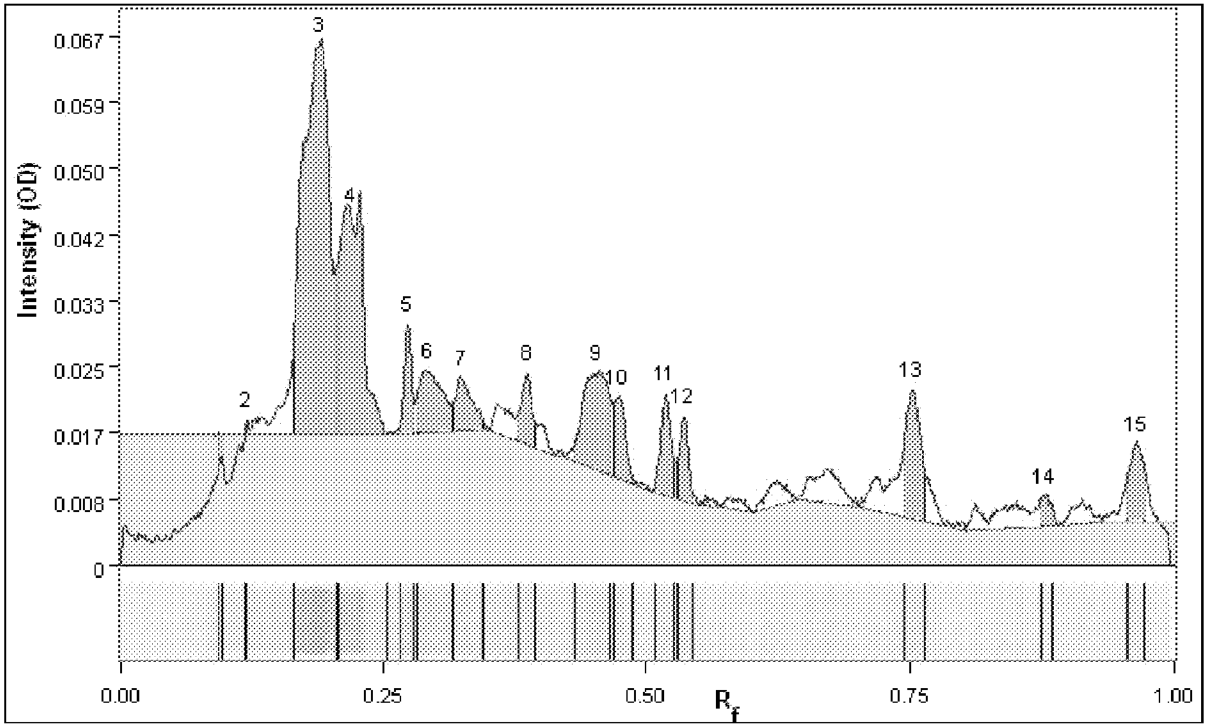
FIG. 33 shows a scanning densitometry plot of BV2384 (SEQ ID NO. 109) purity after purification.
Figure 34:
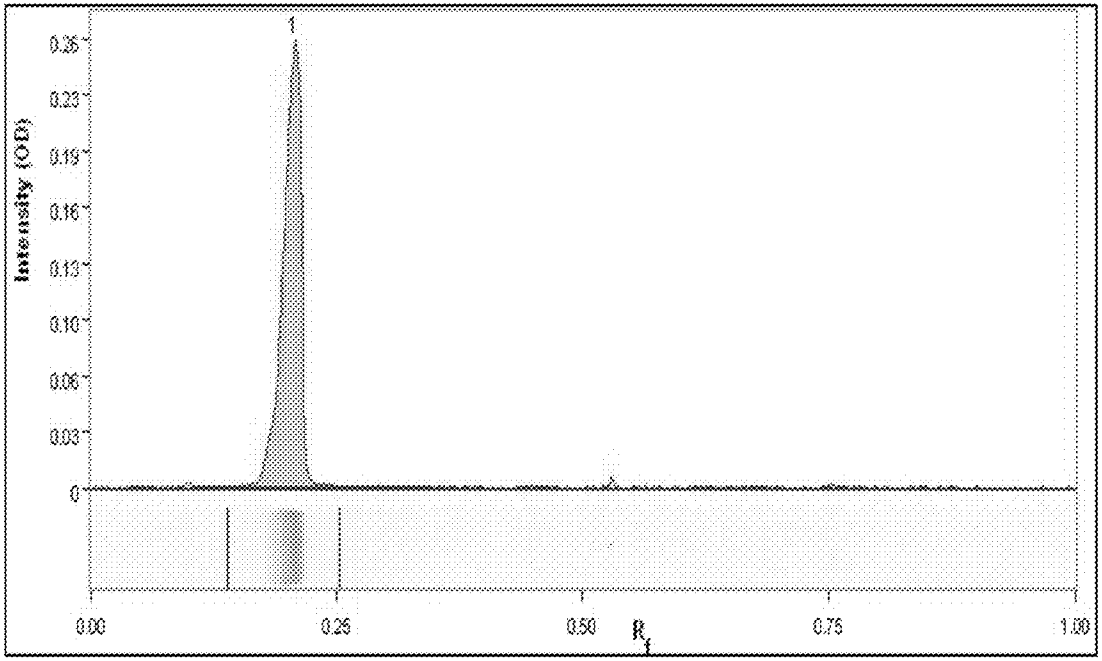
FIG. 34 shows a scanning densitometry plot of BV2373 (SEQ ID NO: 87) purity after purification

Stability of compositions disclosed herein may be measured in a variety of ways. In one approach, a peptide map may be prepared to determine the integrity of the antigen protein after various treatments designed to stress the nanoparticles by mimicking harsh storage conditions. Thus, a measure of stability is the relative abundance of antigen peptides in a stressed sample compared to a control sample. For example, the stability of nanoparticles containing the CoV S polypeptides may be evaluated by exposing the nanoparticles to various pHs, proteases, salt, oxidizing agents, including but not limited to hydrogen peroxide, various temperatures, freeze/thaw cycles, and agitation. FIGS. 12A-B show that BV2373 (SEQ ID NO: 87) and BV2365 (SEQ ID NO: 4) retain binding to hACE2 under a variety of stress conditions. It is thought that the position of the glycoprotein anchored into the detergent core provides enhanced stability by reducing undesirable interactions. For example, the improved protection against protease-based degradation may be achieved through a shielding effect whereby anchoring the glycoproteins into the core at the molar ratios disclosed herein results in steric hindrance blocking protease access. Stability may also be measured by monitoring intact proteins. FIG. 33 and FIG. 34 compare nanoparticles containing CoV polypeptides having amino acid sequences of SEQ ID NOS: 109 and 87, respectively. FIG. 34 indicates that CoV polypeptides having an amino acid sequence of SEQ ID NO: 87 show particularly good stability during purification. The polypeptide of FIG. 34 comprises a furin cleavage site having an amino acid sequence of QQAQ (SEQ ID NO: 7).

Vaccine Compositions Containing CoV S Polypeptide Antigens

The disclosure provides vaccine compositions comprising CoV S polypeptides, for example, in a nanoparticle. In some aspects, the vaccine composition may contain nanoparticles with antigens from more than one viral strain from the same species of virus. In another embodiment, the disclosures provide for a pharmaceutical pack or kit comprising one or more containers filled with one or more of the components of the vaccine compositions.

Compositions disclosed herein may be used either prophylactically or therapeutically, but will typically be prophylactic. Accordingly, the disclosure includes methods for treating or preventing infection. The methods involve administering to the subject a therapeutic or prophylactic amount of the immunogenic compositions of the disclosure. Preferably, the pharmaceutical composition is a vaccine composition that provides a protective effect. In other aspects, the protective effect may include amelioration of a symptom associated with infection in a percentage of the exposed population. For example, the composition may prevent or reduce one or more virus disease symptoms selected from: fever fatigue, muscle pain, headache, sore throat, vomiting, diarrhea, rash, symptoms of impaired kidney and liver function, internal bleeding and external bleeding, compared to an untreated subject.

The nanoparticles may be formulated for administration as vaccines in the presence of various excipients, buffers, and the like. For example, the vaccine compositions may contain sodium phosphate, sodium chloride, and/or histidine. Sodium phosphate may be present at about 10 mM to about 50 mM, about 15 mM to about 25 mM, or about 25 mM; in particular cases, about 22 mM sodium phosphate is present. Histidine may be present about 0.1% (w/v), about 0.5% (w/v), about 0.7% (w/v), about 1% (w/v), about 1.5% (w/v), about 2% (w/v), or about 2.5% (w/v). Sodium chloride, when present, may be about 150 mM. In certain compositions, the sodium chloride may be present in higher concentrations, for example from about 200 mM to about 500 mM. In embodiments, the sodium chloride is present in a high concentration, including but not limited to about 200 mM, about 250 mM, about 300 mM, about 350 mM, about 400 mM, about 450 mM, or about 500 mM.

In embodiments, the nanoparticles described herein have improved stability at certain pH levels. In embodiments, the nanoparticles are stable at slightly acidic pH levels. For example, the nanoparticles that are stable at a slightly acidic pH, for example from pH 5.8 to pH 7.0. In embodiments, the nanoparticles and compositions containing nanoparticles may be stable at pHs ranging from about pH 5.8 to about pH 7.0, including about pH 5.9 to about pH 6.8, about pH 6.0 to about pH 6.5, about pH 6.1 to about pH 6.4, about pH 6.1 to about pH 6.3, or about pH 6.2. In embodiments, the nanoparticles and compositions described herein are stabile at neutral pHs, including from about pH 7.0 to about pH 7.4. In embodiments, the nanoparticles and compositions described herein are stable at slightly alkaline pHs, for example from about pH 7.0 to about pH 8.5, from about pH 7.0 to about pH 8.0, or from about pH 7.0 to about pH 7.5, including all values and ranges in between.

Adjuvants

In certain embodiments, the compositions disclosed herein may be combined with one or more adjuvants to enhance an immune response. In other embodiments, the compositions are prepared without adjuvants, and are thus available to be administered as adjuvant-free compositions. Advantageously, adjuvant-free compositions disclosed herein may provide protective immune responses when administered as a single dose. Alum-free compositions that induce robust immune responses are especially useful in adults about 60 and older.

Aluminum-Based Adjuvants

In embodiments, the adjuvant may be alum (e.g. $AlPO_4$ or $Al(OH)_3$). Typically, the nanoparticle is substantially bound to the alum. For example, the nanoparticle may be at least 80% bound, at least 85% bound, at least 90% bound or at least 95% bound to the alum. Often, the nanoparticle is 92% to 97% bound to the alum in a composition. The amount of alum is present per dose is typically in a range between about 400 μg to about 1250 μg. For example, the alum may be present in a per dose amount of about 300 μg to about 900 μg, about 400 μg to about 800 μg, about 500 μg to about 700 μg, about 400 μg to about 600 μg, or about 400 μg to about 500 μg. Typically, the alum is present at about 400 μg for a dose of 120 μg of the protein nanoparticle.

Saponin Adjuvants

Adjuvants containing saponin may also be combined with the immunogens disclosed herein Saponins are glycosides derived from the bark of the Quillaja saponaria Molina tree. Typically, saponin is prepared using a multi-step purification process resulting in multiple fractions. As used, herein, the term "a saponin fraction from Quillaja saponaria Molina" is used generically to describe a semi-purified or defined saponin fraction of Quillaja saponaria or a substantially pure fraction thereof.

Saponin Fractions

Several approaches for producing saponin fractions are suitable. Fractions A, B, and C are described in U.S. Pat. No. 6,352,697 and may be prepared as follows. A lipophilic fraction from Quil A, a crude aqueous Quillaja saponaria Molina extract, is separated by chromatography and eluted with 70% acetonitrile in water to recover the lipophilic fraction. This lipophilic fraction is then separated by semi-preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of Quillaja saponaria Molina each represent groups or families of chemically closely related molecules with definable properties. The chromatographic conditions under which they are obtained are such that the batch-to-batch reproducibility in terms of elution profile and biological activity is highly consistent.

Other saponin fractions have been described. Fractions B3, B4 and B4b are described in EP 0436620. Fractions QA1-QA22 are described EP03632279 B2, Q-VAC (Nor-Feed, AS Denmark), Quillaja saponaria Molina Spikoside (Isconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9.

The saponin fractions described herein and used for forming adjuvants are often substantially pure fractions; that is, the fractions are substantially free of the presence of contamination from other materials. In particular aspects, a substantially pure saponin fraction may contain up to 40% by weight, up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, or up to 0.1% by weight of other compounds such as other saponins or other adjuvant materials.

ISCOM Structures

Saponin fractions may be administered in the form of a cage-like particle referred to as an ISCOM (Immune Stimulating COMplex). ISCOMs may be prepared as described in EP0109942B1, EP0242380B1 and EP0180546 B1. In particular embodiments a transport and/or a passenger antigen may be used, as described in EP 9600647-3 (PCT/SE97/00289).

Matrix Adjuvants

In embodiments, the ISCOM is an ISCOM matrix complex. An ISCOM matrix complex comprises at least one saponin fraction and a lipid. The lipid is at least a sterol, such as cholesterol. In particular aspects, the ISCOM matrix complex also contains a phospholipid. The ISCOM matrix complexes may also contain one or more other immunomodulatory (adjuvant-active) substances, not necessarily a glycoside, and may be produced as described in EP0436620B1, which is incorporated by reference in its entirety herein.

In other aspects, the ISCOM is an ISCOM complex. An ISCOM complex contains at least one saponin, at least one lipid, and at least one kind of antigen or epitope. The ISCOM complex contains antigen associated by detergent treatment such that that a portion of the antigen integrates into the particle. In contrast, ISCOM matrix is formulated as an admixture with antigen and the association between ISCOM matrix particles and antigen is mediated by electrostatic and/or hydrophobic interactions.

According to one embodiment, the saponin fraction integrated into an ISCOM matrix complex or an ISCOM complex, or at least one additional adjuvant, which also is integrated into the ISCOM or ISCOM matrix complex or mixed therewith, is selected from fraction A, fraction B, or fraction C of Quillaja saponaria, a semipurified preparation of Quillaja saponaria, a purified preparation of Quillaja saponaria, or any purified sub-fraction e.g., QA 1-21.

In particular aspects, each ISCOM particle may contain at least two saponin fractions. Any combinations of weight % of different saponin fractions may be used. Any combination of weight % of any two fractions may be used. For example, the particle may contain any weight % of fraction A and any weight % of another saponin fraction, such as a crude saponin fraction or fraction C, respectively. Accordingly, in particular aspects, each ISCOM matrix particle or each ISCOM complex particle may contain from 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60% by weight, or 50% by weight of one saponin fraction, e.g. fraction A and the rest up to 100% in each case of another saponin e.g. any crude fraction or any other faction e.g. fraction C. The weight is calculated as the total weight of the saponin fractions. Examples of ISCOM matrix complex and ISCOM complex adjuvants are disclosed in U.S. Published Application No. 2013/0129770, which is incorporated by reference in its entirety herein.

In particular embodiments, the ISCOM matrix or ISCOM complex comprises from 5-99% by weight of one fraction, e.g. fraction A and the rest up to 100% of weight of another fraction e.g. a crude saponin fraction or fraction C. The weight is calculated as the total weight of the saponin fractions.

In another embodiment, the ISCOM matrix or ISCOM complex comprises from 40% to 99% by weight of one fraction, e.g. fraction A and from 1% to 60% by weight of another fraction, e.g. a crude saponin fraction or fraction C. The weight is calculated as the total weight of the saponin fractions.

In yet another embodiment, the ISCOM matrix or ISCOM complex comprises from 70% to 95% by weight of one fraction e.g., fraction A, and from 30% to 5% by weight of another fraction, e.g., a crude saponin fraction, or fraction C. The weight is calculated as the total weight of the saponin fractions. In other embodiments, the saponin fraction from Quillaja saponaria Molina is selected from any one of QA 1-21.

In addition to particles containing mixtures of saponin fractions, ISCOM matrix particles and ISCOM complex particles may each be formed using only one saponin fraction. Compositions disclosed herein may contain multiple particles wherein each particle contains only one saponin fraction. That is, certain compositions may contain one or more different types of ISCOM-matrix complexes particles and/or one or more different types of ISCOM complexes particles, where each individual particle contains one saponin fraction from Quillaja saponaria Molina, wherein the saponin fraction in one complex is different from the saponin fraction in the other complex particles.

In particular aspects, one type of saponin fraction or a crude saponin fraction may be integrated into one ISCOM matrix complex or particle and another type of substantially pure saponin fraction, or a crude saponin fraction, may be integrated into another ISCOM matrix complex or particle. A composition or vaccine may comprise at least two types of complexes or particles each type having one type of saponins integrated into physically different particles.

In the compositions, mixtures of ISCOM matrix complex particles and/or ISCOM complex particles may be used in which one saponin fraction Quillaja saponaria Molina and another saponin fraction Quillaja saponaria Molina are separately incorporated into different ISCOM matrix complex particles and/or ISCOM complex particles.

The ISCOM matrix or ISCOM complex particles, which each have one saponin fraction, may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of an ISCOM matrix or complex containing a first saponin fraction with the remaining portion made up by an ISCOM matrix or complex containing a different saponin fraction. In some aspects, the remaining portion is one or more ISCOM matrix or complexes where each matrix or complex particle contains only one saponin fraction. In other aspects, the ISCOM matrix or complex particles may contain more than one saponin fraction.

In particular compositions, the only saponin fraction in a first ISCOM matrix or ISCOM complex particle is Fraction A and the only saponin fraction in a second ISCOM matrix or ISCOM complex particle is Fraction C.

Preferred compositions comprise a first ISCOM matrix containing Fraction A and a second ISCOM matrix containing Fraction C, wherein the Fraction A ISCOM matrix constitutes about 70% per weight of the total saponin adjuvant, and the Fraction C ISCOM matrix constitutes about 30% per weight of the total saponin adjuvant. In another preferred composition, the Fraction A ISCOM matrix constitutes about 85% per weight of the total saponin adjuvant, and the Fraction C ISCOM matrix constitutes about 15% per weight of the total saponin adjuvant. Thus, in certain compositions, the Fraction A ISCOM matrix is present in a range of about 70% to about 85%, and Fraction C ISCOM matrix is present in a range of about 15% to about 30%, of the total weight amount of saponin adjuvant in the composition. In embodiments, the Fraction A ISCOM matrix accounts for 50-96% by weight and Fraction C ISCOM matrix accounts for the remainder, respectively, of the sums of the weights of Fraction A ISCOM matrix and Fraction C ISCOM in the adjuvant. In a particularly preferred composition, referred to herein as MATRIX-M™, the Fraction A ISCOM matrix is present at about 85% and Fraction C ISCOM matrix is present at about 15% of the total weight amount of saponin adjuvant in the composition. MATRIX-M™ may be referred to interchangeably as Matrix-M1.

Exemplary QS-7 and QS-21 fractions, their production and their use is described in U.S. Pat. Nos. 5,057,540; 6,231,859; 6,352,697; 6,524,584; 6,846,489; 7,776,343, and 8,173,141, which are incorporated by reference herein.

In some, compositions other adjuvants may be used in addition or as an alternative. The inclusion of any adjuvant described in Vogel et al., "A Compendium of Vaccine Adjuvants and Excipients (2nd Edition)," herein incorporated by reference in its entirety for all purposes, is envisioned within the scope of this disclosure. Other adjuvants include complete Freund's adjuvant (a non-specific stimulator of the immune response containing killed Mycobacterium tuberculosis), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/TWEEN® polysorbate 80 emulsion. In embodiments, the adjuvant may be a paucilamellar lipid vesicle; for example, NOVASOMES®. NOVASOMES® are paucilamellar non-phospholipid vesicles ranging from about 100 nm to about 500 nm. They comprise BRIJ® alcohol ethoxylate 72, cholesterol, oleic acid and squalene. NOVASOMES® have been shown to be an effective adjuvant (see, U.S. Pat. Nos. 5,629,021, 6,387,373, and 4,911,928.

Administration and Dosage

In embodiments, the disclosure provides a method for eliciting an immune response against one or more coronaviruses. In embodiments, the response is against one or more of the SARS-CoV-2 virus, MERS, and SARS. The method involves administering an immunologically effective amount of a composition containing a nanoparticle or containing a recombinant CoV Spike (S) polypeptide to a subject. Advantageously, the proteins disclosed herein induce one or more of particularly useful anti-coronavirus responses.

In embodiments, the nanoparticles or CoV S polypeptides are administered with an adjuvant. In other aspects, the nanoparticles or CoV S polypeptides are administered without an adjuvant. In some aspects, the adjuvant may be bound to the nanoparticle, such as by a non-covalent interaction. In other aspects, the adjuvant is co-administered with the nanoparticle but the adjuvant and nanoparticle do not interact substantially.

In embodiments, the nanoparticles may be used for the prevention and/or treatment of one or more of a SARS-CoV-2 infection, a SARS infection, or a MERS infection. Thus, the disclosure provides a method for eliciting an immune response against one or more of the SARS-CoV-2 virus, MERS, and SARS. The method involves administering an immunologically effective amount of a composition containing a nanoparticle or a CoV S polypeptide to a subject. Advantageously, the proteins disclosed herein induce particularly useful anti-coronavirus responses.

Compositions disclosed herein may be administered via a systemic route or a mucosal route or a transdermal route or directly into a specific tissue. As used herein, the term "systemic administration" includes parenteral routes of administration. In particular, parenteral administration includes subcutaneous, intraperitoneal, intravenous, intraarterial, intramuscular, or intrasternal injection, intravenous, or kidney dialytic infusion techniques. Typically, the systemic, parenteral administration is intramuscular injection. As used herein, the term "mucosal administration" includes oral, intranasal, intravaginal, intra-rectal, intra-tracheal, intestinal and ophthalmic administration. Preferably, administration is intramuscular.

Compositions may be administered on a single dose schedule or a multiple dose schedule. Multiple doses may be used in a primary immunization schedule or in a booster immunization schedule. In a multiple dose schedule the various doses may be given by the same or different routes e.g., a parenteral prime and mucosal boost, a mucosal prime and parenteral boost, etc. In some aspects, a follow-on boost dose is administered about 2 weeks, about 3 weeks, about 4 weeks, about 5 weeks, or about 6 weeks after the prior dose. In embodiments, the follow-on boost dose is administered 3 weeks after administration of the prior dose. In embodiments, the first dose is administered at day 0, and the boost dose is administered at day 21. In embodiments, the first dose is administered at day 0, and the boost dose is administered at day 28.

In embodiments, the dose, as measured in μg, may be the total weight of the dose including the solute, or the weight of the CoV S polypeptide nanoparticles, or the weight of the CoV S polypeptide. Dose is measured using protein concentration assay either A280 or ELISA The dose of antigen, including for pediatric administration, may be in the range of about 5 μg to about 25 μg, about 1 μg to about 300 μg, about 90 μg to about 270 μg, about 100 μg to about 160 μg, about 110 μg to about 150 μg, about 120 μg to about 140 μg, or about 140 μg to about 160 μg. In embodiments, the dose is about 120 μg, administered with alum. In some aspects, a pediatric dose may be in the range of about 1 μg to about 90 μg. In embodiments, the dose of CoV Spike (S) polypeptide is about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21, about 22, about 23, about 24, about 25 μg, about 26 μg, about 27 μg, about 28 μg, about 29 μg, about 30 μg, about 40 μg, about 50, about 60, about 70, about 80, about 90 about 100 μg, about 110 μg, about 120 μg, about 130 μg, about 140 μg, about 150 μg, about 160 μg, about 170 μg, about 180 μg, about 190 μg, about 200 μg, about 210 μg, about 220 μg, about 230 μg, about 240 μg, about 250 μg, about 260 μg, about 270 μg, about 280 μg, about 290 μg, or about 300 μg, including all values and ranges in between. In embodiments, the dose of CoV S polypeptide is 5 μg. In embodiments, the dose of CoV S polypeptide is 25 μg.

Certain populations may be administered with or without adjuvants. In certain aspects, compositions may be free of added adjuvant. In such circumstances, the dose may be increased by about 10%.

In embodiments, the dose of the adjuvant administered with a non-naturally occurring CoV S polypeptide is from about 1 μg to about 100 μg, for example, about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21, about 22, about 23, about 24, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg, about 75 μg, about 76 μg, about 77 μg, about 78 μg, about 79 μg, about 80 μg, about 81 μg, about 82 μg, about 83 μg, about 84 μg, about 85 μg, about 86 μg, about 87 μg, about 88 μg, about 89 μg, about 90 μg, about 91 μg, about 92 μg, about 93 μg, about 94 μg, about 95 μg, about 96 μg, about 97 μg, about 98 μg, about 99 μg, or about 100 μg of adjuvant. In embodiments, the dose of adjuvant is about 50 μg. In embodiments, the adjuvant is a saponin adjuvant, e.g., MATRIX-M™.

In embodiments, the dose is administered in a volume of about 0.1 mL to about 1.5 mL, for example, about 0.1 mL, about 0.2 mL, about 0.25 mL, about 0.3 mL, about 0.4 mL, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, or about 1.5 mL. In embodiments, the dose is administered in a volume of 0.25 mL. In embodiments, the dose is administered in a volume of 0.5 mL. In embodiments, the dose is administered in a volume of 0.6 mL.

In particular embodiments for a vaccine against MERS, SARS, or the SARS-CoV-2 coronavirus, the dose may comprise a CoV S polypeptide concentration of about 1 μg/mL to about 50 μg/mL, 10 μg/mL to about 100 μg/mL, about 10 μg/mL to about 50 μg/mL, about 175 μg/mL to about 325 μg/mL, about 200 μg/mL to about 300 μg/mL, about 220 μg/mL to about 280 μg/mL, or about 240 μg/mL to about 260 μg/mL.

In another embodiment, the disclosure provides a method of formulating a vaccine composition that induces immunity to an infection or at least one disease symptom thereof to a mammal, comprising adding to the composition an effective dose of a nanoparticle or a CoV S polypeptide. The disclosed CoV S polypeptides and nanoparticles are useful for preparing compositions that stimulate an immune response that confers immunity or substantial immunity to infectious agents. Thus, in one embodiment, the disclosure provides a method of inducing immunity to infections or at least one disease symptom thereof in a subject, comprising administering at least one effective dose of a nanoparticle and/or a CoV S polypeptide.

In embodiments, the CoV S polypeptides or nanoparticles comprising the same are administered in combination with an additional immunogenic composition. In embodiments, the additional immunogenic composition induces an immune response against SARS-CoV-2. In embodiments, the additional immunogenic composition is administered within about 1 minute, about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days of the disclosed CoV S polypeptides or nanoparticles comprising the same. In embodiments, the additional composition is administered with a first dose of a composition comprising a CoV S polypeptide or nanoparticle comprising the same. In embodiments, the additional composition is administered with a boost dose of a composition comprising a CoV S polypeptide or nanoparticle comprising the same.

In embodiments, the additional immunogenic composition comprises an mRNA encoding a SARS-Cov-2 Spike glycoprotein, a plasmid DNA encoding a SARS-Cov-2 Spike glycoprotein, an viral vector encoding a SARS-Cov-2 Spike glycoprotein, or an inactivated SARS-CoV-2 virus.

In embodiments, the additional immunogenic composition comprises mRNA that encodes for a CoV S polypeptide. In embodiments, the mRNA encodes for a CoV S polypeptide comprising proline substitutions at positions 986 and 987 of SEQ ID NO: 1. In embodiments, the mRNA encodes for a CoV S polypeptide comprising an intact furin cleavage site. In embodiments, the mRNA encodes for a CoV S polypeptide comprising proline substitutions at positions 986 and 987 of SEQ ID NO: 1 and an intact furin cleavage site. In embodiments, the mRNA encodes for a CoV S polypeptide comprising proline substitutions at positions 986 and 987 of SEQ ID NO: 1 and an inactive furin cleavage site. In embodiments, the mRNA encodes for a CoV S polypeptide having an amino acid sequence of SEQ ID NO:

87. In embodiments, the mRNA encoding for a CoV S polypeptide is encapsulated in a lipid nanoparticle. An exemplary immunogenic composition comprising mRNA that encodes for a CoV S polypeptide is described in Jackson et al. N. Eng. J. Med. 2020. An mRNA Vaccine against SARS-CoV-2-preliminary report, which is incorporated by reference in its entirety herein. In embodiments, the composition comprising mRNA that encodes for a CoV S polypeptide is administered at a dose of 25 μg, 100 μg, or 250 μg.

In embodiments, the additional immunogenic composition comprises an adenovirus vector encoding for a CoV S polypeptide. In embodiments, the AAV vector encodes for a wild-type CoV S polypeptide. In embodiments, the AAV vector encodes for a CoV S polypeptide comprising proline substitutions at positions 986 and 987 of SEQ ID NO: 1 and an intact furin cleavage site. In embodiments, the AAV vector encodes for a CoV S polypeptide comprising proline substitutions at positions 986 and 987 of SEQ ID NO: 1 and an inactive furin cleavage site. In embodiments, the AAV vector encodes for a CoV S polypeptide having an amino acid sequence of SEQ ID NO: 87. The following publications describe immunogenic compositions comprising an adenovirus vector encoding for a CoV S polypeptide, each of which is incorporated by reference in its entirety herein: van Doremalen N. et al. A single dose of ChAdOx1 MERS provides protective immunity in rhesus macaques. Science Advances, 2020, van Doremalen N. et al. ChAdOx1 nCOV-19 vaccination prevents SARS-CoV-2 pneumonia in rhesus macaques. bioRxiv, (2020).

In embodiments, the additional immunogenic composition comprises deoxyribonucleic acid (DNA). In embodiments, the additional immunogenic composition comprises plasmid DNA. In embodiments, the plasmid DNA encodes for a CoV S polypeptide. In embodiments, the DNA encodes for a CoV S polypeptide comprising proline substitutions at positions 986 and 987 of SEQ ID NO: 1 and an intact furin cleavage site. In embodiments, the DNA encodes for a CoV S polypeptide comprising proline substitutions at positions 986 and 987 of SEQ ID NO: 1 and an inactive furin cleavage site. In embodiments, the DNA encodes for a CoV S polypeptide having an amino acid sequence of SEQ ID NO: 87.

In embodiments, the additional immunogenic composition comprises an inactivated virus vaccine.

In embodiments, the CoV S proteins or nanoparticles comprising CoV S proteins are useful for preparing immunogenic compositions to stimulate an immune response that confers immunity or substantial immunity to one or more of MERS, SARS, and SARS-CoV-2. Both mucosal and cellular immunity may contribute to immunity to infection and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. The antibodies produced in a host after immunization with the nanoparticles disclosed herein can also be administered to others, thereby providing passive administration in the subject.

In embodiments, the present disclosure provides a method of producing one or more of high affinity anti-MERS-CoV, anti-SARS-CoV, and anti-SARS-CoV-2 virus antibodies. The high affinity antibodies produced by immunization with the nanoparticles disclosed herein are produced by administering an immunogenic composition comprising an S CoV polypeptide or a nanoparticle comprising an S CoV polypeptide to an animal, collecting the serum and/or plasma from the animal, and purifying the antibody from the serum/and or plasma. In one embodiment, the animal is a human. In embodiments, the animal is a chicken, mouse, guinea pig, rat, rabbit, goat, human, horse, sheep, or cow. In one embodiment, the animal is bovine or equine. In another embodiment, the bovine or equine animal is transgenic. In yet a further embodiment, the transgenic bovine or equine animal produces human antibodies. In embodiments, the animal produces monoclonal antibodies. In embodiments, the animal produces polyclonal antibodies. In one embodiment, the method further comprises administration of an adjuvant or immune stimulating compound. In a further embodiment, the purified high affinity antibody is administered to a human subject. In one embodiment, the human subject is at risk for infection with one or more of MERS, SARS, and SARS-CoV-2.

All patents, patent applications, references, and journal articles cited in this disclosure are expressly incorporated herein by reference in their entireties for all purposes.

EXAMPLES

Example 1

Figure 4:
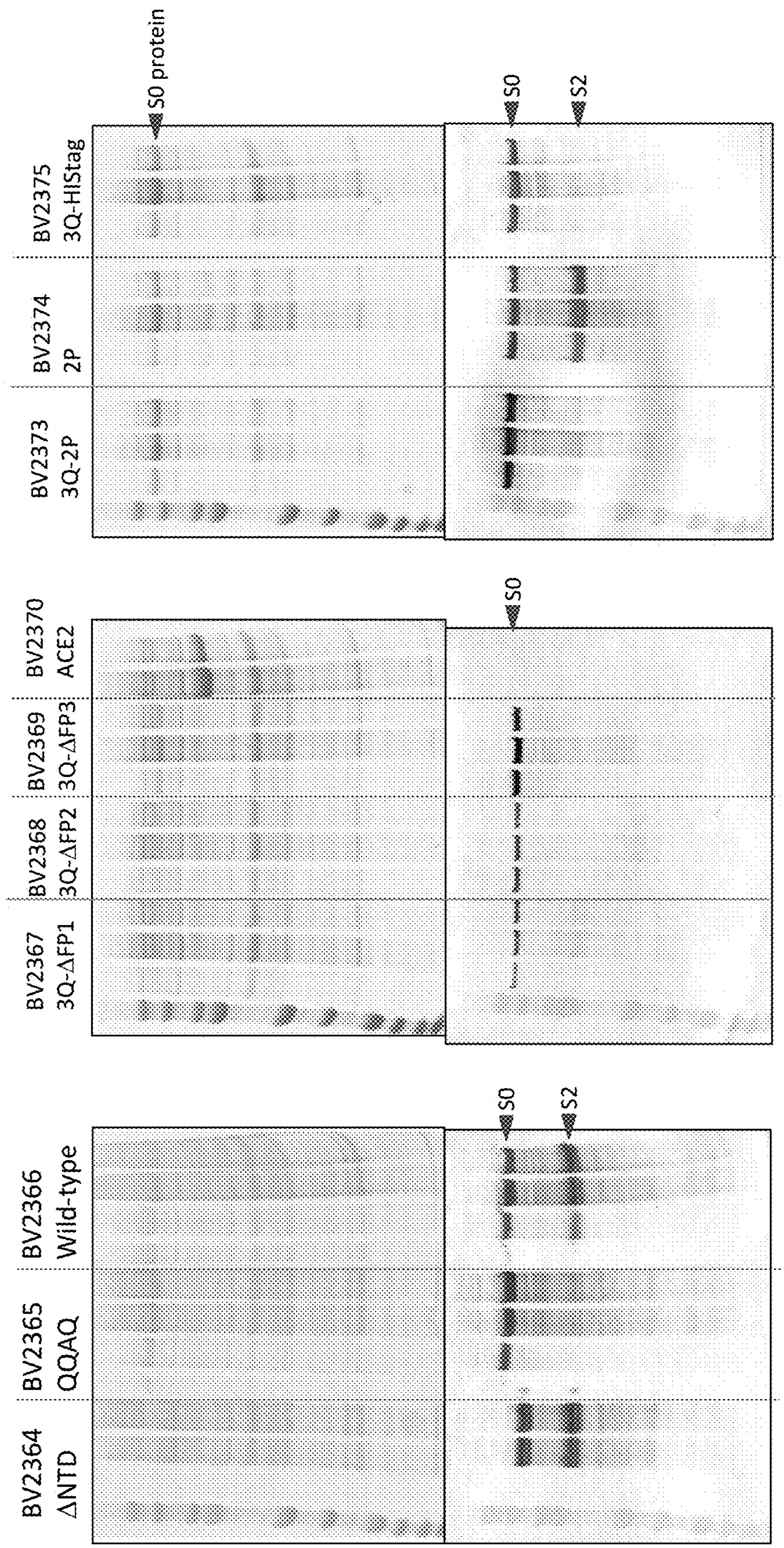
FIG. 4 shows purification of the CoV S polypeptides BV2364, BV2365, BV2366, BV2367, BV2368, BV2369, BV2373, BV2374, and BV2375. The data reveal that BV2365 (SEQ ID NO. 4) and BV2373 (SEQ ID NO: 87) which has an inactive furin cleavage site having an amino acid sequence of QQAQ (SEQ ID NO: 7) is expressed as a single chain (S0). In contrast, CoV S polypeptides containing an intact furin cleavage site (e.g. BV2364, BV2366, and BV2374) are cleaved, as evident by the presence of the cleavage product S2.
Figure 5:
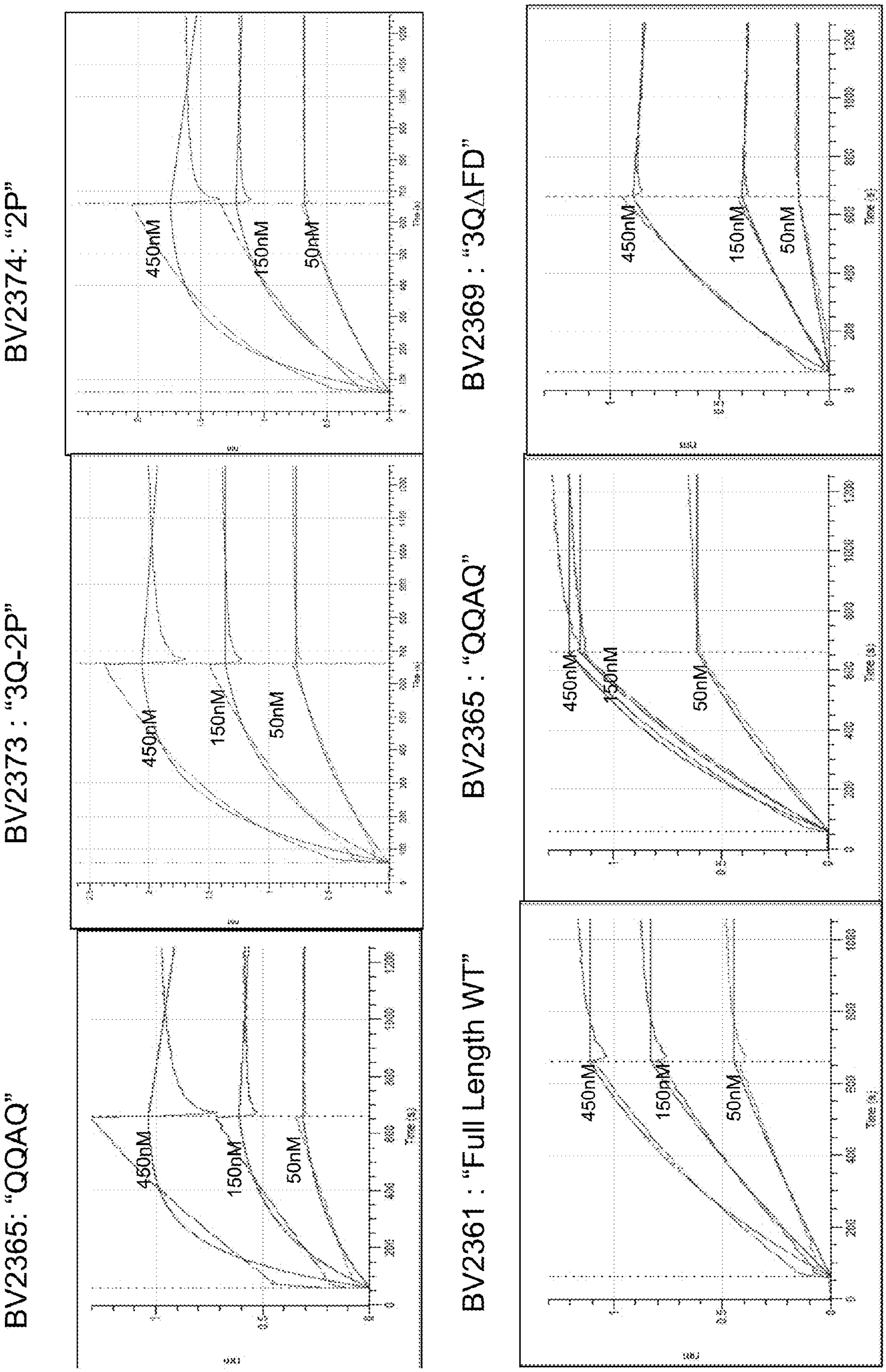
FIG. 5 shows that the CoV S polypeptides BV2361, BV2365, BV2369, BV2365, BV2373, and BV2374 bind to human angiotensin-converting enzyme 2 precursor (hACE2) by bio-layer interferometry.
Figure 6:
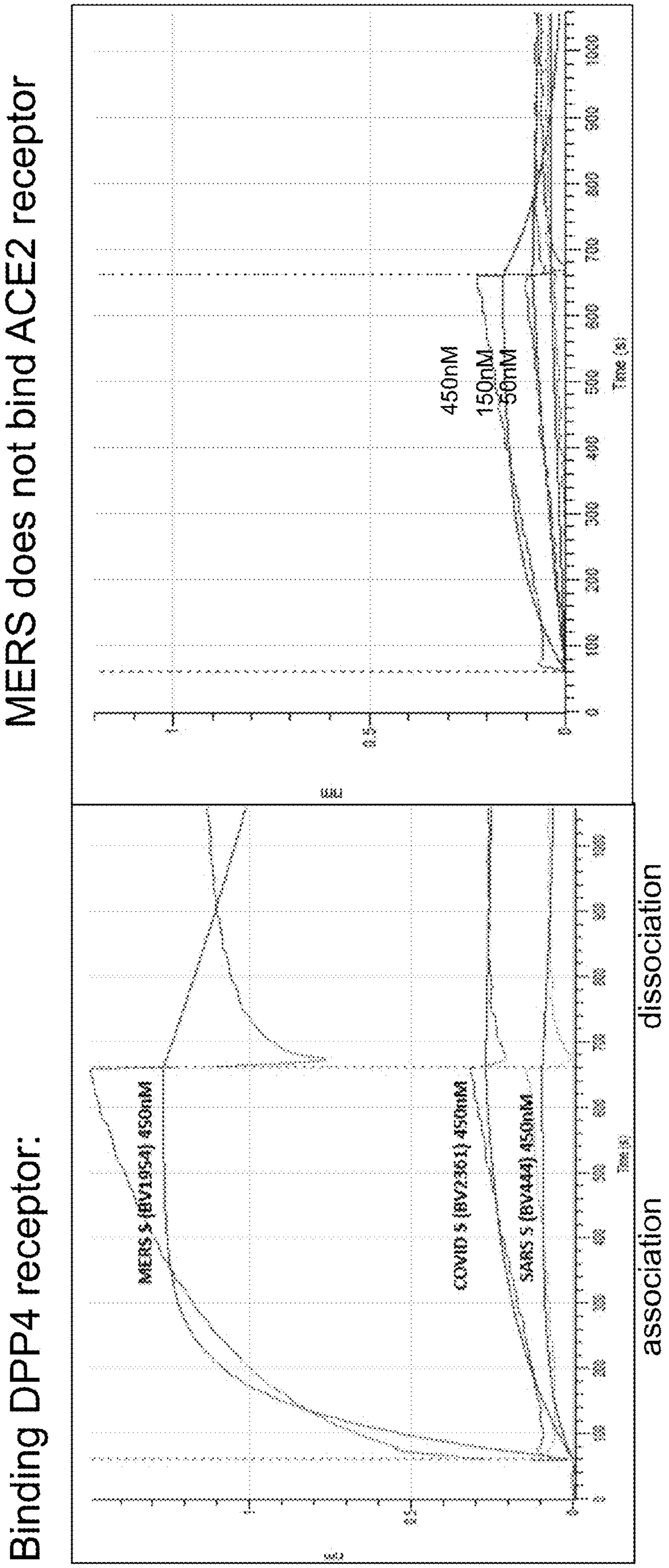
FIG. 6 shows that BV2361 from SARS-CoV-2 does not bind the MERS-CoV receptor, dipeptidyl peptidase IV (DPP4) and the MERS S protein does not bind to human angiotensin-converting enzyme 2 precursor (hACE2) by bio-layer interferometry.
Figure 7:
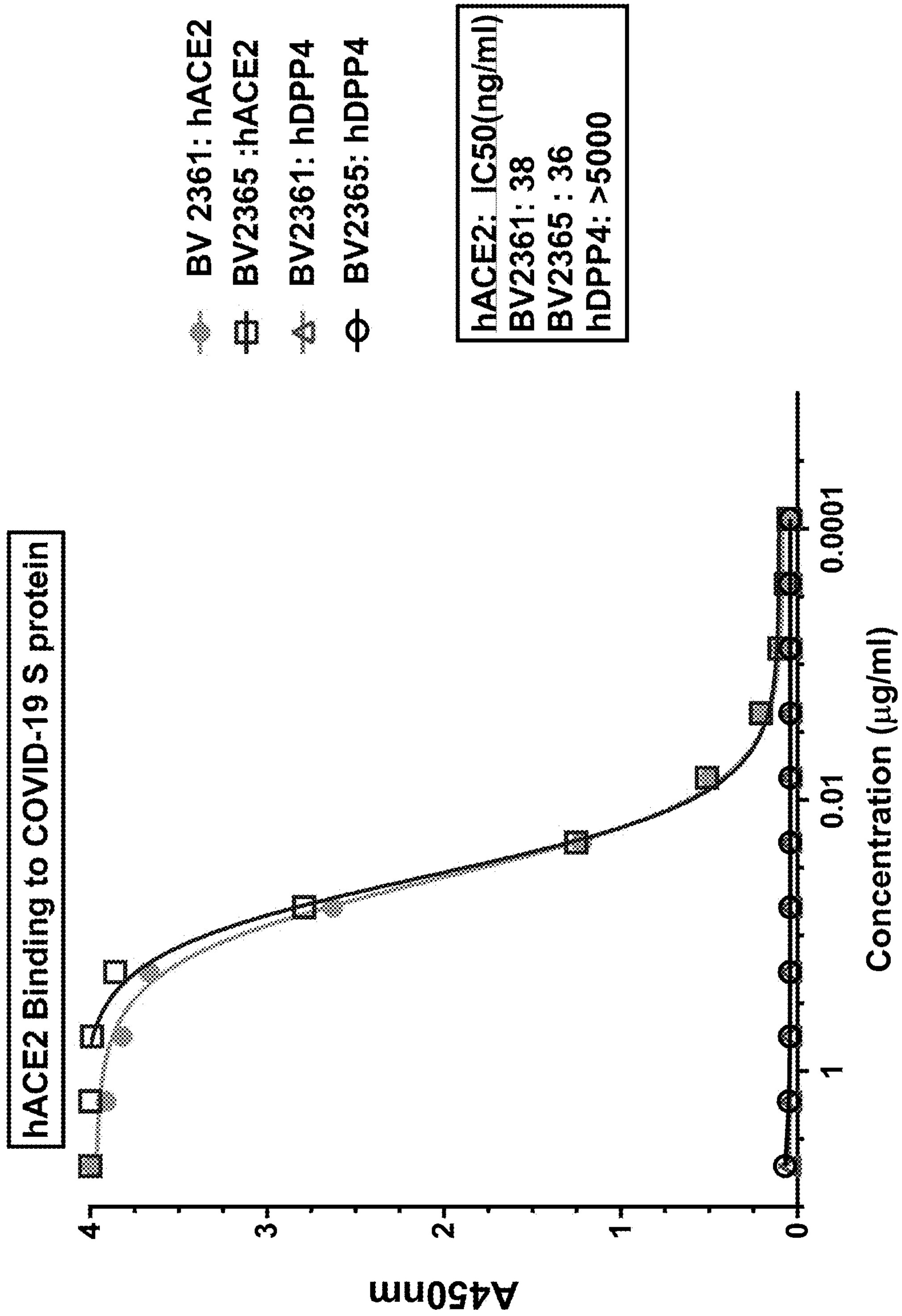
FIG. 7 shows that BV2361 binds to hACE2 by enzyme-linked immunosorbent assay (ELISA).
Figure 9:
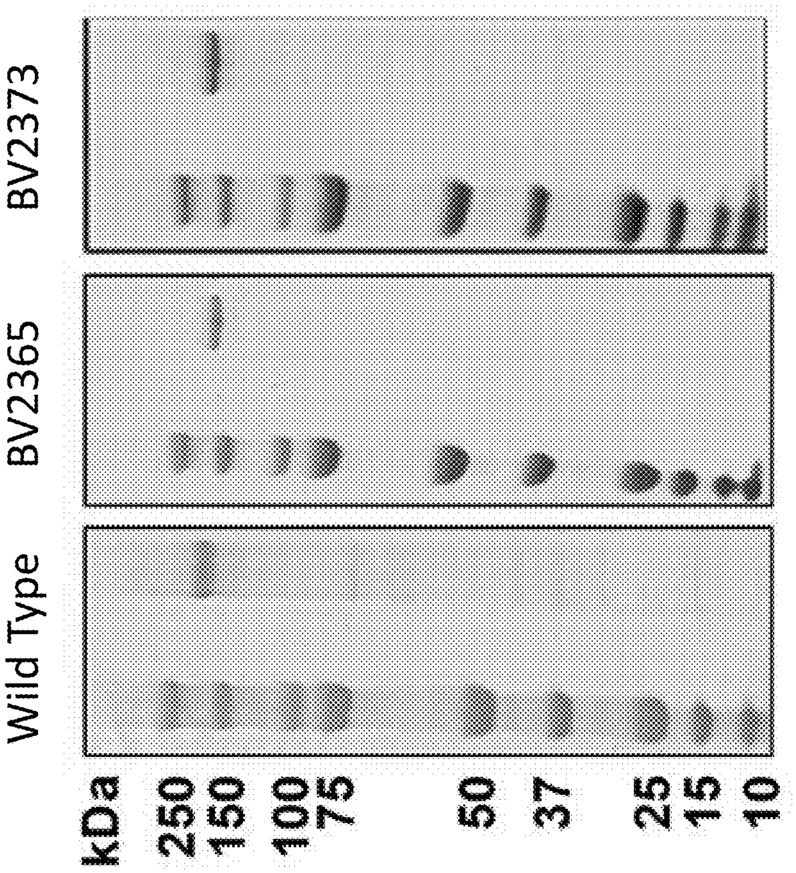
FIG. 9 shows purification of the wild type CoV S polypeptide and the CoV S polypeptides BV2365 and BV2373.

Expression and Purification of Coronavirus Spike (S) Polypeptide Nanoparticles The native coronavirus Spike (S) polypeptide (SEQ ID NO: 1 and SEQ ID NO:2) and CoV Spike polypeptides which have amino acid sequences corresponding to SEQ ID NOS: 3, 4, 38, 41, 44, 48, 51, 54, 58, 61, 63, 65, 67, 73, 75, 78, 79, 82, 83, 85, 87, 106, 108, and 89 have been expressed in a baculovirus expression system and recombinant plaques expressing the coronavirus Spike (S) polypeptides were picked and confirmed. In each case the signal peptide is SEQ ID NO: 5. FIG. 4 and FIG. 9 show successful purification of the CoV Spike polypeptides BV2364, BV2365, BV2366, BV2367, BV2368, BV2369, BV2373, BV2374, and BV2375. Table 2 shows the sequence characteristics of the aforementioned CoV Spike polypeptides.

TABLE 2

Selected CoV Spike Polypeptides

| CoV S polypeptide | Modification | SEQ ID NO. |
|---|---|---|
| BV2364 | Deleted N-Terminal Domain | 48 |
| BV2365 | Inactive furin cleavage site | 4 |
| BV2361/BV2366 | Wild-type | 2 |
| BV2367 | Deletion of amino acids 676-685, inactive furin cleavage site | 63 |
| BV2368 | Deletion of amino acids 702-711, inactive furin cleavage site | 65 |
| BV2369 | Deletion of amino acids 806-815, inactive furin cleavage site | 67 |
| BV2373, formulated into a composition referred to herein as “NVX-CoV2373” | Inactive furin cleavage site, K973P mutation, V974P mutation | 87 |
| BV2374 | K973P mutation, V974P mutation | 85 |
| BV2374 | Inactive furin cleavage site and His-tag | 58 |
| BV2384 | Inactive furin cleavage site (GSAS), K973P, V974P mutation | 110 |

The wild-type BV2361 protein (SEQ ID NO: 2) binds to human angiotensin-converting enzyme 2 precursor (hACE2). Bio-layer interferometry and ELISA were performed to assess binding of the CoV S polypeptides.

Bio-Layer Interferometry (BLI):

The BLI experiments were performed using an Octet QK384 system (Pall Forté Bio, Fremont, CA). His-tagged human ACE2 (2 μg mL-1) was immobilized on nickel-charged Ni-NTA biosensor tips. After baseline, SARS-CoV-2 S protein containing samples were 2-fold serially diluted and were allowed to associate for 600 seconds followed by dissociation for an additional 900 sec. Data was analyzed with Octet software HT 101:1 global curve fit.

Figures 11A, 11B, 11C, 11D, 11E, 11F:
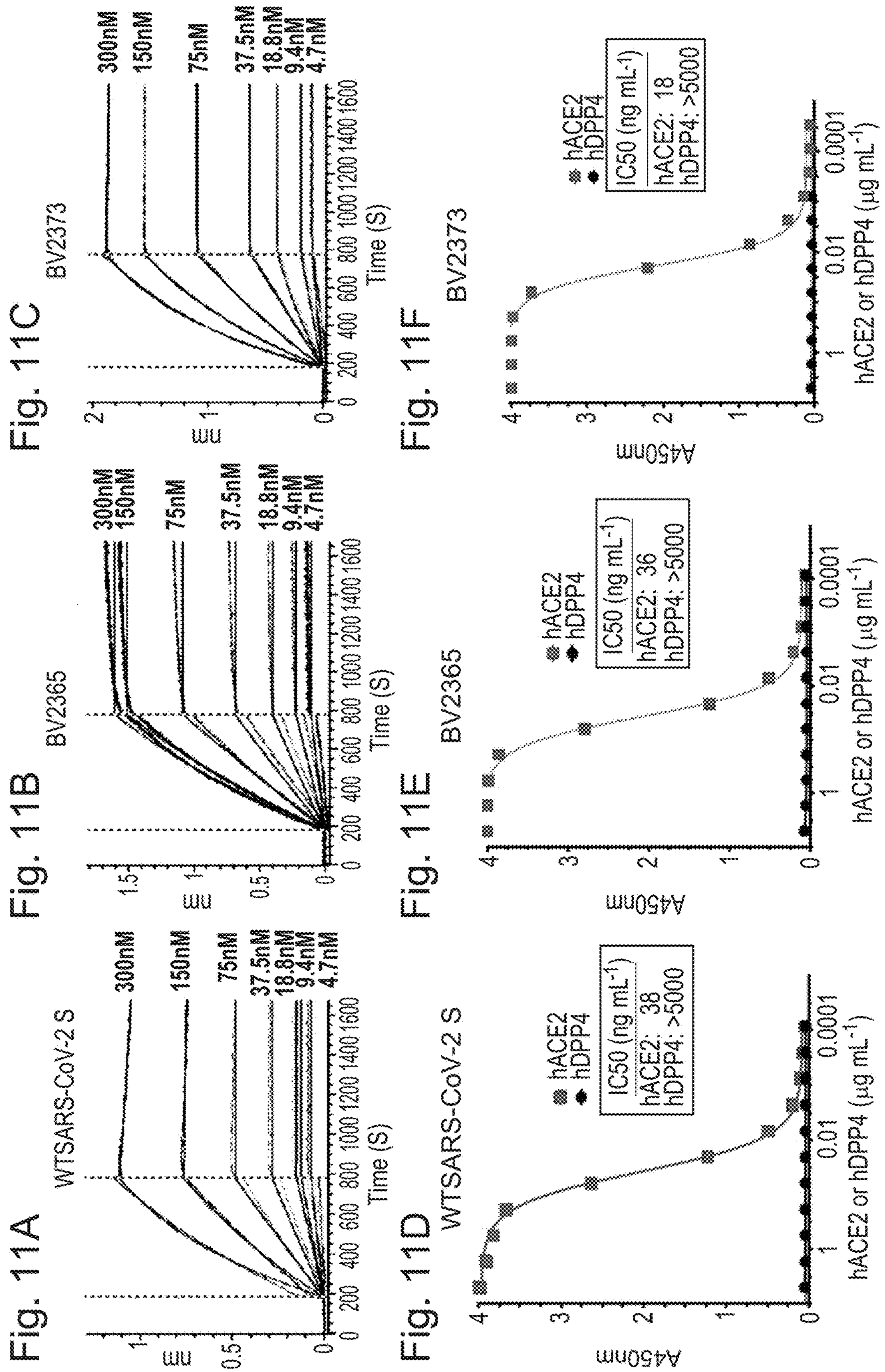
FIGS. 11A-F show that the CoV S Spike polypeptides BV2365 and BV2373 bind to hACE2. Bio-layer interferometry reveals that BV2365 (FIG. 11B) and BV2373 (FIG. 11C) bind to hACE2 with similar dissociation kinetics to the wild-type CoV S polypeptide (FIG. 11A) ELISA shows that the wild-type CoV S polypeptide (FIG. 11D) and BV2365 (FIG. 11E) bind to hACE2 with similar affinity while BV2373 binds to hACE2 at a higher affinity (FIG. 11F).

The CoV S polypeptides BV2361, BV2365, BV2369, BV2365, BV2373, BV2374 retain the ability to bind to hACE2 (FIG. 5, FIGS. 11A-C). Dissociation kinetics showed that the S-proteins remained tightly bound as evident by minimal or no dissociation over 900 seconds of observation in the absence of fluid phase S protein (FIGS. 11A-C).

Furthermore, binding is specific. The wild-type CoV S protein, BV2361 and the CoV S polypeptides BV2365 and BV2373 do not bind the MERS-CoV receptor, dipeptidyl peptidase IV (DPP4). Additionally, the MERS S protein does not bind to human angiotensin-converting enzyme 2 precursor (hACE2) (FIG. 6 and FIGS. 11D-F).

ELISA

The specificity of the CoV S polypeptides for hACE2 was confirmed by ELISA. Ninety-six well plates were coated with 100 μL SARS-CoV-2 spike protein (2 μg/mL) overnight at 4° C. Plates were washed with phosphate buffered saline with 0.05% Tween (PBS-T) buffer and blocked with TBS Startblock blocking buffer (ThermoFisher, Scientific). His-tagged hACE2 and hDPP4 receptors were 3-fold serially diluted (5-0.0001 μg mL-1) and added to coated wells for 2 hours at room temperature. The plates were washed with PBS-T. Optimally diluted horseradish peroxidase (HRP) conjugated anti-histidine was added and color developed by addition of and 3,3',5,5'-tetramethylbenzidine peroxidase substrate (TMB, T0440-IL, Sigma, St. Louis, MO, USA). Plates were read at an OD of 450 nm with a SpectraMax Plus plate reader (Molecular Devices, Sunnyvale, CA, USA) and data analyzed with SoftMax software. EC50 values were calculated by 4-parameter fitting using GraphPad Prism 7.05 software.

The ELISA results showed that the wild-type CoV S polypeptide (BV2361), BV2365, and BV2373 proteins specifically bound hACE2 but failed to bind the hDPP-4 receptor used by MERS-CoV ($IC_{50}$>5000 ng mL-1). The wild-type CoV S polypeptide and BV2365 bound to hACE2 with similar affinity ($IC_{50}$=36-38 ng/mL), while BV2373 attained 50% saturation of hACE2 binding at 2-fold lower concentration ($IC_{50}$=18 ng/mL) (FIG. 7, FIGS. 11D-F)

Protein and Nanoparticle Production

The recombinant virus is amplified by infection of Sf9 insect cells. A culture of insect cells is infected at ~3 MOI (Multiplicity of infection=virus ffu or pfu/cell) with baculovirus. The culture and supernatant is harvested 48-72 hrs post-infection. The crude cell harvest, approximately 30 mL, is clarified by centrifugation for 15 minutes at approximately 800×g. The resulting crude cell harvests containing the coronavirus Spike (S) protein are purified as nanoparticles as described below.

To produce nanoparticles, non-ionic surfactant TERGITOL® nonylphenol ethoxylate NP-9 is used in the membrane protein extraction protocol. Crude extraction is further purified by passing through anion exchange chromatography, lentil lectin affinity/HIC and cation exchange chromatography. The washed cells are lysed by detergent treatment and then subjected to low pH treatment which leads to precipitation of BV and Sf9 host cell DNA and protein. The neutralized low pH treatment lysate is clarified and further purified on anion exchange and affinity chromatography before a second low pH treatment is performed.

Affinity chromatography is used to remove Sf9/BV proteins, DNA and NP-9, as well as to concentrate the coronavirus Spike (S) protein. Briefly, lentil lectin is a metalloprotein containing calcium and manganese, which reversibly binds polysaccharides and glycosylated proteins containing glucose or mannose. The coronavirus Spike (S) protein-containing anion exchange flow through fraction is loaded onto the lentil lectin affinity chromatography resin (Capto Lentil Lectin, GE Healthcare). The glycosylated coronavirus Spike (S) protein is selectively bound to the resin while non-glycosylated proteins and DNA are removed in the column flow through. Weakly bound glycoproteins are removed by buffers containing high salt and low molar concentration of methyl alpha-D-mannopyranoside (MMP).

The column washes are also used to detergent exchange the NP-9 detergent with the surfactant polysorbate 80 (PS80). The coronavirus Spike (S) polypeptides are eluted in nanoparticle structure from the lentil lectin column with a high concentration of MMP. After elution, the coronavirus Spike (S) protein trimers are assembled into nanoparticles composed of coronavirus Spike (S) protein trimers and PS80 contained in a detergent core.

Example 2

Immunogenicity of Coronavirus Spike (S) Polypeptide Nanoparticle Vaccines in Mice The coronavirus Spike (S) protein composition comprising a CoV S polypeptide of SEQ ID NO: 87 (also called "BV2373") as described in Example 1 was evaluated for immunogenicity and toxicity in a murine model, using female BALB/c mice (7-9 weeks old; Harlan Laboratories Inc., Frederick, MD). The compositions were evaluated in the presence and in the absence of a saponin adjuvant, e.g., MATRIX-M™. Compositions containing MATRIX-M™ contained 5 μg of MATRIX-M™. Vaccines containing coronavirus Spike (S) polypeptide at various doses, including 0.01 μg, 0.1 μg, 1 μg, and 10 μg, were administered intramuscularly as a single dose (also referred to as a single priming dose) (study day 14) or as two doses (also referred to as a prime/boost regimen) spaced 14-days apart (study day 0 and 14). A placebo group served as a non-immunized control. Serum was collected for analysis on study days-1, 13, 21, and 28. Vaccinated and control animals were intranasally challenged with SARS-CoV-2 42 days following one (a single dose) or two (two doses) immunizations.

Vaccine Immunogenicity

Figure 13A:
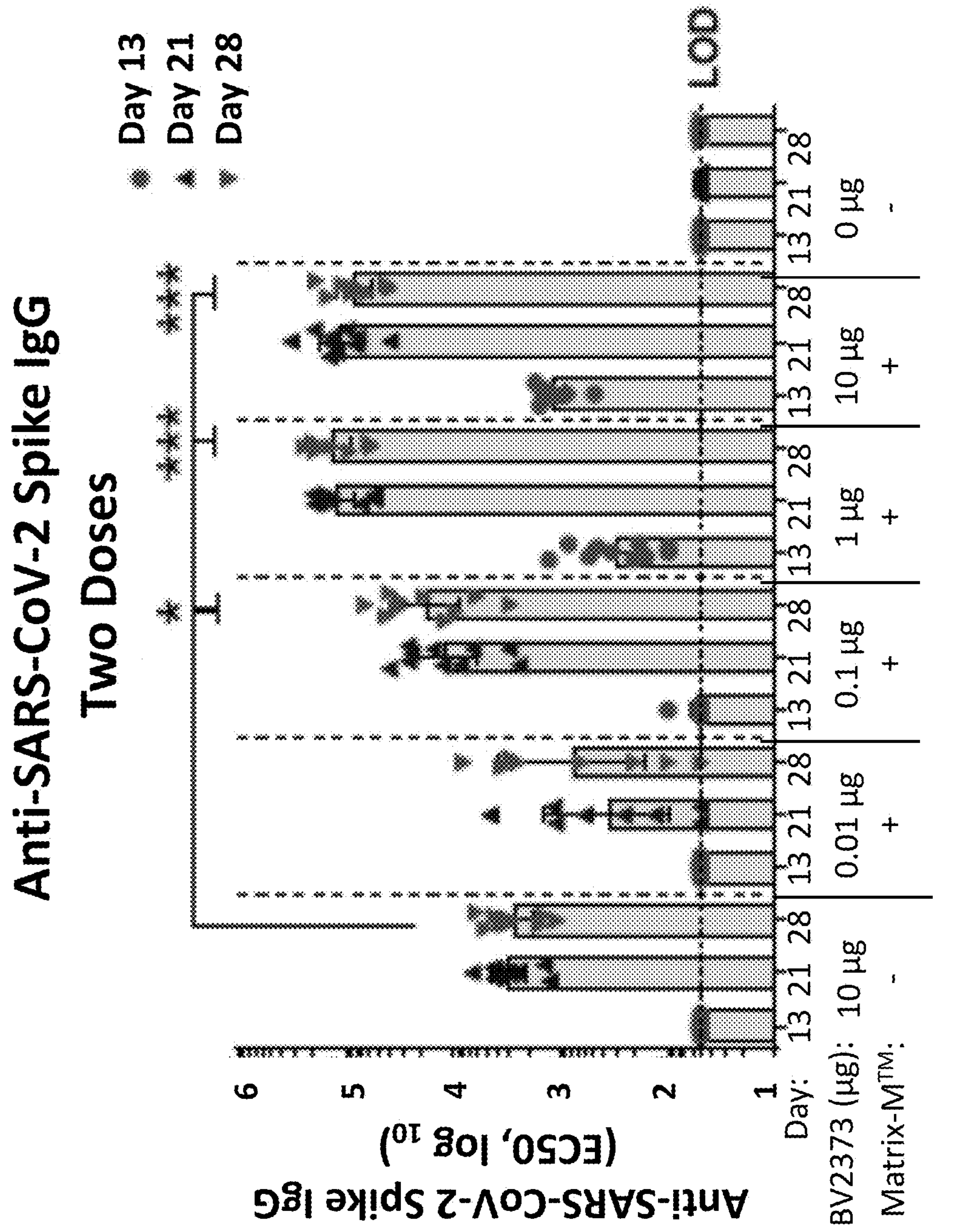
FIGS. 13A-B show anti-CoV S polypeptide IgG titers 13 days, 21 days, and 28 days after immunization of mice with two doses (FIG. 13A) and one dose of 0.1 μg to 10 μg of BV2373 with or without Fraction A and Fraction C iscom matrix (e.g., MATRIX-M™) (FIG. 13B).
Figure 13B:
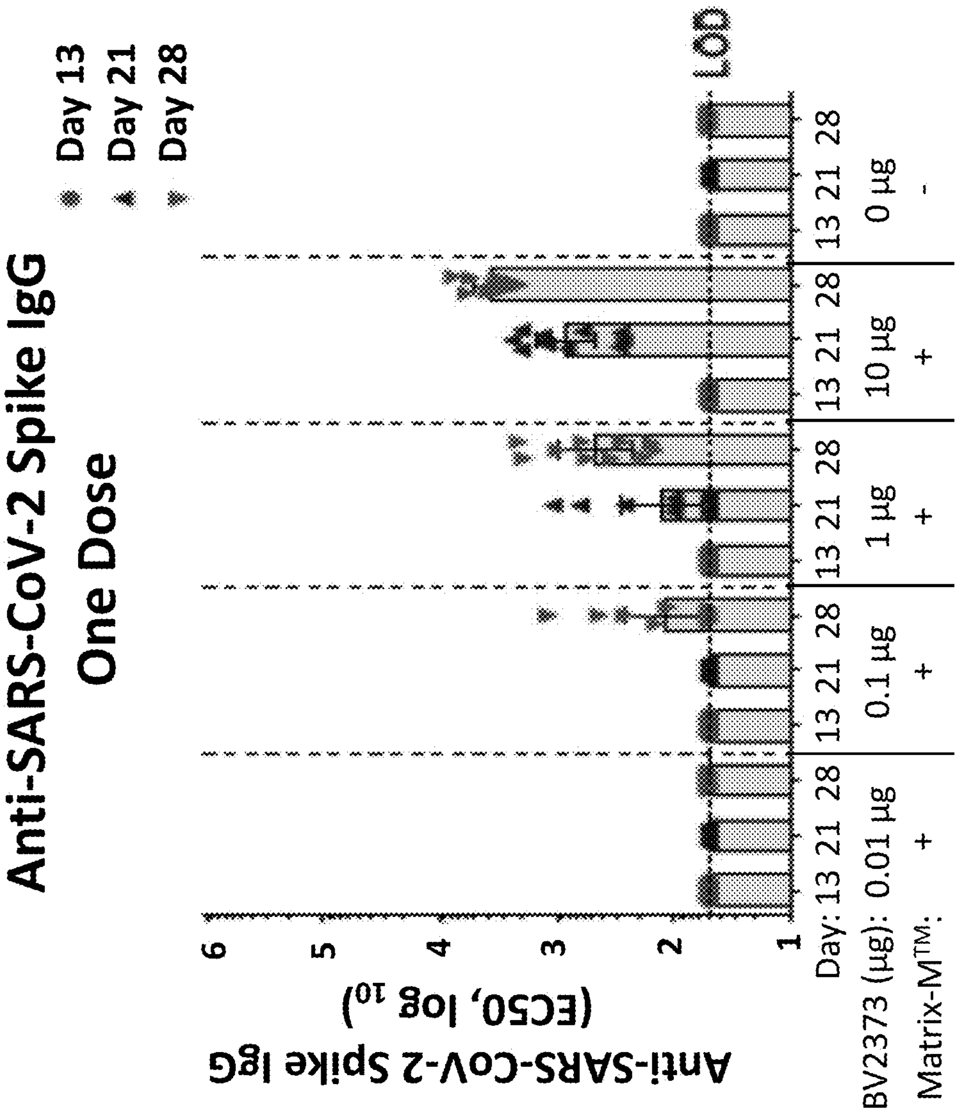
Figure 14:
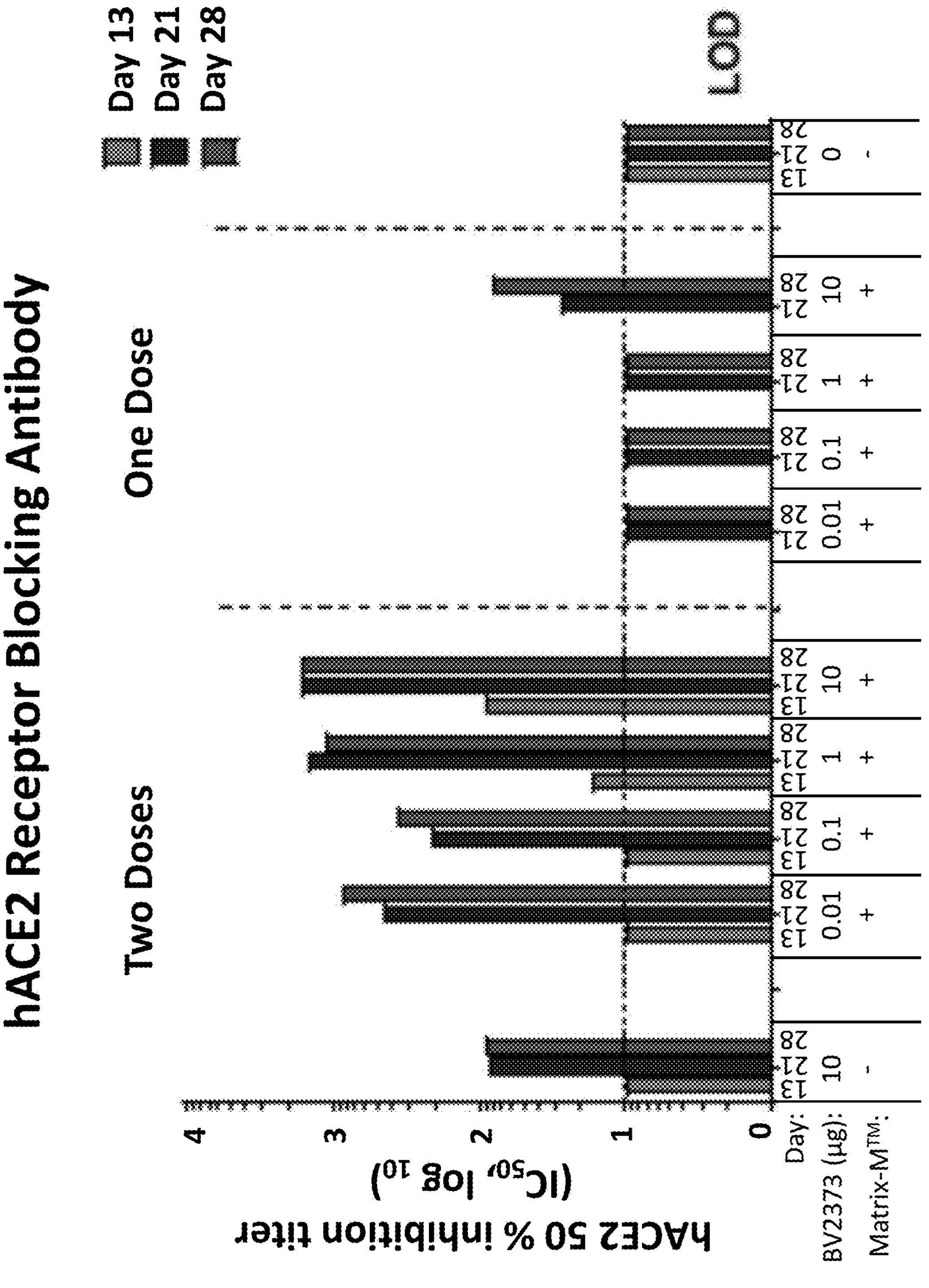
FIG. 14 shows the induction of antibodies that block interaction of hACE2 in mice immunized with one dose or two doses of 0.1 μg to 10 μg of BV2373 with or without MATRIX-M™.
Figure 15:
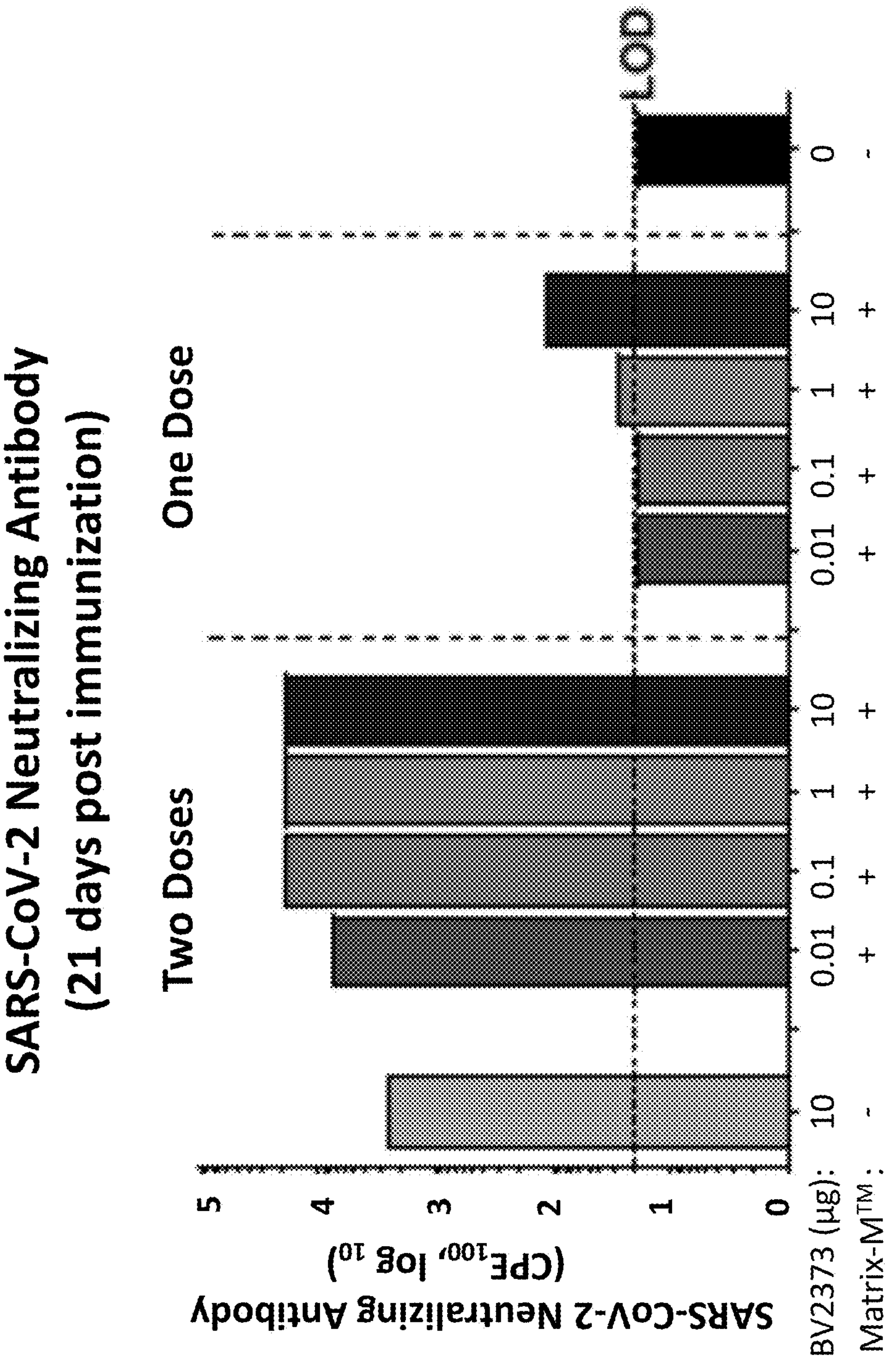
FIG. 15 shows virus neutralizing antibodies detected in mice immunized with one dose or two doses of 0.1 μg to 10 μg of BV2373 with or without MATRIX-M™.

Animals immunized with a single priming dose of 0.1-10 μg BV2373 and MATRIX-M™ had elevated anti-S IgG titers that were detected 21-28 days after a single immunization (FIG. 13B). Mice immunized with a 10 g dose of BV2373 and MATRIX-M™ produced antibodies that blocked hACE2 receptor binding to the CoV S protein and virus neutralizing antibodies that were detected 21-28 days after a single priming dose (FIG. 14 and FIG. 15). Animals immunized with the prime/boost regimen (two doses) had significantly elevated anti-S IgG titers that were detected 7-16 days following the booster immunization across all dose levels (FIG. 13A). Animals immunized with BV2373 (1 μg and 10 μg) and MATRIX-M™ had similar high anti-S IgG titers following immunization (GMT=139,000 and 84,000, respectively). Mice immunized with BV2373 (0.1 μg, 1 μg, or 10 μg) and MATRIX-M™ bad significantly ($p \leq 0.05$ and $p \leq 0.0001$) higher anti-S IgG titers compared to mice immunized with 10 μg BV2373 without adjuvant (FIG. 13A). These results indicate the potential for 10- to 100-fold dose sparing provided by the MATRIX-M™ adjuvant. Furthermore, immunization with two doses of BV2373 and MATRIX-M™ elicited high titer antibodies that blocked hACE2 receptor binding to S-protein (IC50=218 –1642) and neutralized the cytopathic effect (CPE) of SARS-CoV-2 on Vero E6 cells (100% blocking of CPE=7680-20,000) across all dose levels (FIG. 14 and FIG. 15).

SARS CoV-2 Challenge

To evaluate the induction of protective immunity, immunized mice were challenged with SARS-CoV-2. Since mice do not support replication of the wild-type SARS-CoV-2 virus, on day 52 post initial vaccination, mice were intranasally infected with an adenovirus expressing hACE2 (Ad/hACE2) to render them permissive. Mice were intranasally inoculated with $1.5 \times 10^5$ pfu of SARS-CoV-2 in 50 μL divided between nares. Challenged mice were weighed on the day of infection and daily for up to 7 days post infection. At 4- and 7-days post infection, 5 mice were sacrificed from each vaccination and control group, and lungs were harvested and prepared for pulmonary histology.

Figure 16:
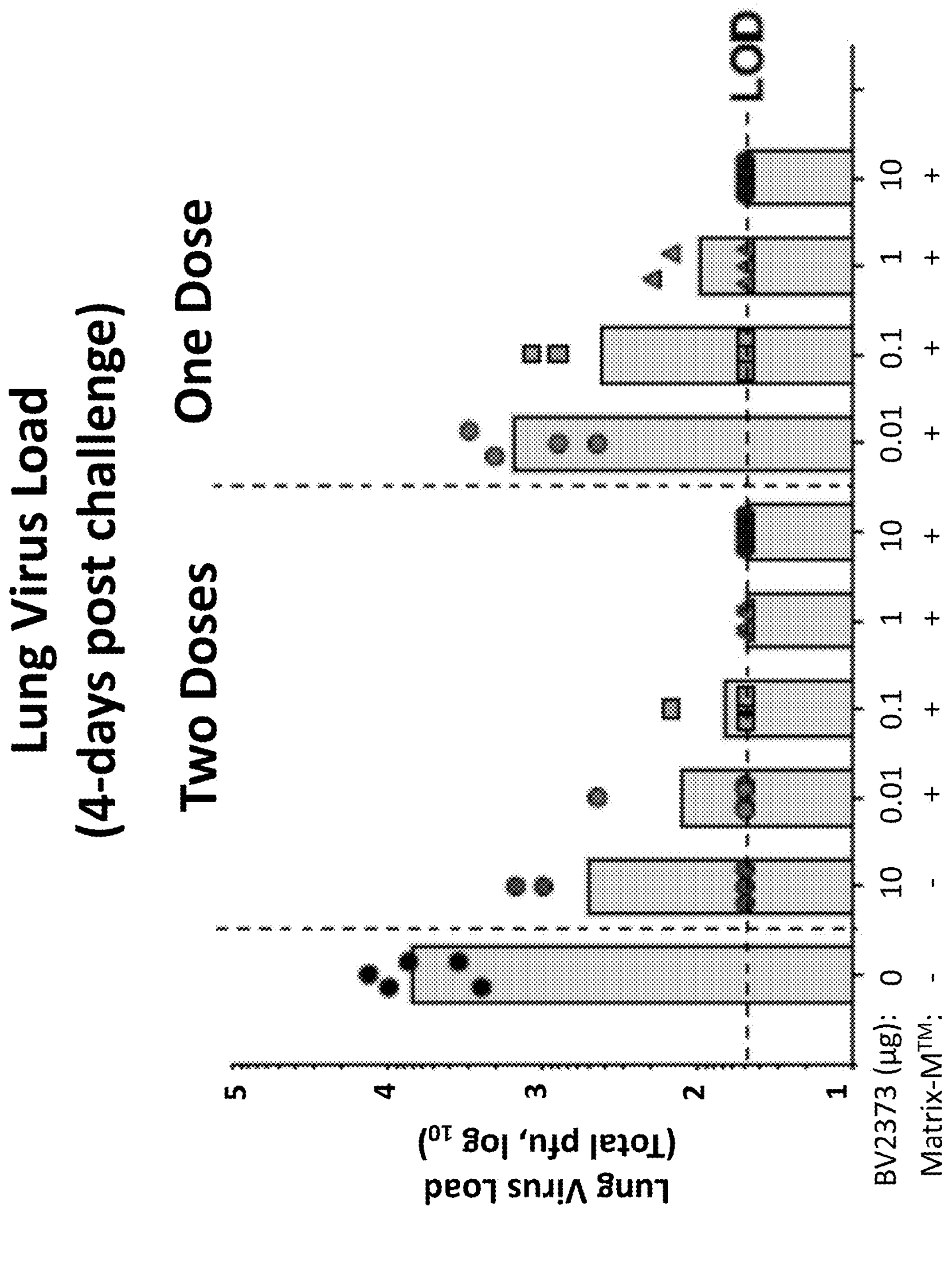
FIG. 16 shows the virus load (SARS-CoV-2) in the lungs of Ad/CMV/hACE2 mice immunized with either a single dose of BV2373 or two doses of BV2373 spaced 14 days apart with or without MATRIX-M™.

The viral titer was quantified by a plaque assay. Briefly, the harvested lungs were homogenized in PBS using 1.0 mm glass beads (Sigma Aldrich) and a Beadruptor (Omini International Inc.). Homogenates were added to Vero E6 near confluent cultures and SARS-CoV-2 virus titers determined by counting plaque forming units (pfu) using a 6-point dilution curve At 4 days post infection, placebo-treated mice had 104 SARS-CoV-2 pfu/lung, while the mice immunized with BV2363 without MATRIX-M™ had 103 pfu/lung (FIG. 16). The BV2373 with MATRIX-M™ prime-only groups of mice exhibited a dose dependent reduction in virus titer, with recipients of the 10 μg BV2373 dose having no detectable virus at day 4 post infection. Mice receiving 1 μg, 0.1 μg and 0.01 μg BV2373 doses all showed a marked reduction in titer compared to placebo-vaccinated mice. In the prime/boost groups, mice immunized with 10 μg, 1 μg and 0.1 μg doses had almost undetectable lung virus loads, while the 0.01 μg group displayed a reduction of 1 log reduction relative to placebo animals.

Figure 17A:
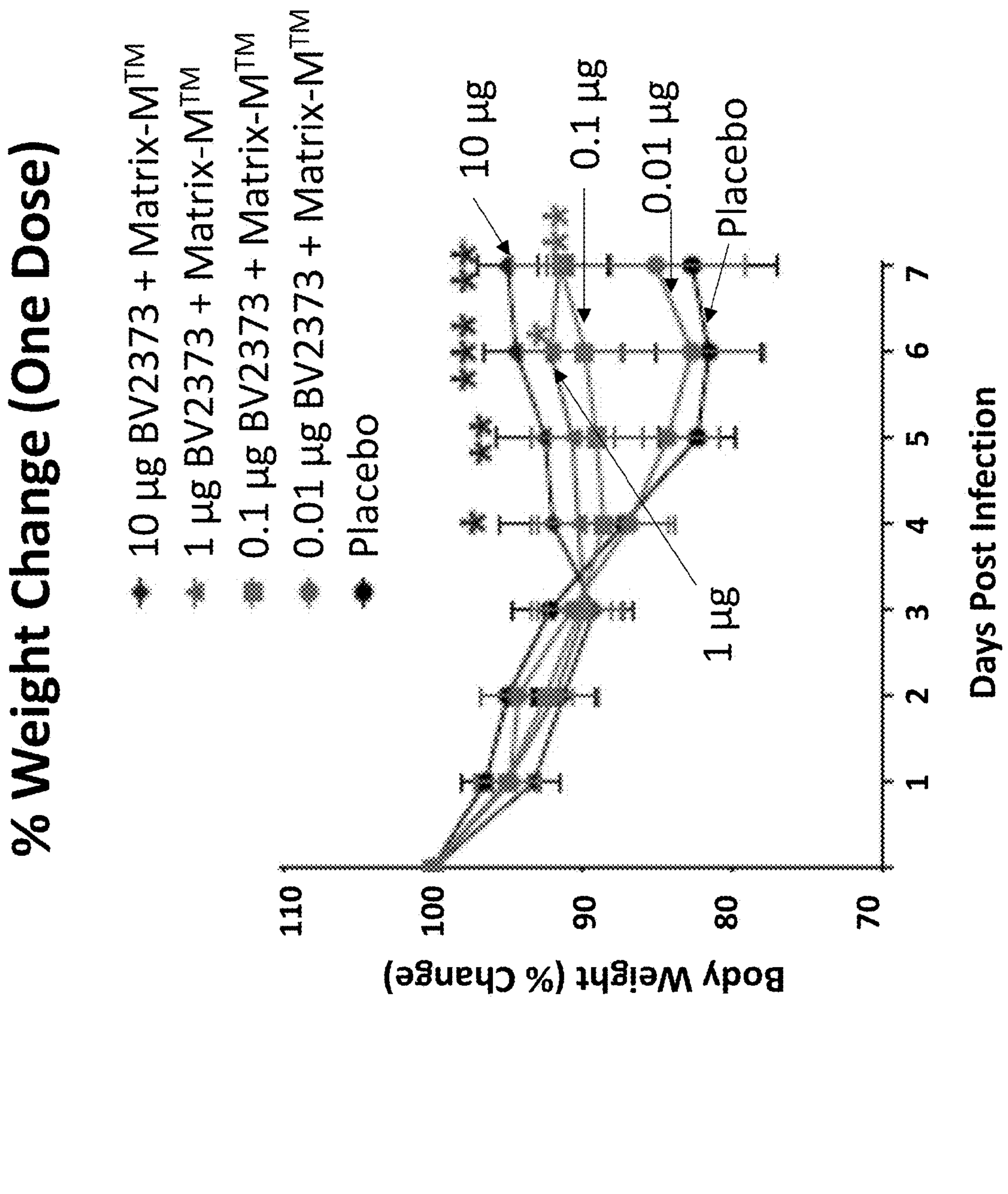
FIGS. 17A-C shows weight loss exhibited by mice after immunization with BV2373.
Figure 17B:
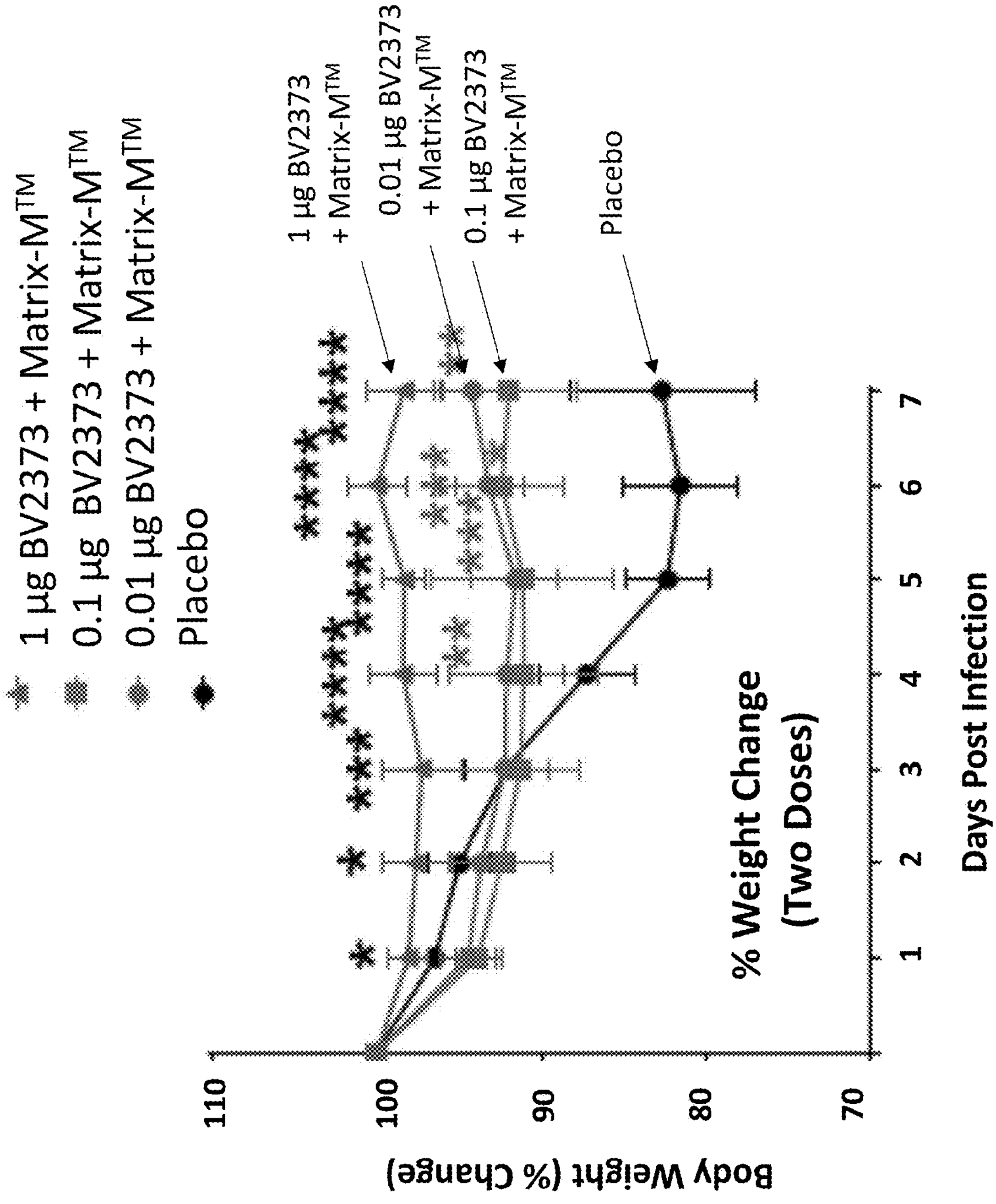
Figure 17C:
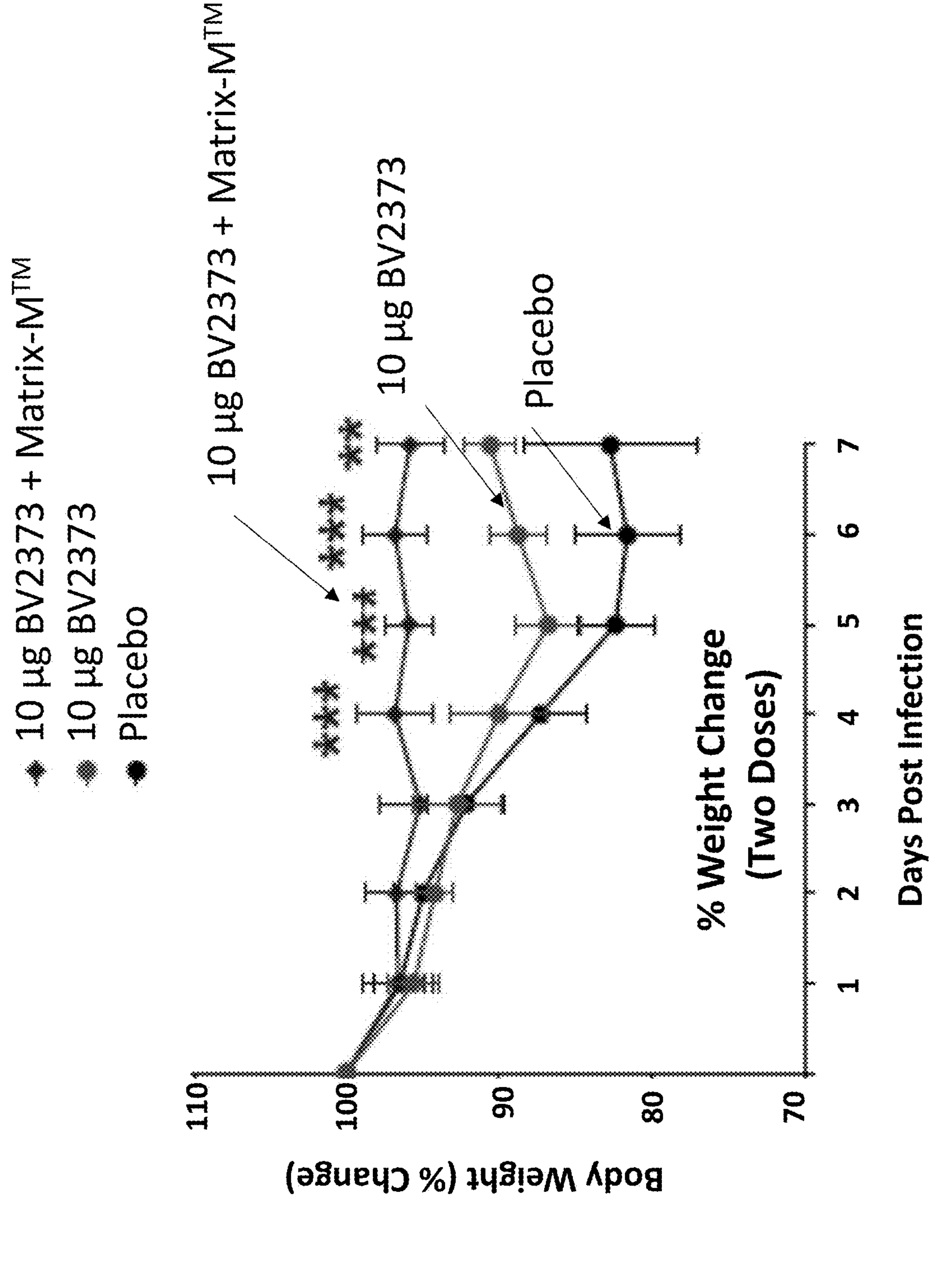

Weight loss paralleled the viral load findings. Animals receiving a single dose of BV2373 (0.1 μg, 1 μg, and 10 μg) and MATRIX-M™ showed marked protection from weight loss compared to the unvaccinated placebo animals (FIG. 17A). The mice receiving a prime and boost dose with adjuvant also demonstrated significant protection against weight loss at all dose levels (FIGS. 17B-C). The effect of the presence of adjuvant on protection against weight loss was evaluated. Mice receiving the prime/boost (two doses) plus adjuvant were significantly protected from weight loss relative to placebo, while the group immunized without adjuvant was not (FIG. 17C). These results showed that BV2373 confers protection against SARS-CoV-2 and that low doses of the vaccine associated with lower serologic responses do not exacerbate weight loss or demonstrate exaggerated illness.

Figure 18A:
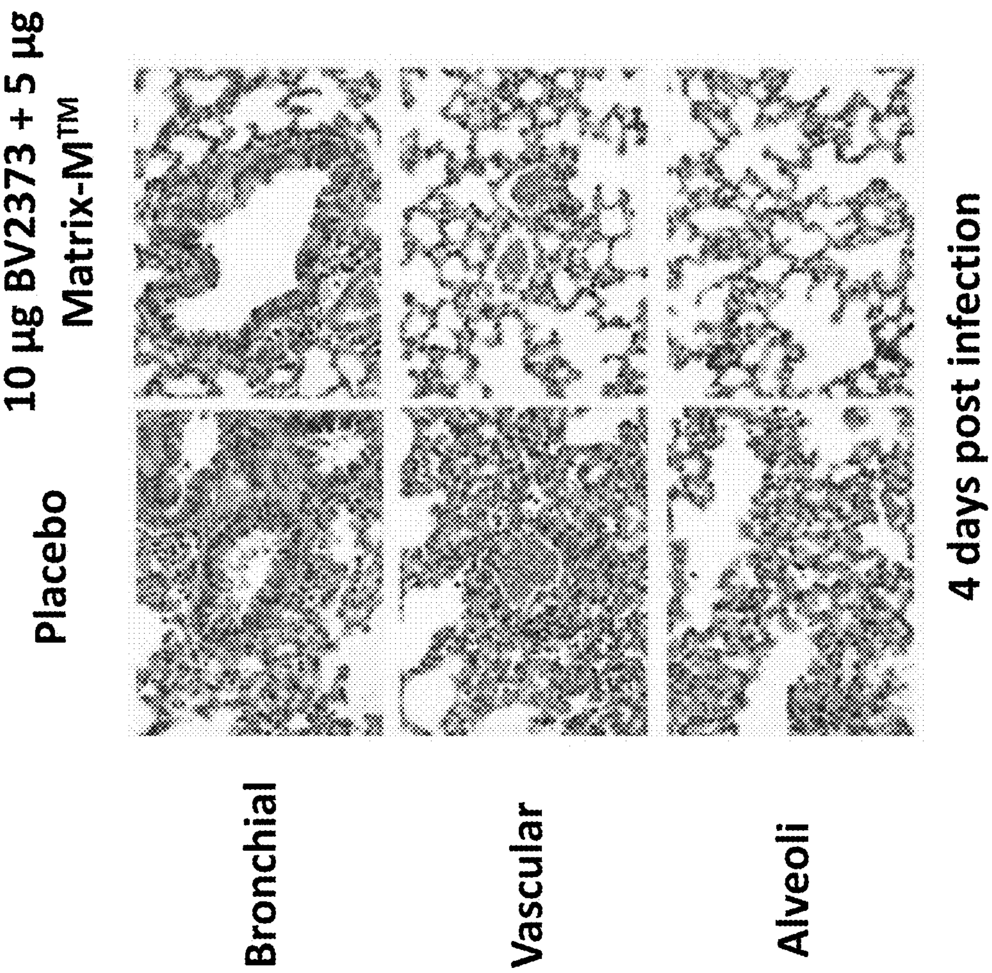
FIGS. 18A-B shows the effect of BV2373 on lung histopathology of mice four days (FIG. 18A) or seven days (FIG. 18B) after infection with SARS-CoV-2.
Figure 18B:
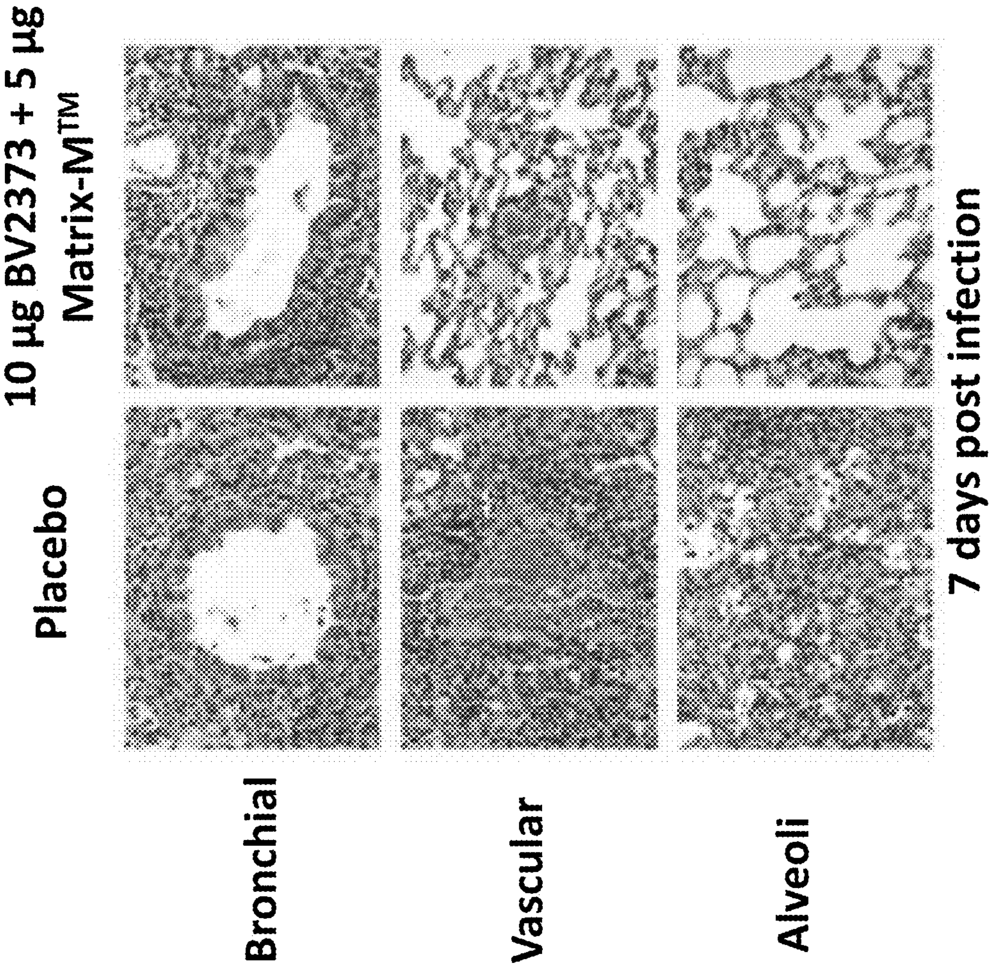

Lung histopathology was evaluated on days 4 and day 7 post infection (FIG. 18A and FIG. 18B). At day 4 post infection, placebo-immunized mice showed denudation of epithelial cells in the large airways with thickening of the alveolar septa surrounded by a mixed inflammatory cell population. Periarteriolar cuffing was observed throughout the lungs with inflammatory cells consisting primarily of neutrophils and macrophages. By day 7 post infection, the placebo-treated mice displayed peribronchiolar inflammation with increased periarteriolar cuffing. The thickened alveolar septa remained with increased diffuse interstitial inflammation throughout the alveolar septa (FIG. 18B).

The BV2373 immunized mice showed significant reduction in lung pathology at both day 4 and day 7 post infection in a dose-dependent manner. The prime only group displays reduced inflammation at the 10 μg and 1 μg dose with a reduction in inflammation surrounding the bronchi and arterioles compared to placebo mice. In the lower doses of the prime-only groups, lung inflammation resembles that of the placebo groups, correlating with weight loss and lung virus titer. The prime/boost immunized groups displayed a significant reduction in lung inflammation for all doses tested, which again correlated with lung viral titer and weight loss data. The epithelial cells in the large and small bronchi at day 4 and 7 were substantially preserved with minimal bronchiolar sloughing and signs of viral infection. The arterioles of animals immunized with 10 μg, 1 μg and 0.1 μg doses have minimal inflammation with only moderate cuffing seen with the 0.01 μg dose, similar to placebo. Alveolar inflammation was reduced in animals that received the higher doses with only the lower 0.01 μg dose associated with inflammation (FIGS. 18A-18B). These data demonstrate that BV2373 reduces lung inflammation after challenge and that even doses and regimens of BV2373 that elicit minimal or no detectable neutralizing activity are not associated with exacerbation of the inflammatory response to the virus. Furthermore, the vaccine does not cause vaccine associated enhanced respiratory disease (VAERD) in challenged mice.

T Cell Response

The effect of the vaccine composition comprising a CoV S polypeptide of SEQ ID NO: 87 on the T cell response was evaluated. BALB/c mice (N=6 per group) were immunized intramuscularly with 10 μg BV2373 with or without 5 μg MATRIX-M™ in 2 doses spaced 21-days apart. Spleens were collected 7-days after the second immunization (study day 28). A non-vaccinated group (N=3) served as a control.

Figure 19:
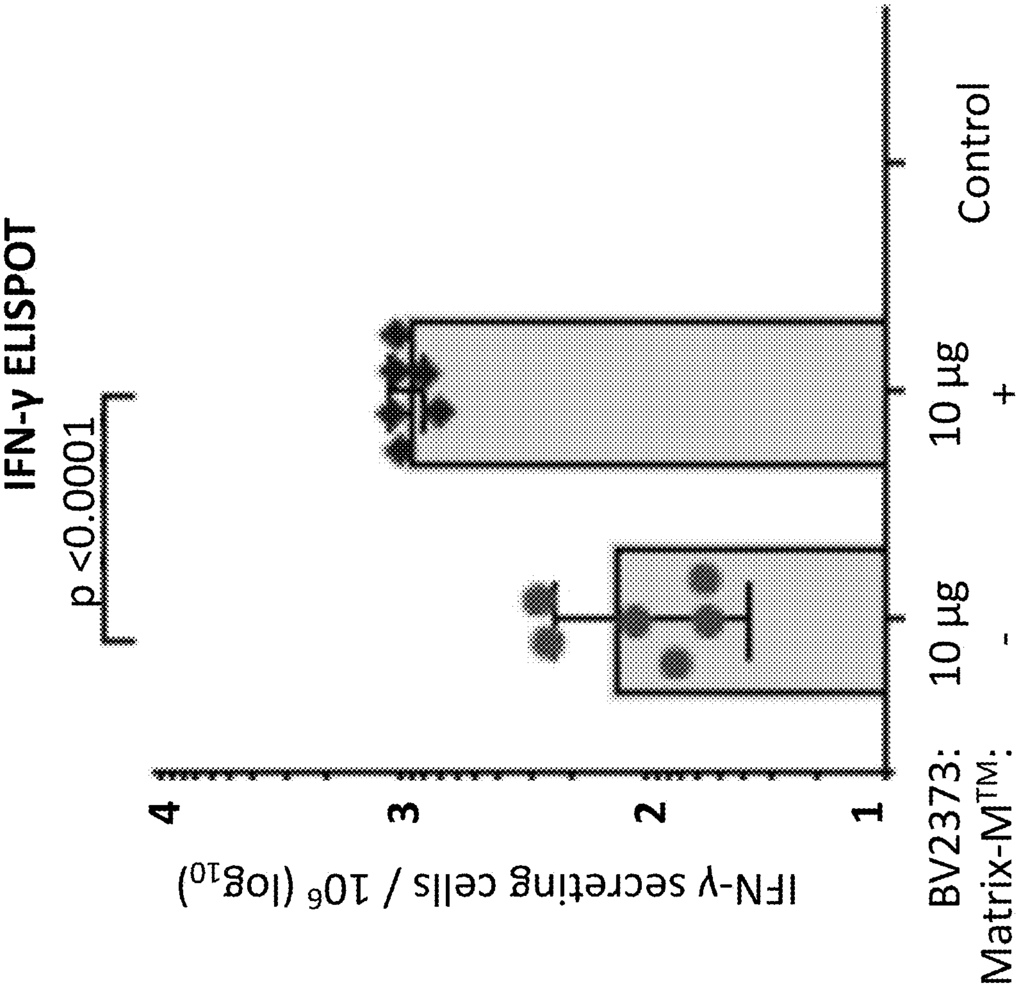
FIG. 19 shows the number of IFN-γ secreting cells after ex vivo stimulation in the spleens of mice immunized with BV2373 in the absence of adjuvant compared to mice immunized with BV2373 in the presence of MATRIX-M™.
Figure 20A:
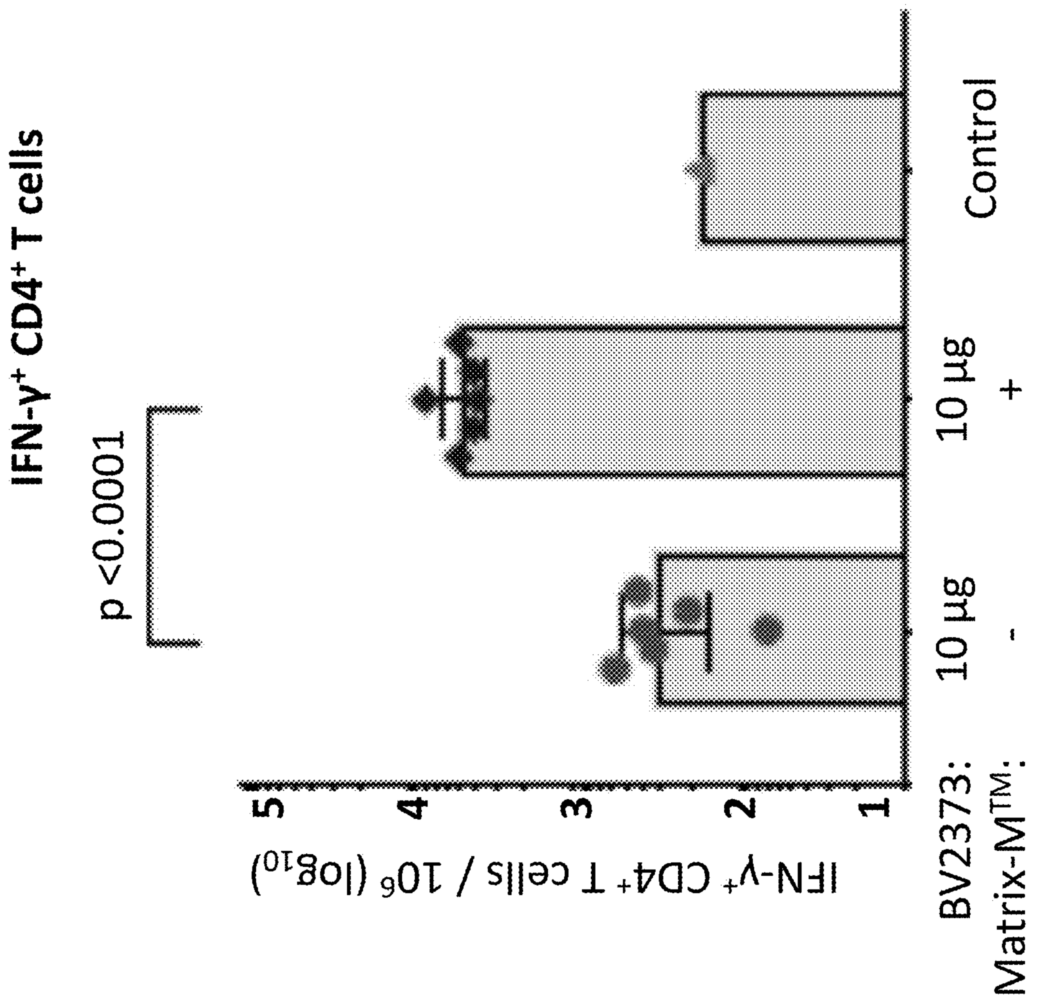
FIGS. 20A-E shows the frequency of cytokine secreting CD4+ T cells in the spleens of mice immunized with BV2373 in the presence or absence of MATRIX-M™.
Figure 20B:
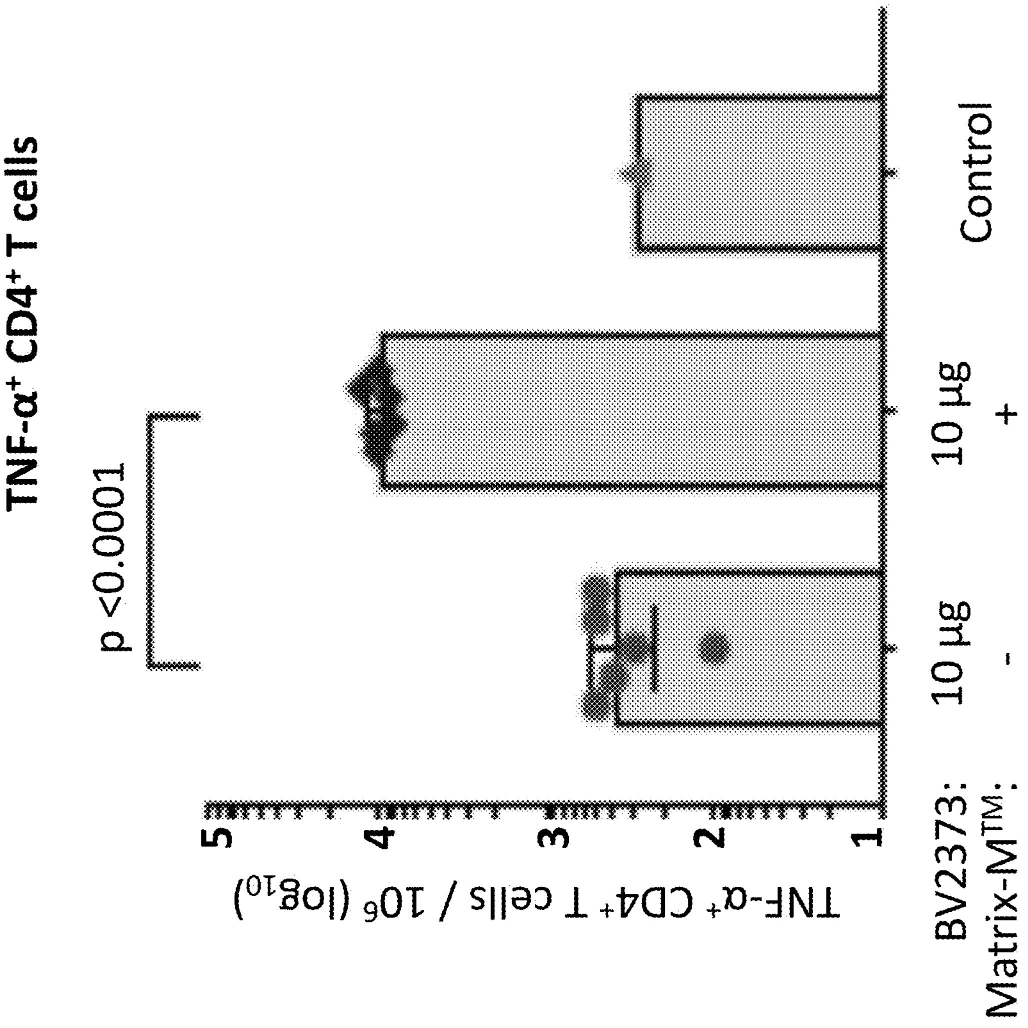
Figure 20C:
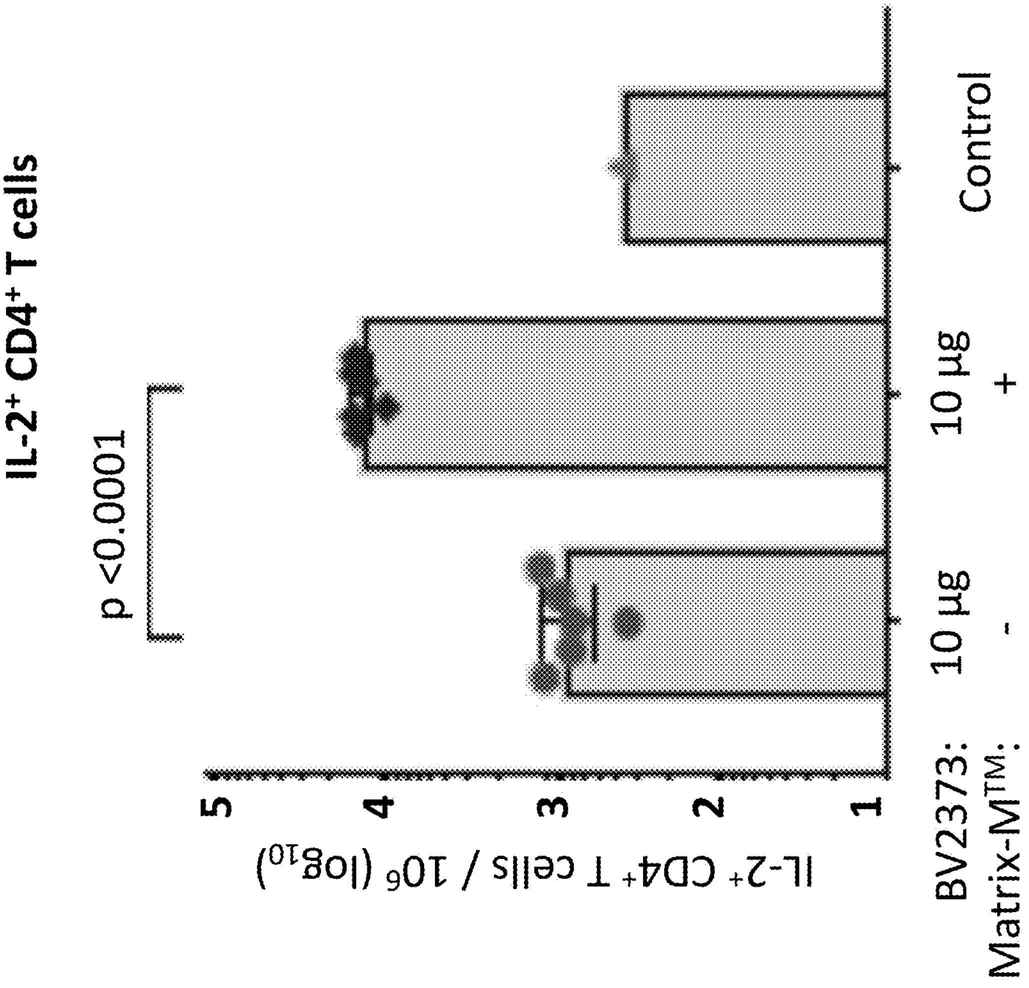
Figure 20D:
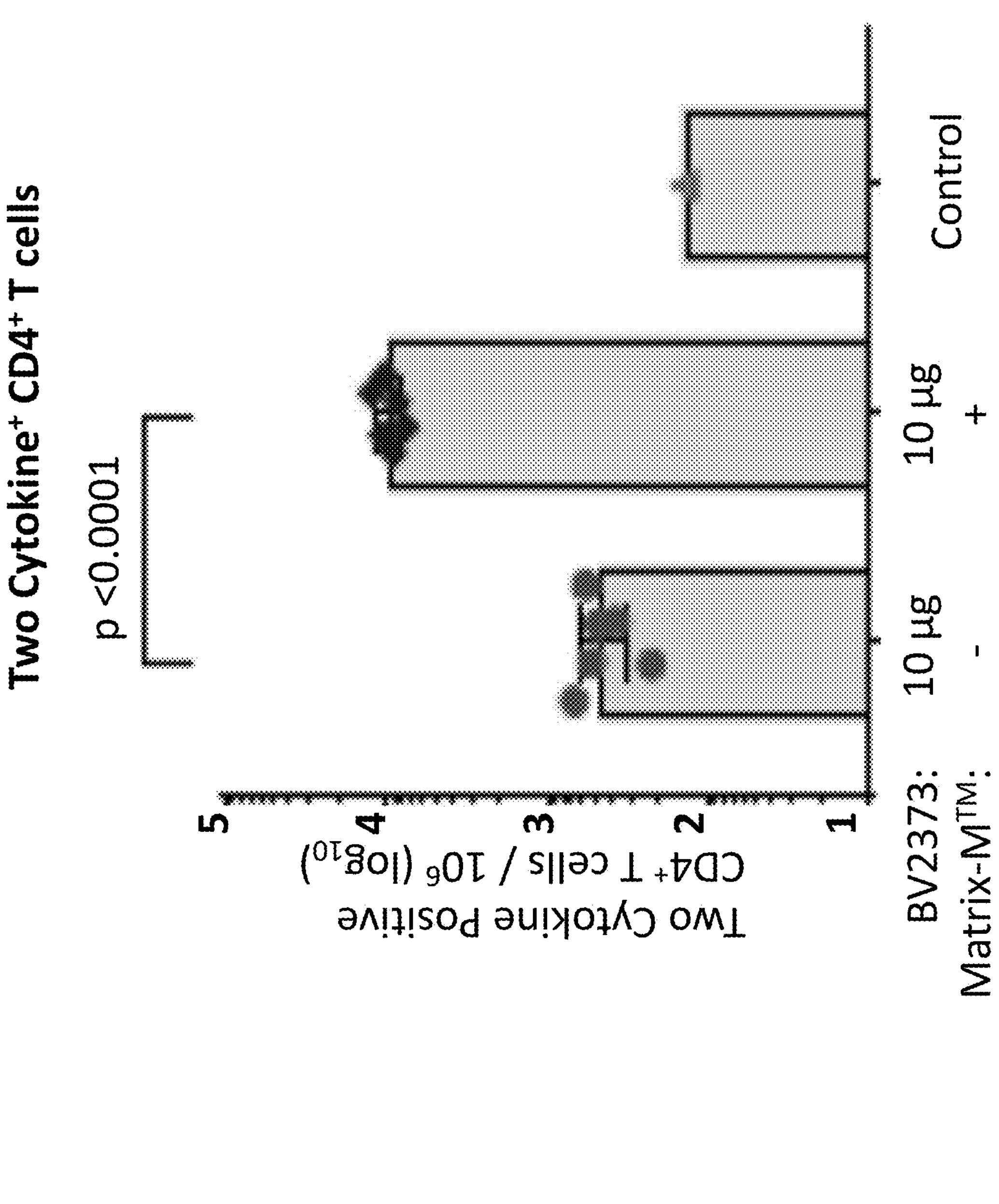
Figure 20E:
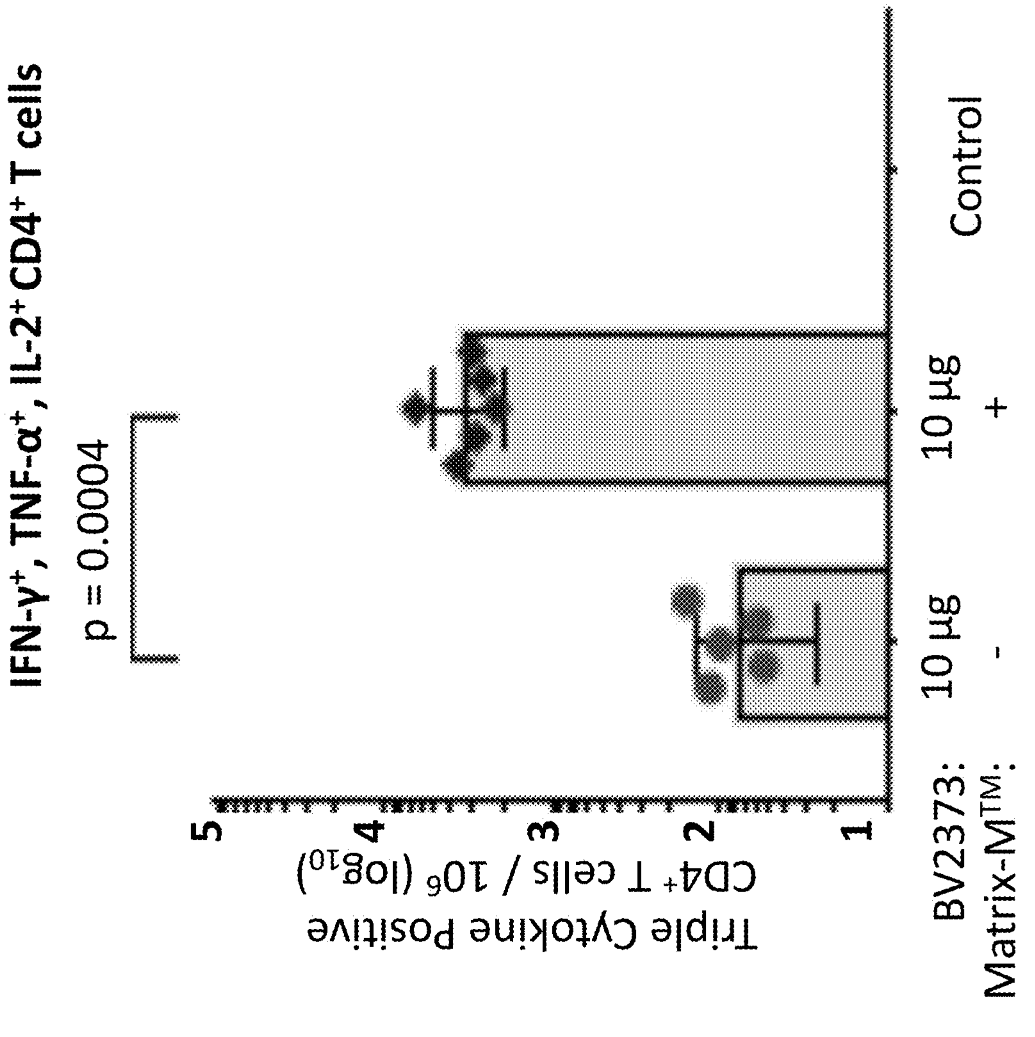
Figure 21A:
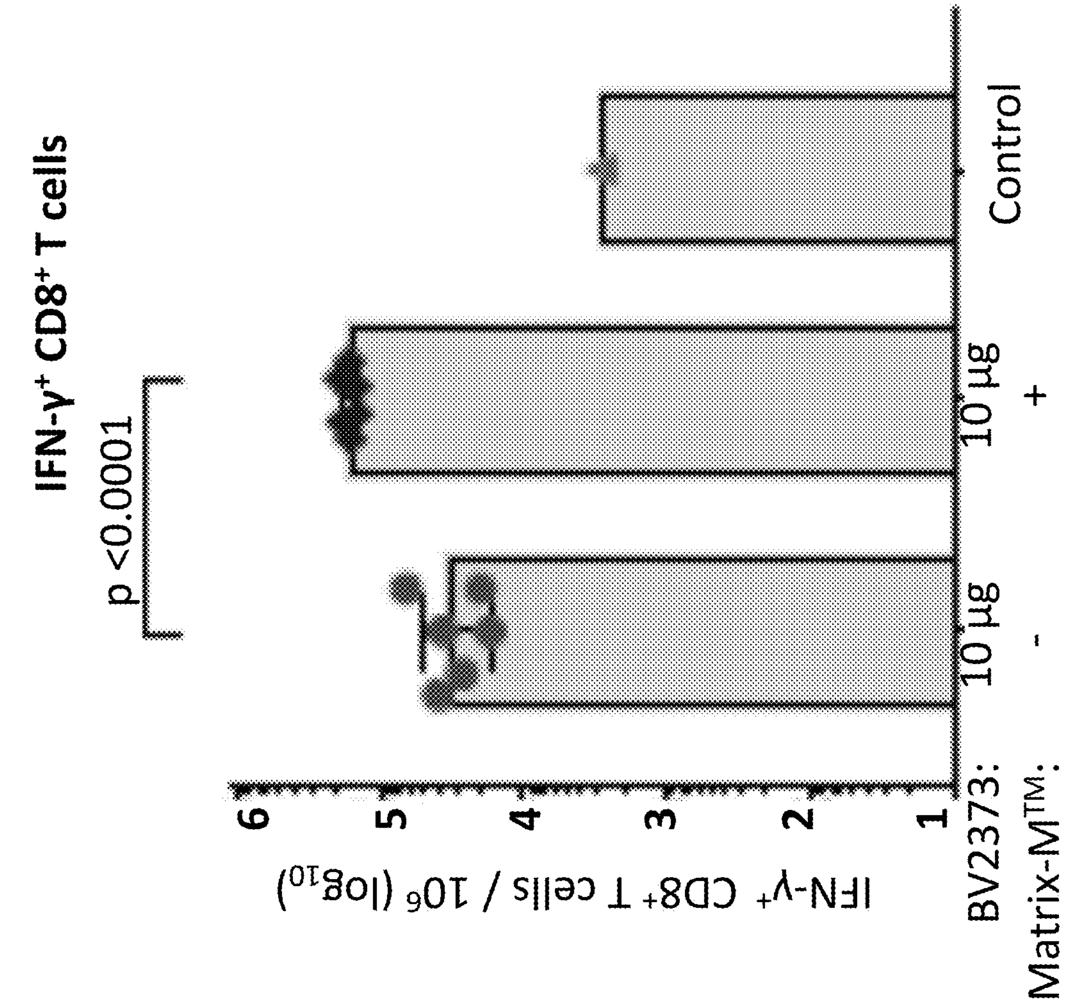
FIGS. 21A-E shows the frequency of cytokine secreting CD8 T cells in the spleens of mice immunized with BV2373 in the presence or absence of MATRIX-M™.
Figure 21B:
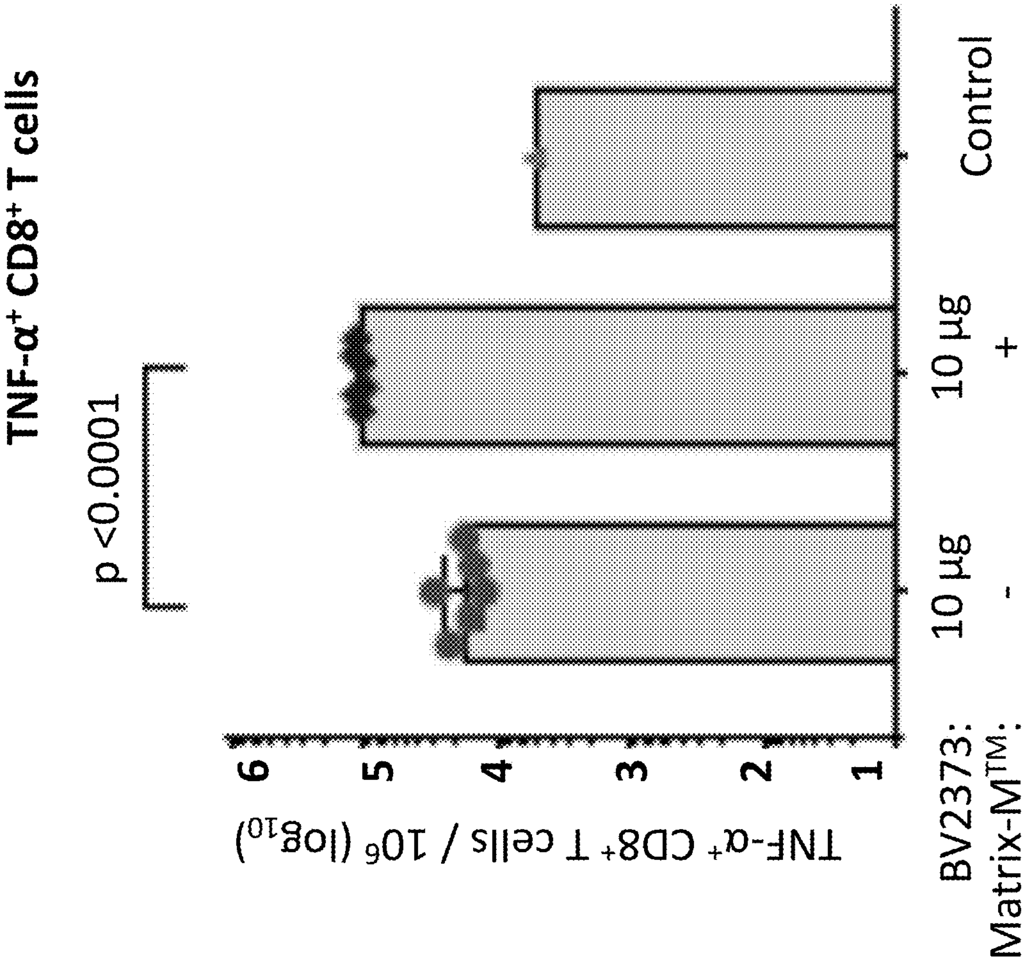
Figure 21C:
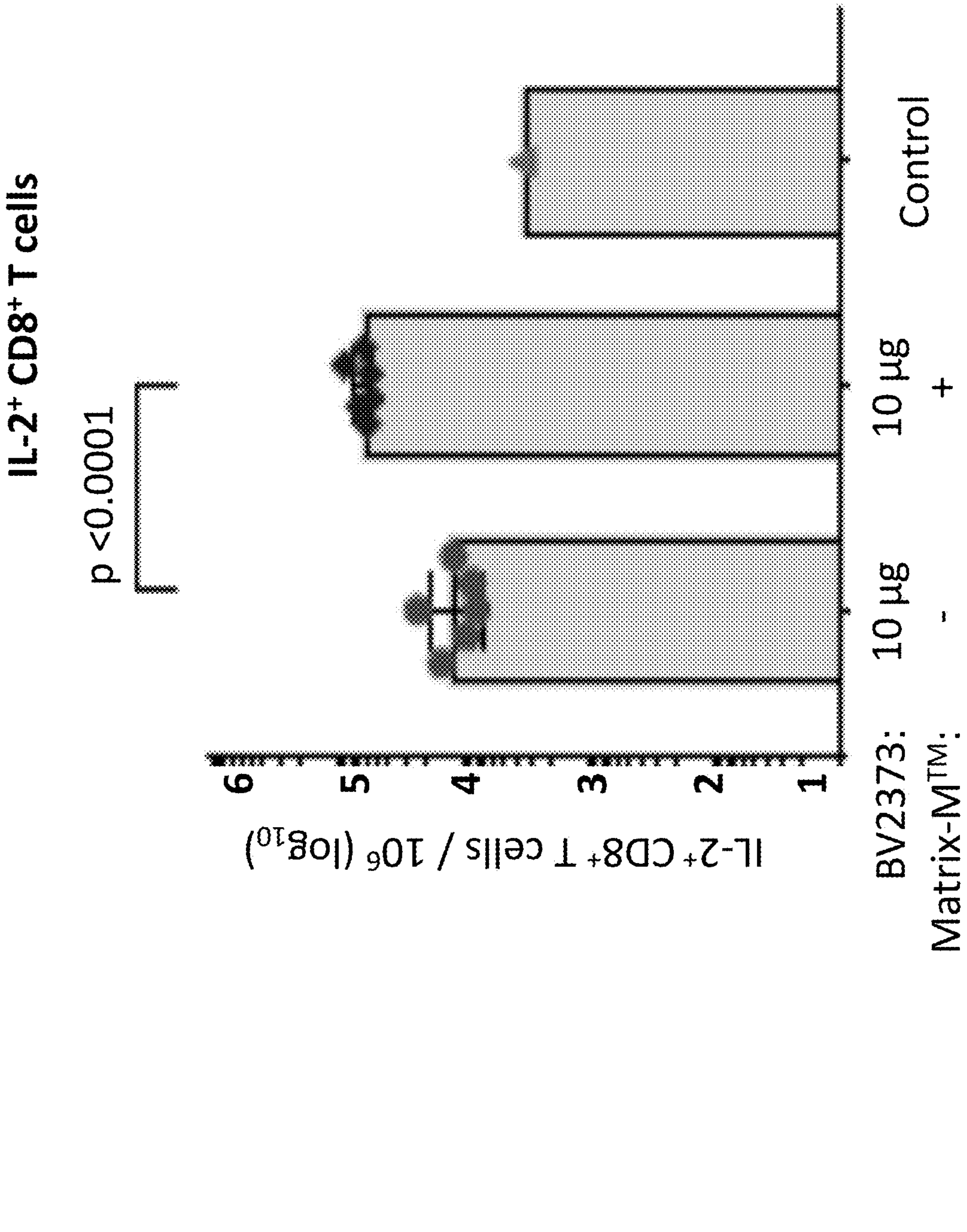
Figure 21D:
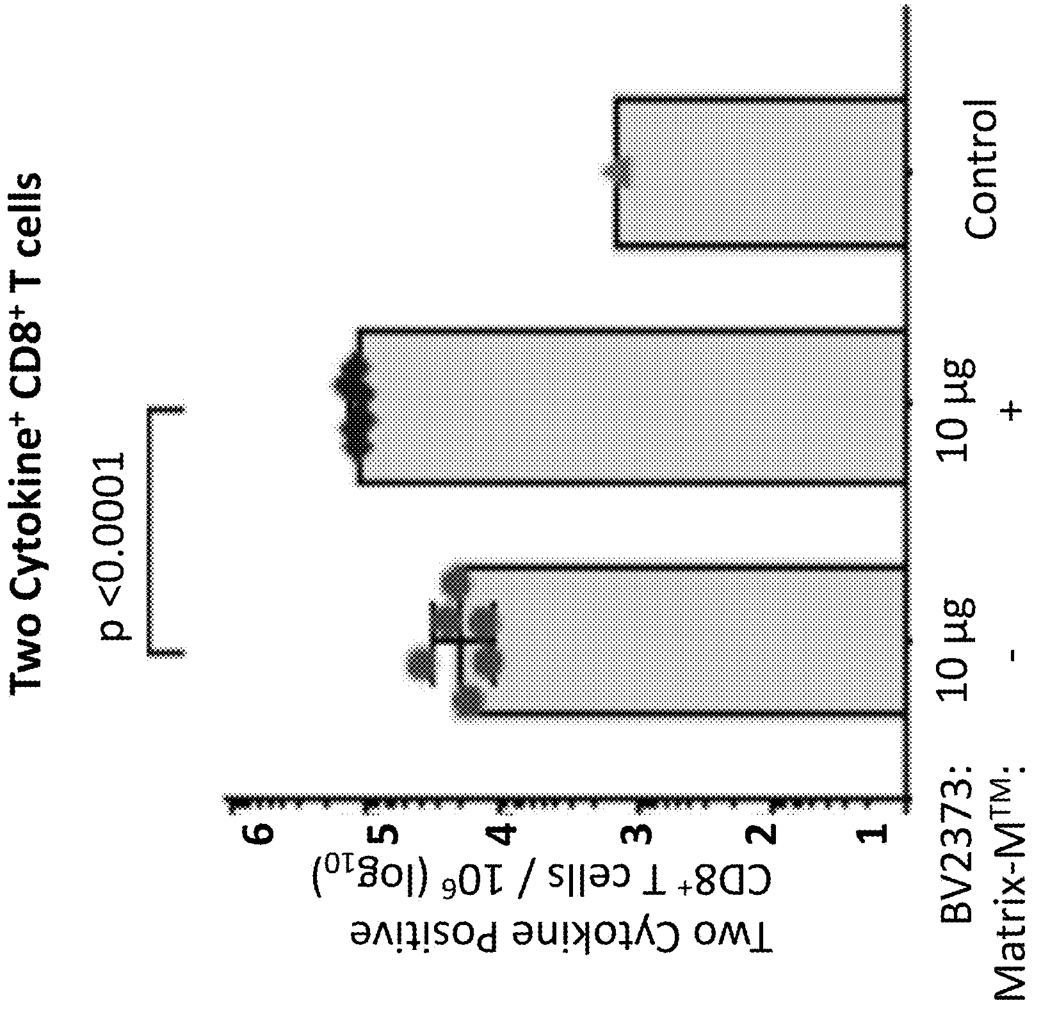
Figure 21E:
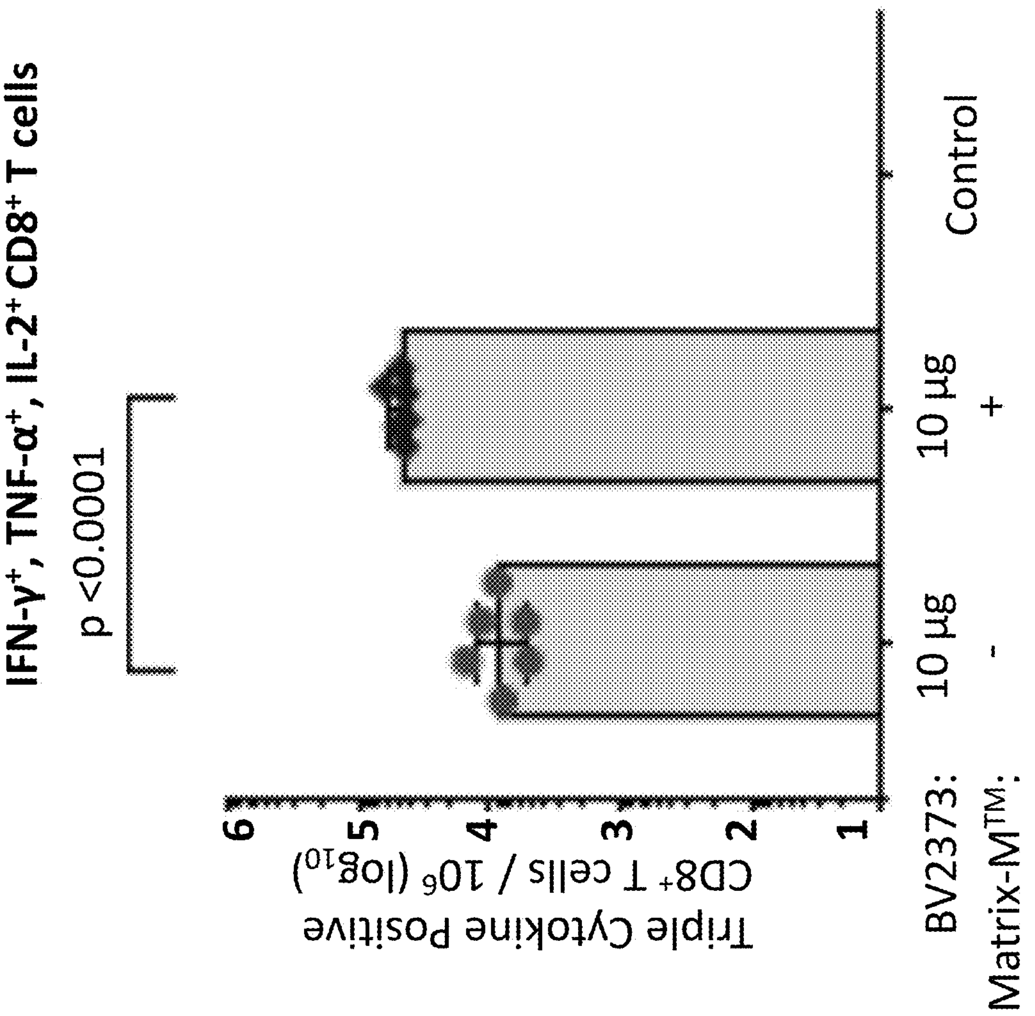
Figure 22:
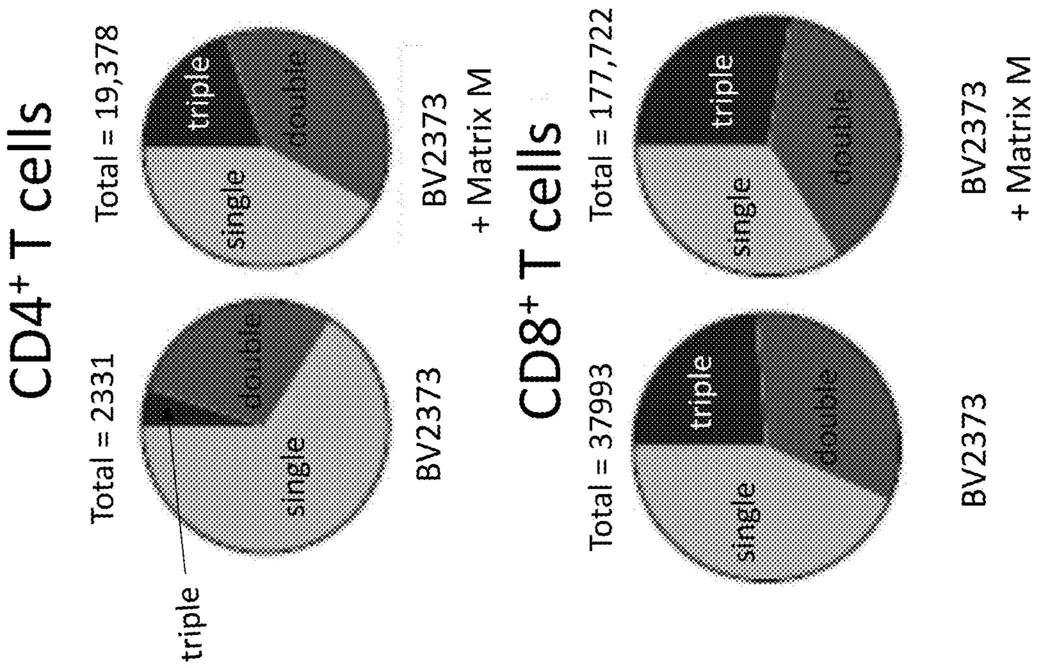
FIG. 22 illustrates the frequency of $CD4^+$ or $CD8^+$ cells that express one (single), two (double), or three (triple) cytokines selected from IFN-γ, TNF-α, and IL-2 in the spleens of mice immunized with BV2373 in the presence or absence of MATRIX-M™.

Antigen-specific T cell responses were measured by ELISPOT™ enzyme linked immunosorbent assay and intracellular cytokine staining (ICCS) from spleens collected 7-days after the second immunization (study day 28). The number of IFN-γ secreting cells after ex vivo stimulation increased 20-fold ($p=0.002$) in spleens of mice immunized with BV2373 and MATRIX-M™ compared to BV2373 alone as measured by the ELISPOT™ assay (FIG. 19) In order to examine CD4+ and CD8+ T cell responses separately, ICCS assays were performed in combination with surface marker staining. Data shown are gated on CD44hi CD62L-effector memory T cell population. The frequency of IFN-γ+, TNF-α+, and IL-2+ cytokine-secreting CD4+ and CD8+ T cells was significantly higher ($p < 0.0001$) in spleens from mice immunized with BV2373 as compared to mice immunized without adjuvant (FIG. 20A-C and FIG. 21A-C). Further, the frequency of multifunctional CD4+ and CD8+ T cells, which simultaneously produce at least two or three cytokines was also significantly increased ($p < 0.0001$) in spleens from the BV2373/MATRIX-M™ immunized mice as compared to mice immunized in the absence of adjuvant (FIGS. 20D-E and FIGS. 21D-E). Immunization with BV2373/ MATRIX-M™ resulted in higher proportions of multifunctional phenotypes (e.g., T cells that secrete more than one of IFN-γ, TNF-α, and IL-2) within both CD4+ and CD8+ T cell populations. The proportions of multifunctional phenotypes detected in memory CD4+ T cells were higher than those in CD8+ T cells (FIG. 22).

Figure 23A:
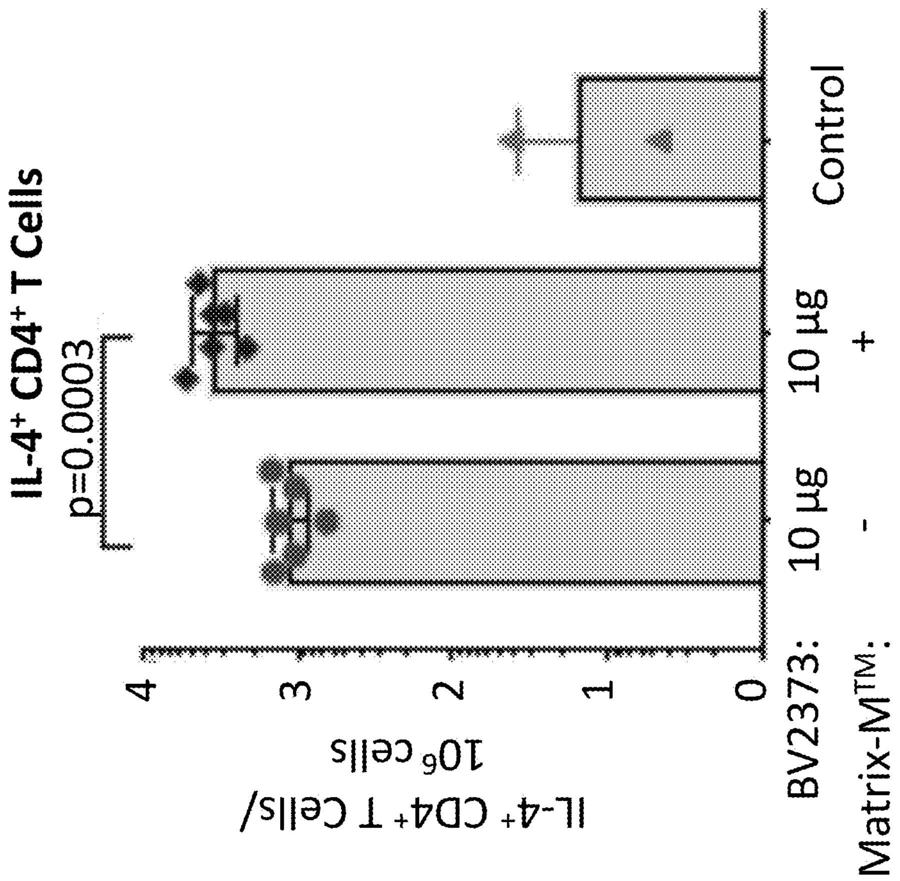
FIGS. 23A-C illustrate the effect of immunization with BV2373 in the presence or absence of MATRIX-M™ on type 2 cytokine secretion from $CD4^+$ T cells.
Figure 23B:
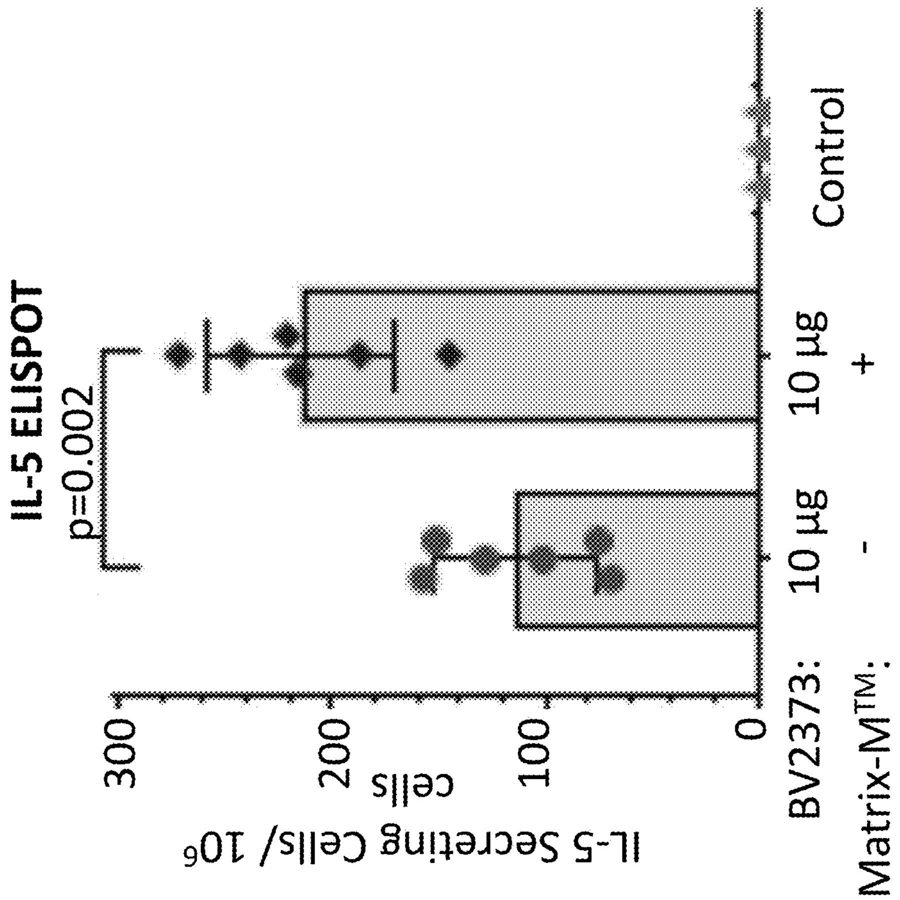
Figure 23C:
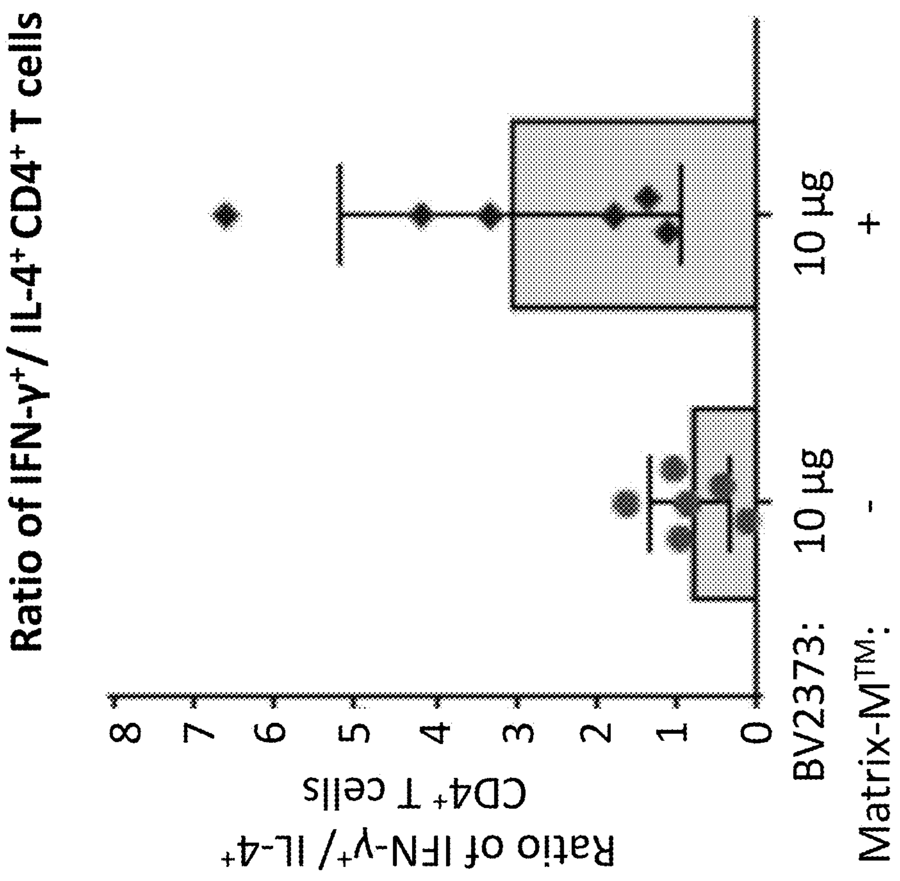
Figure 24A:
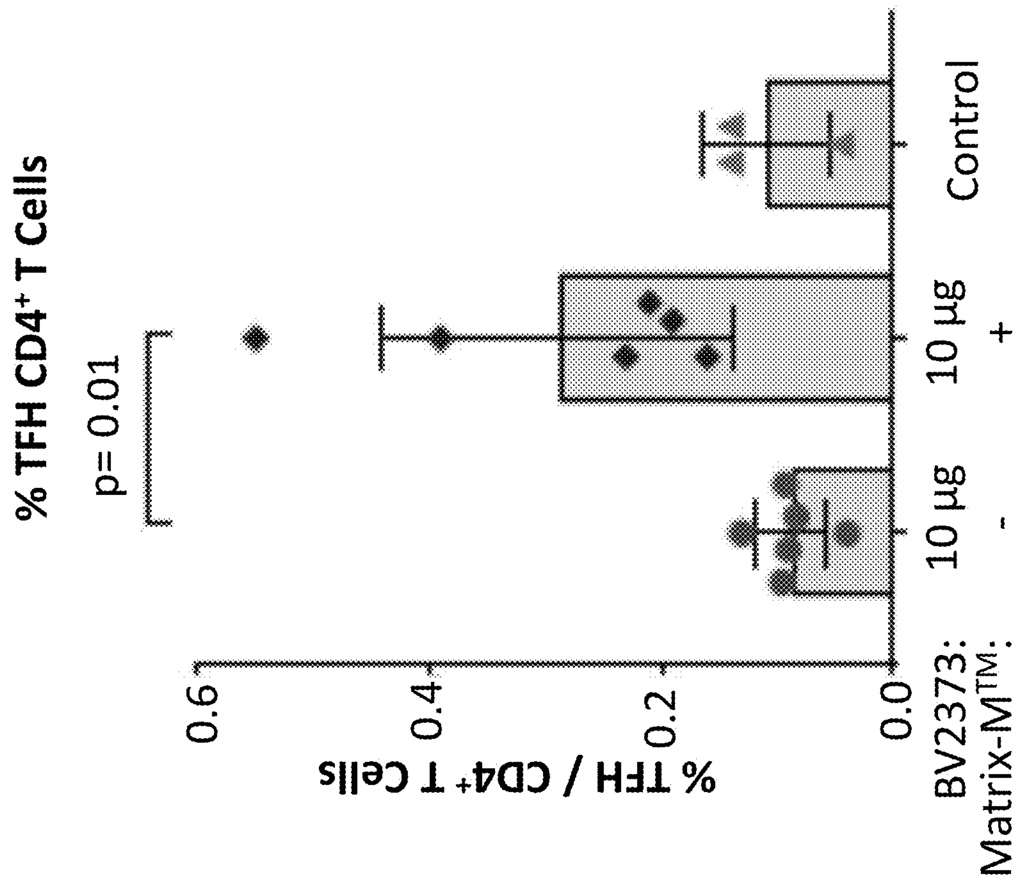
FIGS. 24A-B illustrate the effect of mouse immunization with BV2373 in the presence or absence of MATRIX-M™ on germinal center formation by assessing the presence of $CD4^+$ T follicular helper cells (TFH).
Figure 24B:
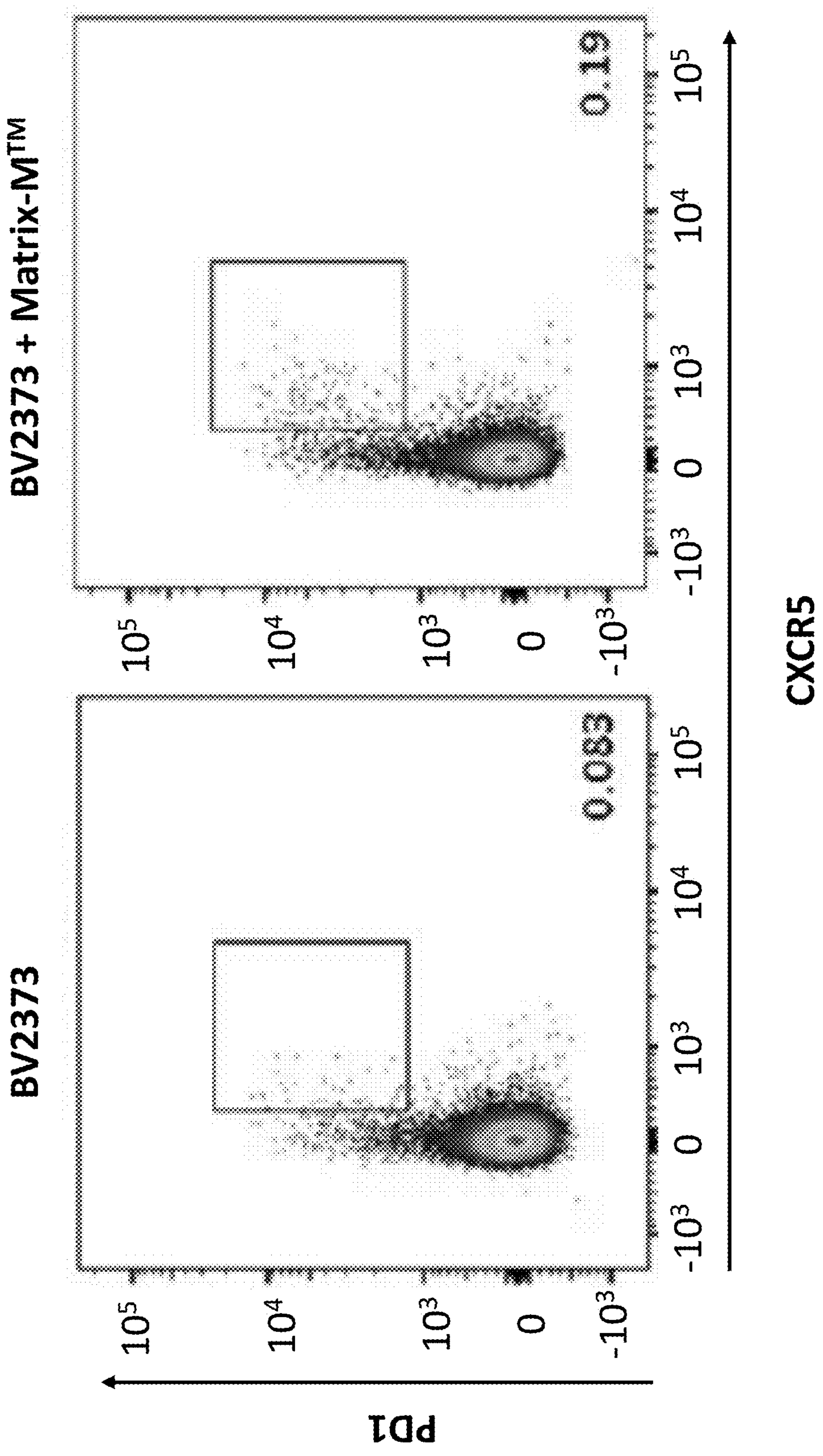
Figure 25A:
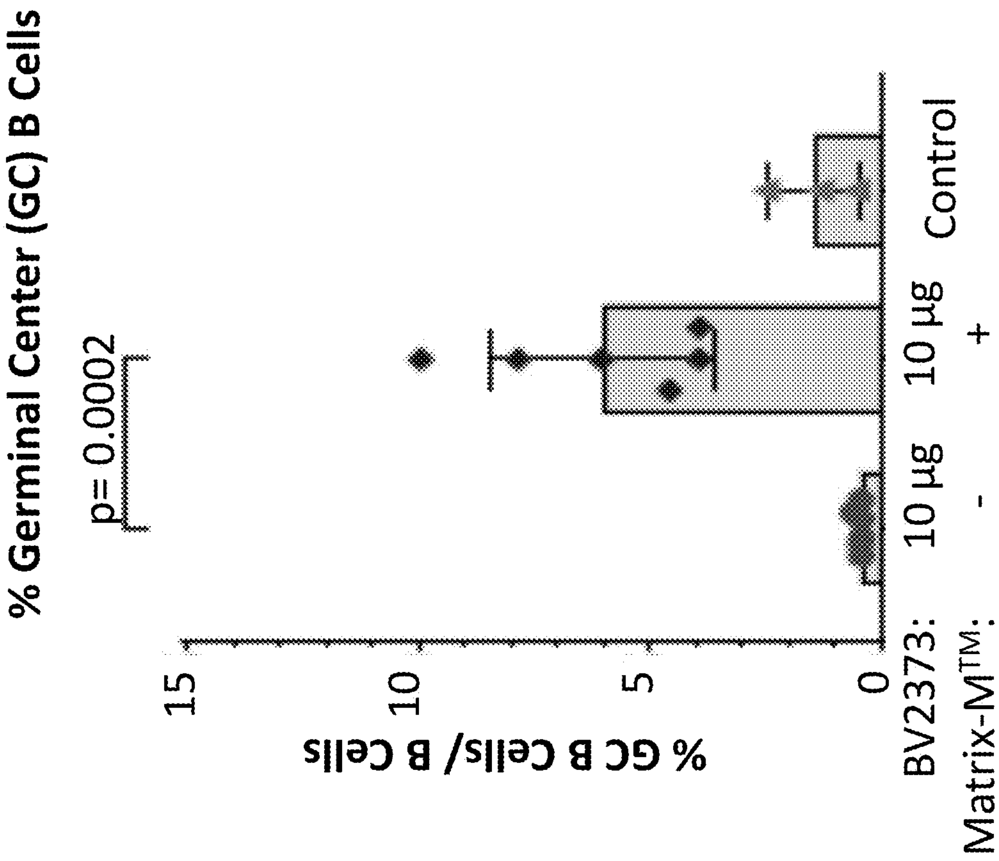
FIGS. 25A-B illustrate the effect of mouse immunization with BV2373 in the presence or absence of MATRIX-M™ on germinal center formation by assessing the presence of germinal center (GC) B cells.
Figure 25B:
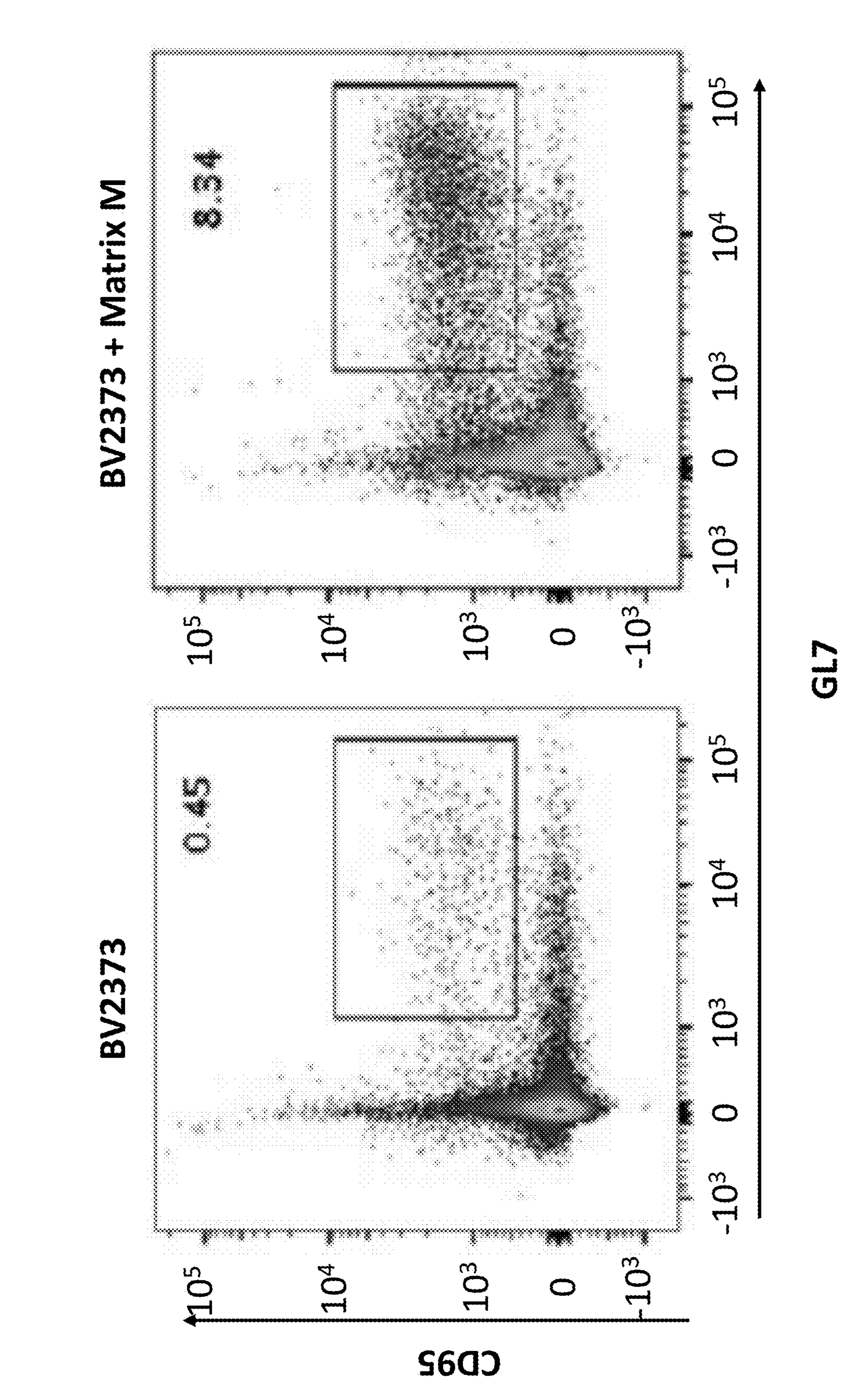

Type 2 cytokine IL-4 and IL-5 secretion from CD4+ T cells was also determined by ICCS and ELISPOT™ respectively. Immunization with BV2373/ MATRIX-M™ also increased type 2 cytokine IL-4 and IL-5 secretion (2-fold) compared to immunization with BV2373 alone, but to a lesser degree than enhancement of type 1 cytokine production (e.g. IFN-γ increased 20-fold) (FIGS. 23A-C). These results indicate that administration of the MATRIX-M™ adjuvant skewed the CD4+ T cell development toward Th1 responses.

The effect of immunization on germinal center formation was assessed by measuring the frequency of CD4+ T follicular helper (TFH) cells and germinal center (GC) B cells in spleens. MATRIX-M™ administration significantly increased the frequency of TFH cells (CD4+ CXCR5+ PD-1+) was significantly increased (p=0.01), as well as the frequency of GC B cells (CD19+GL7+CD95+) (p=0.0002) in spleens (FIGS. 24A-B and FIGS. 25A-B).

Example 3

Figure 26A:
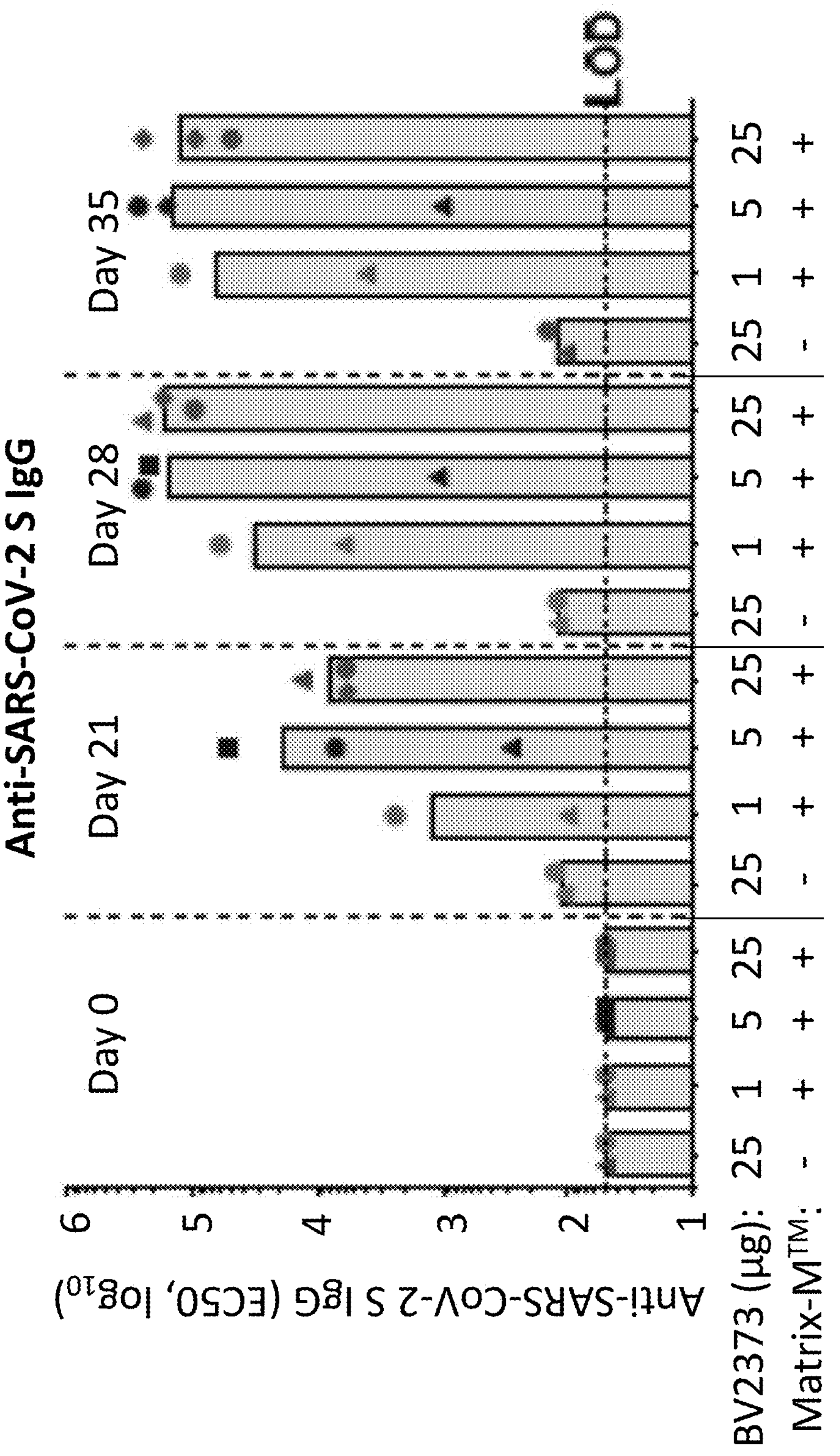
FIGS. 26A-C show the effect of immunization with BV2373 in the presence or absence of MATRIX-M™ on antibody response in olive baboons.

Immunogenicity of Coronavirus Spike (S) Polypeptide Nanoparticle Vaccines in Olive Baboons The immunogenicity of a vaccine composition comprising BV2373 in baboons was assessed. Adult olive baboons were immunized with a dose range (1 μg, 5 μg and 25 μg) of BV2373 and 50 μg MATRIX-M™ adjuvant administered by intramuscular (IM) injection in two doses spaced 21-days apart. To assess the adjuvanting activity of MATRIX-M™ in non-human primates, another group of animals was immunized with 25 μg of BV2373 without MATRIX-M™. Anti-S protein IgG titers were detected within 21-days of a single priming immunization in animals immunized with BV2373/ MATRIX-M™ across all the dose levels (GMT=1249-19, 000). Anti-S protein IgG titers increased over a log (GMT=33,000-174,000) within 1 to 2 weeks following a booster immunization (days 28 and 35) across all of the dose levels. (FIG. 26A).

Figure 26B:
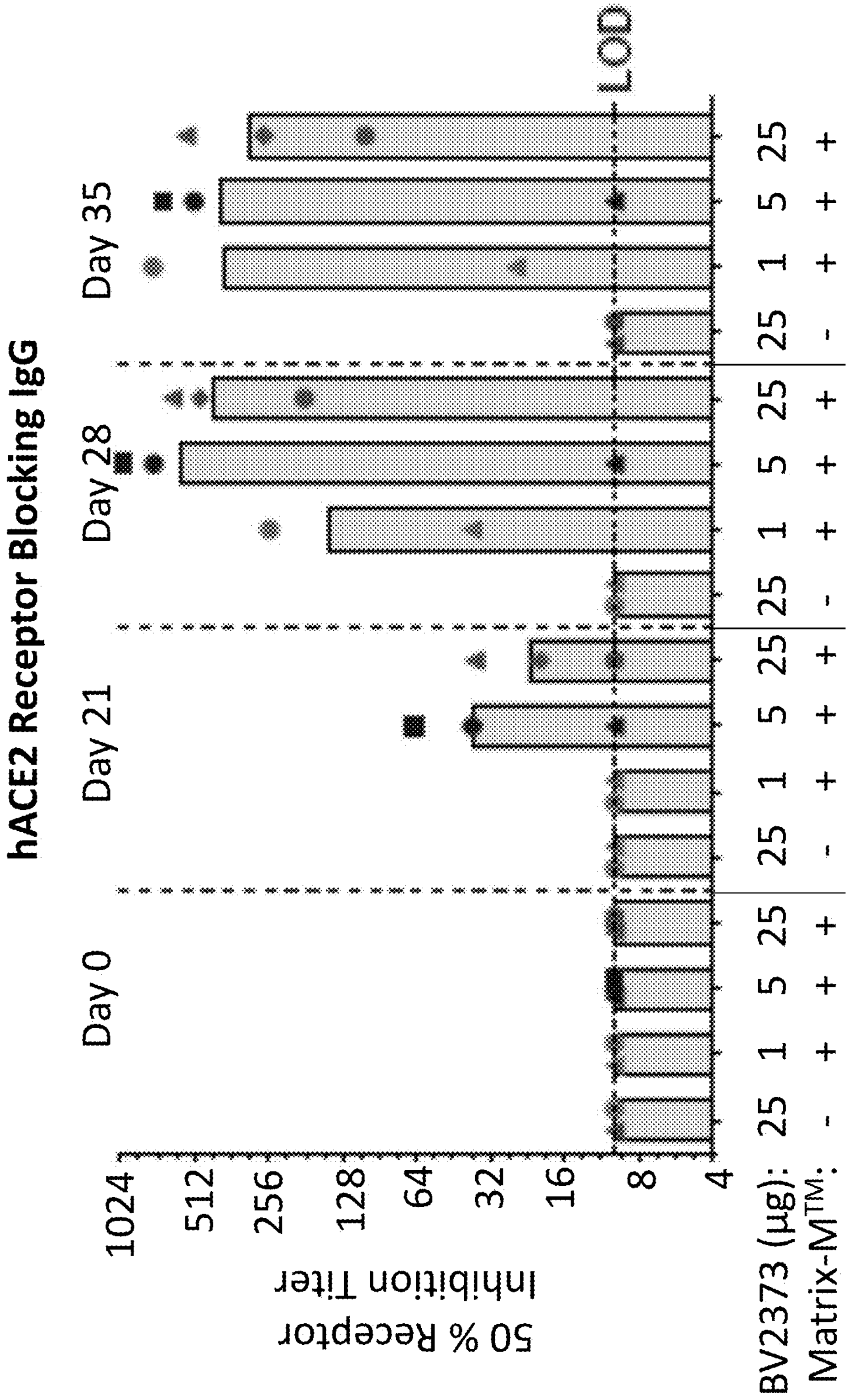
Figure 26C:
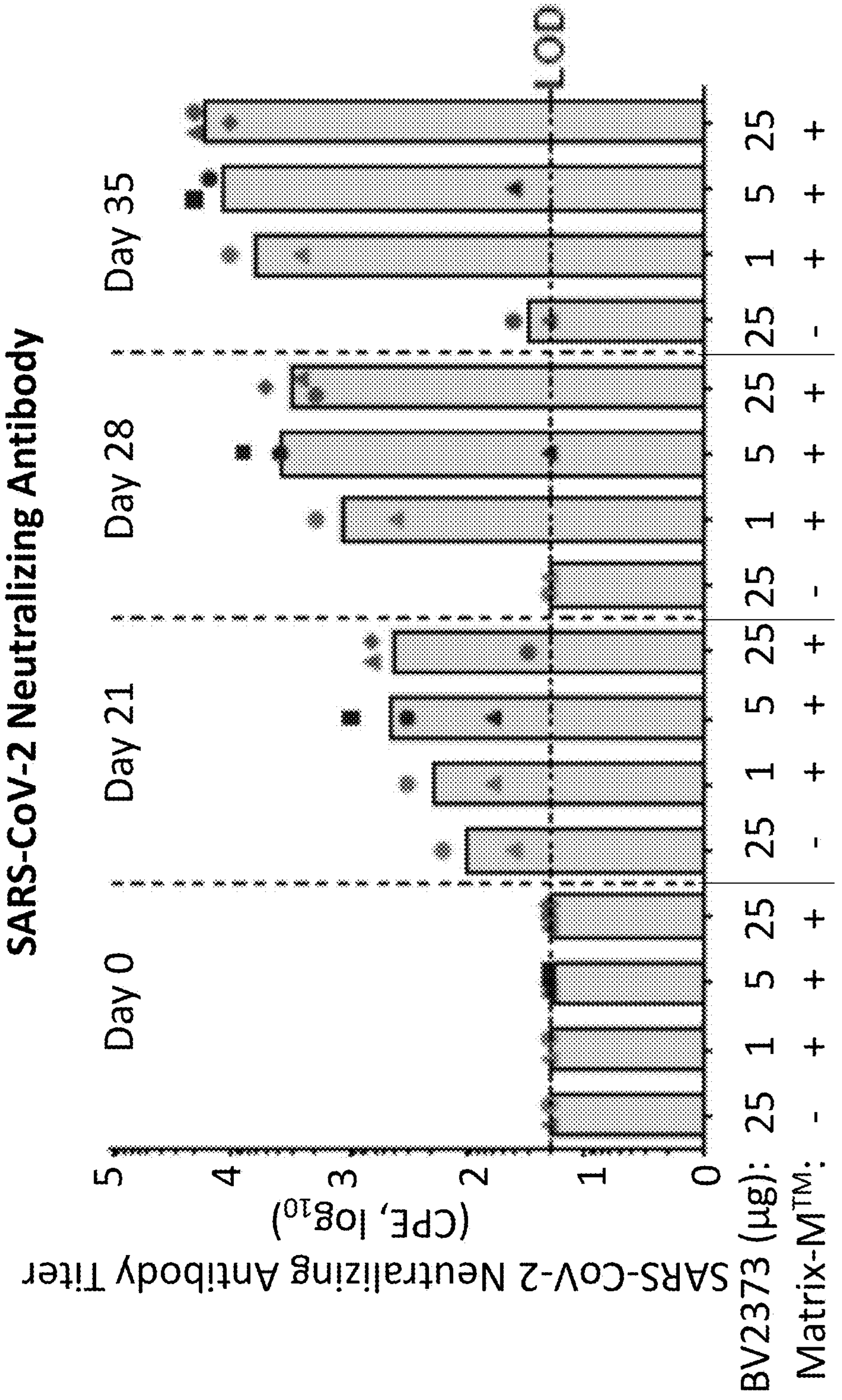
Figure 27:
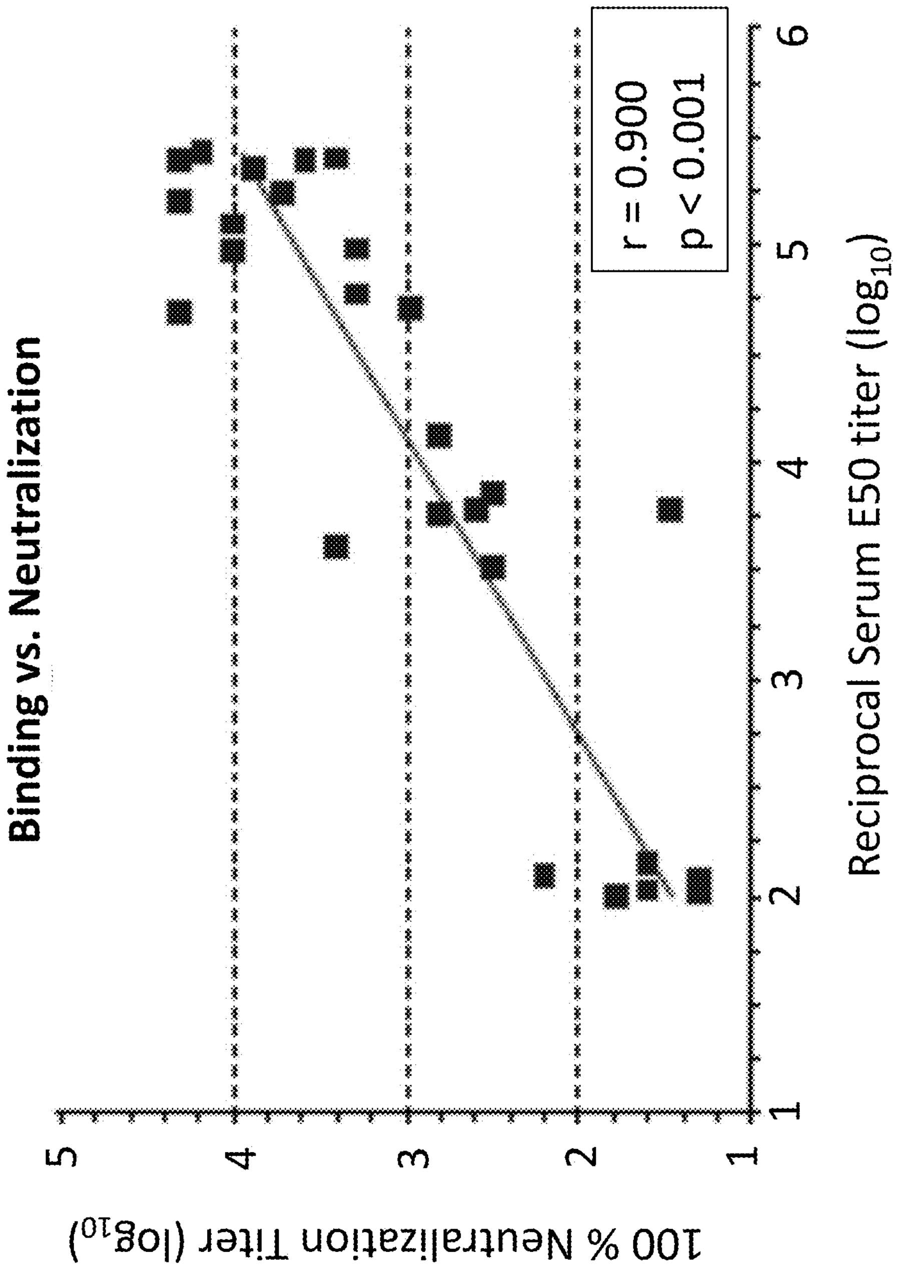
FIG. 27 shows the significant correlation between anti-SARS-CoV-2 S polypeptide IgG and neutralizing antibody titers in olive baboons after immunization with BV2373.

Low levels of hACE2 receptor blocking antibodies were detected in animals following a single immunization with BV2373 (5 μg or 25 μg) and MATRIX-M™ (GMT=22-37). Receptor blocking antibody titers were significantly increased within one to two weeks of the booster immunization across all groups immunized with BV2373/ MATRIX-M™ (GMT=150-600) (FIG. 26B). Virus neutralizing antibodies were elevated (GMT=190-446) across all dose groups after a single immunization with BV2373/ MATRIX-M™. Animals immunized with 25 μg BV2373 alone had no detectable antibodies that block S-protein binding to hACE2 (FIG. 26C). Neutralizing titers were increased 6- to 8-fold one week following the booster immunization (GMT=1160-3846). Neutralizing titers increased an additional 25- to 38-fold following the second immunization (GMT=6400-17,000) (FIG. 26C). There was a significant correlation (p <0.0001) between anti-S IgG levels and neutralizing antibody titers (FIG. 27). The immunogenicity of the adjuvanted vaccine in nonhuman primates is consistent with the results of Example 2 and further supports the role of MATRIX-M™ in promoting the generation of neutralizing antibodies and dose sparing.

Figure 28:
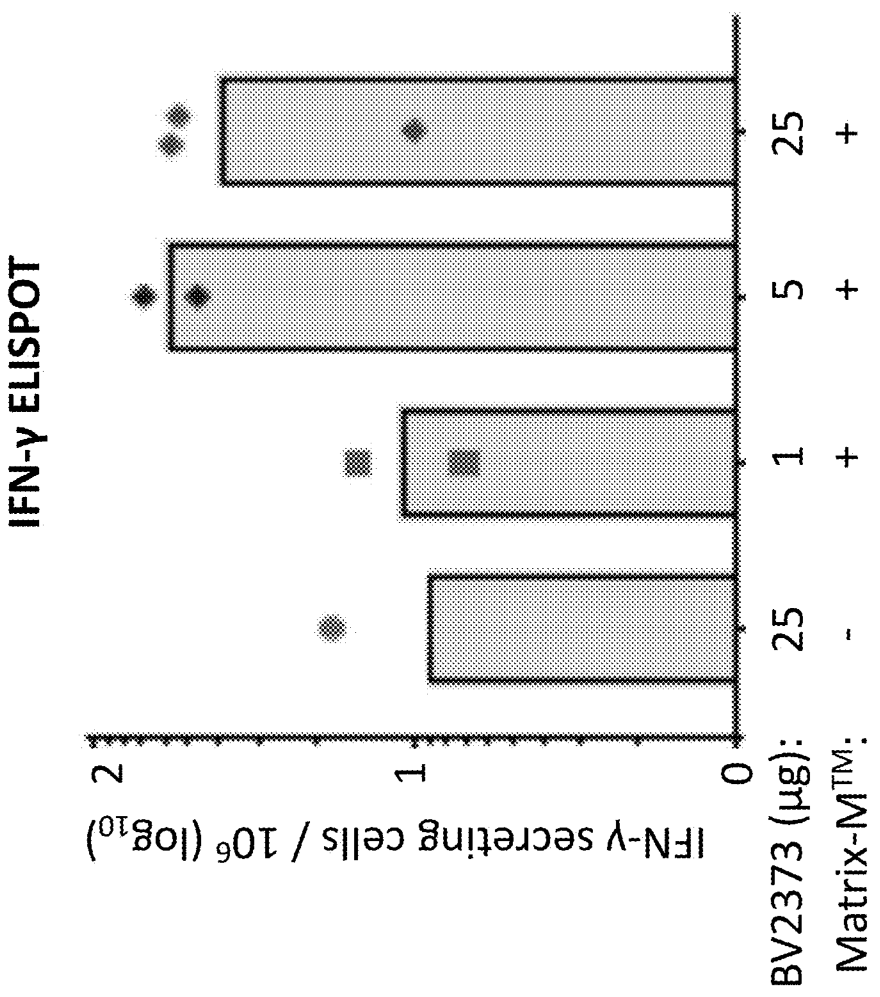
FIG. 28 shows the frequency of IFN-γ secreting cells in peripheral blood mononuclear cells (PBMC) of olive baboons immunized with BV2373 in the presence or absence of MATRIX-M™.
Figure 29A:
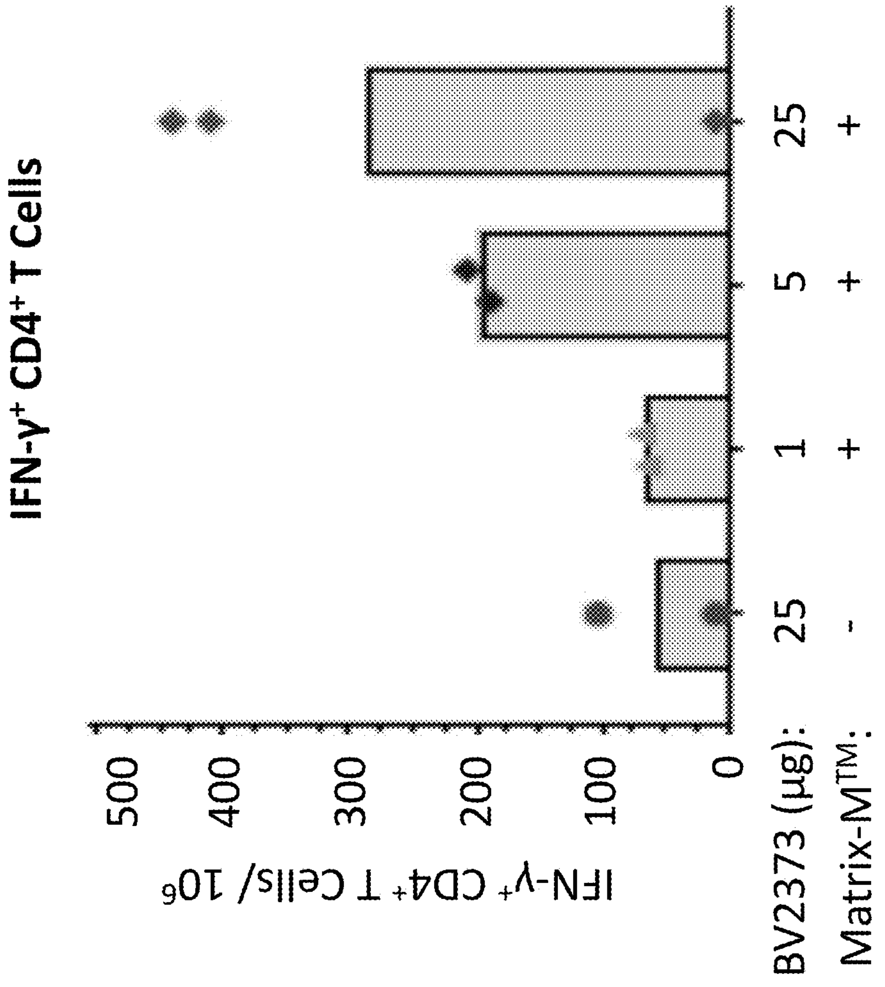
FIGS. 29A-E shows the frequency of cytokine secreting CD4+ T cells in the PBMC of olive baboons immunized with BV2373 in the presence or absence of MATRIX-M™.
Figure 29B:
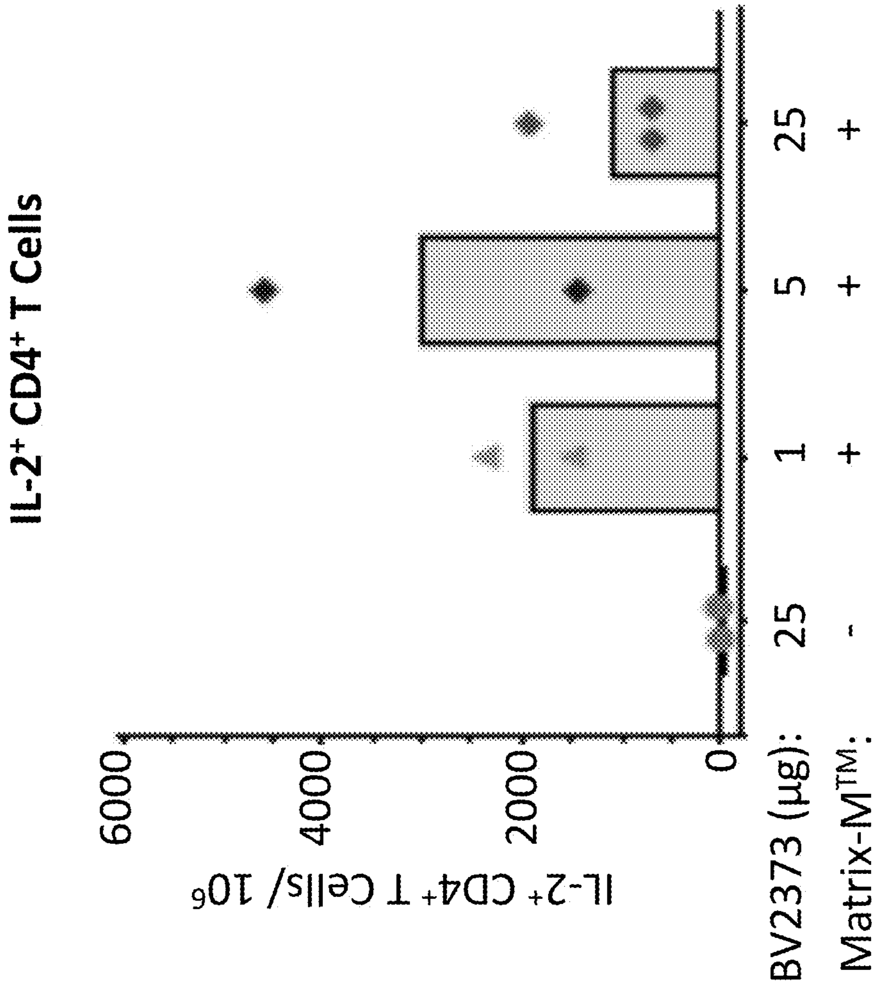
Figure 29C:
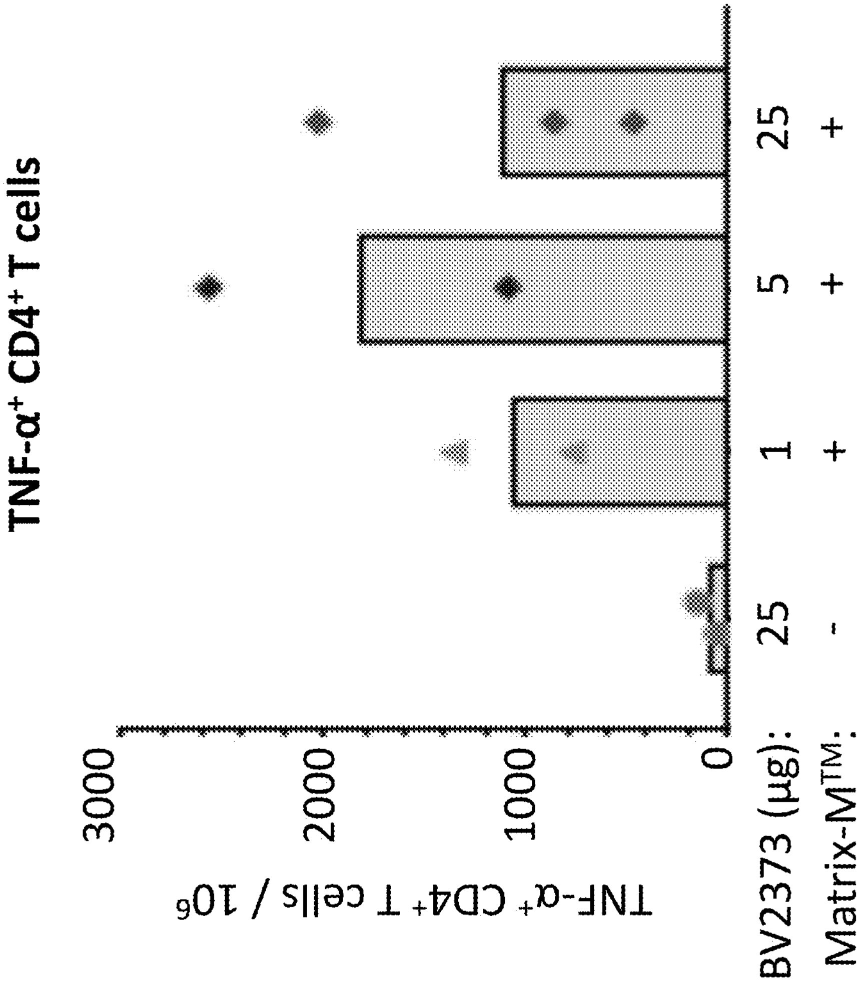
Figure 29D:
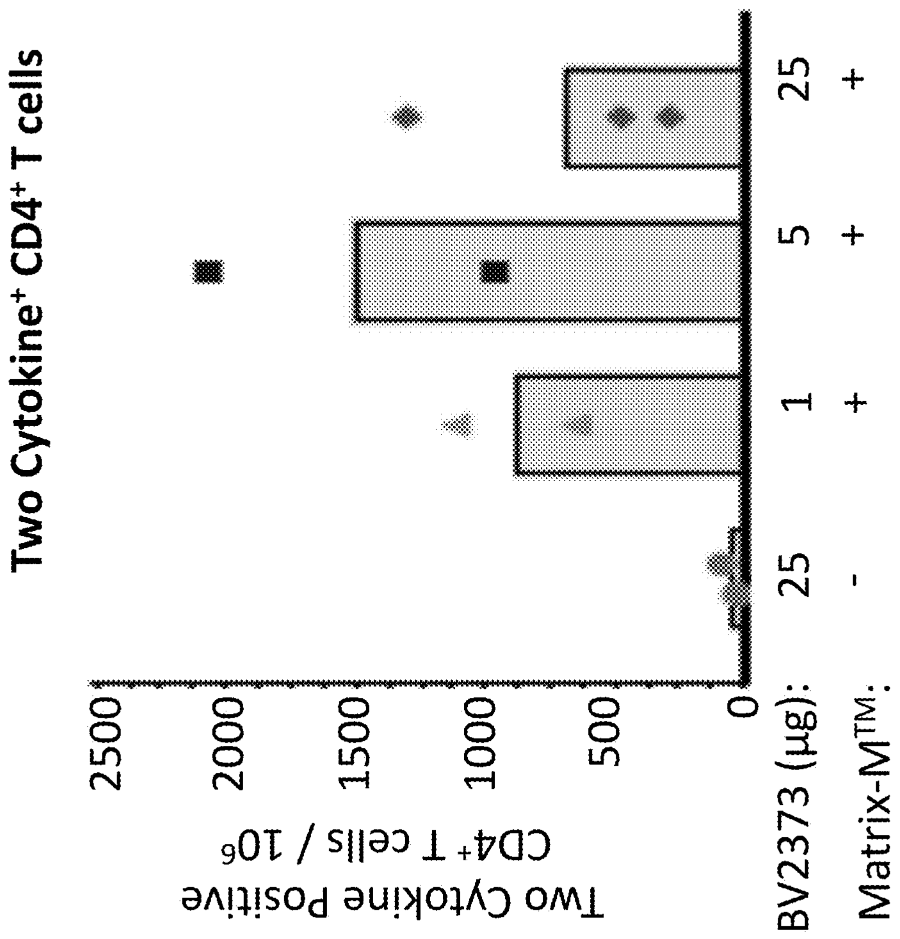
Figure 29E:
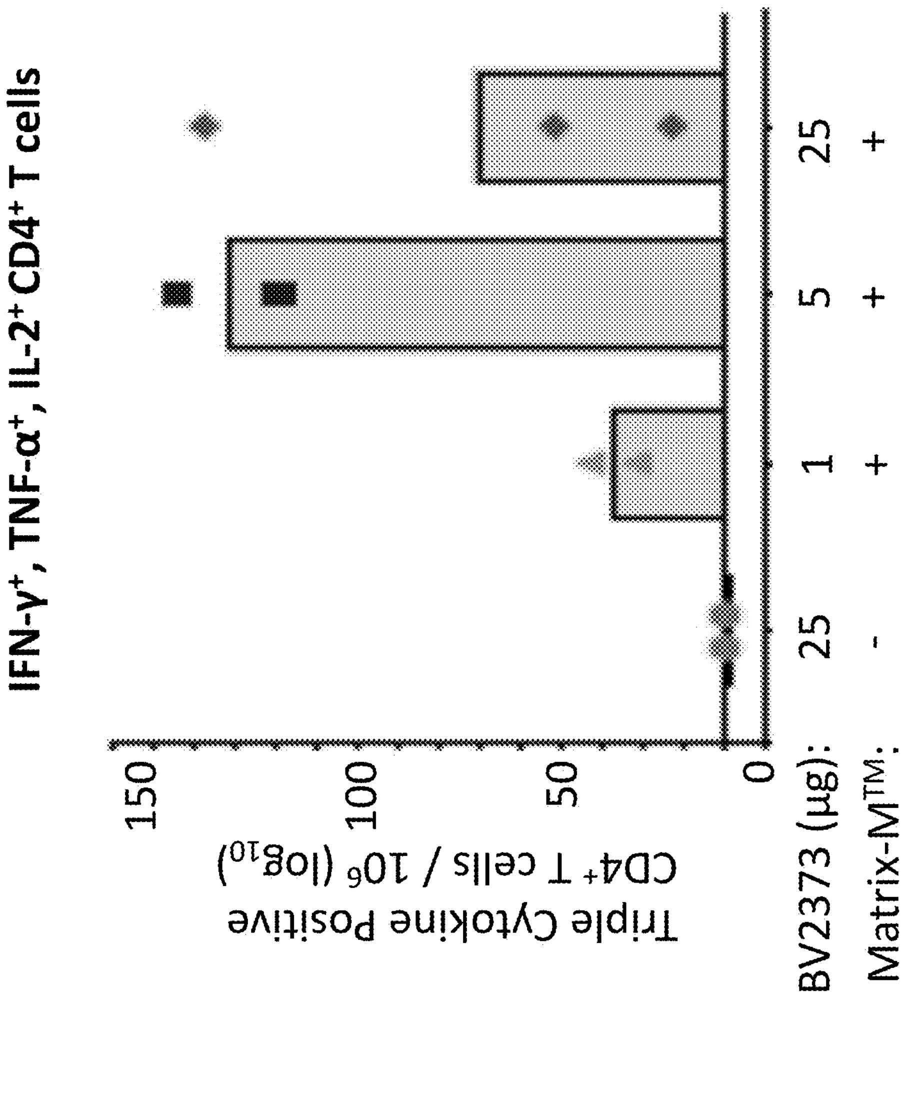

PBMCs were collected 7 days after the second immunization (day 28), and the T cell response was measured by ELISPOT assay. PBMCs from animals immunized with BV2373 (5 μg or 25 μg) and MATRIX-M™ had the highest number of IFN-γ secreting cells, which was 5-fold greater compared to animals immunized with 25 μg BV2373 alone or BV2373 (1 μg) and MATRIX-M™ (FIG. 28). By ICCS analysis, immunization with BV2373 (5 μg) and MATRIX-M™ showed the highest frequency of IFN-γ+, IL-2+, and TNF-α+CD4+ T cells (FIGS. 29A-C). This trend was also true for multifunctional CD4+ T cells, in which at least two or three type 1 cytokines were produced simultaneously (FIGS. 29D-E).

Example 4

Structural Characterization of Coronavirus Spike (S) Polypeptide Nanoparticle Vaccines Transmission electron microscopy (TEM) and two dimensional (2D) class averaging were used to determine the ultrastructure of BV2373. High magnification (67,000× and 100,000×) TEM images of negatively stained BV2373 showed particles corresponding to S-protein homotrimers.

An automated picking protocol was used to construct 2D class average images (Lander G.C. et al. *J Struct Biol.* 166, 95-102 (2009), Sorzano C.O. et al., *J Struct Biol.* 148, 194-204 (2004).). Two rounds of 2D class averaging of homotrimeric structures revealed a triangular particle appearance with a 15 nm length and 13 nm width (FIG. 10, top left). Overlaying the recently solved cryoEM structure of the SARS-CoV-2 spike protein (EMD ID: 21374) over the 2D BV2373 image showed a good fit with the crown-shaped S1 (NTD and RBD) and the S2 stem (FIG. 10, bottom left). Also apparent in the 2D images was a faint projection that protruded from the tip of the trimeric structure opposite of the NTD/RBD crown (FIG. 10, top right). 2D class averaging using a larger box size showed these faint projections form a connection between the S-trimer and an amorphous structure. (FIG. 10, bottom right).

Dynamic light scattering (DLS) show that the wild-type CoV S protein had a Z-avg particle diameter of 69.53 nm compared to a 2-fold smaller particle size of BV2365 (33.4 nm) and BV2373 (27.2 nm). The polydispersity index (PDI) indicated that BV2365 and BV2373 particles were generally uniform in size, shape, and mass (PDI=0.25-0.29) compared to the wild-type spike-protein (PDI=0.46) (Table 3).

TABLE 3

Particle Size and Thermostability of SARS-CoV-2 Trimeric Spike Proteins

| SARS-CoV-2 S protein | Differential Scanning Calorimetry (DSC) $T_{max}$ (° C.)[1] | Differential Scanning Calorimetry (DSC) ΔHcal (kJ/mol) | Dynamic Light Scattering (DLS) Z-avg diameter[2] (nm) | Dynamic Light Scattering (DLS) PDI[3] |
|---|---|---|---|---|
| Wild-type | 58.6 | 153 | 69.53 | 0.46 |
| BV2365 | 61.3 | 466 | 33.40 | 0.25 |
| BV2373 | 60.4 | 732 | 27.21 | 0.29 |

[1]$T_{max}$: melting temperature
[2]Z-avg: Z-average particle size
[3]PDI: polydispersity index The thermal stability of the S-trimers was determined by differential scanning calorimetry (DSC). The thermal transition temperature of the wild-type CoV S- protein ($T_{max}$=58.6° C. was similar to BV2365 and BV2373 with a $T_{max}$=61.3° C. and 60.4° C., respectively (Table 3). Of greater significance, was the 3-5 fold increased enthalpy of transition required to unfold the BV2365 and BV2373 variants (ΔHcal=466 and 732 KJ/mol, respectively) compared to the lower enthalpy required to unfold the WT spike protein (ΔHcal=153 KJ/mol). These results are consistent with improved thermal stability of the BV2365 and BV2373 compared to that of WT spike protein (Table 3).

The stability of the CoV Spike (S) polypeptide nanoparticle vaccines was evaluated by dynamic light scattering. Various pHs, temperatures, salt concentrations, and proteases were used to compare the stability of the CoV Spike (S) polypeptide nanoparticle vaccines to nanoparticle vaccines containing the native CoV Spike (S) polypeptide.

Example 5

Stability of Coronavirus Spike (S) Polypeptide Nanoparticle Vaccines

The stability of the CoV Spike (S) polypeptide nanoparticle vaccines was evaluated by dynamic light scattering. Various pHs, temperatures, salt concentrations, and proteases were used to compare the stability of the CoV Spike (S) polypeptide nanoparticle vaccines to nanoparticle vaccines containing the native CoV Spike (S) polypeptide. The stability of BV2365 without the 2-proline substitutions and BV2373 with two prolines substitution was assessed under different environmental stress conditions using the hACE2 capture ELISA. Incubation of BV2373 at pH extremes (48 hours at pH 4 and pH 9), with prolonged agitation (48 hours), and through freeze/thaw (2 cycles), and elevated temperature (48 hours at 25° C. and 37° C.) had no effect on hACE2 receptor binding (IC50=14.0-18.3 ng mL-1).

Oxidizing conditions with hydrogen peroxide reduced binding of hACE2 binding to BV2373 8-fold (IC50=120 ng mL-1) (FIG. 12A). BV2365 without the 2-proline substitutions was less stable as determined by a significant loss of hACE2 binding under multiple conditions (FIG. 12B).

Figure 32:
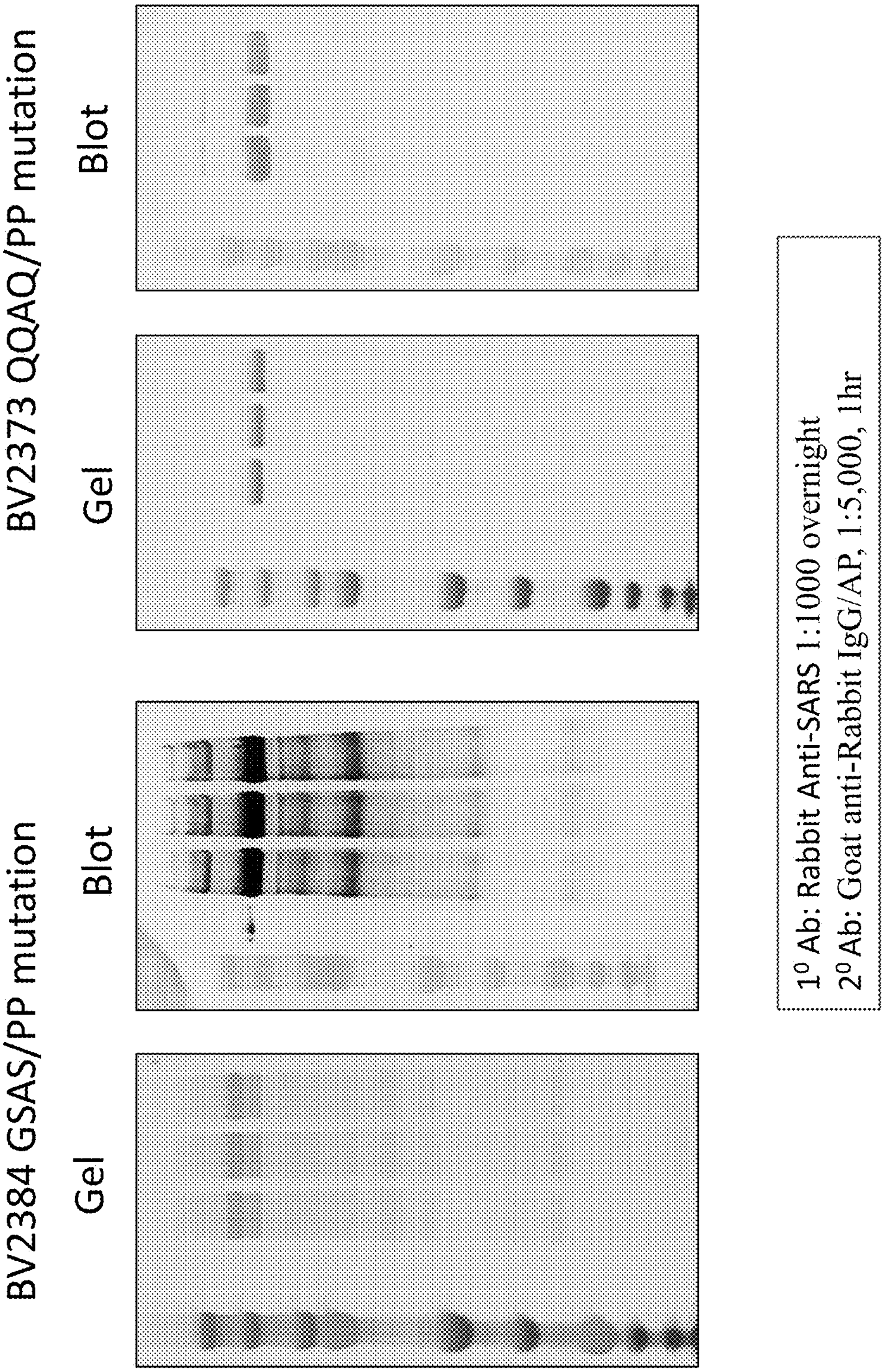
FIG. 32 shows purification of the CoV S polypeptides BV2373 (SEQ ID NO: 87) and BV2384 (SEQ ID NO: 109).

The stability of BV2384 (SEQ ID NO: 110) and BV2373 (SEQ ID NO: 87) were compared. BV2384 has a furin cleavage site sequence of GSAS (SEQ ID NO: 97), whereas BV2373 has a furin cleavage site of QQAQ (SEQ ID NO: 7). As demonstrated by SDS-PAGE and Western Blot, BV2384 showed extensive degradation in comparison to BV2373 (FIG. 32). Furthermore, scanning densitometry and recovery data demonstrate the unexpected loss of full length CoV S protein BV2384, lower purity, and recovery (FIG. 33) in comparison to BV2373 (FIG. 34).

Example 6

Immune Response in Cynomolgus Macaques

We assessed the immune response induced by BV2373 in a Cynomolgus macaque model of SARS-CoV-2 infection. Groups 1-6 were treated as shown in Table 4.

TABLE 4

Groups 1-6 of Cynomolgus macaque study

| Group (N = 4) | BV2373 Dose | MATRIX-M ™ Dose | Immunization (Days) | Blood Draw (days) | Challenge (Day) |
|---|---|---|---|---|---|
| 1 | Placebo | — | 0, 21 | 0, 21, 33 | 35 |
| 2 | 2.5 μg | 25 μg | 0, 21 | 0, 21, 33 | 35 |
| 3 | 5 μg | 25 μg | 0 | 0, 21, 33 | 35 |
| 4 | 5 μg | 50 μg | 0, 21 | 0, 21, 33 | 35 |
| 5 | 5 μg | 50 μg | 0 | 0, 21, 33 | 35 |
| 6 | 25 μg | 50 μg | 0, 21 | 0, 21, 33 | 35 |

Figure 35A:
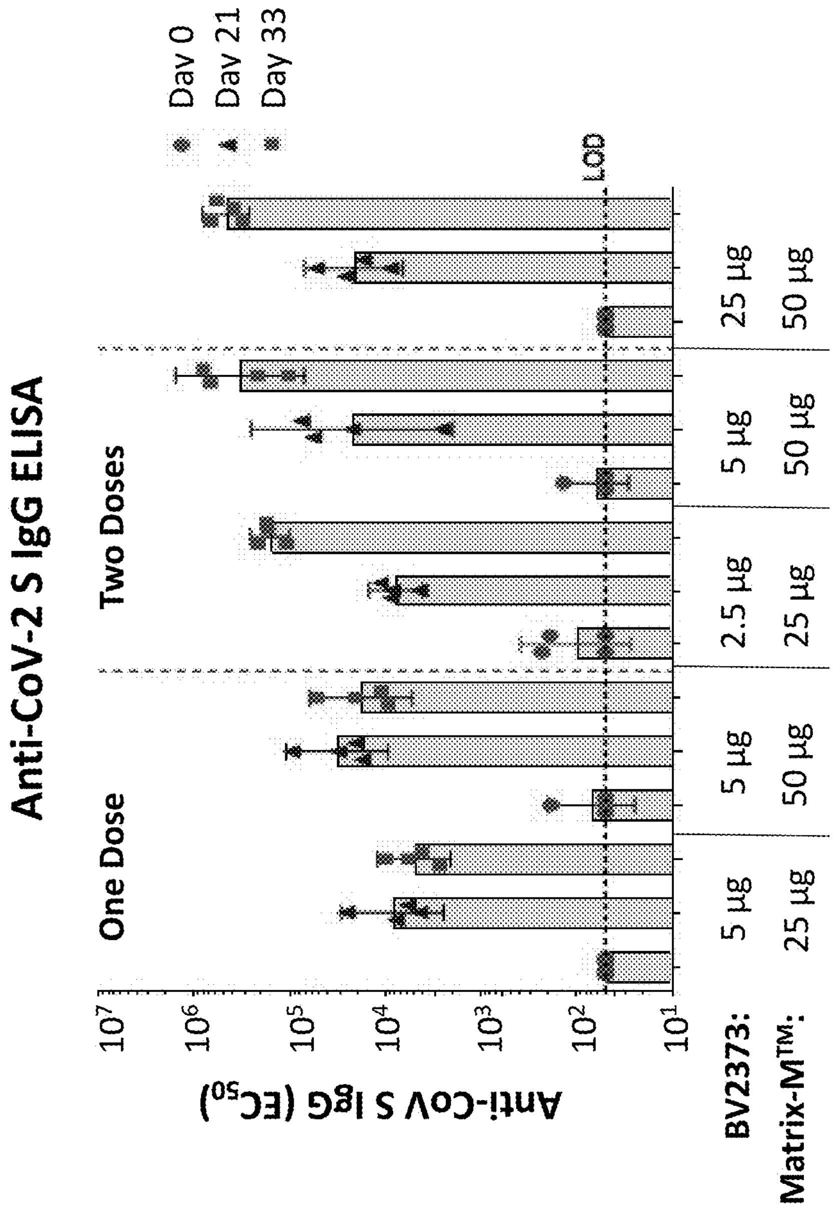
FIGS. 35A-B illustrates induction of anti-S antibodies (FIG. 35A) and neutralizing antibodies (FIG. 35B) in response to administration of BV2373 and MATRIX-M™. Cynomolgus macaques were administered one or two doses (Day 0 and Day 21) of 2.5 μg, 5 μg, or 25 μg of BV2373 with 25 μg or 50 μg MATRIX-M™adjuvant. Controls received neither BV2373 or MATRIX-M™. Antibodies were measured at Days 21 and 33.
Figure 35B:
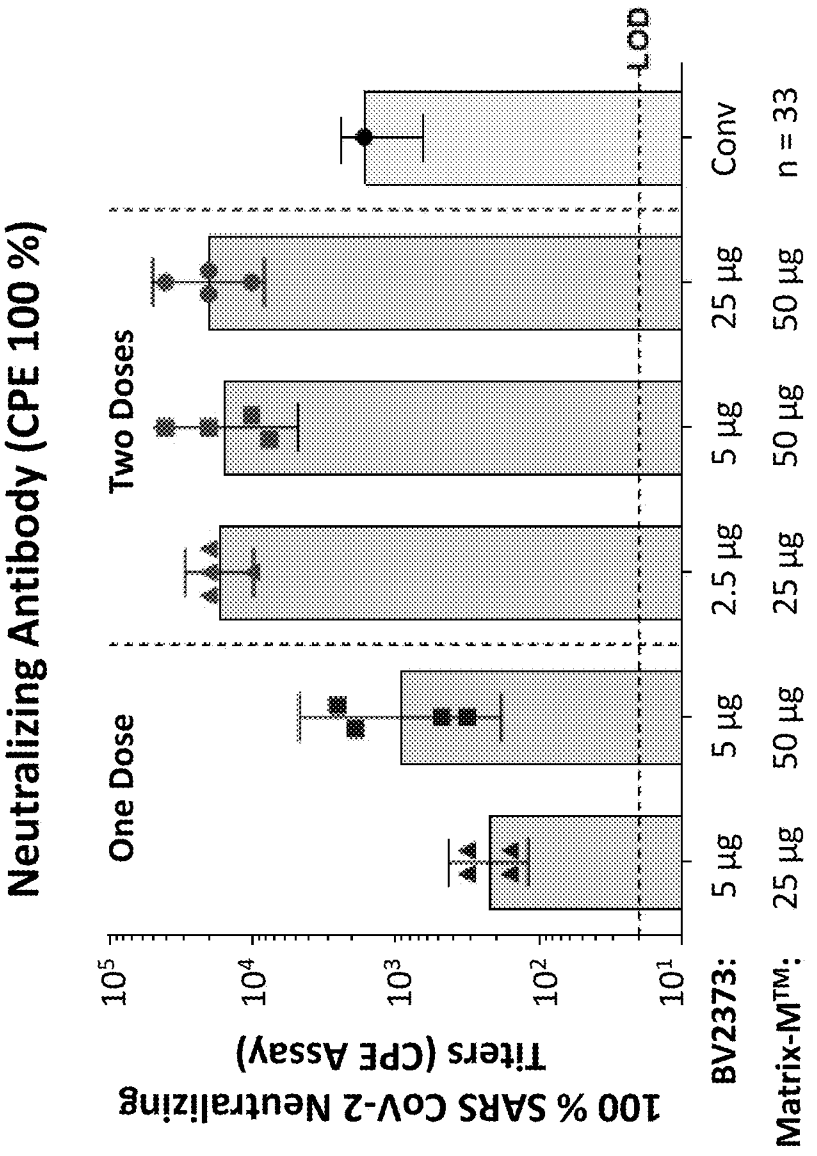
Figure 38A:
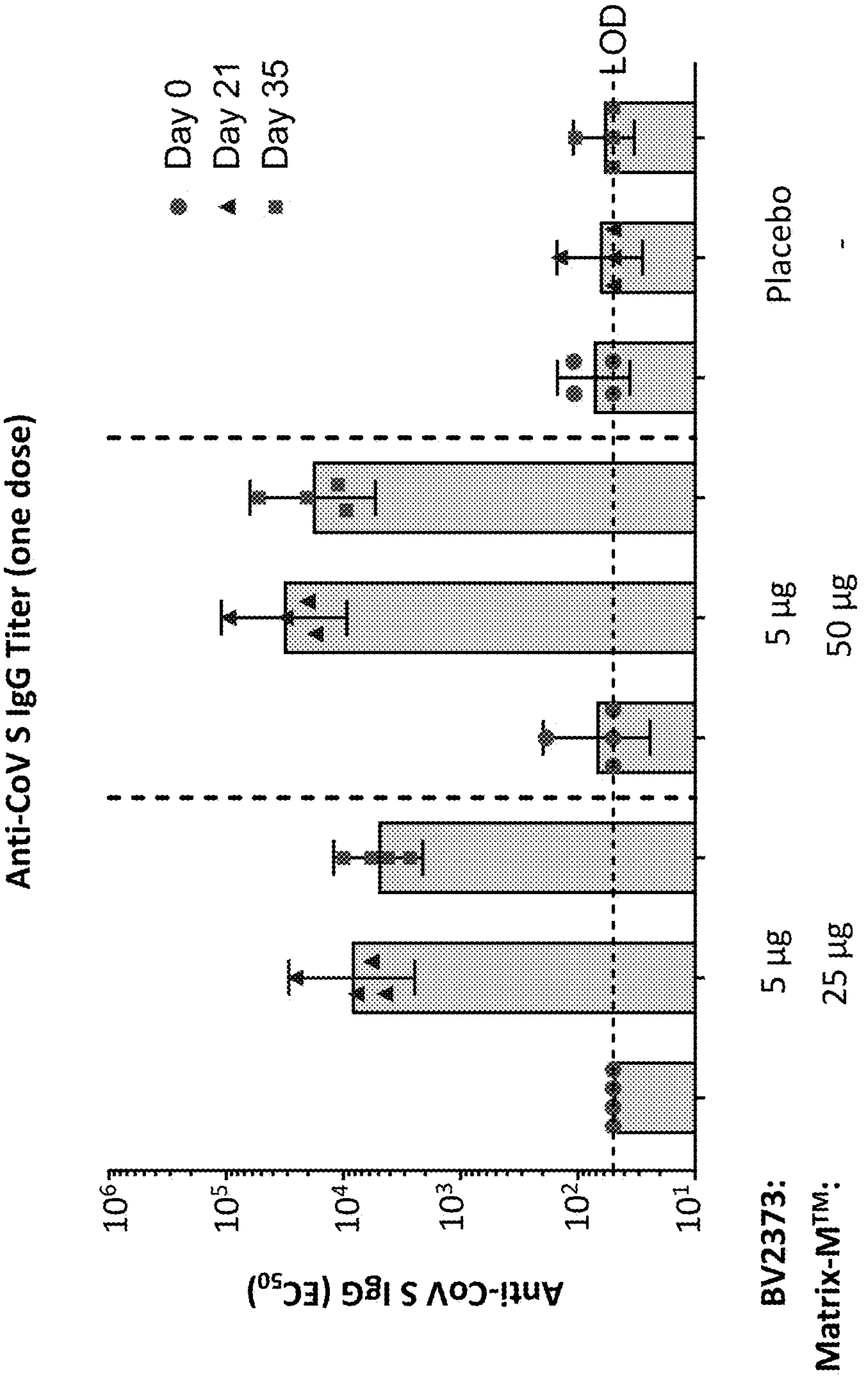
FIGS. 38A-B show anti-CoV S polypeptide IgG titers 21 days and 35 days after immunization of Cynomolgus macaques with one dose (FIG. 38A) or two doses of BV2373 and 25 μg or 50 μg of MATRIX-M™ (FIG. 38B).
Figure 38B:
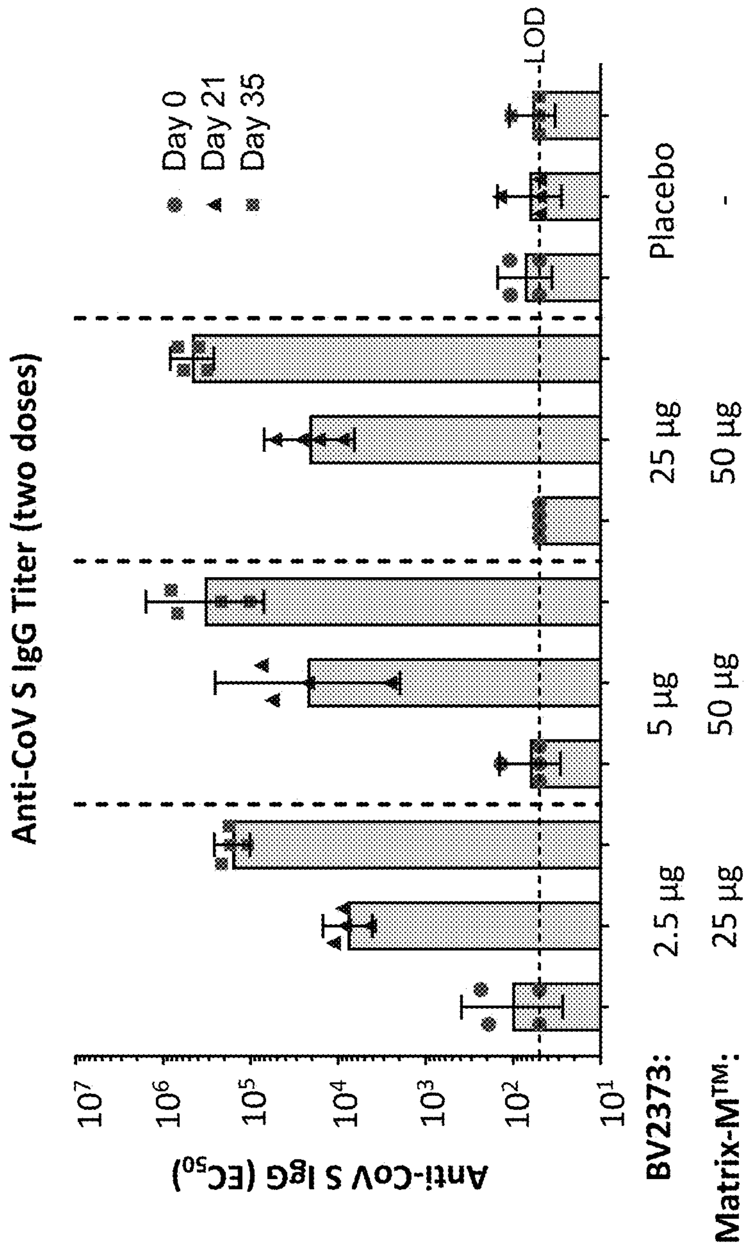
Figure 38C:
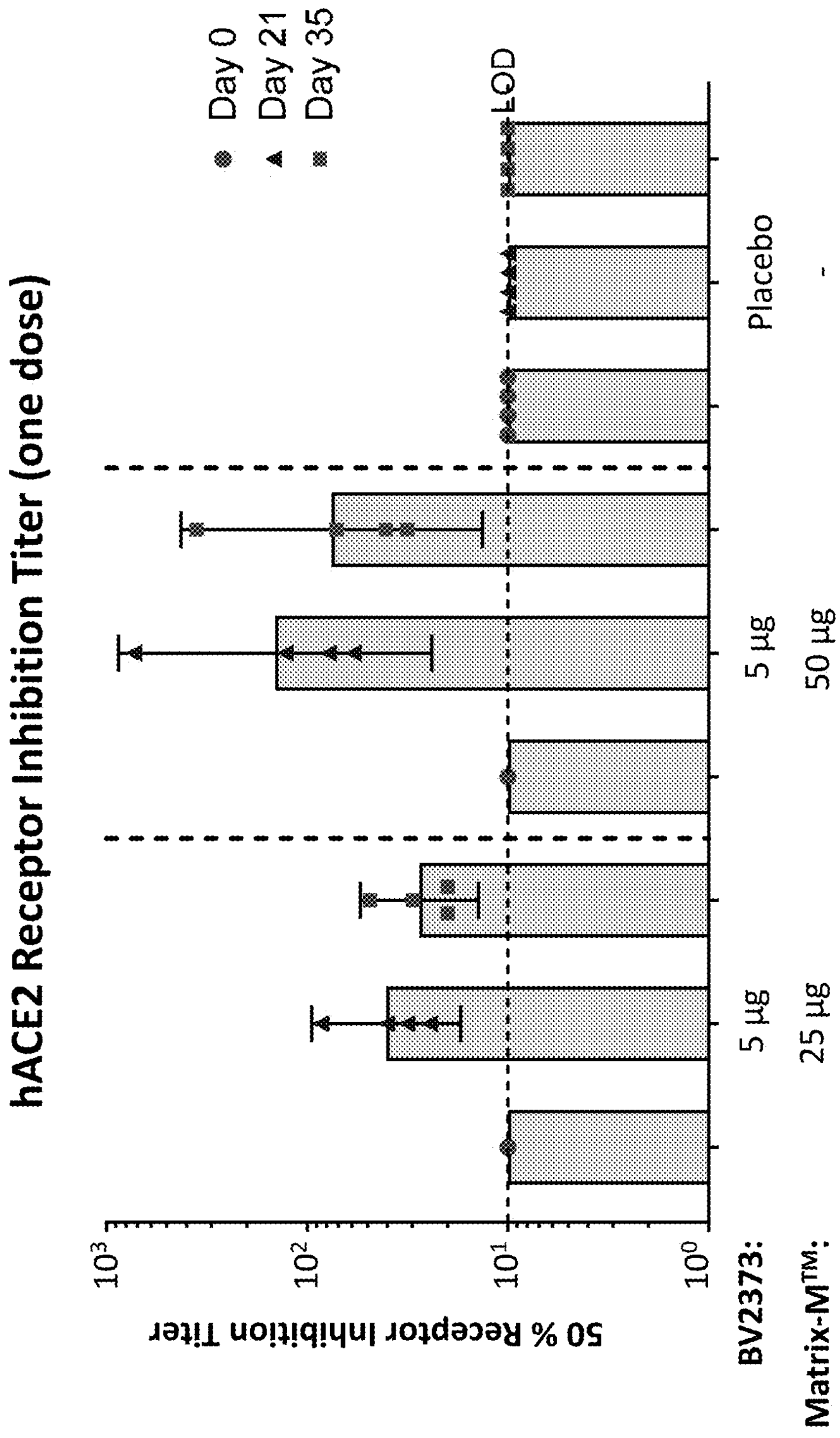
FIGS. 38C-38D shows the hACE2 inhibition titer of Cynomolgus macaques 21 days and 35 days after immunization of Cynomolgus macaques with one dose (FIG. 38C) or two doses of BV2373 (5 μg) and MATRIX-M™ (25 μg or 50 μg) (FIG. 38D).
Figure 38D:
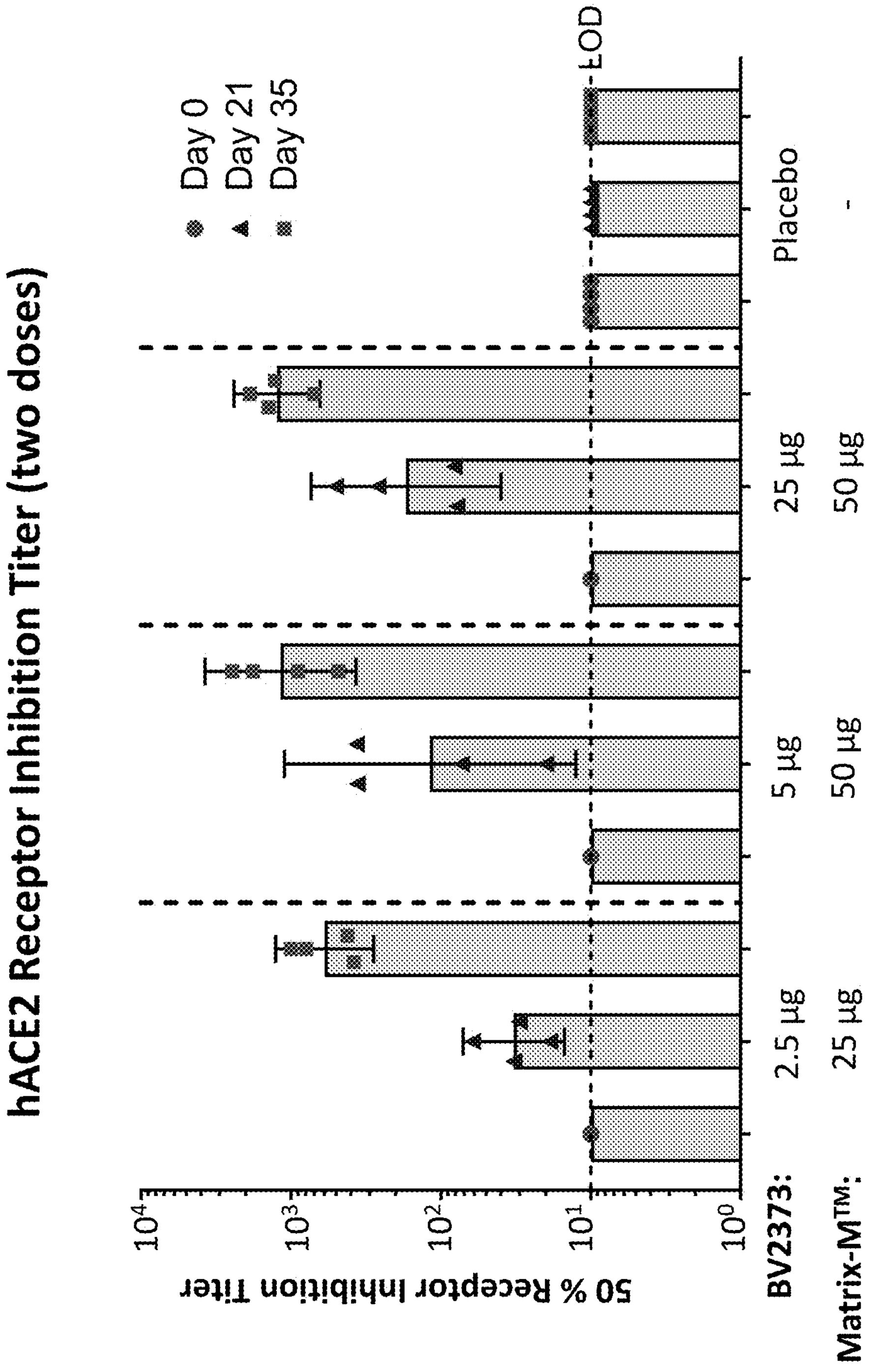
Figure 38E:
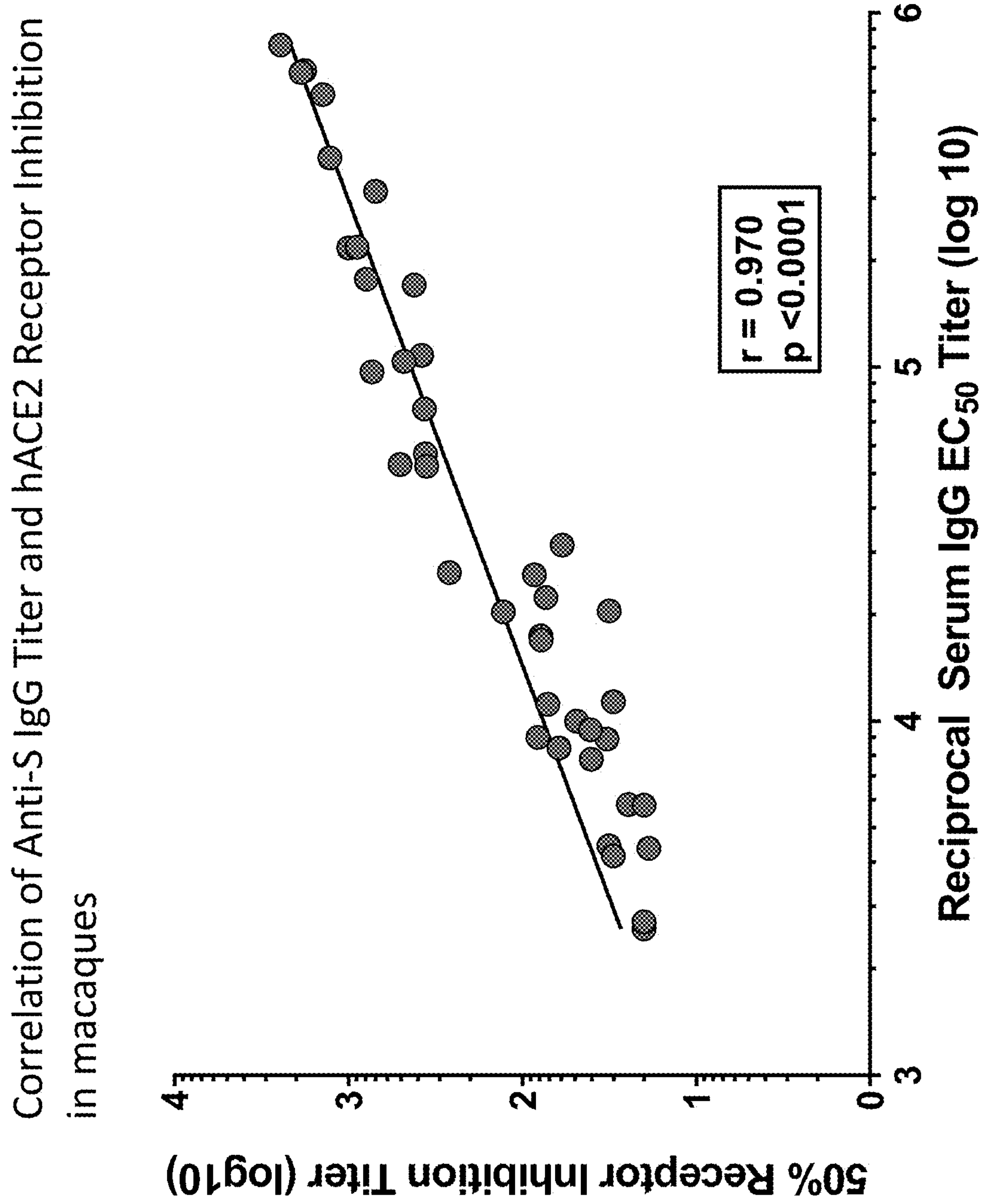
FIG. 38E shows the significant correlation between anti-CoV S polypeptide IgG titer and hACE2 inhibition titer in Cynomolgus macaques after administration of BV2373 and MATRIX-M™ Data is shown for Groups 2-6 of Table 4.
Figure 40A:
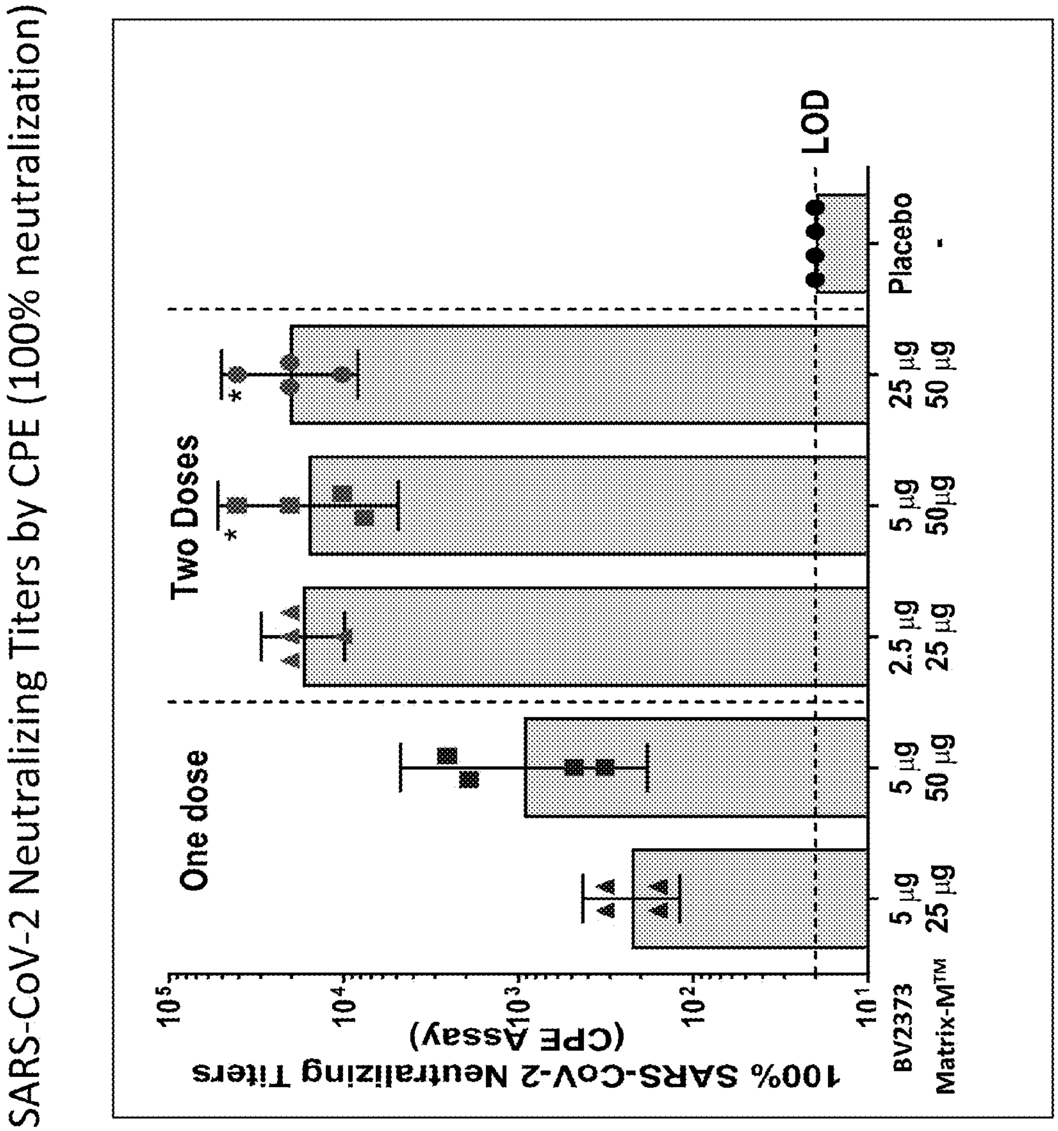
FIGS. 40A-B shows the SARS-CoV-2 neutralizing titers of Cynomolgus macaques immunized with BV2373 and MATRIX-M™ as determined by cytopathic effect (CPE) (FIG. 40A) and plaque reduction neutralization test (PRNT) (FIG. 40B).
Figure 40B:
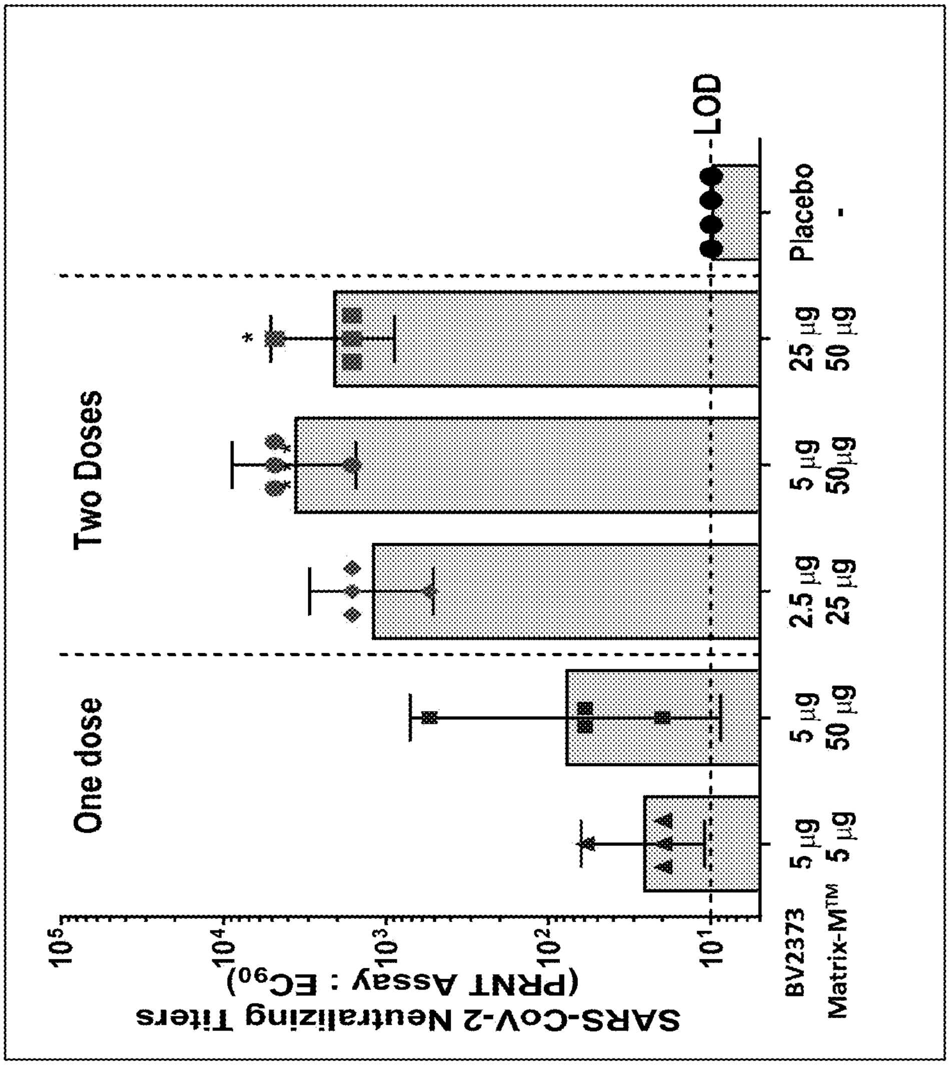

Administration of a vaccine comprising BV2373 resulted in the induction of anti-CoV-S antibodies (FIG. 35A) including neutralizing antibodies (FIG. 35B). Anti-CoV-S antibodies were induced after administration of one (FIG. 38A) or two doses (FIG. 38B) of BV2373. Administration of the vaccine comprising BV2373 also resulted in the production of antibodies that blocked binding of the CoV S protein to hACE2 (FIG. 38C and FIG. 38D). There was a significant correlation between anti-CoV S polypeptide IgG titer and hACE2 inhibition titer in Cynomolgus macaques after administration of BV2373 (FIG. 38E). The ability of BV2373 to induce the production of neutralizing antibodies was evaluated by cytopathic effect (CPE) (FIG. 40A) and plaque reduction neutralization test (PRNT) (FIG. 40B). The data revealed that vaccine formulations of Table 4 produced SARS-CoV-2 neutralizing titers, in contrast to the control.

Figure 39:
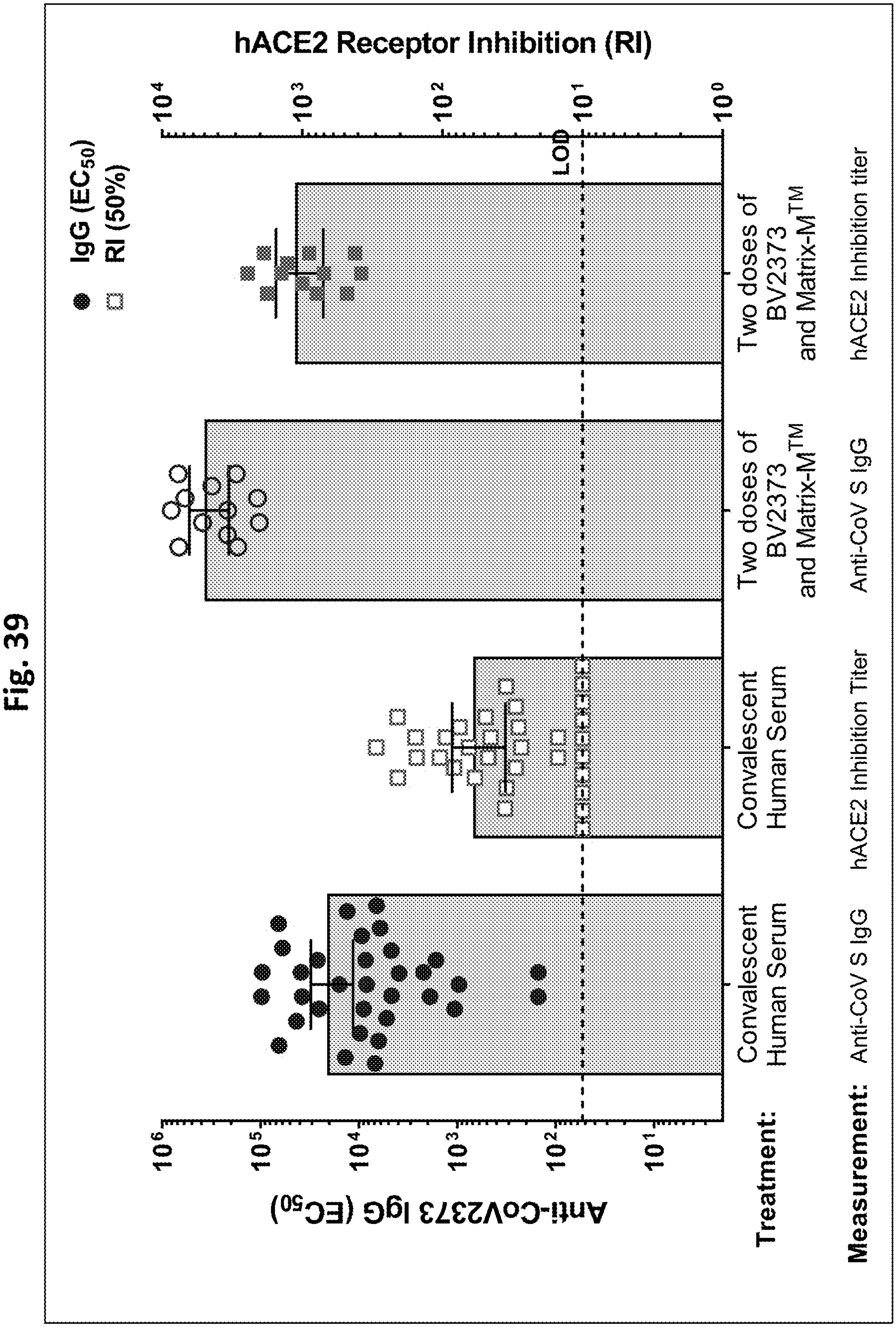
FIG. 39 shows the anti-CoV S polypeptide titers and hACE2 inhibition titer of Cynomolgus macaques 35 days after immunization with two doses of BV2373 and MATRIX-M™ or after immunization with convalescent human serum (Groups 2, 4, and 6) of Table 4. These data show that the anti-CoV S polypeptide and hACE2 inhibition titers of Cynomologus macaques immunized with BV2373 and MATRIX-M™ is superior to Cynomolgus macaques immunized with convalescent serum.

The vaccine comprising BV2373's ability to induce anti-CoV-S antibodies and antibodies that block binding of hACE2 to the CoV S protein in Cynomolgus macaques was compared to human convalescent serum. The data revealed that the BV2373 vaccine formulation induced superior anti-CoV S polypeptide and hACE2 inhibition titers as compared to human convalescent serum (FIG. 39).

Figure 36A:
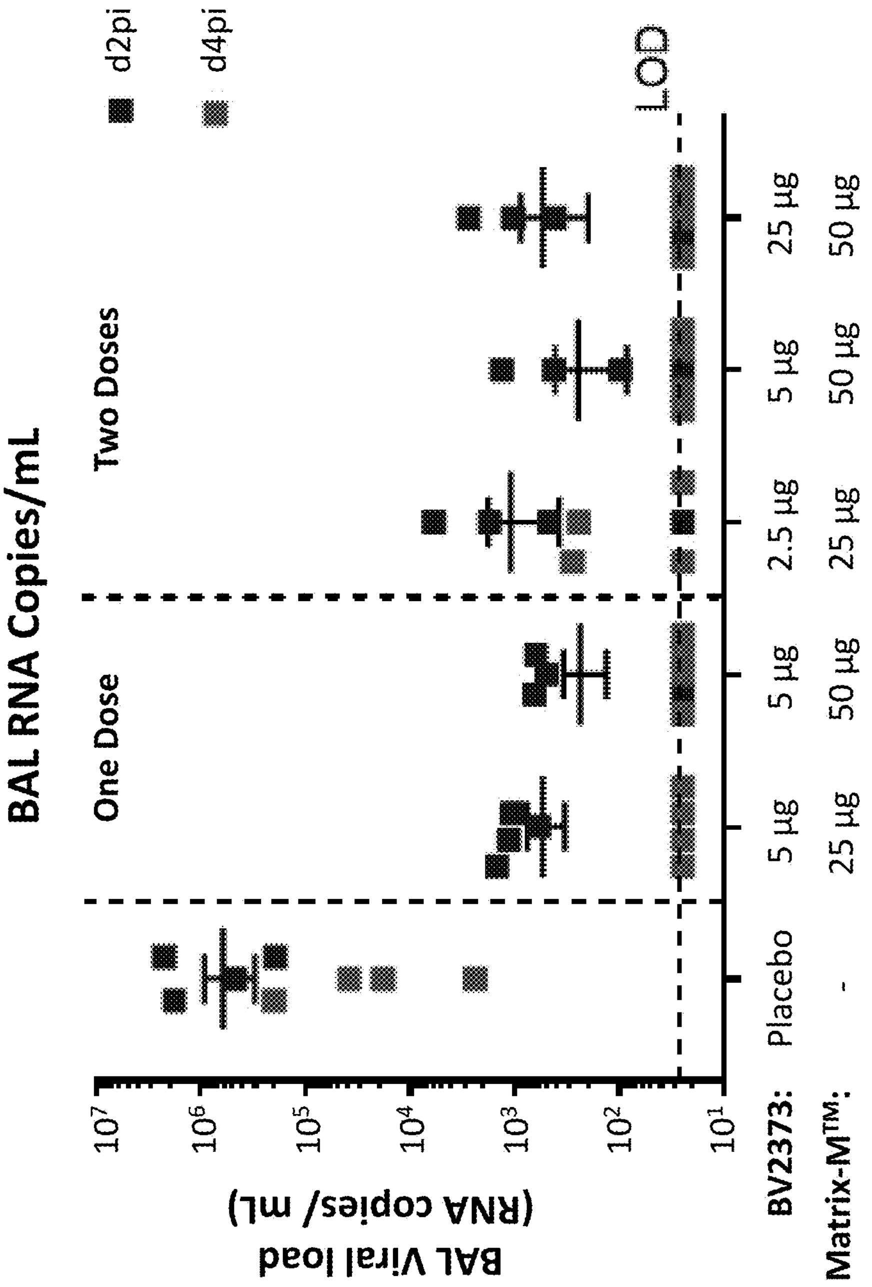
FIGS. 36A-B illustrates a decrease of SARS-CoV-2 viral replication by vaccine formulations disclosed herein as assessed in broncheoalveol lavage (BAL) in Cynomolgus macaques. Cynomolgus macaques were administered BV2373 and MATRIX-M™ as shown. Subjects were immunized Day 0 and in the groups with two doses Day 0 and Day 21. Subject animals were challenged Day 37 with $1\times10^4$ pfu SARS-CoV-2 virus. Viral RNA (FIG. 36A, corresponding to total RNA present) and viral sub-genomic RNA (FIG. 36B, corresponding to replicating virus) levels were assessed in bronchiolar lavage (BAL) at 2 days and 4 days post-challenge with infectious virus (d2pi and d4pi). Most subjects showed no viral RNA. At Day 2 small amounts of RNA were measured in some subjects. By Day 4, no RNA was measured except for two subjects at the lowest dose of 2.5 μg. Sub-genomic RNA was not detected at either 2 Days or 4 days except for 1 subject, again at the lowest dose.
Figure 36B:
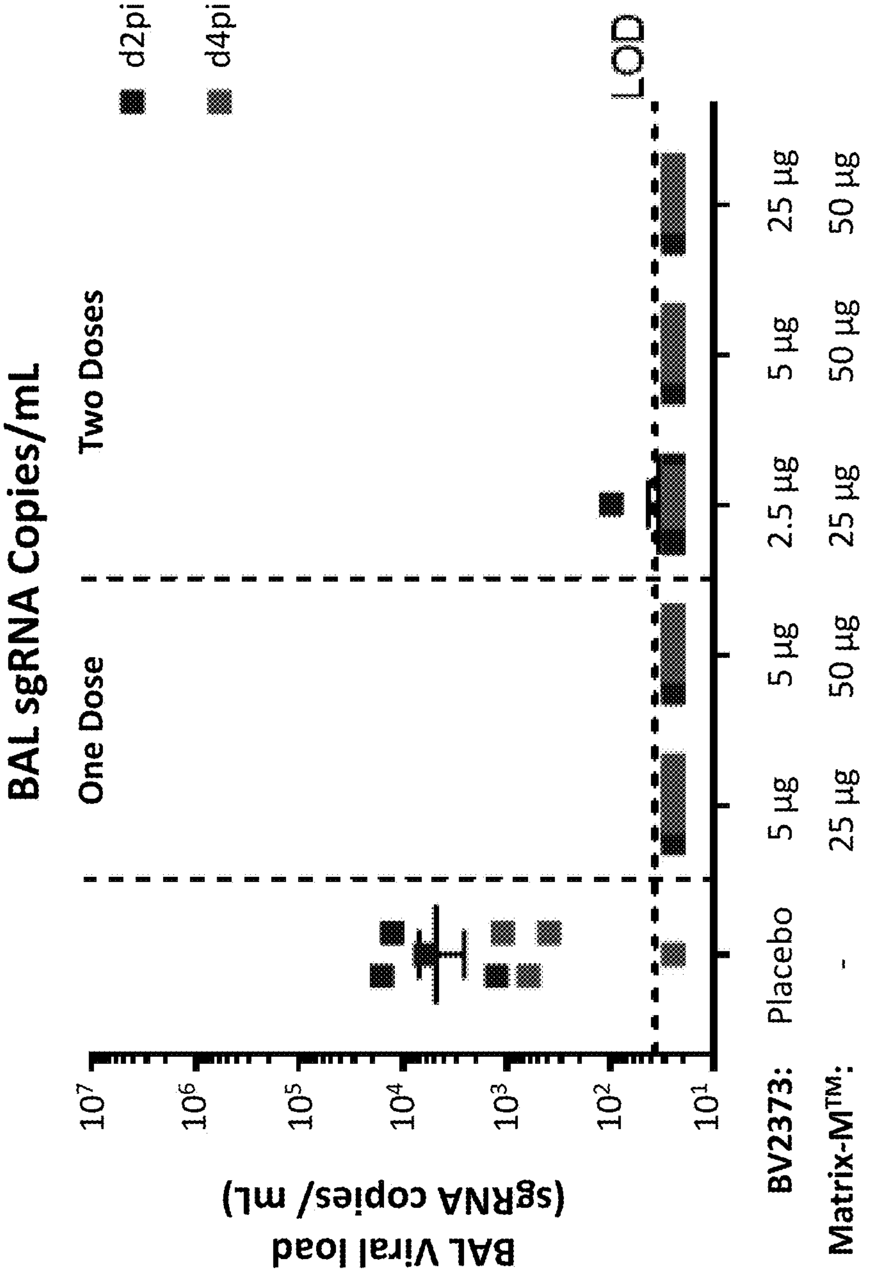
Figure 37A:
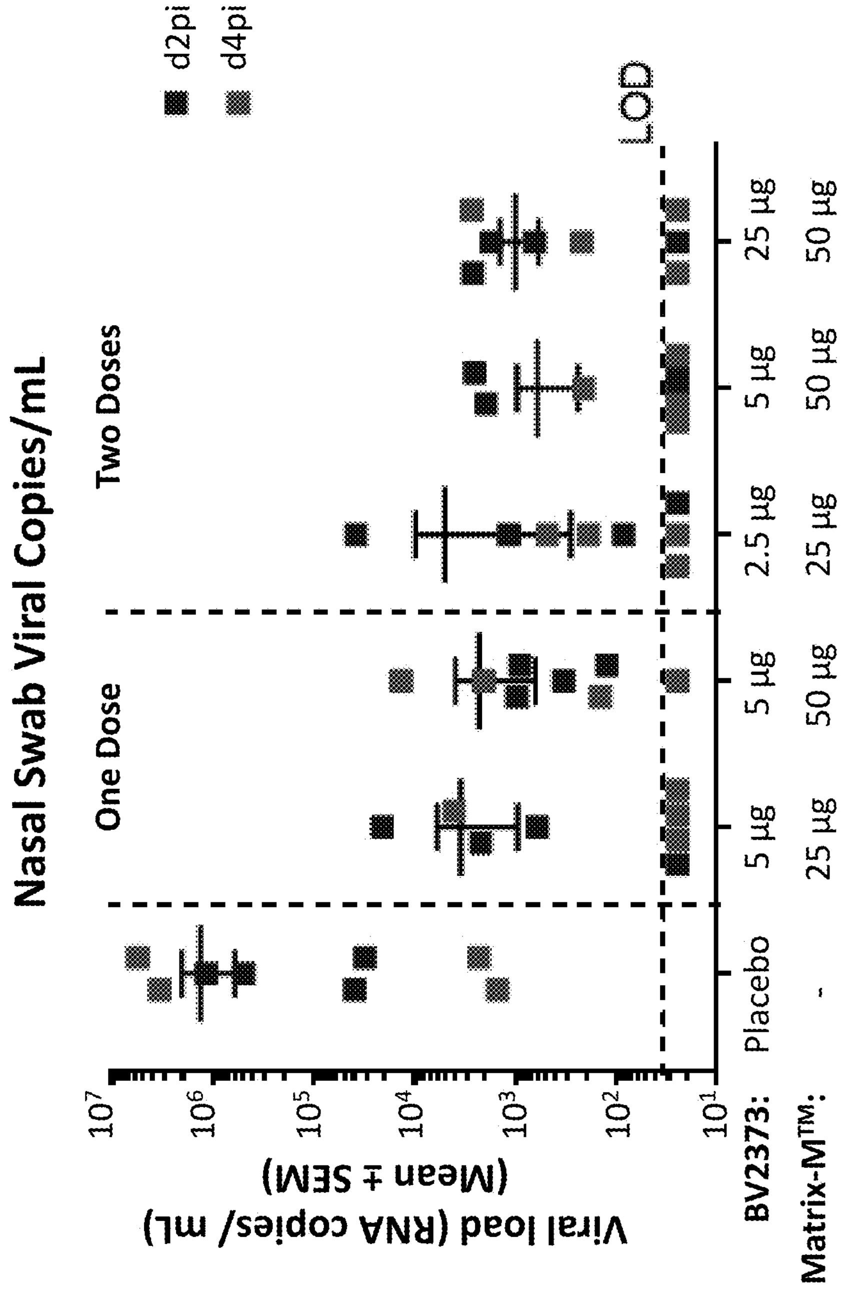
FIGS. 37A-B illustrates a decrease of SARS-CoV-2 viral replication by vaccine formulations disclosed herein as assessed in nasal swab in Cynomolgus macaques. Cynomolgus macaques were administered BV2373 with MATRIX-M™ as shown. Subjects were immunized Day 0 and in the groups with two doses Day 0 and Day 21. Subject animals were challenged Day 37 with $1\times10^4$ SARS-CoV-2 virus. Viral RNA (FIG. 37A) and viral sub-genomic (sg) RNA (FIG. 37B) were assessed by nasal swab at 2 days and 4 days post-infection (d2pi and d4pi). Most subjects showed no viral RNA. At Day 2 and Day 4 small amounts of RNA were measured in some subjects. Sub-genomic RNA was not detected at either 2 Days or 4 days. Subjects were immunized Day 0 and in the groups with two doses Day 0 and Day 21. These data show that the vaccine decreases nose total virus RNA by 100-1000 fold and sgRNA to undetectable levels, and confirm that immune response to the vaccine will block viral replication and prevent viral spread.
Figure 37B:
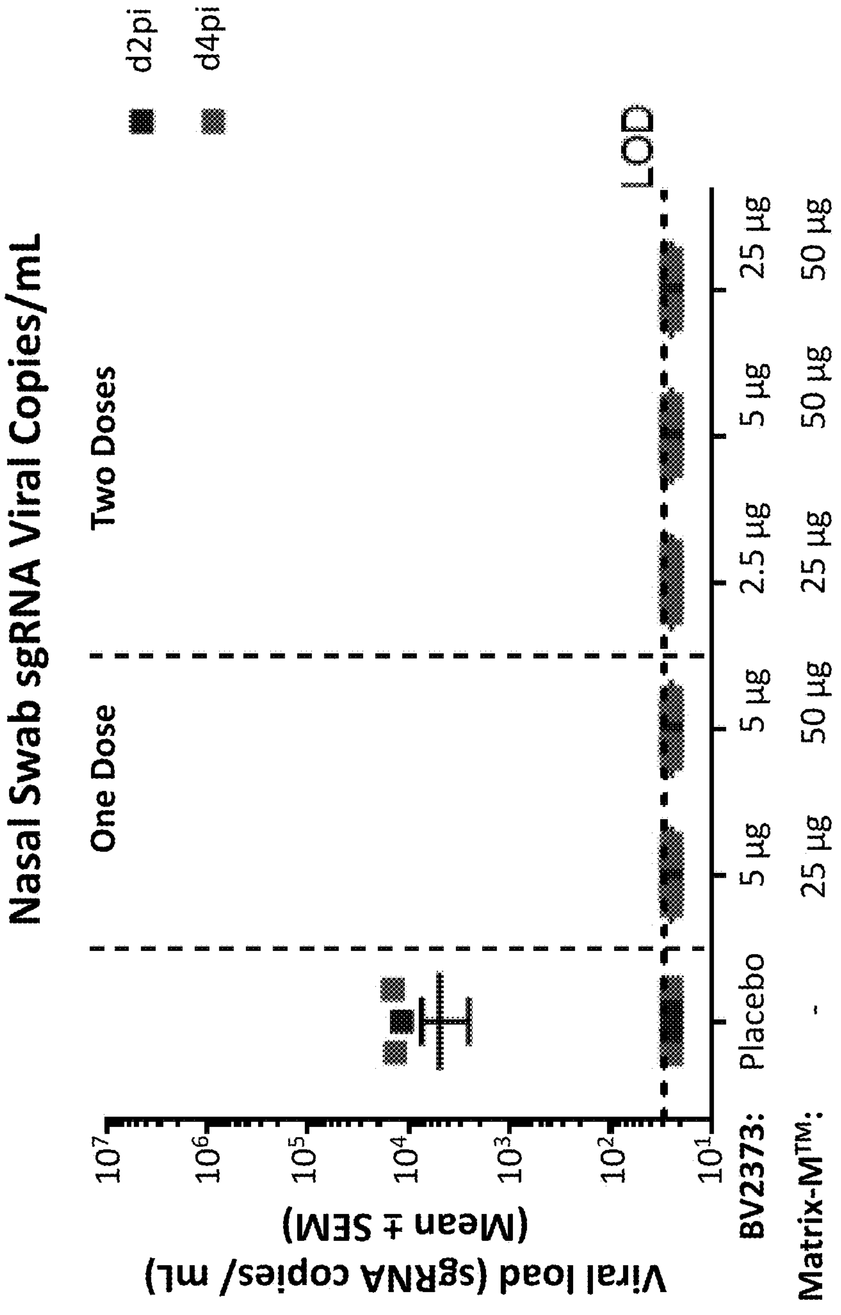

The BV2373 vaccine formulation also caused a decrease of SARS-CoV-2 viral replication (FIGS. 36A-B). Viral RNA (FIG. 36A, corresponding to total RNA present) and viral sub-genomic RNA (sgRNA) (FIG. 36B, corresponding to replicating virus) levels were assessed in bronchiolar lavage (BAL) at 2 days and 4 days post-challenge with infectious virus (d2pi and d4pi). Most subjects showed no viral RNA. At Day 2 small amounts of RNA were measured in some subjects. By Day 4, no RNA was measured except for two subjects at the lowest dose of 2.5 μg. Sub-genomic RNA was not detected at either 2 days or 4 days except for 1 subject, again at the lowest dose. Viral RNA (FIG. 37A) and viral sub-genomic (sg) RNA (FIG. 37B) were assessed by nasal swab at 2 days and 4 days post-infection (d2pi and d4pi). Most subjects showed no viral RNA. At Day 2 and Day 4 small amounts of RNA were measured in some subjects. Sub-genomic RNA was not detected at either 2 Days or 4 days. Subjects were immunized Day 0 and in the groups with two doses Day 0 and Day 21. These data show that the vaccine decreases nose total virus RNA by 100-1000 fold and sgRNA to undetectable levels, and confirm that immune response to the vaccine will block viral replication and prevent viral spread.

Example 7

Evaluation of CoV S Polypeptide Nanoparticle Vaccines in Humans

We assessed the safety and efficacy of a vaccine comprising BV2373 in a randomized, observer-blinded, placebo-controlled Phase 1 clinical trial in 131 healthy participants 18-59 years of age. Participants were immunized with two intramuscular injections, 21 days apart. Participants received BV2373 with or without MATRIX-M™ (n=106) or placebo (n=25). Groups A-E were treated as shown in Table 5. FIG. 41 shows a timeline of the evaluation of clinical endpoints.

TABLE 5

Groups A-E of Phase 1 Human Study

| | Participants | | Day 0 | | Day 21 (+5 days) | |
|---|---|---|---|---|---|---|
| Group (N = 25) | Ran-domized | Sentinel | BV2373 Dose | MATRIX-M ™ Dose | BV2373 Dose | MATRIX-M ™ Dose |
| A | 25 | — | 0 µg | 0 µg | 0 µg | 0 µg |
| B | 25 | — | 25 µg | 0 µg | 25 µg | 0 µg |
| C | 25 | 3 | 5 µg | 50 µg | 5 µg | 50 µg |
| D | 25 | 3 | 25 µg | 50 µg | 25 µg | 50 µg |
| E | 25 | — | 25 µg | 50 µg | 0 µg | 0 µg |

Figure 42A:
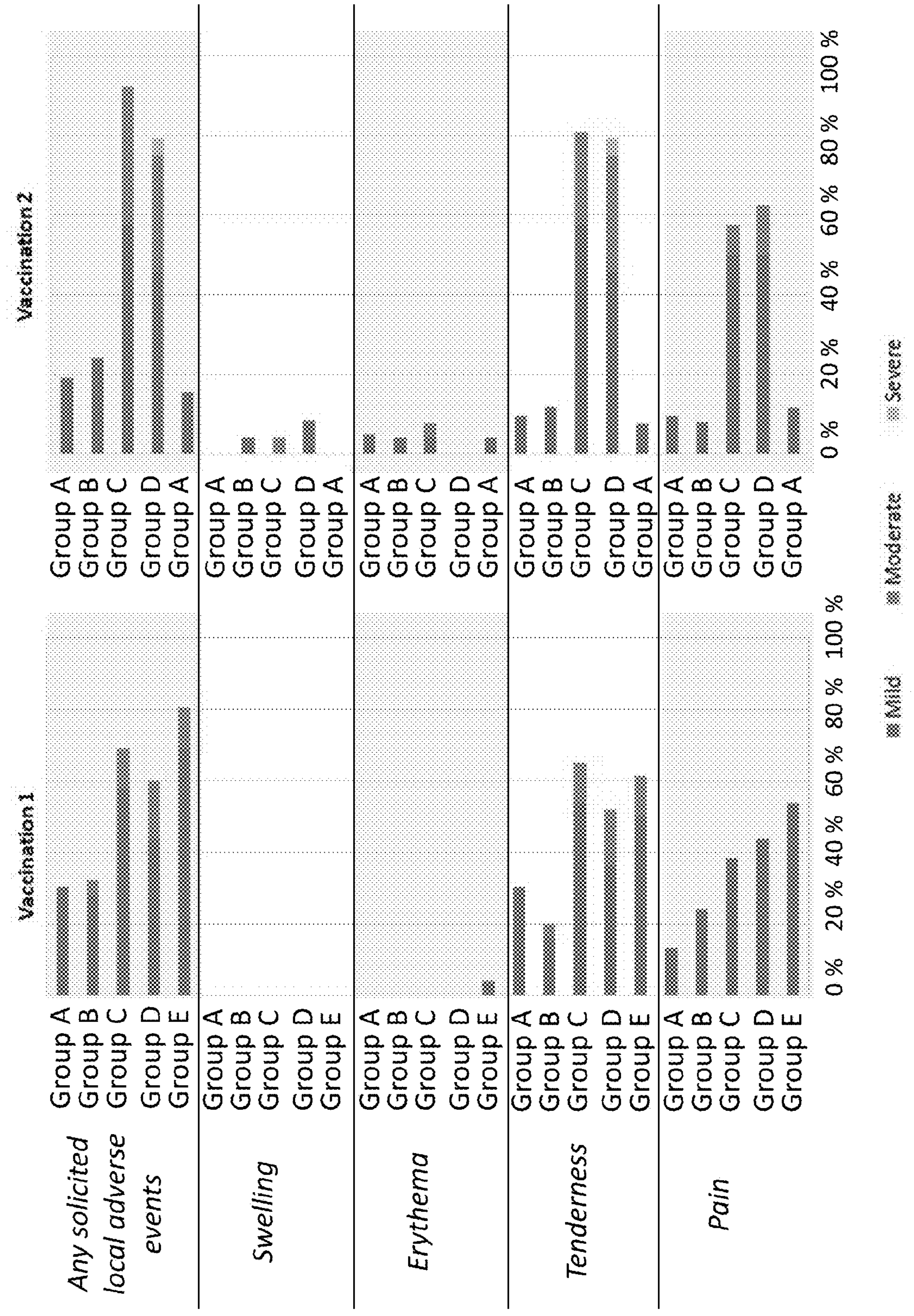
FIGS. 42A-B show the local (FIG. 42A) and systemic adverse events (FIG. 42B) experienced by patients in a clinical trial which evaluated a vaccine comprising BV2373 and MATRIX-M™. Groups A-E are identified in Table 5. The data shows that the vaccine was well tolerated and safe.
Figure 42B:
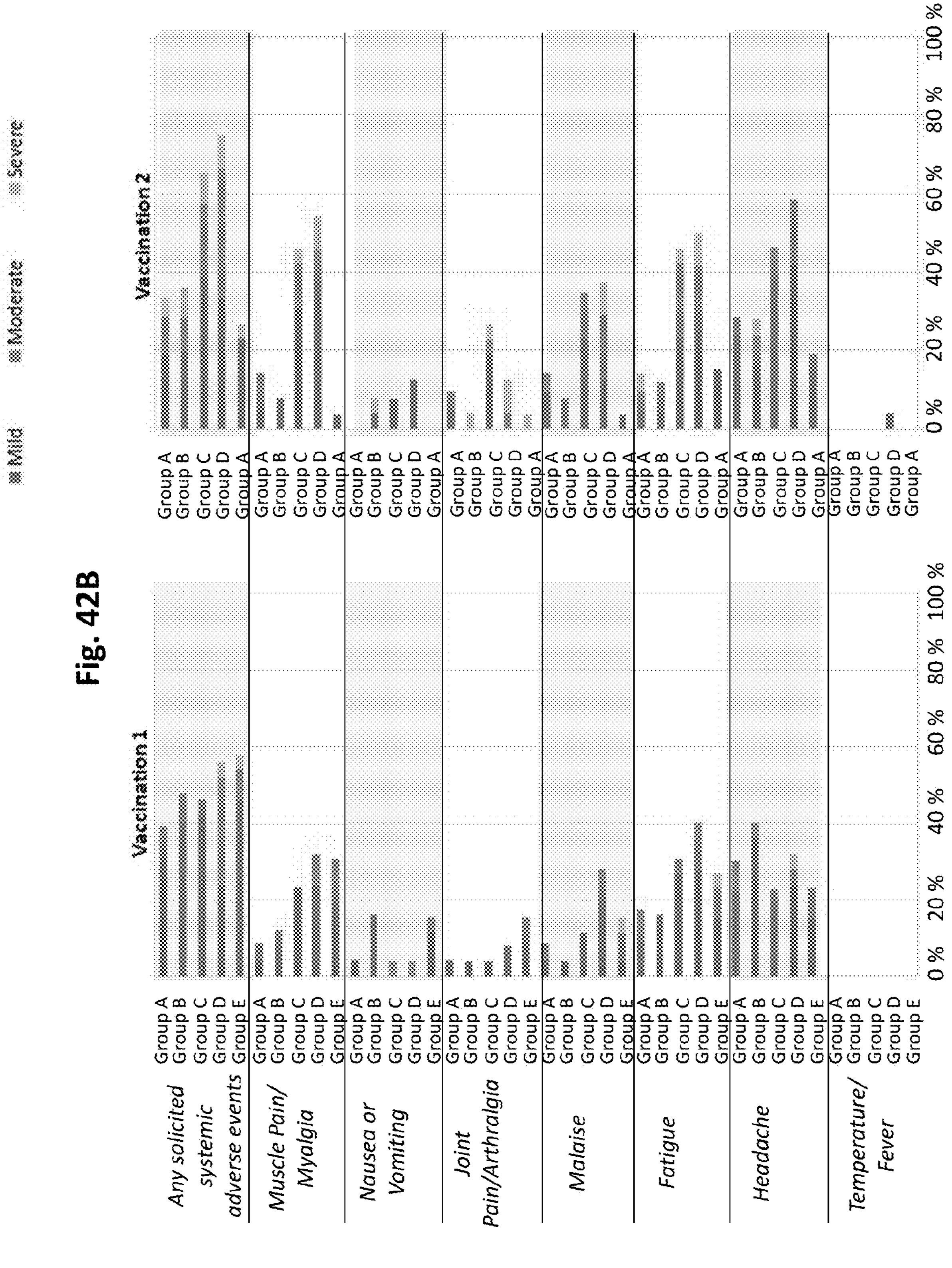

Overall reactogenicity was mild, and the vaccinations were well tolerated. Local reactogenicity was more frequent in patients treated with BV2373 and MATRIX-™ (FIGS. 42A-B).

Figure 43A:
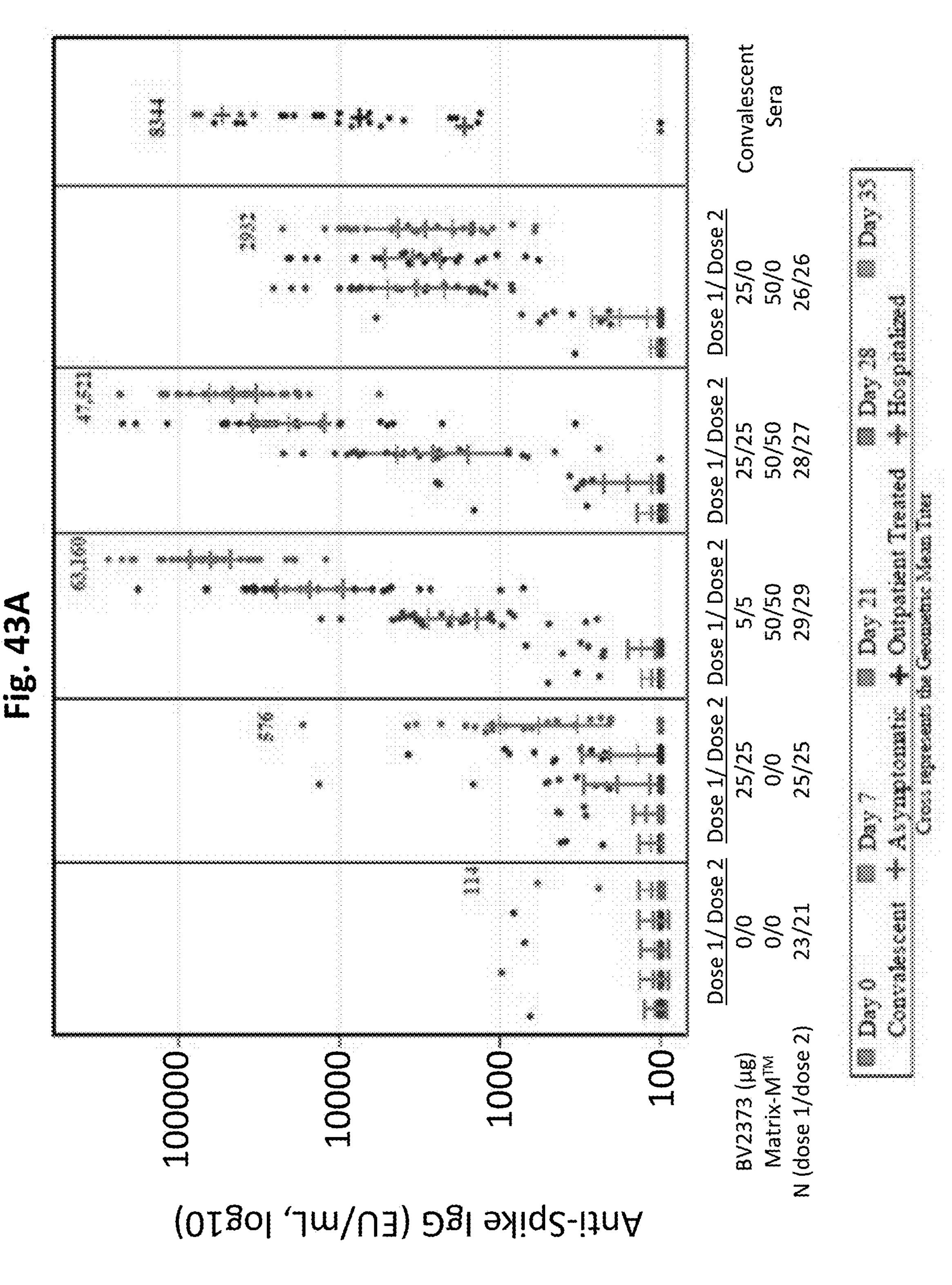
FIGS. 43A-B show the anti-CoV S polypeptide IgG (FIG. 43A) and neutralization titers (FIG. 43B) 21 days and 35 days after immunization of participants in a clinical trial which evaluated a vaccine comprising BV2373 and MATRIX-M™. Horizontal bars represent interquartile range (IRQ) and median area under the curve, respectively. Whisker endpoints are equal to the maximum and minimum values below or above the median ±1.5 times the IQR. The convalescent serum panel includes specimens from PCR-confirmed COVID-19 participants from Baylor College of Medicine (29 specimens for ELISA and 32 specimens for microneutralization (MN $IC_{>99}$). Severity of COVID-19 is denoted as a red mark for hospitalized patients (including intensive care setting), a blue mark for outpatient-treated patients (sample collected in emergency department), and a green mark for asymptomatic (exposed) patients (sample collected from contact/exposure assessment).

The immunogenicity of BV2373 with and without MATRIX-M™ was evaluated. 21 days after vaccination, anti-CoV-S antibodies were detected for all vaccine regimens (FIG. 43A). Geometric mean fold rises (GMFR) in vaccine regimens comprising MATRIX-M™ exceeded those induced by unadjuvanted BV2373. 7 days after a second vaccination (day 28), the anti-CoV-S titer increased an additional eight-fold over responses seen with first vaccination and within 14 days (Day 35) responses had more than doubled yet again, achieving GMFRs approximately 100-fold over those observed with BV2373 alone. A single vaccination with BV2373/ MATRIX-M™ achieved similar anti-CoV-S titer levels to those in asymptomatic (exposed) COVID-19 patients. A second vaccination achieved GMEU levels that exceeded convalescent serum from outpatient-treated COVID-19 patients by six-fold, achieved levels similar to convalescent serum from patients hospitalized with COVID-19, and exceeded overall convalescent serum anti-CoV-S antibodies by nearly six-fold. The responses in the two-dose 5-µg and 25-µg BV2373/ MATRIX-M™ regimens were similar. This highlights the ability of the adjuvant (MATRIX-M™) to enable dose sparing.

Figure 43B:
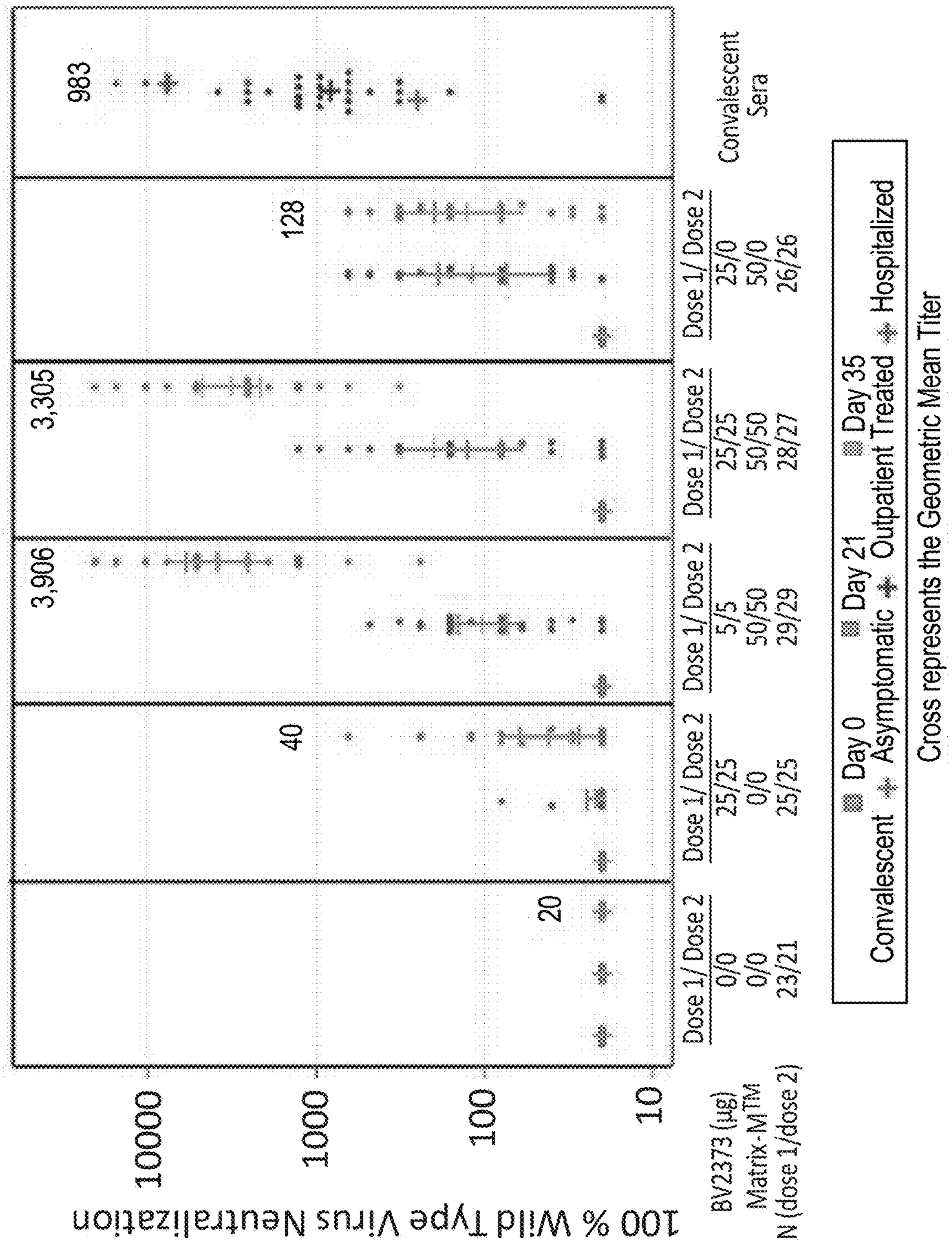

Neutralizing antibodies were induced in all groups treated with BV2373 (FIG. 43B). Groups treated with BV2373 and MATRIX-M™ regimens exhibited an approximately five-fold GMFR than groups treated with BV2373 alone(FIG. 43B). Second vaccinations with adjuvant had a profound effect on neutralizing antibody titers—inducing >100 fold rise over single vaccinations without adjuvant. When compared to convalescent serum, second vaccinations with BV2373/MATRIX-M™ achieved GMT levels four-fold greater than outpatient-treated COVID-19 patients, levels spanning those of patients hospitalized with COVID-19, and exceeded overall convalescent serum GMT by four fold.

Convalescent serum, obtained from COVID-19 patients with clinical symptoms requiring medical care, demonstrated proportional anti-CoV-S IgG and neutralization titers that increased with illness severity (FIGS. 43A-B).

Figure 44A:
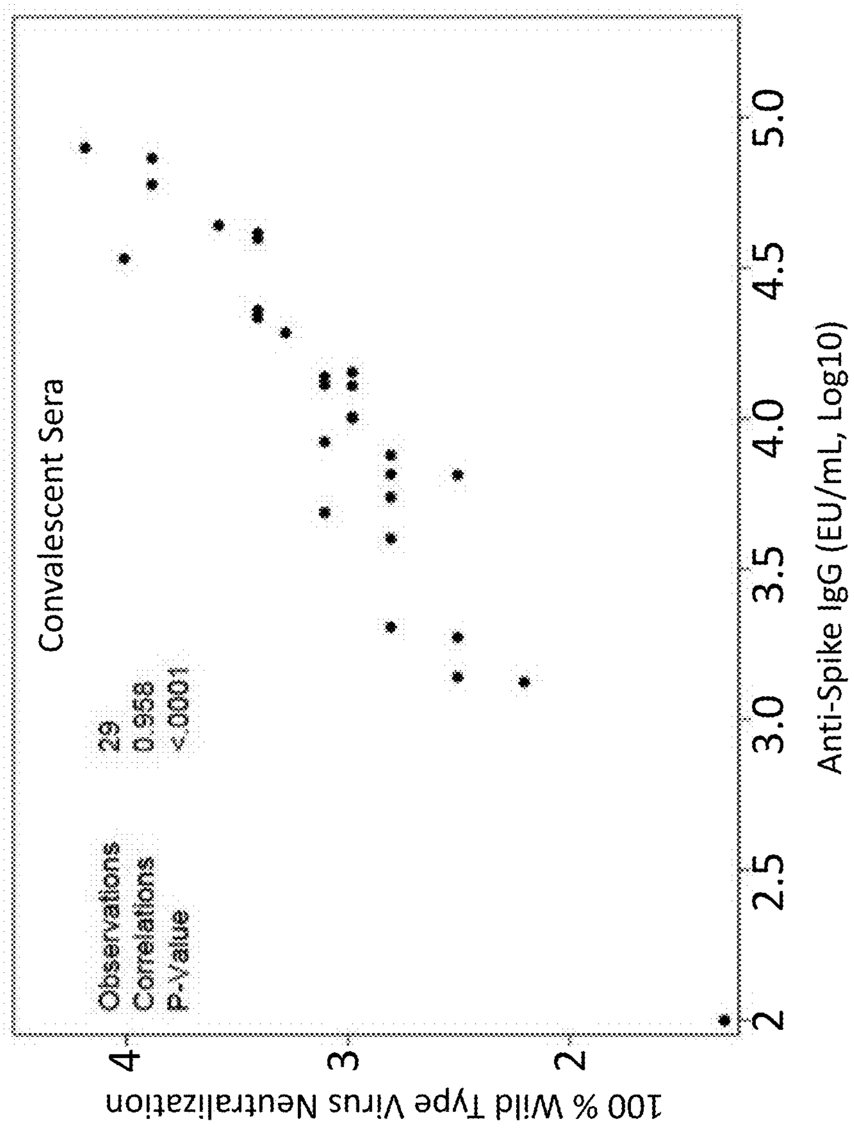
FIGS. 44A-C shows the correlation between anti-CoV S polypeptide IgG and neutralizing antibody titers in patients administered convalescent sera (FIG. 44A), two 25 μg doses of BV2373 (FIG. 44B), and two doses (5 μg and 25 μg) of BV2373 with MATRIX-M™ (FIG. 44C). A strong correlation was observed between neutralizing antibody titers and anti-CoV-S IgG titers in patients treated with convalescent sera or with adjuvanted BV2373, but not in patients treated with BV2373 in the absence of adjuvant.
Figure 44B:
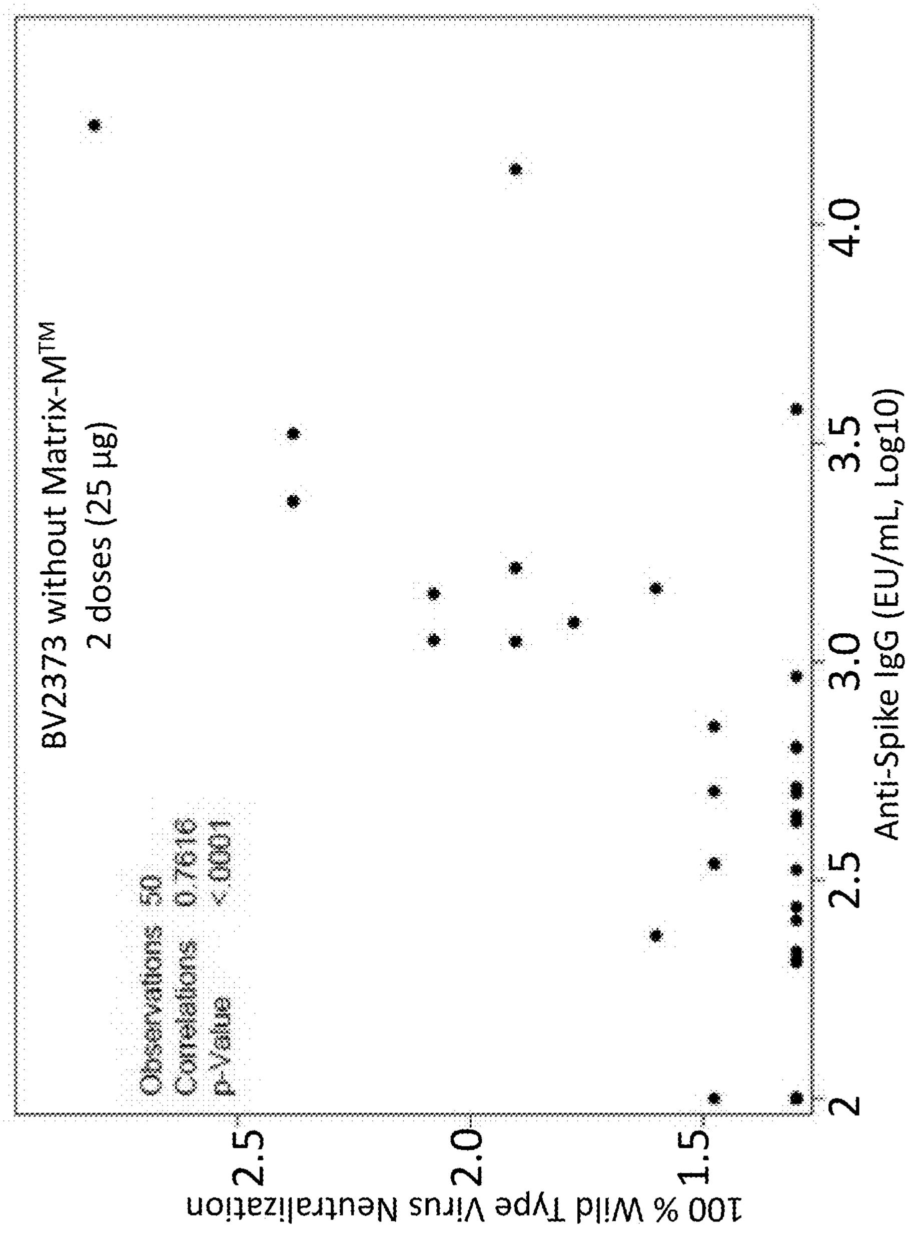
Figure 44C:
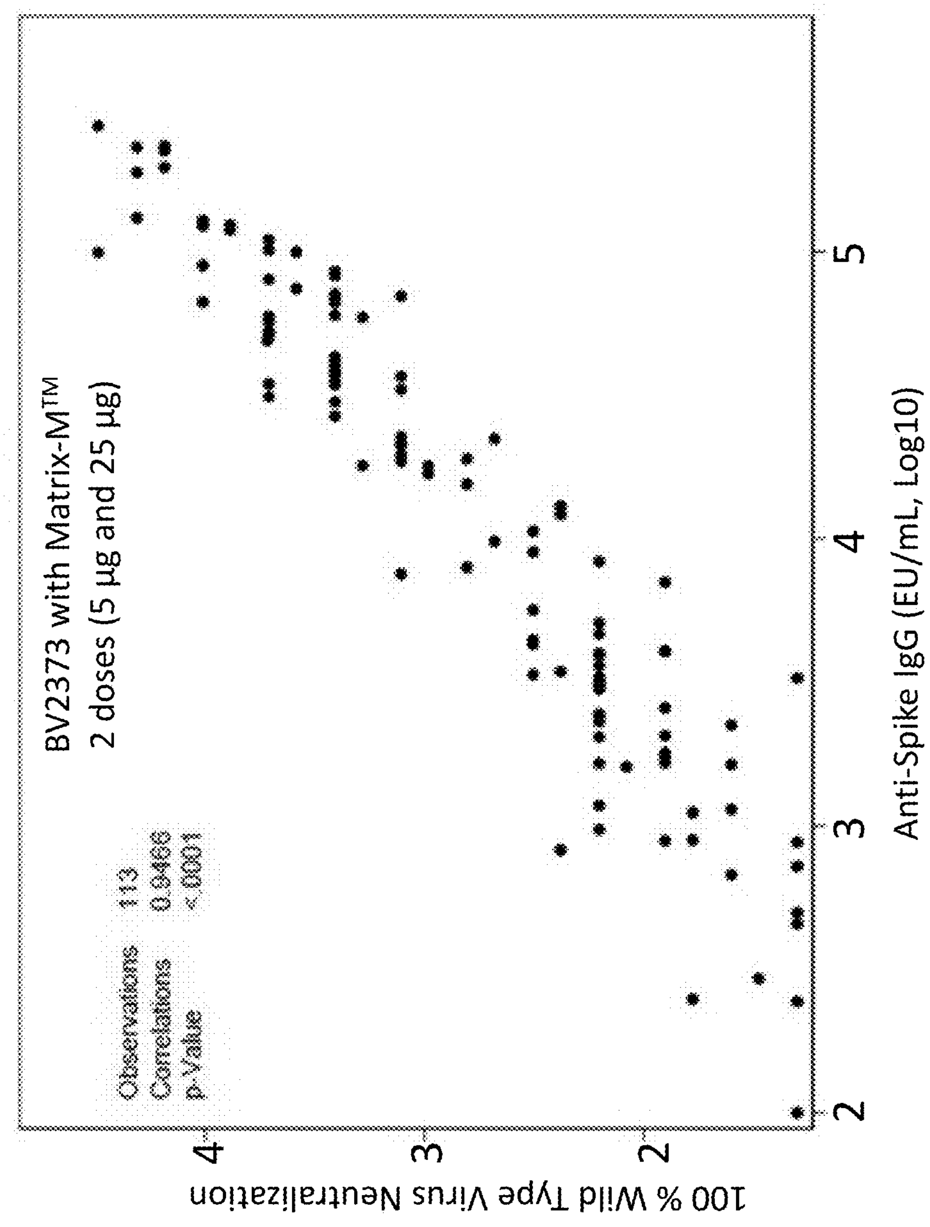
Figure 45A:
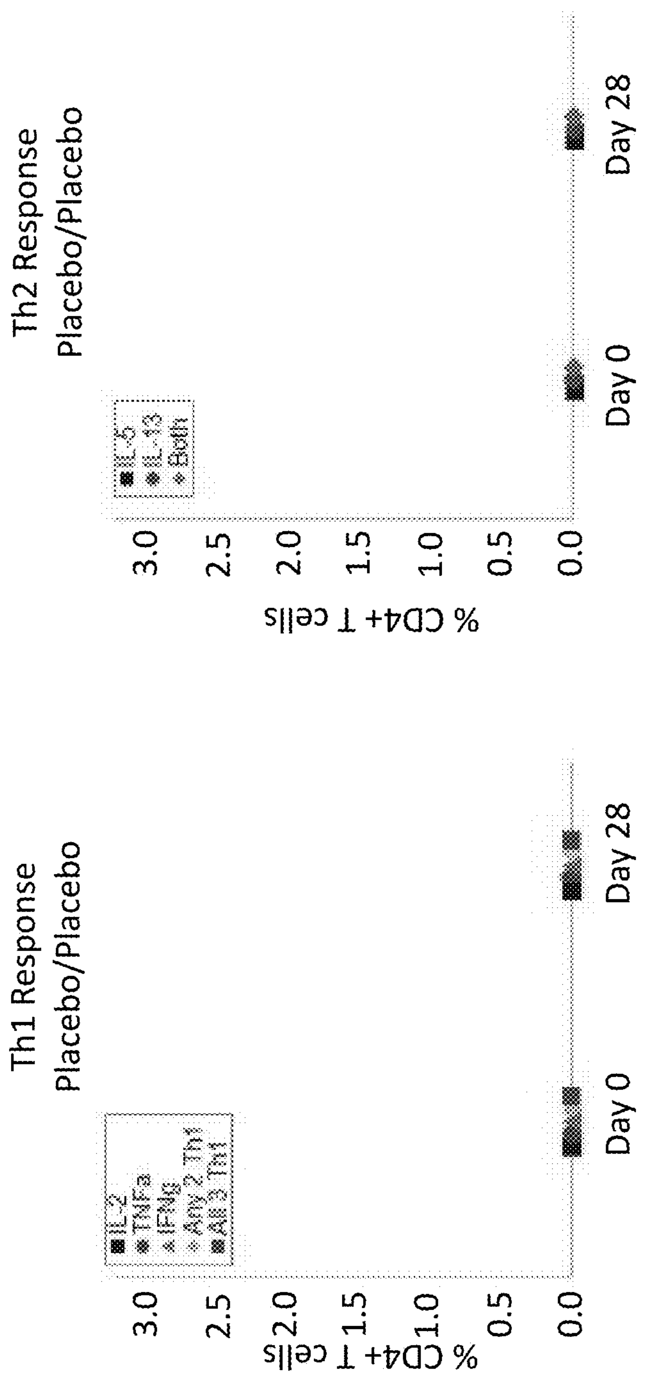
FIGS. 45A-D show the frequencies of antigen-specific $CD4^+$ T cells producing T helper 1 (Th1) cytokines interferon-gamma (IFN-γ), tumor necrosis factor-alpha (TNF-α), and interleukin (IL)-2 and T helper 2 (Th2) cytokines IL-5 and IL-13 indicated cytokines from participants in Groups A (placebo, FIG. 45A), B (25 μg BV2373, FIG. 45B), C (5 μg BV2373 and 50 μg MATRIX-M™, FIG. 45C), and D (25 μg BV2373 and 50 μg MATRIX-M™, FIG. 45D) following stimulation with BV2373. "Any 2" in Th1 cytokine panel means $CD4^+$ T cells that can produce two types of Th1 cytokines at the same time. "All 3" indicates $CD4^+$ T cells that produce IFN-γ, TNF-α, and IL-2 simultaneously. "Both" in Th2 panel means $CD4^+$ T cells that can produce Th2 cytokines IL-5 and IL-13 at the same time.
Figure 45B:
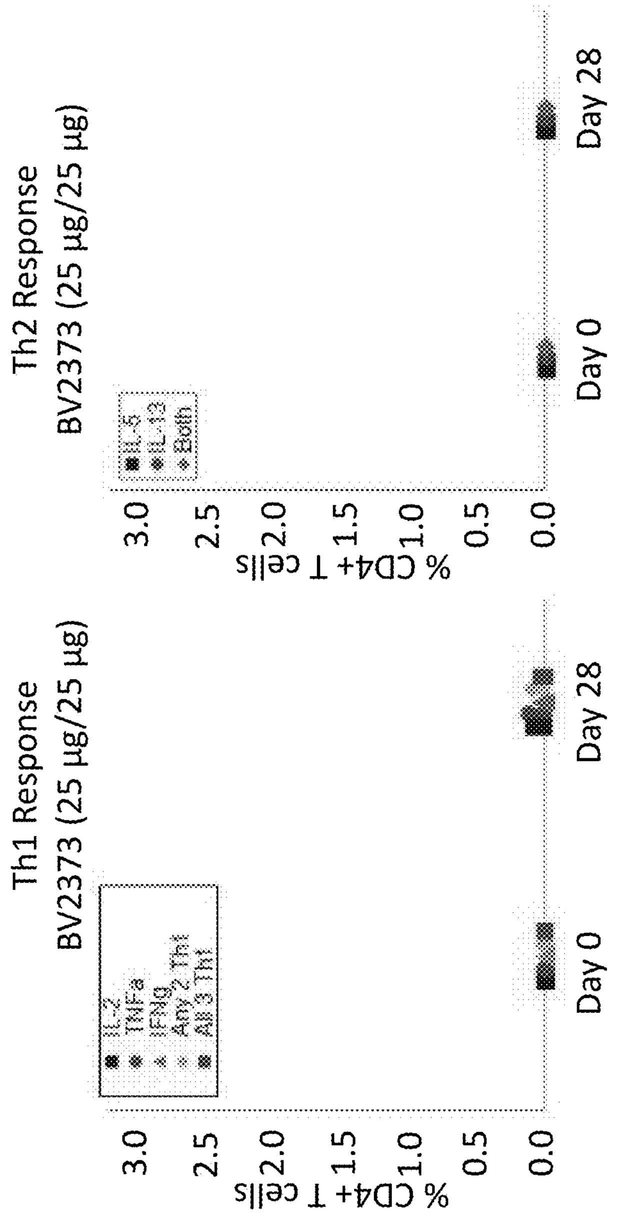
Figure 45C:
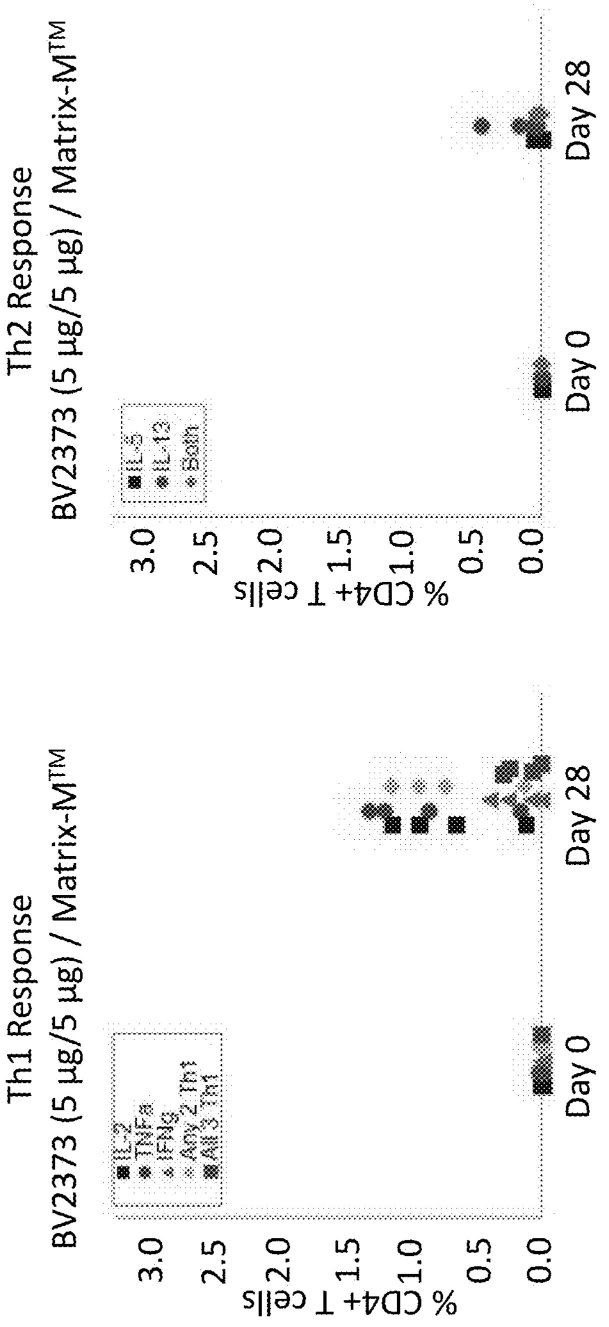
Figure 45D:
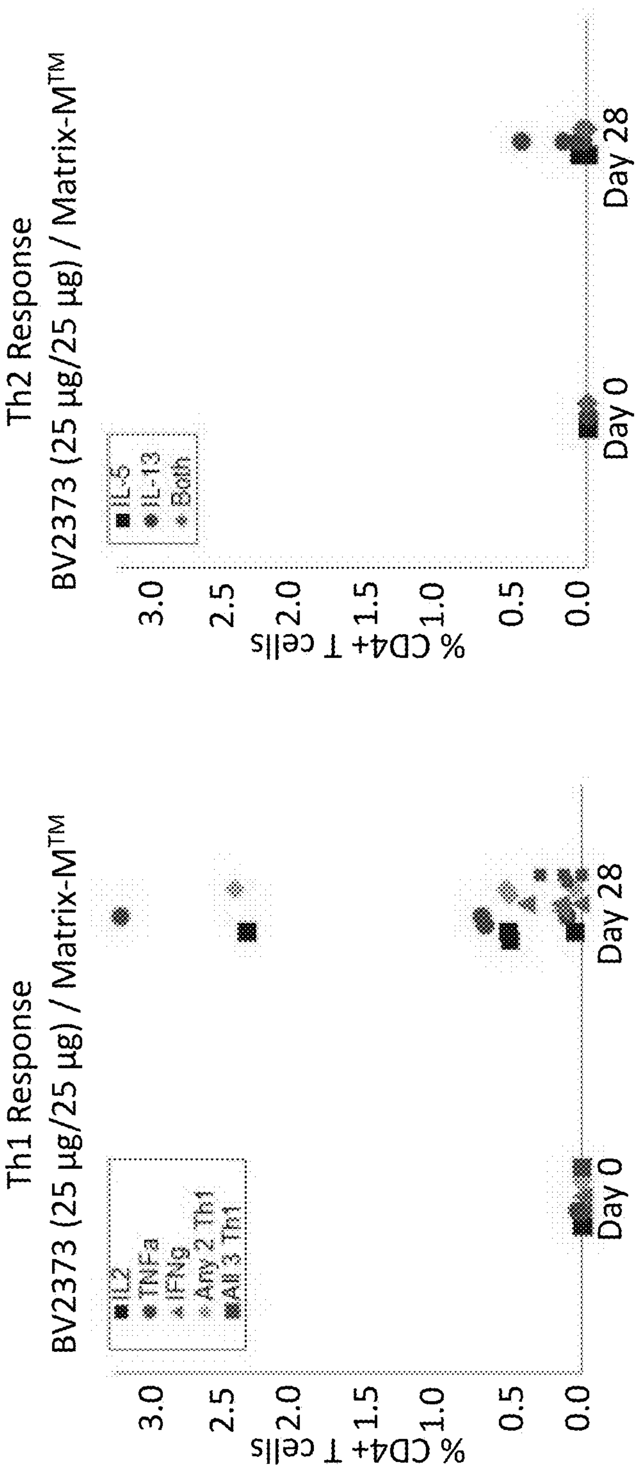

A strong correlation was observed between neutralizing antibody titers and anti-CoV-S IgG in patients treated with BV2373 and MATRIX-M™ (r=0.9466, FIG. 44C) similar to that observed in patients treated with convalescent sera (r=0.958) (FIG. 44A). This correlation was not observed in subjected administered unadjuvanted BV2373 (r=0.7616) (FIG. 44B). Both 5 µg and 25 µg BV2373/ MATRIX-M™ groups (groups C-E of Table 5) demonstrated similar magnitudes of two-dose responses and every participant sero-converted using either assay measurement when a two-dose regimen was utilized.

T-cell responses in 16 participants (four participants from each of Groups A through D) showed that BV2373/MATRIX-M™ regimens induced antigen-specific polyfunctional CD4+ T-cell responses in terms of IFN-γ, IL-2, and TNF-α production upon stimulation with BV2373. There was a strong bias toward production of Th1 cytokines (FIGS. 45A-D).

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

SEQUENCE LISTING

```
Sequence total quantity: 111
SEQ ID NO: 1            moltype = AA  length = 1273
FEATURE                 Location/Qualifiers
source                  1..1273
                        mol_type = protein
                        organism = Betacoronavirus severe acute respiratory
                         syndrome coronavirus 2
SEQUENCE: 1
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
```

```
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 2            moltype = AA  length = 1260
FEATURE                 Location/Qualifiers
source                  1..1260
                        mol_type = protein
                        organism = Betacoronavirus severe acute respiratory
                         syndrome coronavirus 2
SEQUENCE: 2
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPRR ARSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDKVEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260

SEQ ID NO: 3            moltype = AA  length = 1273
FEATURE                 Location/Qualifiers
REGION                  1..1273
                        note = RECOMBINANT S PROTEIN
source                  1..1273
                        mol_type = protein
                        organism = synthetic construct
SEQUENCE: 3
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 4            moltype = AA  length = 1260
FEATURE                 Location/Qualifiers
REGION                  1..1260
                        note = RECOMBINANT S PROTEIN
source                  1..1260
                        mol_type = protein
                        organism = synthetic construct
SEQUENCE: 4
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
```

```
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDKVEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260

SEQ ID NO: 5            moltype = AA  length = 13
FEATURE                 Location/Qualifiers
REGION                  1..13
                        note = SIGNAL PEPTIDE
source                  1..13
                        mol_type = protein
                        organism = synthetic construct
SEQUENCE: 5
MFVFLVLLPL VSS                                                      13

SEQ ID NO: 6            moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 6
RRAR                                                                4

SEQ ID NO: 7            moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 7
QQAQ                                                                4

SEQ ID NO: 8            moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 8
QRAR                                                                4

SEQ ID NO: 9            moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 9
RQAR                                                                4

SEQ ID NO: 10           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 10
RRAQ                                                                4
```

-continued

```
SEQ ID NO: 11           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 11
QQAR                                                                  4

SEQ ID NO: 12           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 12
RQAQ                                                                  4

SEQ ID NO: 13           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 13
QRAQ                                                                  4

SEQ ID NO: 14           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 14
NNAN                                                                  4

SEQ ID NO: 15           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 15
NRAR                                                                  4

SEQ ID NO: 16           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 16
RNAR                                                                  4

SEQ ID NO: 17           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 17
RRAN                                                                  4

SEQ ID NO: 18           moltype = AA  length = 4
FEATURE                 Location/Qualifiers
REGION                  1..4
                        note = RECOMBINANT FURIN CLEAVAGE SITE
source                  1..4
                        mol_type = protein
                        organism = synthetic construct
SEQUENCE: 18
NNAR                                                                  4
```

```
SEQ ID NO: 19          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 19
RNAN                                                                 4

SEQ ID NO: 20          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 20
NRAN                                                                 4

SEQ ID NO: 21          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 21
AAAA                                                                 4

SEQ ID NO: 22          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 22
ARAR                                                                 4

SEQ ID NO: 23          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 23
RAAR                                                                 4

SEQ ID NO: 24          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 24
RRAA                                                                 4

SEQ ID NO: 25          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 25
AAAR                                                                 4

SEQ ID NO: 26          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 26
```

```
RAAA                                                                    4

SEQ ID NO: 27          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 27
ARAA                                                                    4

SEQ ID NO: 28          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 28
GGAG                                                                    4

SEQ ID NO: 29          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 29
GRAR                                                                    4

SEQ ID NO: 30          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 30
RGAR                                                                    4

SEQ ID NO: 31          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 31
RRAG                                                                    4

SEQ ID NO: 32          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 32
GGAR                                                                    4

SEQ ID NO: 33          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
SEQUENCE: 33
RGAG                                                                    4

SEQ ID NO: 34          moltype = AA  length = 4
FEATURE                Location/Qualifiers
REGION                 1..4
                       note = RECOMBINANT FURIN CLEAVAGE SITE
source                 1..4
                       mol_type = protein
                       organism = synthetic construct
```

```
SEQUENCE: 34
GRAG                                                            4

SEQ ID NO: 35          moltype = DNA  length = 3819
FEATURE                Location/Qualifiers
misc_feature           1..3819
                       note = RECOMBINANT SPIKE PROTEIN
source                 1..3819
                       mol_type = other DNA
                       organism = synthetic construct
SEQUENCE: 35
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacgcaggg ctcgctctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctt ggtacatctg gctgggtttc  3660
atcgctggcc tcatcgctat cgtgatggtg accatcatgc tgtgctgcat gacttcatgc  3720
tgctcctgcc tgaagggctg ctgcagctgc ggatcttgct gcaagttcga cgaggacgac  3780
tctgaacccg tcctgaaggg cgtgaagctg cactacacc                        3819

SEQ ID NO: 36          moltype = AA  length = 1279
FEATURE                Location/Qualifiers
REGION                 1..1279
```

```
                        note = RECOMBINANT SPIKE PROTEIN
source                  1..1279
                        mol_type = protein
                        organism = synthetic construct
SEQUENCE: 36
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYTHHHHHH                                              1279

SEQ ID NO: 37           moltype = DNA  length = 3837
FEATURE                 Location/Qualifiers
misc_feature            1..3837
                        note = RECOMBINANT SPIKE PROTEIN
source                  1..3837
                        mol_type = other DNA
                        organism = synthetic construct
SEQUENCE: 37
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacgcaggg ctcgctctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
```

```
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctt ggtacatctg gctgggtttc  3660
atcgctggcc tcatcgctat cgtgatggtg accatcatgc tgtgctgcat gacttcatgc  3720
tgctcctgcc tgaagggctg ctgcagctgc ggatcttgct gcaagttcga cgaggacgac  3780
tctgaacccg tcctgaaggg cgtgaagctg cactacaccc accaccacca ccaccac     3837
```

```
SEQ ID NO: 38           moltype = AA  length = 1266
FEATURE                 Location/Qualifiers
REGION                  1..1266
                        note = RECOMBINANT SPIKE PROTEIN
source                  1..1266
                        mol_type = protein
                        organism = synthetic construct
SEQUENCE: 38
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPRR ARSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDKVEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260
HHHHHH                                                            1266
```

```
SEQ ID NO: 39           moltype = AA  length = 60
FEATURE                 Location/Qualifiers
REGION                  1..60
                        note = RECOMBINANT SPIKE PROTEIN
source                  1..60
                        mol_type = protein
                        organism = synthetic construct
SEQUENCE: 39
WYIWLGFIAG LIAIVMVTIM LCCMTSCCSC LKGCCSCGSC CKFDEDDSEP VLKGVKLHYT  60
```

```
SEQ ID NO: 40           moltype = AA  length = 1213
FEATURE                 Location/Qualifiers
REGION                  1..1213
                        note = RECOMBINANT SPIKE PROTEIN
source                  1..1213
                        mol_type = protein
                        organism = synthetic construct
SEQUENCE: 40
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
```

```
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWP                                                   1213

SEQ ID NO: 41          moltype = AA  length = 1200
FEATURE                Location/Qualifiers
REGION                 1..1200
                       note = RECOMBINANT SPIKE PROTEIN
source                 1..1200
                       mol_type = protein
                       organism = synthetic construct
SEQUENCE: 41
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPRR ARSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDKVEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200

SEQ ID NO: 42          moltype = AA  length = 1219
FEATURE                Location/Qualifiers
REGION                 1..1219
                       note = RECOMBINANT SPIKE PROTEIN
source                 1..1219
                       mol_type = protein
                       organism = synthetic construct
SEQUENCE: 42
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPHHHHHH                                             1219

SEQ ID NO: 43          moltype = DNA  length = 3657
FEATURE                Location/Qualifiers
misc_feature           1..3657
                       note = RECOMBINANT SPIKE PROTEIN
source                 1..3657
                       mol_type = other DNA
```

```
                        organism = synthetic construct
SEQUENCE: 43
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacgcaggg ctcgctctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctc accaccacca ccaccac     3657

SEQ ID NO: 44           moltype = AA  length = 1219
FEATURE                 Location/Qualifiers
REGION                  1..1219
                        note = RECOMBINANT SPIKE PROTEIN
source                  1..1219
                        mol_type = protein
                        organism = synthetic construct
SEQUENCE: 44
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
```

```
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPHHHHHH                                               1219

SEQ ID NO: 45          moltype = AA  length = 318
FEATURE                Location/Qualifiers
REGION                 1..318
                       note = RECOMBINANT SPIKE PROTEIN
source                 1..318
                       mol_type = protein
                       organism = synthetic construct
SEQUENCE: 45
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPN                                                318

SEQ ID NO: 46          moltype = AA  length = 955
FEATURE                Location/Qualifiers
REGION                 1..955
                       note = RECOMBINANT SPIKE PROTEIN
source                 1..955
                       mol_type = protein
                       organism = synthetic construct
SEQUENCE: 46
MFVFLVLLPL VSSITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNFNFNGLTG TGVLTESNKK  240
FLPFQQFGRD IADTTDAVRD PQTLEILDIT PCSFGGVSVI TPGTNTSNQV AVLYQDVNCT  300
EVPVAIHADQ LTPTWRVYST GSNVFQTRAG CLIGAEHVNN SYECDIPIGA GICASYQTQT  360
NSPRRARSVA SQSIIAYTMS LGAENSVAYS NNSIAIPTNF TISVTTEILP VSMTKTSVDC  420
TMYICGDSTE CSNLLLQYGS FCTQLNRALT GIAVEQDKNT QEVFAQVKQI YKTPPIKDFG  480
GFNFSQILPD PSKPSKRSFI EDLLFNKVTL ADAGFIKQYG DCLGDIAARD LICAQKFNGL  540
TVLPPLLTDE MIAQYTSALL AGTITSGWTF GAGAALQIPF AMQMAYRFNG IGVTQNVLYE  600
NQKLIANQFN SAIGKIQDSL SSTASALGKL QDVVNQNAQA LNTLVKQLSS NFGAISSVLN  660
DILSRLDKVE AEVQIDRLIT GRLQSLQTYV TQQLIRAAEI RASANLAATK MSECVLGQSK  720
RVDFCGKGYH LMSFPQSAPH GVVFLHVTYV PAQEKNFTTA PAICHDGKAH FPREGVFVSN  780
GTHWFVTQRN FYEPQIITTD NTFVSGNCDV VIGIVNNTVY DPLQPELDSF KEELDKYFKN  840
HTSPDVDLGD ISGINASVVN IQKEIDRLNE VAKNLNESLI DLQELGKYEQ YIKWPWYIWL  900
GFIAGLIAIV MVTIMLCCMT SCCSCLKGCC SCGSCCKFDE DDSEPVLKGV KLHYT       955

SEQ ID NO: 47          moltype = DNA  length = 2868
FEATURE                Location/Qualifiers
misc_feature           1..2868
                       note = RECOMBINANT SPIKE PROTEIN
source                 1..2868
                       mol_type = other DNA
                       organism = synthetic construct
SEQUENCE: 47
atgttcgtct tcctggtgct gctgcccctg gtgtccagca tcactaacct gtgccccttc  60
ggagaggtct tcaacgccac ccgcttcgct tccgtgtacg cctggaacag gaagagaatc  120
tcaaactgcg tcgctgacta ctccgtgctg tacaactcag cctccttcag caccttcaag  180
tgctacggcg tgtcaccaac taagctgaac gacctgtgct tcaccaacgt ctacgccgac  240
tccttcgtga tcaggggaga cgaggtcaga cagatcgctc ctggccagac tggaaagatc  300
gccgactaca actacaagct gcccgacgac ttcaccggtt gcgtcatcgc ttggaacagc  360
aacaacctgg actctaaagt gggtggcaac tacaactacc tgtaccgcct gttccgtaag  420
tcaaacctga agccattcga gagggacatc agcactgaaa tctaccaggc cggatctacc  480
ccttgcaacg gtgtcgaggg cttcaactgc tacttccccc tgcagtccta cggtttccag  540
ccaactaacg gtgtgggcta ccagccttac agagtggtcg tgctgagctt cgaactgctc  600
cacgctcctg ctactgtgtg cggtccaaag aagtctacca acctggtcaa gaacaagtgc  660
gtgaacttca acttcaacgg cctgaccgga actggtgtcc tgaccgagag caacaagaag  720
ttcctgccct tccagcagtt cggaagggac atcgctgaca ccactgacgc tgtgcgcgac  780
cctcagaccc tggaaatcct ggacatcact ccatgctcat tcggaggtgt ctccgtgatc  840
accccctggca ccaacacttc taaccaggtc gctgtgctgt accaggacgt caactgcacc  900
gaggtccctg tggccatcca cgctgaccag ctgaccccca cttggcgcgt gtactccacc  960
```

-continued

```
ggcagcaacg tgttccagac tcgtgctggt tgcctgatcg gcgccgagca cgtgaacaac  1020
agctacgaat gcgacatccc catcggcgct ggaatctgcg cctcttacca gacccagact  1080
aacagcccac gcagggctcg ctctgtggcc tctcagtcaa tcatcgctta caccatgtca  1140
ctgggcgctg aaaactccgt ggcctactct aacaactcaa tcgccatccc caccaacttc  1200
actatcagcg tgaccactga gatcctgcca gtcagcatga ccaagacttc tgtggactgc  1260
actatgtaca tctgcggaga cagcaccgaa tgctctaacc tgctgctgca gtacggctct  1320
ttctgcaccc agctgaaccg tgctctgact ggaatcgccg tggagcagga caagaacact  1380
caggaagtct tcgctcaggt gaagcaaatc tacaagaccc cacctatcaa ggacttcggc  1440
ggattcaact tctcccagat cctgcctgac ccctccaagc caagcaagcg ctctttcatc  1500
gaggacctgc tgttcaacaa ggtcactctg gccgacgctg gattcatcaa gcagtacgga  1560
gactgcctgg gtgacatcgc cgctcgtgac ctgatctgcg ctcagaagtt caacggtctg  1620
accgtgctgc ccccactgct gactgacgaa atgatcgccc agtacactag cgccctgctg  1680
gctggaacca tcacttctgg ttggaccttc ggtgctggcg ccgctctgca gatccctttc  1740
gctatgcaga tggcctaccg tttcaacgga atcggtgtca cccagaacgt gctgtacgag  1800
aaccagaagc tgatcgctaa ccagttcaac tcagccatcg gaaagatcca ggacagcctg  1860
agctctactg cctctgctct gggcaagctg caggacgtcg tgaaccagaa cgcccaggct  1920
ctgaacaccc tggtcaagca gctgtcatcc aacttcggtg ctatcagctc tgtgctgaac  1980
gacatcctgt cccgcctgga caaggtcgag gccgaagtgc agatcgaccg cctgatcact  2040
ggccgtctgc agtcactgca gacctacgtg actcagcagc tgatcagggc cgctgaaatc  2100
agagcctccg ctaacctggc cgctaccaag atgagcgagt gcgtcctggg tcaatctaag  2160
cgtgtggact tctgcggcaa gggataccac ctgatgtcat tccctcagtc tgctccccac  2220
ggtgtggtgt tcctgcacgt cacctacgtg ccagcccagg agaagaactt caccactgcc  2280
cctgctatct gccacgacgg caaggctcac ttccccaggg aaggtgtctt cgtgagcaac  2340
ggcacccact ggttcgtcac tcagagaaac ttctacgagc cacagatcat caccactgac  2400
aacactttcg tgtctggaaa ctgcgacgtg gtcatcggta tcgtcaacaa caccgtgtac  2460
gacccccctgc agccagagct ggactcattc aaggaggaac tggacaagta cttcaagaac  2520
cacacctccc ctgacgtcga cctgggcgac atctcaggaa tcaacgcttc cgtcgtgaac  2580
atccagaagg agatcgaccg cctgaacgaa gtggccaaga acctgaacga aagcctgatc  2640
gacctgcagg agctgggcaa gtacgaacag tacatcaagt ggccttggta catctggctg  2700
ggtttcatcg ctggcctcat cgctatcgtg atggtgacca tcatgctgtg ctgcatgact  2760
tcatgctgct cctgcctgaa gggctgctgc agctgcggat cttgctgcaa gttcgacgag  2820
gacgactctg aacccgtcct gaagggcgtg aagctgcact acacctaa              2868
```

```
SEQ ID NO: 48          moltype = AA  length = 942
FEATURE                Location/Qualifiers
REGION                 1..942
                       note = RECOMBINANT SPIKE PROTEIN
source                 1..942
                       mol_type = protein
                       organism = synthetic construct
SEQUENCE: 48
ITNLCPFGEV FNATRFASVY AWNRKRISNC VADYSVLYNS ASFSTFKCYG VSPTKLNDLC  60
FTNVYADSFV IRGDEVRQIA PGQTGKIADY NYKLPDDFTG CVIAWNSNNL DSKVGGNYNY  120
LYRLFRKSNL KPFERDISTE IYQAGSTPCN GVEGFNCYFP LQSYGFQPTN GVGYQPYRVV  180
VLSFELLHAP ATVCGPKKST NLVKNKCVNF NFNGLTGTGV LTESNKKFLP FQQFGRDIAD  240
TTDAVRDPQT LEILDITPCS FGGVSVITPG TNTSNQVAVL YQDVNCTEVP VAIHADQLTP  300
TWRVYSTGSN VFQTRAGCLI GAEHVNNSYE CDIPIGAGIC ASYQTQTNSP RRARSVASQS  360
IIAYTMSLGA ENSVAYSNNS IAIPTNFTIS VTTEILPVSM TKTSVDCTMY ICGDSTECSN  420
LLLQYGSFCT QLNRALTGIA VEQDKNTQEV FAQVKQIYKT PPIKDFGGFN FSQILPDPSK  480
PSKRSFIEDL LFNKVTLADA GFIKQYGDCL GDIAARDLIC AQKFNGLTVL PPLLTDEMIA  540
QYTSALLAGT ITSGWTFGAG AALQIPFAMQ MAYRFNGIGV TQNVLYENQK LIANQFNSAI  600
GKIQDSLSST ASALGKLQDV VNQNAQALNT LVKQLSSNFG AISSVLNDIL SRLDKVEAEV  660
QIDRLITGRL QSLQTYVTQQ LIRAAEIRAS ANLAATKMSE CVLGQSKRVD FCGKGYHLMS  720
FPQSAPHGVV FLHVTYVPAQ EKNFTTAPAI CHDGKAHFPR EGVFVSNGTH WFVTQRNFYE  780
PQIITTDNTF VSGNCDVVIG IVNNTVYDPL QPELDSFKEE LDKYFKNHTS PDVDLGDISG  840
INASVVNIQK EIDRLNEVAK NLNESLIDLQ ELGKYEQYIK WPWYIWLGFI AGLIAIVMVT  900
IMLCCMTSCC SCLKGCCSCG SCCKFDEDDS EPVLKGVKLH YT                    942
```

```
SEQ ID NO: 49          moltype = AA  length = 960
FEATURE                Location/Qualifiers
REGION                 1..960
                       note = RECOMBINANT SPIKE PROTEIN
source                 1..960
                       mol_type = protein
                       organism = synthetic construct
SEQUENCE: 49
MFVFLVLLPL VSSITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNFNFNGLTG TGVLTESNKK  240
FLPFQQFGRD IADTTDAVRD PQTLEILDIT PCSFGGVSVI TPGTNTSNQV AVLYQDVNCT  300
EVPVAIHADQ LTPTWRVYST GSNVFQTRAG CLIGAEHVNN SYECDIPIGA GICASYQTQT  360
NSPRRARSVA SQSIIAYTMS LGAENSVAYS NNSIAIPTNF TISVTTEILP VSMTKTSVDC  420
TMYICGDSTE CSNLLLQYGS FCTQLNRALT GIAVEQDKNT QEVFAQVKQI YKTPPIKDFG  480
GFNFSQILPD PSKPSKRSFI EDLLFNKVTL ADAGFIKQYG DCLGDIAARD LICAQKFNGL  540
TVLPPLLTDE MIAQYTSALL AGTITSGWTF GAGAALQIPF AMQMAYRFNG IGVTQNVLYE  600
NQKLIANQFN SAIGKIQDSL SSTASALGKL QDVVNQNAQA LNTLVKQLSS NFGAISSVLN  660
DILSRLDKVE AEVQIDRLIT GRLQSLQTYV TQQLIRAAEI RASANLAATK MSECVLGQSK  720
RVDFCGKGYH LMSFPQSAPH GVVFLHVTYV PAQEKNFTTA PAICHDGKAH FPREGVFVSN  780
```

```
GTHWFVTQRN FYEPQIITTD NTFVSGNCDV VIGIVNNTVY DPLQPELDSF KEELDKYFKN  840
HTSPDVDLGD ISGINASVVN IQKEIDRLNE VAKNLNESLI DLQELGKYEQ YIKWPWYIWL  900
GFIAGLIAIV MVTIMLCCMT SCCSCLKGCC SCGSCCKFDE DDSEPVLKGV KLHYTHHHHH  960

SEQ ID NO: 50          moltype = DNA  length = 2883
FEATURE                Location/Qualifiers
misc_feature           1..2883
                       note = RECOMBINANT SPIKE PROTEIN
source                 1..2883
                       mol_type = other DNA
                       organism = synthetic construct
SEQUENCE: 50
atgttcgtct tcctggtgct gctgcccctg gtgtccagca tcactaacct gtgccccttc  60
ggagaggtct tcaacgccac ccgcttcgct tccgtgtacg cctggaacag gaagagaatc  120
tcaaactgcg tcgctgacta ctccgtgctg tacaactcag cctccttcag caccttcaag  180
tgctacggcg tgtcaccaac taagctgaac gacctgtgct tcaccaacgt ctacgccgac  240
tccttcgtga tcaggggaga cgaggtcaga cagatcgctc ctggccagac tggaaagatc  300
gccgactaca actacaagct gcccgacgac ttcaccggtt gcgtcatcgc ttggaacagc  360
aacaacctgg actctaaagt gggtggcaac tacaactacc tgtaccgcct gttccgtaag  420
tcaaacctga agccattcga gagggacatc agcactgaaa tctaccaggc cggatctacc  480
ccttgcaacg gtgtcgaggg cttcaactgc tacttccccc tgcagtccta cggtttccag  540
ccaactaacg gtgtgggcta ccagccttac agagtggtcg tgctgagctt cgaactgctc  600
cacgctcctg ctactgtgtg cggtccaaag aagtctacca acctggtcaa gaacaagtgc  660
gtgaacttca acttcaacgg cctgaccgga actggtgtcc tgaccgagag caacaagaag  720
ttcctgccct tccagcagtt cggaagggac atcgctgaca ccactgacgc tgtgcgcgac  780
cctcagaccc tggaaatcct ggacatcact ccatgctcat tcggaggtgt ctccgtgatc  840
acccctggca ccaacacttc taaccaggtc gctgtgctgt accaggacgt caactgcacc  900
gaggtccctg tggccatcca cgctgaccag ctgaccccca cttggcgcgt gtactccacc  960
ggcagcaacg tgttccagac tcgtgctggt tgcctgatcg gcgccgagca cgtgaacaac  1020
agctacgaat gcgacatccc catcggcgct ggaatctgcg cctcttacca gacccagact  1080
aacagcccac gcagggctcg ctctgtggcc tctcagtcaa tcatcgctta caccatgtca  1140
ctgggcgctg aaaactccgt ggcctactct aacaactcaa tcgccatccc caccaacttc  1200
actatcagcg tgaccactga gatcctgcca gtcagcatga ccaagacttc tgtggactgc  1260
actatgtaca tctgcggaga cagcaccgaa tgctctaacc tgctgctgca gtacggctct  1320
ttctgcaccc agctgaaccg tgctctgact ggaatcgccg tggagcagga caagaacact  1380
caggaagtct tcgctcaggt gaagcaaatc tacaagaccc cacctatcaa ggacttcggc  1440
ggattcaact tctcccagat cctgcctgac ccctccaagc caagcaagcg ctctttcatc  1500
gaggacctgc tgttcaacaa ggtcactctg gccgacgctg gattcatcaa gcagtacgga  1560
gactgcctgg gtgacatcgc cgctcgtgac ctgatctgcg ctcagaagtt caacggtctg  1620
accgtgctgc ccccactgct gactgacgaa atgatcgccc agtacactag cgccctgctg  1680
gctggaacca tcacttctgg ttggaccttc ggtgctggcg ccgctctgca gatccctttc  1740
gctatgcaga tggcctaccg tttcaacgga atcggtgtca cccagaacgt gctgtacgag  1800
aaccagaagc tgatcgctaa ccagttcaac tcagccatcg gaaagatcca ggacagcctg  1860
agctctactg cctctgctct gggcaagctg caggacgtcg tgaaccagaa cgcccaggct  1920
ctgaacaccc tggtcaagca gctgtcatcc aacttcggtg ctatcagctc tgtgctgaac  1980
gacatcctgt cccgcctgga caaggtcgag gccgaagtgc agatcgaccg cctgatcact  2040
ggccgtctgc agtcactgca gacctacgtg actcagcagc tgatcagggc cgctgaaatc  2100
agagcctccg ctaacctggc cgctaccaag atgagcgagt gcgtcctggg tcaatctaag  2160
cgtgtggact tctgcggcaa gggataccac ctgatgtcat tccctcagtc tgctccccac  2220
ggtgtggtgt tcctgcacgt cacctacgtg ccagcccagg agaagaactt caccactgcc  2280
cctgctatct gccacgacgg caaggctcac ttccccaggg aaggtgtctt cgtgagcaac  2340
ggcacccact ggttcgtcac tcagagaaac ttctacgagc cacagatcat caccactgac  2400
aacactttcg tgtctggaaa ctgcgacgtg gtcatcggta tcgtcaacaa caccgtgtac  2460
gacccccctgc agccagagct ggactcattc aaggaggaac tggacaagta cttcaagaac  2520
cacacctccc ctgacgtcga cctgggcgac atctcaggaa tcaacgcttc cgtcgtgaac  2580
atccagaagg agatcgaccg cctgaacgaa gtggccaaga acctgaacga aagcctgatc  2640
gacctgcagg agctgggcaa gtacgaacag tacatcaagt ggccttggta catctggctg  2700
ggtttcatcg ctggcctcat cgctatcgtg atggtgacca tcatgctgtg ctgcatgact  2760
tcatgctgct cctgcctgaa gggctgctgc agctgcggat cttgctgcaa gttcgacgag  2820
gacgactctg aacccgtcct gaagggcgtg aagctgcact acacccacca ccaccaccac  2880
cac                                                                2883

SEQ ID NO: 51          moltype = AA  length = 947
FEATURE                Location/Qualifiers
REGION                 1..947
                       note = RECOMBINANT SPIKE PROTEIN
source                 1..947
                       mol_type = protein
                       organism = synthetic construct
SEQUENCE: 51
ITNLCPFGEV FNATRFASVY AWNRKRISNC VADYSVLYNS ASFSTFKCYG VSPTKLNDLC  60
FTNVYADSFV IRGDEVRQIA PGQTGKIADY NYKLPDDFTG CVIAWNSNNL DSKVGGNYNY  120
LYRLFRKSNL KPFERDISTE IYQAGSTPCN GVEGFNCYFP LQSYGFQPTN GVGYQPYRVV  180
VLSFELLHAP ATVCGPKKST NLVKNKCVNF NFNGLTGTGV LTESNKKFLP FQQFGRDIAD  240
TTDAVRDPQT LEILDITPCS FGGVSVITPG TNTSNQVAVL YQDVNCTEVP VAIHADQLTP  300
TWRVYSTGSN VFQTRAGCLI GAEHVNNSYE CDIPIGAGIC ASYQTQTNSP RRARSVASQS  360
IIAYTMSLGA ENSVAYSNNS IAIPTNFTIS VTTEILPVSM TKTSVDCTMY ICGDSTECSN  420
LLLQYGSFCT QLNRALTGIA VEQDKNTQEV FAQVKQIYKT PPIKDFGGFN FSQILPDPSK  480
PSKRSFIEDL LFNKVTLADA GFIKQYGDCL GDIAARDLIC AQKFNGLTVL PPLLTDEMIA  540
```

```
QYTSALLAGT ITSGWTFGAG AALQIPFAMQ MAYRFNGIGV TQNVLYENQK LIANQFNSAI  600
GKIQDSLSST ASALGKLQDV VNQNAQALNT LVKQLSSNFG AISSVLNDIL SRLDKVEAEV  660
QIDRLITGRL QSLQTYVTQQ LIRAAEIRAS ANLAATKMSE CVLGQSKRVD FCGKGYHLMS  720
FPQSAPHGVV FLHVTYVPAQ EKNFTTAPAI CHDGKAHFPR EGVFVSNGTH WFVTQRNFYE  780
PQIITTDNTF VSGNCDVVIG IVNNTVYDPL QPELDSFKEE LDKYFKNHTS PDVDLGDISG  840
INASVVNIQK EIDRLNEVAK NLNESLIDLQ ELGKYEQYIK WPWYIWLGFI AGLIAIVMVT  900
IMLCCMTSCC SCLKGCCSCG SCCKFDEDDS EPVLKGVKLH YTHHHHH                947

SEQ ID NO: 52           moltype = AA  length = 901
FEATURE                 Location/Qualifiers
REGION                  1..901
                        note = RECOMBINANT SPIKE PROTEIN
source                  1..901
                        mol_type = protein
                        organism = synthetic construct
SEQUENCE: 52
MFVFLVLLPL VSSITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNFNFNGLTG TGVLTESNKK  240
FLPFQQFGRD IADTTDAVRD PQTLEILDIT PCSFGGVSVI TPGTNTSNQV AVLYQDVNCT  300
EVPVAIHADQ LTPTWRVYST GSNVFQTRAG CLIGAEHVNN SYECDIPIGA GICASYQTQT  360
NSPRRARSVA SQSIIAYTMS LGAENSVAYS NNSIAIPTNF TISVTTEILP VSMTKTSVDC  420
TMYICGDSTE CSNLLLQYGS FCTQLNRALT GIAVEQDKNT QEVFAQVKQI YKTPPIKDFG  480
GFNFSQILPD PSKPSKRSFI EDLLFNKVTL ADAGFIKQYG DCLGDIAARD LICAQKFNGL  540
TVLPPLLTDE MIAQYTSALL AGTITSGWTF GAGAALQIPF AMQMAYRFNG IGVTQNVLYE  600
NQKLIANQFN SAIGKIQDSL SSTASALGKL QDVVNQNAQA LNTLVKQLSS NFGAISSVLN  660
DILSRLDKVE AEVQIDRLIT GRLQSLQTYV TQQLIRAAEI RASANLAATK MSECVLGQSK  720
RVDFCGKGYH LMSFPQSAPH GVVFLHVTYV PAQEKNFTTA PAICHDGKAH FPREGVFVSN  780
GTHWFVTQRN FYEPQIITTD NTFVSGNCDV VIGIVNNTVY DPLQPELDSF KEELDKYFKN  840
HTSPDVDLGD ISGINASVVN IQKEIDRLNE VAKNLNESLI DLQELGKYEQ YIKWPHHHHH  900
H                                                                 901

SEQ ID NO: 53           moltype = DNA  length = 2706
FEATURE                 Location/Qualifiers
misc_feature            1..2706
                        note = RECOMBINANT SPIKE PROTEIN
source                  1..2706
                        mol_type = other DNA
                        organism = synthetic construct
SEQUENCE: 53
atgttcgtct tcctggtgct gctgcccctg gtgtccagca tcactaacct gtgccccttc  60
ggagaggtct tcaacgccac ccgcttcgct tccgtgtacg cctggaacag gaagagaatc  120
tcaaactgcg tcgctgacta ctccgtgctg tacaactcag cctccttcag caccttcaag  180
tgctacggcg tgtcaccaac taagctgaac gacctgtgct tcaccaacgt ctacgccgac  240
tccttcgtga tcaggggaga cgaggtcaga cagatcgctc ctggccagac tggaaagatc  300
gccgactaca actacaagct gcccgacgac ttcaccggtt gcgtcatcgc ttggaacagc  360
aacaacctgg actctaaagt gggtggcaac tacaactacc tgtaccgcct gttccgtaag  420
tcaaacctga agccattcga gagggacatc agcactgaaa tctaccaggc cggatctacc  480
ccttgcaacg gtgtcgaggg cttcaactgc tacttccccc tgcagtccta cggtttccag  540
ccaactaacg gtgtgggcta ccagccttac agagtggtcg tgctgagctt cgaactgctc  600
cacgctcctg ctactgtgtg cggtccaaag aagtctacca acctggtcaa gaacaagtgc  660
gtgaacttca acttcaacgg cctgaccgga actggtgtcc tgaccgagag caacaagaag  720
ttcctgccct tccagcagtt cggaagggac atcgctgaca ccactgacgc tgtgcgcgac  780
cctcagaccc tggaaatcct ggacatcact ccatgctcat tcggaggtgt ctccgtgatc  840
accccctggca ccaacacttc taaccaggtc gctgtgctgt accaggacgt caactgcacc  900
gaggtccctg tggccatcca cgctgaccag ctgacccccca cttggcgcgt gtactccacc  960
ggcagcaacg tgttccagac tcgtgctggt tgcctgatcg gcgccgagca cgtgaacaac  1020
agctacgaat gcgacatccc catcggcgct ggaatctgcg cctcttacca gacccagact  1080
aacagcccac gcagggctcg ctctgtggcc tctcagtcaa tcatcgctta caccatgtca  1140
ctgggcgctg aaaactccgt ggcctactct aacaactcaa tcgccatccc caccaacttc  1200
actatcagcg tgaccactga gatcctgcca gtcagcatga ccaagacttc tgtggactgc  1260
actatgtaca tctgcggaga cagcaccgaa tgctctaacc tgctgctgca gtacggctct  1320
ttctgcaccc agctgaaccg tgctctgact ggaatcgccg tggagcagga caagaacact  1380
caggaagtct tcgctcaggt gaagcaaatc tacaagaccc cacctatcaa ggacttcggc  1440
ggattcaact tctcccagat cctgcctgac ccctccaagc caagcaagcg ctctttcatc  1500
gaggacctgc tgttcaacaa ggtcactctg gccgacgctg gattcatcaa gcagtacgga  1560
gactgcctgg gtgacatcgc cgctcgtgac ctgatctgcg ctcagaagtt caacggtctg  1620
accgtgctgc ccccactgct gactgacgaa atgatcgccc agtacactag cgccctgctg  1680
gctggaacca tcacttctgg ttggaccttc ggtgctggcg ccgctctgca gatccctttc  1740
gctatgcaga tggcctaccg tttcaacgga atcggtgtca cccagaacgt gctgtacgag  1800
aaccagaagc tgatcgctaa ccagttcaac tcagccatcg gaaagatcca ggacagcctg  1860
agctctactg cctctgctct gggcaagctg caggacgtcg tgaaccagaa cgcccaggct  1920
ctgaacaccc tggtcaagca gctgtcatcc aacttcggtg ctatcagctc tgtgctgaac  1980
gacatcctgt cccgcctgga caaggtcgag gccgaagtgc agatcgaccg cctgatcact  2040
ggccgtctgc agtcactgca gacctacgtg actcagcagc tgatcagggc cgctgaaatc  2100
agagcctccg ctaacctggc cgctaccaag atgagcgagt gcgtcctggg tcaatctaag  2160
cgtgtggact tctgcggcaa gggataccac ctgatgtcat tccctcagtc tgctccccac  2220
ggtgtggtgt tcctgcacgt cacctacgtg ccagcccagg agaagaactt caccactgcc  2280
```

```
cctgctatct gccacgacgg caaggctcac ttccccaggg aaggtgtctt cgtgagcaac  2340
ggcacccact ggttcgtcac tcagagaaac ttctacgagc cacagatcat caccactgac  2400
aacactttcg tgtctggaaa ctgcgacgtg gtcatcggta tcgtcaacaa caccgtgtac  2460
gaccccctgc agccagagct ggactcattc aaggaggaac tggacaagta cttcaagaac  2520
cacacctccc ctgacgtcga cctgggcgac atctcaggaa tcaacgcttc cgtcgtgaac  2580
atccagaagg agatcgaccg cctgaacgaa gtggccaaga acctgaacga aagcctgatc  2640
gacctgcagg agctgggcaa gtacgaacag tacatcaagt ggcctcacca ccaccaccac  2700
caccac                                                             2706

SEQ ID NO: 54           moltype = AA  length = 888
FEATURE                 Location/Qualifiers
REGION                  1..888
                        note = RECOMBINANT SPIKE PROTEIN
source                  1..888
                        mol_type = protein
                        organism = synthetic construct
SEQUENCE: 54
ITNLCPFGEV FNATRFASVY AWNRKRISNC VADYSVLYNS ASFSTFKCYG VSPTKLNDLC  60
FTNVYADSFV IRGDEVRQIA PGQTGKIADY NYKLPDDFTG CVIAWNSNNL DSKVGGNYNY  120
LYRLFRKSNL KPFERDISTE IYQAGSTPCN GVEGFNCYFP LQSYGFQPTN GVGYQPYRVV  180
VLSFELLHAP ATVCGPKKST NLVKNKCVNF NFNGLTGTGV LTESNKKFLP FQQFGRDIAD  240
TTDAVRDPQT LEILDITPCS FGGVSVITPG TNTSNQVAVL YQDVNCTEVP VAIHADQLTP  300
TWRVYSTGSN VFQTRAGCLI GAEHVNNSYE CDIPIGAGIC ASYQTQTNSP RRARSVASQS  360
IIAYTMSLGA ENSVAYSNNS IAIPTNFTIS VTTEILPVSM TKTSVDCTMY ICGDSTECSN  420
LLLQYGSFCT QLNRALTGIA VEQDKNTQEV FAQVKQIYKT PPIKDFGGFN FSQILPDPSK  480
PSKRSFIEDL LFNKVTLADA GFIKQYGDCL GDIAARDLIC AQKFNGLTVL PPLLTDEMIA  540
QYTSALLAGT ITSGWTFGAG AALQIPFAMQ MAYRFNGIGV TQNVLYENQK LIANQFNSAI  600
GKIQDSLSST ASALGKLQDV VNQNAQALNT LVKQLSSNFG AISSVLNDIL SRLDKVEAEV  660
QIDRLITGRL QSLQTYVTQQ LIRAAEIRAS ANLAATKMSE CVLGQSKRVD FCGKGYHLMS  720
FPQSAPHGVV FLHVTYVPAQ EKNFTTAPAI CHDGKAHFPR EGVFVSNGTH WFVTQRNFYE  780
PQIITTDNTF VSGNCDVVIG IVNNTVYDPL QPELDSFKEE LDKYFKNHTS PDVDLGDISG  840
INASVVNIQK EIDRLNEVAK NLNESLIDLQ ELGKYEQYIK WPHHHHHH                888

SEQ ID NO: 55           moltype = DNA  length = 3819
FEATURE                 Location/Qualifiers
misc_feature            1..3819
                        note = RECOMBINANT SPIKE PROTEIN
source                  1..3819
                        mol_type = other DNA
                        organism = synthetic construct
SEQUENCE: 55
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacagcagg ctcagtctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
```

```
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctt ggtacatctg gctgggtttc  3660
atcgctggcc tcatcgctat cgtgatggtg accatcatgc tgtgctgcat gacttcatgc  3720
tgctcctgcc tgaagggctg ctgcagctgc ggatcttgct gcaagttcga cgaggacgac  3780
tctgaacccg tcctgaaggg cgtgaagctg cactacacc                         3819
```

```
SEQ ID NO: 56           moltype = AA  length = 1279
FEATURE                 Location/Qualifiers
REGION                  1..1279
                        note = RECOMBINANT SPIKE PROTEIN
source                  1..1279
                        mol_type = protein
                        organism = synthetic construct
SEQUENCE: 56
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYTHHHHHH                                              1279
```

```
SEQ ID NO: 57           moltype = DNA  length = 3837
FEATURE                 Location/Qualifiers
misc_feature            1..3837
                        note = RECOMBINANT SPIKE PROTEIN
source                  1..3837
                        mol_type = other DNA
                        organism = synthetic construct
SEQUENCE: 57
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
```

-continued

```
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacagcagg ctcagtctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctt ggtacatctg gctgggtttc  3660
atcgctggcc tcatcgctat cgtgatggtg accatcatgc tgtgctgcat gacttcatgc  3720
tgctcctgcc tgaagggctg ctgcagctgc ggatcttgct gcaagttcga cgaggacgac  3780
tctgaacccg tcctgaaggg cgtgaagctg cactacaccc accaccacca ccaccac     3837

SEQ ID NO: 58          moltype = AA  length = 1266
FEATURE                Location/Qualifiers
REGION                 1..1266
                       note = RECOMBINANT SPIKE PROTEIN
source                 1..1266
                       mol_type = protein
                       organism = synthetic construct
SEQUENCE: 58
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDKVEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
```

```
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260
HHHHHH                                                            1266

SEQ ID NO: 59          moltype = AA  length = 1219
FEATURE                Location/Qualifiers
REGION                 1..1219
                       note = RECOMBINANT SPIKE PROTEIN
source                 1..1219
                       mol_type = protein
                       organism = synthetic construct
SEQUENCE: 59
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPHHHHHH                                              1219

SEQ ID NO: 60          moltype = DNA  length = 3657
FEATURE                Location/Qualifiers
misc_feature           1..3657
                       note = RECOMBINANT SPIKE PROTEIN
source                 1..3657
                       mol_type = other DNA
                       organism = synthetic construct
SEQUENCE: 60
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacagcagg ctcagtctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
```

-continued

```
tacatctgcg gagacagcac cgaatgctct aacctgctgc tgcagtacgg ctctttctgc  2280
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctc accaccacca ccaccac     3657

SEQ ID NO: 61          moltype = AA  length = 1205
FEATURE                Location/Qualifiers
REGION                 1..1205
                       note = RECOMBINANT SPIKE PROTEIN
source                 1..1205
                       mol_type = protein
                       organism = synthetic construct
SEQUENCE: 61
CVNLTTRTQL PPAYTNSFTR GVYYPDKVFR SSVLHSTQDL FLPFFSNVTW FHAIHVSGTN  60
GTKRFDNPVL PFNDGVYFAS TEKSNIIRGW IFGTTLDSKT QSLLIVNNAT NVVIKVCEFQ  120
FCNDPFLGVY YHKNNKSWME SEFRVYSSAN NCTFEYVSQP FLMDLEGKQG NFKNLREFVF  180
KNIDGYFKIY SKHTPINLVR DLPQGFSALE PLVDLPIGIN ITRFQTLLAL HRSYLTPGDS  240
SSGWTAGAAA YYVGYLQPRT FLLKYNENGT ITDAVDCALD PLSETKCTLK SFTVEKGIYQ  300
TSNFRVQPTE SIVRFPNITN LCPFGEVFNA TRFASVYAWN RKRISNCVAD YSVLYNSASF  360
STFKCYGVSP TKLNDLCFTN VYADSFVIRG DEVRQIAPGQ TGKIADYNYK LPDDFTGCVI  420
AWNSNNLDSK VGGNYNYLYR LFRKSNLKPF ERDISTEIYQ AGSTPCNGVE GFNCYFPLQS  480
YGFQPTNGVG YQPYRVVVLS FELLHAPATV CGPKKSTNLV KNKCVNFNFN GLTGTGVLTE  540
SNKKFLPFQQ FGRDIADTTD AVRDPQTLEI LDITPCSFGG VSVITPGTNT SNQVAVLYQD  600
VNCTEVPVAI HADQLTPTWR VYSTGSNVFQ TRAGCLIGAE HVNNSYECDI PIGAGICASY  660
QTQTNSPQQA QSVASQSIIA YTMSLGAENS VAYSNNSIAI PTNFTISVTT EILPVSMTKT  720
SVDCTMYICG DSTECSNLLL QYGSFCTQLN RALTGIAVEQ DKNTQEVFAQ VKQIYKTPPI  780
KDFGGFNFSQ ILPDPSKPSK RSFIEDLLFN KVTLADAGFI KQYGDCLGDI AARDLICAQK  840
FNGLTVLPPL LTDEMIAQYT SALLAGTITS GWTFGAGAAL QIPFAMQMAY RFNGIGVTQN  900
VLYENQKLIA NQFNSAIGKI QDSLSSTASA LGKLQDVVNQ NAQALNTLVK QLSSNFGAIS  960
SVLNDILSRL DKVEAEVQID RLITGRLQSL QTYVTQQLIR AAEIRASANL AATKMSECVL  1020
GQSKRVDFCG KGYHLMSFPQ SAPHGVVFLH VTYVPAQEKN FTTAPAICHD GKAHFPREGV  1080
FVSNGTHWFV TQRNFYEPQI ITTDNTFVSG NCDVVIGIVN NTVYDPLQPE LDSFKEELDK  1140
YFKNHTSPDV DLGDISGINA SVVNIQKEID RLNEVAKNLN ESLIDLQELG KYEQYIKWPH  1200
HHHHH                                                              1205

SEQ ID NO: 62          moltype = AA  length = 1263
FEATURE                Location/Qualifiers
REGION                 1..1263
                       note = RECOMBINANT SPIKE PROTEIN
source                 1..1263
                       mol_type = protein
                       organism = synthetic construct
SEQUENCE: 62
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVALG AENSVAYSNN SIAIPTNFTI SVTTEILPVS  720
MTKTSVDCTM YICGDSTECS NLLLQYGSFC TQLNRALTGI AVEQDKNTQE VFAQVKQIYK  780
TPPIKDFGGF NFSQILPDPS KPSKRSFIED LLFNKVTLAD AGFIKQYGDC LGDIAARDLI  840
CAQKFNGLTV LPPLLTDEMI AQYTSALLAG TITSGWTFGA GAALQIPFAM QMAYRFNGIG  900
VTQNVLYENQ KLIANQFNSA IGKIQDSLSS TASALGKLQD VVNQNAQALN TLVKQLSSNF  960
```

```
GAISSVLNDI LSRLDKVEAE VQIDRLITGR LQSLQTYVTQ QLIRAAEIRA SANLAATKMS  1020
ECVLGQSKRV DFCGKGYHLM SFPQSAPHGV VFLHVTYVPA QEKNFTTAPA ICHDGKAHFP  1080
REGVFVSNGT HWFVTQRNFY EPQIITTDNT FVSGNCDVVI GIVNNTVYDP LQPELDSFKE  1140
ELDKYFKNHT SPDVDLGDIS GINASVVNIQ KEIDRLNEVA KNLNESLIDL QELGKYEQYI  1200
KWPWYIWLGF IAGLIAIVMV TIMLCCMTSC CSCLKGCCSC GSCCKFDEDD SEPVLKGVKL  1260
HYT                                                               1263

SEQ ID NO: 63          moltype = AA  length = 1250
FEATURE                Location/Qualifiers
REGION                 1..1250
                       note = RECOMBINANT SPIKE PROTEIN
source                 1..1250
                       mol_type = protein
                       organism = synthetic construct
SEQUENCE: 63
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVALGAEN SVAYSNNSIA IPTNFTISVT TEILPVSMTK TSVDCTMYIC  720
GDSTECSNLL LQYGSFCTQL NRALTGIAVE QDKNTQEVFA QVKQIYKTPP IKDFGGFNFS  780
QILPDPSKPS KRSFIEDLLF NKVTLADAGF IKQYGDCLGD IAARDLICAQ KFNGLTVLPP  840
LLTDEMIAQY TSALLAGTIT SGWTFGAGAA LQIPFAMQMA YRFNGIGVTQ NVLYENQKLI  900
ANQFNSAIGK IQDSLSSTAS ALGKLQDVVN QNAQALNTLV KQLSSNFGAI SSVLNDILSR  960
LDKVEAEVQI DRLITGRLQS LQTYVTQQLI RAAEIRASAN LAATKMSECV LGQSKRVDFC  1020
GKGYHLMSFP QSAPHGVVFL HVTYVPAQEK NFTTAPAICH DGKAHFPREG VFVSNGTHWF  1080
VTQRNFYEPQ IITTDNTFVS GNCDVVIGIV NNTVYDPLQP ELDSFKEELD KYFKNHTSPD  1140
VDLGDISGIN ASVVNIQKEI DRLNEVAKNL NESLIDLQEL GKYEQYIKWP WYIWLGFIAG  1200
LIAIVMVTIM LCCMTSCCSC LKGCCSCGSC CKFDEDDSEP VLKGVKLHYT            1250

SEQ ID NO: 64          moltype = AA  length = 1263
FEATURE                Location/Qualifiers
REGION                 1..1263
                       note = RECOMBINANT SPIKE PROTEIN
source                 1..1263
                       mol_type = protein
                       organism = synthetic construct
SEQUENCE: 64
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIEILPVS  720
MTKTSVDCTM YICGDSTECS NLLLQYGSFC TQLNRALTGI AVEQDKNTQE VFAQVKQIYK  780
TPPIKDFGGF NFSQILPDPS KPSKRSFIED LLFNKVTLAD AGFIKQYGDC LGDIAARDLI  840
CAQKFNGLTV LPPLLTDEMI AQYTSALLAG TITSGWTFGA GAALQIPFAM QMAYRFNGIG  900
VTQNVLYENQ KLIANQFNSA IGKIQDSLSS TASALGKLQD VVNQNAQALN TLVKQLSSNF  960
GAISSVLNDI LSRLDKVEAE VQIDRLITGR LQSLQTYVTQ QLIRAAEIRA SANLAATKMS  1020
ECVLGQSKRV DFCGKGYHLM SFPQSAPHGV VFLHVTYVPA QEKNFTTAPA ICHDGKAHFP  1080
REGVFVSNGT HWFVTQRNFY EPQIITTDNT FVSGNCDVVI GIVNNTVYDP LQPELDSFKE  1140
ELDKYFKNHT SPDVDLGDIS GINASVVNIQ KEIDRLNEVA KNLNESLIDL QELGKYEQYI  1200
KWPWYIWLGF IAGLIAIVMV TIMLCCMTSC CSCLKGCCSC GSCCKFDEDD SEPVLKGVKL  1260
HYT                                                               1263

SEQ ID NO: 65          moltype = AA  length = 1250
FEATURE                Location/Qualifiers
REGION                 1..1250
                       note = RECOMBINANT SPIKE PROTEIN
source                 1..1250
                       mol_type = protein
                       organism = synthetic construct
SEQUENCE: 65
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
```

```
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVASQSII AYTMSLGAEN SVAYSNNSIA IEILPVSMTK TSVDCTMYIC  720
GDSTECSNLL LQYGSFCTQL NRALTGIAVE QDKNTQEVFA QVKQIYKTPP IKDFGGFNFS  780
QILPDPSKPS KRSFIEDLLF NKVTLADAGF IKQYGDCLGD IAARDLICAQ KFNGLTVLPP  840
LLTDEMIAQY TSALLAGTIT SGWTFGAGAA LQIPFAMQMA YRFNGIGVTQ NVLYENQKLI  900
ANQFNSAIGK IQDSLSSTAS ALGKLQDVVN QNAQALNTLV KQLSSNFGAI SSVLNDILSR  960
LDKVEAEVQI DRLITGRLQS LQTYVTQQLI RAAEIRASAN LAATKMSECV LGQSKRVDFC  1020
GKGYHLMSFP QSAPHGVVFL HVTYVPAQEK NFTTAPAICH DGKAHFPREG VFVSNGTHWF  1080
VTQRNFYEPQ IITTDNTFVS GNCDVVIGIV NNTVYDPLQP ELDSFKEELD KYFKNHTSPD  1140
VDLGDISGIN ASVVNIQKEI DRLNEVAKNL NESLIDLQEL GKYEQYIKWP WYIWLGFIAG  1200
LIAIVMVTIM LCCMTSCCSC LKGCCSCGSC CKFDEDDSEP VLKGVKLHYT             1250

SEQ ID NO: 66           moltype = AA  length = 1263
FEATURE                 Location/Qualifiers
REGION                  1..1263
                        note = RECOMBINANT SPIKE PROTEIN
source                  1..1263
                        mol_type = protein
                        organism = synthetic construct
SEQUENCE: 66
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIAD AGFIKQYGDC LGDIAARDLI  840
CAQKFNGLTV LPPLLTDEMI AQYTSALLAG TITSGWTFGA GAALQIPFAM QMAYRFNGIG  900
VTQNVLYENQ KLIANQFNSA IGKIQDSLSS TASALGKLQD VVNQNAQALN TLVKQLSSNF  960
GAISSVLNDI LSRLDKVEAE VQIDRLITGR LQSLQTYVTQ QLIRAAEIRA SANLAATKMS  1020
ECVLGQSKRV DFCGKGYHLM SFPQSAPHGV VFLHVTYVPA QEKNFTTAPA ICHDGKAHFP  1080
REGVFVSNGT HWFVTQRNFY EPQIITTDNT FVSGNCDVVI GIVNNTVYDP LQPELDSFKE  1140
ELDKYFKNHT SPDVDLGDIS GINASVVNIQ KEIDRLNEVA KNLNESLIDL QELGKYEQYI  1200
KWPWYIWLGF IAGLIAIVMV TIMLCCMTSC CSCLKGCCSC GSCCKFDEDD SEPVLKGVKL  1260
HYT                                                                1263

SEQ ID NO: 67           moltype = AA  length = 1250
FEATURE                 Location/Qualifiers
REGION                  1..1250
                        note = RECOMBINANT SPIKE PROTEIN
source                  1..1250
                        mol_type = protein
                        organism = synthetic construct
SEQUENCE: 67
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIADAGF IKQYGDCLGD IAARDLICAQ KFNGLTVLPP  840
LLTDEMIAQY TSALLAGTIT SGWTFGAGAA LQIPFAMQMA YRFNGIGVTQ NVLYENQKLI  900
ANQFNSAIGK IQDSLSSTAS ALGKLQDVVN QNAQALNTLV KQLSSNFGAI SSVLNDILSR  960
LDKVEAEVQI DRLITGRLQS LQTYVTQQLI RAAEIRASAN LAATKMSECV LGQSKRVDFC  1020
GKGYHLMSFP QSAPHGVVFL HVTYVPAQEK NFTTAPAICH DGKAHFPREG VFVSNGTHWF  1080
VTQRNFYEPQ IITTDNTFVS GNCDVVIGIV NNTVYDPLQP ELDSFKEELD KYFKNHTSPD  1140
VDLGDISGIN ASVVNIQKEI DRLNEVAKNL NESLIDLQEL GKYEQYIKWP WYIWLGFIAG  1200
LIAIVMVTIM LCCMTSCCSC LKGCCSCGSC CKFDEDDSEP VLKGVKLHYT             1250
```

```
SEQ ID NO: 68          moltype = AA  length = 31
FEATURE                Location/Qualifiers
REGION                 1..31
                       note = Foldon
source                 1..31
                       mol_type = protein
                       organism = synthetic construct
SEQUENCE: 68
SAIGGYIPEA PRDGQAYVRK DGEWVLLSTF L                                31

SEQ ID NO: 69          moltype = AA  length = 202
FEATURE                Location/Qualifiers
source                 1..202
                       mol_type = protein
                       organism = Betacoronavirus severe acute respiratory
                        syndrome coronavirus 2
SEQUENCE: 69
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KK                                          202

SEQ ID NO: 70          moltype = AA  length = 201
FEATURE                Location/Qualifiers
source                 1..201
                       mol_type = protein
                       organism = Betacoronavirus Severe acute respiratory
                        syndrome-related coronavirus
SEQUENCE: 70
RFPNITNLCP FGEVFNATKF PSVYAWERKK ISNCVADYSV LYNSTFFSTF KCYGVSATKL  60
NDLCFSNVYA DSFVVKGDDV RQIAPGQTGV IADYNYKLPD DFMGCVLAWN TRNIDATSTG  120
NYNYKYRYLR HGKLRPFERD ISNVPFSPDG KPCTPPALNC YWPLNDYGFY TTTGIGYQPY  180
RVVVLSFELL NAPATVCGPK L                                           201

SEQ ID NO: 71          moltype = AA  length = 239
FEATURE                Location/Qualifiers
source                 1..239
                       mol_type = protein
                       organism = Betacoronavirus Middle East respiratory
                        syndrome-related coronavirus
SEQUENCE: 71
FEAKPSGSVV AEGVECDFSP LLSGTPPQVY NFKRLVFTNC NYNLTKLLSL FSVNDFTCSQ  60
ISPAAIASNC YSSLILDYFS YPLSMKSDLS VSSAGPISQF NYKQSFSNPT CLILATVPHN  120
LTTITKPLKY SYINKCSRLL SDDRTEVPQL VNANQYSPCV SIVPSTVWED GDYYRKQLSP  180
LEGGGWLVAS GSTVAMTEQL QMGFGITVQY GTDTNSVCPK LEFANDTKIA SQLGNCVEY   239

SEQ ID NO: 72          moltype = AA  length = 544
FEATURE                Location/Qualifiers
REGION                 1..544
                       note = RECOMBINANT SPIKE PROTEIN
source                 1..544
                       mol_type = protein
                       organism = synthetic construct
SEQUENCE: 72
MFVFLVLLPL VSSRFPNITN LCPFGEVFNA TRFASVYAWN RKRISNCVAD YSVLYNSASF  60
STFKCYGVSP TKLNDLCFTN VYADSFVIRG DEVRQIAPGQ TGKIADYNYK LPDDFTGCVI  120
AWNSNNLDSK VGGNYNYLYR LFRKSNLKPF ERDISTEIYQ AGSTPCNGVE GFNCYFPLQS  180
YGFQPTNGVG YQPYRVVVLS FELLHAPATV CGPKKSTNLV KNKCVNFNFN GLTGTGVLTE  240
SNKKFLPFQQ FGRDIADTTD AVRDPQTLEI LDITPCSFGG VSVITPGTNT SNQVAVLYQD  300
VNCTERFPNI TNLCPFGEVF NATRFASVYA WNRKRISNCV ADYSVLYNSA SFSTFKCYGV  360
SPTKLNDLCF TNVYADSFVI RGDEVRQIAP GQTGKIADYN YKLPDDFTGC VIAWNSNNLD  420
SKVGGNYNYL YRLFRKSNLK PFERDISTEI YQAGSTPCNG VEGFNCYFPL QSYGFQPTNG  480
VGYQPYRVVV LSFELLHAPA TVCGPKKSAI GGYIPEAPRD GQAYVRKDGE WVLLSTFLHH  540
HHHH                                                              544

SEQ ID NO: 73          moltype = AA  length = 531
FEATURE                Location/Qualifiers
REGION                 1..531
                       note = RECOMBINANT SPIKE PROTEIN
source                 1..531
                       mol_type = protein
                       organism = synthetic construct
SEQUENCE: 73
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KKSTNLVKNK CVNFNFNGLT GTGVLTESNK KFLPFQQFGR  240
DIADTTDAVR DPQTLEILDI TPCSFGGVSV ITPGTNTSNQ VAVLYQDVNC TERFPNITNL  300
```

-continued

```
CPFGEVFNAT RFASVYAWNR KRISNCVADY SVLYNSASFS TFKCYGVSPT KLNDLCFTNV  360
YADSFVIRGD EVRQIAPGQT GKIADYNYKL PDDFTGCVIA WNSNNLDSKV GGNYNYLYRL  420
FRKSNLKPFE RDISTEIYQA GSTPCNGVEG FNCYFPLQSY GFQPTNGVGY QPYRVVVLSF  480
ELLHAPATVC GPKKSAIGGY IPEAPRDGQA YVRKDGEWVL LSTFLHHHHH H           531

SEQ ID NO: 74           moltype = AA  length = 544
FEATURE                 Location/Qualifiers
REGION                  1..544
                        note = RECOMBINANT SPIKE PROTEIN
source                  1..544
                        mol_type = protein
                        organism = synthetic construct
SEQUENCE: 74
MFVFLVLLPL VSSRFPNITN LCPFGEVFNA TRFASVYAWN RKRISNCVAD YSVLYNSASF  60
STFKCYGVSP TKLNDLCFTN VYADSFVIRG DEVRQIAPGQ TGKIADYNYK LPDDFTGCVI  120
AWNSNNLDSK VGGNYNYLYR LFRKSNLKPF ERDISTEIYQ AGSTPCNGVE GFNCYFPLQS  180
YGFQPTNGVG YQPYRVVVLS FELLHAPATV CGPKKSTNLV KNKCVNFNFN GLTGTGVLTE  240
SNKKFLPFQQ FGRDIADTTD AVRDPQTLEI LDITPCSFGG VSVITPGTNT SNQVAVLYQD  300
VNCTERFPNI TNLCPFGEVF NATRFASVYA WNRKRISNCV ADYSVLYNSA SFSTFKCYGV  360
SPTKLNDLCF TNVYADSFVI RGDEVRQIAP GQTGKIADYN YKLPDDFTGC VIAWNSNNLD  420
SKVGGNYNYL YRLFRKSNLK PFERDISTEI YQAGSTPCNG VEGFNCYFPL QSYGFQPTNG  480
VGYQPYRVVV LSFELLHAPA TVCGPKKSAI GGYIPEAPRD GQAYVRKDGE WVLLSTFLHH  540
HHHH                                                              544

SEQ ID NO: 75           moltype = AA  length = 531
FEATURE                 Location/Qualifiers
REGION                  1..531
                        note = RECOMBINANT SPIKE PROTEIN
source                  1..531
                        mol_type = protein
                        organism = synthetic construct
SEQUENCE: 75
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KKSTNLVKNK CVNFNFNGLT GTGVLTESNK KFLPFQQFGR  240
DIADTTDAVR DPQTLEILDI TPCSFGGVSV ITPGTNTSNQ VAVLYQDVNC TERFPNITNL  300
CPFGEVFNAT RFASVYAWNR KRISNCVADY SVLYNSASFS TFKCYGVSPT KLNDLCFTNV  360
YADSFVIRGD EVRQIAPGQT GKIADYNYKL PDDFTGCVIA WNSNNLDSKV GGNYNYLYRL  420
FRKSNLKPFE RDISTEIYQA GSTPCNGVEG FNCYFPLQSY GFQPTNGVGY QPYRVVVLSF  480
ELLHAPATVC GPKKSAIGGY IPEAPRDGQA YVRKDGEWVL LSTFLHHHHH H           531

SEQ ID NO: 76           moltype = AA  length = 470
FEATURE                 Location/Qualifiers
REGION                  1..470
                        note = RECOMBINANT SPIKE PROTEIN
source                  1..470
                        mol_type = protein
                        organism = synthetic construct
SEQUENCE: 76
MFVFLVLLPL VSSRFPNITN LCPFGEVFNA TRFASVYAWN RKRISNCVAD YSVLYNSASF  60
STFKCYGVSP TKLNDLCFTN VYADSFVIRG DEVRQIAPGQ TGKIADYNYK LPDDFTGCVI  120
AWNSNNLDSK VGGNYNYLYR LFRKSNLKPF ERDISTEIYQ AGSTPCNGVE GFNCYFPLQS  180
YGFQPTNGVG YQPYRVVVLS FELLHAPATV CGPKKSGGGS GGGSGGGSGG GSRFPNITNL  240
CPFGEVFNAT KFPSVYAWER KKISNCVADY SVLYNSTFFS TFKCYGVSAT KLNDLCFSNV  300
YADSFVVKGD DVRQIAPGQT GVIADYNYKL PDDFMGCVLA WNTRNIDATS TGNYNYKYRY  360
LRHGKLRPFE RDISNVPFSP DGKPCTPPAL NCYWPLNDYG FYTTTGIGYQ PYRVVVLSFE  420
LLNAPATVCG PKLSAIGGYI PEAPRDGQAY VRKDGEWVLL STFLHHHHHH            470

SEQ ID NO: 77           moltype = AA  length = 464
FEATURE                 Location/Qualifiers
REGION                  1..464
                        note = RECOMBINANT SPIKE PROTEIN
source                  1..464
                        mol_type = protein
                        organism = synthetic construct
SEQUENCE: 77
MFVFLVLLPL VSSRFPNITN LCPFGEVFNA TRFASVYAWN RKRISNCVAD YSVLYNSASF  60
STFKCYGVSP TKLNDLCFTN VYADSFVIRG DEVRQIAPGQ TGKIADYNYK LPDDFTGCVI  120
AWNSNNLDSK VGGNYNYLYR LFRKSNLKPF ERDISTEIYQ AGSTPCNGVE GFNCYFPLQS  180
YGFQPTNGVG YQPYRVVVLS FELLHAPATV CGPKKSGGGS GGGSGGGSGG GSRFPNITNL  240
CPFGEVFNAT KFPSVYAWER KKISNCVADY SVLYNSTFFS TFKCYGVSAT KLNDLCFSNV  300
YADSFVVKGD DVRQIAPGQT GVIADYNYKL PDDFMGCVLA WNTRNIDATS TGNYNYKYRY  360
LRHGKLRPFE RDISNVPFSP DGKPCTPPAL NCYWPLNDYG FYTTTGIGYQ PYRVVVLSFE  420
LLNAPATVCG PKLSAIGGYI PEAPRDGQAY VRKDGEWVLL STFL                  464

SEQ ID NO: 78           moltype = AA  length = 457
FEATURE                 Location/Qualifiers
REGION                  1..457
```

```
                         note = RECOMBINANT SPIKE PROTEIN
source                   1..457
                         mol_type = protein
                         organism = synthetic construct
SEQUENCE: 78
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KKSGGGSGGG SGGGSGGGSR FPNITNLCPF GEVFNATKFP  240
SVYAWERKKI SNCVADYSVL YNSTFFSTFK CYGVSATKLN DLCFSNVYAD SFVVKGDDVR  300
QIAPGQTGVI ADYNYKLPDD FMGCVLAWNT RNIDATSTGN YNYKYRYLRH GKLRPFERDI  360
SNVPFSPDGK PCTPPALNCY WPLNDYGFYT TTGIGYQPYR VVVLSFELLN APATVCGPKL  420
SAIGGYIPEA PRDGQAYVRK DGEWVLLSTF LHHHHHH                          457

SEQ ID NO: 79            moltype = AA  length = 451
FEATURE                  Location/Qualifiers
REGION                   1..451
                         note = RECOMBINANT SPIKE PROTEIN
source                   1..451
                         mol_type = protein
                         organism = synthetic construct
SEQUENCE: 79
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KKSGGGSGGG SGGGSGGGSR FPNITNLCPF GEVFNATKFP  240
SVYAWERKKI SNCVADYSVL YNSTFFSTFK CYGVSATKLN DLCFSNVYAD SFVVKGDDVR  300
QIAPGQTGVI ADYNYKLPDD FMGCVLAWNT RNIDATSTGN YNYKYRYLRH GKLRPFERDI  360
SNVPFSPDGK PCTPPALNCY WPLNDYGFYT TTGIGYQPYR VVVLSFELLN APATVCGPKL  420
SAIGGYIPEA PRDGQAYVRK DGEWVLLSTF L                                451

SEQ ID NO: 80            moltype = AA  length = 726
FEATURE                  Location/Qualifiers
REGION                   1..726
                         note = RECOMBINANT SPIKE PROTEIN
source                   1..726
                         mol_type = protein
                         organism = synthetic construct
SEQUENCE: 80
MFVFLVLLPL VSSRFPNITN LCPFGEVFNA TRFASVYAWN RKRISNCVAD YSVLYNSASF  60
STFKCYGVSP TKLNDLCFTN VYADSFVIRG DEVRQIAPGQ TGKIADYNYK LPDDFTGCVI  120
AWNSNNLDSK VGGNYNYLYR LFRKSNLKPF ERDISTEIYQ AGSTPCNGVE GFNCYFPLQS  180
YGFQPTNGVG YQPYRVVVLS FELLHAPATV CGPKKSGGGS GGGSGGGSGG GSFEAKPSGS  240
VVAEGVECDF SPLLSGTPPQ VYNFKRLVFT NCNYNLTKLL SLFSVNDFTC SQISPAAIAS  300
NCYSSLILDY FSYPLSMKSD LSVSSAGPIS QFNYKQSFSN PTCLILATVP HNLTTITKPL  360
KYSYINKCSR LLSDDRTEVP QLVNANQYSP CVSIVPSTVW EDGDYYRKQL SPLEGGGWLV  420
ASGSTVAMTE QLQMGFGITV QYGTDTNSVC PKLEFANDTK IASQLGNCVE YSGGGSGGGS  480
GGGSGGGSRF PNITNLCPFG EVFNATKFPS VYAWERKKIS NCVADYSVLY NSTFFSTFKC  540
YGVSATKLND LCFSNVYADS FVVKGDDVRQ IAPGQTGVIA DYNYKLPDDF MGCVLAWNTR  600
NIDATSTGNY NYKYRYLRHG KLRPFERDIS NVPFSPDGKP CTPPALNCYW PLNDYGFYTT  660
TGIGYQPYRV VVLSFELLNA PATVCGPKLS AIGGYIPEAP RDGQAYVRKD GEWVLLSTFL  720
HHHHHH                                                            726

SEQ ID NO: 81            moltype = AA  length = 720
FEATURE                  Location/Qualifiers
REGION                   1..720
                         note = RECOMBINANT SPIKE PROTEIN
source                   1..720
                         mol_type = protein
                         organism = synthetic construct
SEQUENCE: 81
MFVFLVLLPL VSSRFPNITN LCPFGEVFNA TRFASVYAWN RKRISNCVAD YSVLYNSASF  60
STFKCYGVSP TKLNDLCFTN VYADSFVIRG DEVRQIAPGQ TGKIADYNYK LPDDFTGCVI  120
AWNSNNLDSK VGGNYNYLYR LFRKSNLKPF ERDISTEIYQ AGSTPCNGVE GFNCYFPLQS  180
YGFQPTNGVG YQPYRVVVLS FELLHAPATV CGPKKSGGGS GGGSGGGSGG GSFEAKPSGS  240
VVAEGVECDF SPLLSGTPPQ VYNFKRLVFT NCNYNLTKLL SLFSVNDFTC SQISPAAIAS  300
NCYSSLILDY FSYPLSMKSD LSVSSAGPIS QFNYKQSFSN PTCLILATVP HNLTTITKPL  360
KYSYINKCSR LLSDDRTEVP QLVNANQYSP CVSIVPSTVW EDGDYYRKQL SPLEGGGWLV  420
ASGSTVAMTE QLQMGFGITV QYGTDTNSVC PKLEFANDTK IASQLGNCVE YSGGGSGGGS  480
GGGSGGGSRF PNITNLCPFG EVFNATKFPS VYAWERKKIS NCVADYSVLY NSTFFSTFKC  540
YGVSATKLND LCFSNVYADS FVVKGDDVRQ IAPGQTGVIA DYNYKLPDDF MGCVLAWNTR  600
NIDATSTGNY NYKYRYLRHG KLRPFERDIS NVPFSPDGKP CTPPALNCYW PLNDYGFYTT  660
TGIGYQPYRV VVLSFELLNA PATVCGPKLS AIGGYIPEAP RDGQAYVRKD GEWVLLSTFL  720

SEQ ID NO: 82            moltype = AA  length = 713
FEATURE                  Location/Qualifiers
REGION                   1..713
                         note = RECOMBINANT SPIKE PROTEIN
source                   1..713
```

```
                         mol_type = protein
                         organism = synthetic construct
SEQUENCE: 82
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KKSGGGSGGG SGGGSGGGSF EAKPSGSVVA EGVECDFSPL  240
LSGTPPQVYN FKRLVFTNCN YNLTKLLSLF SVNDFTCSQI SPAAIASNCY SSLILDYFSY  300
PLSMKSDLSV SSAGPISQFN YKQSFSNPTC LILATVPHNL TTITKPLKYS YINKCSRLLS  360
DDRTEVPQLV NANQYSPCVS IVPSTVWEDG DYYRKQLSPL EGGGWLVASG STVAMTEQLQ  420
MGFGITVQYG TDTNSVCPKL EFANDTKIAS QLGNCVEYSG GGSGGGSGGG SGGGSRFPNI  480
TNLCPFGEVF NATKFPSVYA WERKKISNCV ADYSVLYNST FFSTFKCYGV SATKLNDLCF  540
SNVYADSFVV KGDDVRQIAP GQTGVIADYN YKLPDDFMGC VLAWNTRNID ATSTGNYNYK  600
YRYLRHGKLR PFERDISNVP FSPDGKPCTP PALNCYWPLN DYGFYTTTGI GYQPYRVVVL  660
SFELLNAPAT VCGPKLSAIG GYIPEAPRDG QAYVRKDGEW VLLSTFLHHH HHH        713

SEQ ID NO: 83            moltype = AA  length = 707
FEATURE                  Location/Qualifiers
REGION                   1..707
                         note = RECOMBINANT SPIKE PROTEIN
source                   1..707
                         mol_type = protein
                         organism = synthetic construct
SEQUENCE: 83
RFPNITNLCP FGEVFNATRF ASVYAWNRKR ISNCVADYSV LYNSASFSTF KCYGVSPTKL  60
NDLCFTNVYA DSFVIRGDEV RQIAPGQTGK IADYNYKLPD DFTGCVIAWN SNNLDSKVGG  120
NYNYLYRLFR KSNLKPFERD ISTEIYQAGS TPCNGVEGFN CYFPLQSYGF QPTNGVGYQP  180
YRVVVLSFEL LHAPATVCGP KKSGGGSGGG SGGGSGGGSF EAKPSGSVVA EGVECDFSPL  240
LSGTPPQVYN FKRLVFTNCN YNLTKLLSLF SVNDFTCSQI SPAAIASNCY SSLILDYFSY  300
PLSMKSDLSV SSAGPISQFN YKQSFSNPTC LILATVPHNL TTITKPLKYS YINKCSRLLS  360
DDRTEVPQLV NANQYSPCVS IVPSTVWEDG DYYRKQLSPL EGGGWLVASG STVAMTEQLQ  420
MGFGITVQYG TDTNSVCPKL EFANDTKIAS QLGNCVEYSG GGSGGGSGGG SGGGSRFPNI  480
TNLCPFGEVF NATKFPSVYA WERKKISNCV ADYSVLYNST FFSTFKCYGV SATKLNDLCF  540
SNVYADSFVV KGDDVRQIAP GQTGVIADYN YKLPDDFMGC VLAWNTRNID ATSTGNYNYK  600
YRYLRHGKLR PFERDISNVP FSPDGKPCTP PALNCYWPLN DYGFYTTTGI GYQPYRVVVL  660
SFELLNAPAT VCGPKLSAIG GYIPEAPRDG QAYVRKDGEW VLLSTFL               707

SEQ ID NO: 84            moltype = AA  length = 1273
FEATURE                  Location/Qualifiers
REGION                   1..1273
                         note = RECOMBINANT SPIKE PROTEIN
source                   1..1273
                         mol_type = protein
                         organism = synthetic construct
SEQUENCE: 84
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 85            moltype = AA  length = 1260
FEATURE                  Location/Qualifiers
REGION                   1..1260
                         note = RECOMBINANT SPIKE PROTEIN
source                   1..1260
                         mol_type = protein
                         organism = synthetic construct
SEQUENCE: 85
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
```

```
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPRR ARSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDPPEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260

SEQ ID NO: 86           moltype = AA  length = 1273
FEATURE                 Location/Qualifiers
REGION                  1..1273
                        note = RECOMBINANT SPIKE PROTEIN
source                  1..1273
                        mol_type = protein
                        organism = synthetic construct
SEQUENCE: 86
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                  1273

SEQ ID NO: 87           moltype = AA  length = 1260
FEATURE                 Location/Qualifiers
REGION                  1..1260
                        note = RECOMBINANT SPIKE PROTEIN
source                  1..1260
                        mol_type = protein
                        organism = synthetic construct
SEQUENCE: 87
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDPPEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260
```

```
SEQ ID NO: 88          moltype = AA  length = 1219
FEATURE                Location/Qualifiers
REGION                 1..1219
                       note = RECOMBINANT SPIKE PROTEIN
source                 1..1219
                       mol_type = protein
                       organism = synthetic construct
SEQUENCE: 88
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPHHHHHH                                              1219

SEQ ID NO: 89          moltype = AA  length = 1206
FEATURE                Location/Qualifiers
REGION                 1..1206
                       note = RECOMBINANT SPIKE PROTEIN
source                 1..1206
                       mol_type = protein
                       organism = synthetic construct
SEQUENCE: 89
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPQQ AQSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDPPEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
HHHHHH                                                            1206

SEQ ID NO: 90          moltype = AA  length = 17
FEATURE                Location/Qualifiers
REGION                 1..17
                       note = Linker
source                 1..17
                       mol_type = protein
                       organism = synthetic construct
SEQUENCE: 90
SGGGSGGGSG GGSGGGS                                                17

SEQ ID NO: 91          moltype = AA  length = 4
FEATURE                Location/Qualifiers
REGION                 1..4
                       note = Linker
source                 1..4
                       mol_type = protein
                       organism = synthetic construct
SEQUENCE: 91
```

```
SGGG                                                             4

SEQ ID NO: 92          moltype = AA  length = 4
FEATURE                Location/Qualifiers
REGION                 1..4
                       note = Linker
source                 1..4
                       mol_type = protein
                       organism = synthetic construct
SEQUENCE: 92
GGGS                                                             4

SEQ ID NO: 93          moltype = AA  length = 5
FEATURE                Location/Qualifiers
REGION                 1..5
                       note = Linker
source                 1..5
                       mol_type = protein
                       organism = synthetic construct
SEQUENCE: 93
GGGGS                                                            5

SEQ ID NO: 94          moltype = AA  length = 90
FEATURE                Location/Qualifiers
REGION                 1..90
                       note = RECOMBINANT SPIKE PROTEIN
source                 1..90
                       mol_type = protein
                       organism = synthetic construct
SEQUENCE: 94
STNLVKNKCV NFNFNGLTGT GVLTESNKKF LPFQQFGRDI ADTTDAVRDP QTLEILDITP  60
CSFGGVSVIT PGTNTSNQVA VLYQDVNCTE                                   90

SEQ ID NO: 95          moltype = DNA  length = 3639
FEATURE                Location/Qualifiers
misc_feature           1..3639
                       note = RECOMBINANT SPIKE PROTEIN
source                 1..3639
                       mol_type = other DNA
                       organism = synthetic construct
SEQUENCE: 95
atgttcgtct tcctggtgct gctgccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacgcaggg ctcgctctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
```

```
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggacaaggt cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcct                        3639
```

```
SEQ ID NO: 96           moltype = DNA  length = 3822
FEATURE                 Location/Qualifiers
misc_feature            1..3822
                        note = RECOMBINANT SPIKE PROTEIN
source                  1..3822
                        mol_type = other DNA
                        organism = synthetic construct
SEQUENCE: 96
atgttcgtct tcctggtgct gctgcccctg gtgtccagcc agtgcgtgaa cctgaccact  60
aggactcagc tgcctcccgc ttacaccaac tcattcactc gcggtgtgta ctaccctgac  120
aaggtcttcc gttcttcagt gctgcactca actcaggacc tgttcctgcc cttcttctcc  180
aacgtcacct ggttccacgc catccacgtg tccggcacca acggcactaa gcgcttcgac  240
aacccagtgc tgcctttcaa cgacggtgtc tacttcgctt caaccgagaa gtccaacatc  300
atccgtggat ggatcttcgg caccactctg gacagcaaga ctcagtctct gctgatcgtc  360
aacaacgcca ccaacgtggt catcaaggtc tgcgaattcc agttctgcaa cgacccattc  420
ctgggcgtct actaccacaa gaacaacaag tcatggatgg agtccgaatt ccgcgtctac  480
tccagcgcta acaactgcac tttcgagtac gtgtcccagc ctttcctgat ggacctggaa  540
ggaaagcagg gtaacttcaa gaacctgagg gagttcgtgt tcaagaacat cgacggatac  600
ttcaagattt acagcaagca caccccaatc aacctggtgc gcgacctgcc tcagggtttc  660
tctgctctgg agccactggt ggacctgcct atcggcatca acatcacccg cttccagact  720
ctgctggctc tgcaccgttc ctacctgact ccaggcgact catcttctgg atggactgct  780
ggagctgctg cttactacgt gggctacctg cagcctcgca ccttcctgct gaagtacaac  840
gaaaacggaa ccatcactga cgccgtcgac tgcgctctgg accctctgtc agaaaccaag  900
tgcactctga agtccttcac cgtggagaag ggcatctacc agacttcaaa cttcagggtg  960
cagcccaccg aatccatcgt cagattccct aacatcacta acctgtgccc cttcggagag  1020
gtcttcaacg ccacccgctt cgcttccgtg tacgcctgga acaggaagag aatctcaaac  1080
tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc taccccttgc  1440
aacggtgtcg agggcttcaa ctgctacttc cccctgcagt cctacggttt ccagccaact  1500
aacggtgtgg gctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacagcagg ctcagtctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
acccagctga accgtgctct gactggaatc gccgtggagc aggacaagaa cactcaggaa  2340
gtcttcgctc aggtgaagca aatctacaag accccaccta tcaaggactt cggcggattc  2400
aacttctccc agatcctgcc tgacccctcc aagccaagca agcgctcttt catcgaggac  2460
ctgctgttca acaaggtcac tctggccgac gctggattca tcaagcagta cggagactgc  2520
ctgggtgaca tcgccgctcg tgacctgatc tgcgctcaga agttcaacgg tctgaccgtg  2580
ctgcccccac tgctgactga cgaaatgatc gcccagtaca ctagcgccct gctggctgga  2640
accatcactt ctggttggac cttcggtgct ggcgccgctc tgcagatccc tttcgctatg  2700
cagatggcct accgtttcaa cggaatcggt gtcacccaga acgtgctgta cgagaaccag  2760
aagctgatcg ctaaccagtt caactcagcc atcggaaaga tccaggacag cctgagctct  2820
```

```
actgcctctg ctctgggcaa gctgcaggac gtcgtgaacc agaacgccca ggctctgaac  2880
accctggtca agcagctgtc atccaacttc ggtgctatca gctctgtgct gaacgacatc  2940
ctgtcccgcc tggaccctcc cgaggccgaa gtgcagatcg accgcctgat cactggccgt  3000
ctgcagtcac tgcagaccta cgtgactcag cagctgatca gggccgctga aatcagagcc  3060
tccgctaacc tggccgctac caagatgagc gagtgcgtcc tgggtcaatc taagcgtgtg  3120
gacttctgcg gcaagggata ccacctgatg tcattccctc agtctgctcc ccacggtgtg  3180
gtgttcctgc acgtcaccta cgtgccagcc caggagaaga acttcaccac tgcccctgct  3240
atctgccacg acggcaaggc tcacttcccc agggaaggtg tcttcgtgag caacggcacc  3300
cactggttcg tcactcagag aaacttctac gagccacaga tcatcaccac tgacaacact  3360
ttcgtgtctg gaaactgcga cgtggtcatc ggtatcgtca acaacaccgt gtacgacccc  3420
ctgcagccag agctggactc attcaaggag gaactggaca agtacttcaa gaaccacacc  3480
tcccctgacg tcgacctggg cgacatctca ggaatcaacg cttccgtcgt gaacatccag  3540
aaggagatcg accgcctgaa cgaagtggcc aagaacctga acgaaagcct gatcgacctg  3600
caggagctgg gcaagtacga acagtacatc aagtggcctt ggtacatctg gctgggtttc  3660
atcgctggcc tcatcgctat cgtgatggtg accatcatgc tgtgctgcat gacttcatgc  3720
tgctcctgcc tgaagggctg ctgcagctgc ggatcttgct gcaagttcga cgaggacgac  3780
tctgaacccg tcctgaaggg cgtgaagctg cactacacct aa                    3822

SEQ ID NO: 97          moltype = AA  length = 4
FEATURE                Location/Qualifiers
REGION                 1..4
                       note = Recombinant Furin Cleavage Site
source                 1..4
                       mol_type = protein
                       organism = synthetic construct
SEQUENCE: 97
GSAS                                                                4

SEQ ID NO: 98          moltype = AA  length = 8
FEATURE                Location/Qualifiers
REGION                 1..8
                       note = HRV3C Cleavage Site
source                 1..8
                       mol_type = protein
                       organism = synthetic construct
SEQUENCE: 98
LEVLFQGP                                                            8

SEQ ID NO: 99          moltype = AA  length = 8
FEATURE                Location/Qualifiers
REGION                 1..8
                       note = Strep-tag
source                 1..8
                       mol_type = protein
                       organism = synthetic construct
SEQUENCE: 99
WSHPQFEK                                                            8

SEQ ID NO: 100         moltype = AA  length = 6
FEATURE                Location/Qualifiers
REGION                 1..6
                       note = 6X-His Tag
source                 1..6
                       mol_type = protein
                       organism = synthetic construct
SEQUENCE: 100
HHHHHH                                                              6

SEQ ID NO: 101         moltype = AA  length = 10
FEATURE                Location/Qualifiers
REGION                 1..10
                       note = His-Tag
VARIANT                6
                       note = May be present or absent
VARIANT                7
                       note = May be present or absent
VARIANT                8
                       note = May be present or absent
VARIANT                9
                       note = May be present or absent
VARIANT                10
                       note = May be present or absent
source                 1..10
                       mol_type = protein
                       organism = synthetic construct
SEQUENCE: 101
HHHHHHHHHH                                                          10

SEQ ID NO: 102         moltype = AA  length = 8
```

```
FEATURE                 Location/Qualifiers
REGION                  1..8
                        note = 8X-His Tag
source                  1..8
                        mol_type = protein
                        organism = synthetic construct
SEQUENCE: 102
HHHHHHHH                                                          8

SEQ ID NO: 103          moltype = AA  length = 30
FEATURE                 Location/Qualifiers
REGION                  1..30
                        note = FOLDON
source                  1..30
                        mol_type = protein
                        organism = synthetic construct
SEQUENCE: 103
GYIPEAPRDG QAYVRKDGEW VLLSTFLSPA                                  30

SEQ ID NO: 104          moltype = AA  length = 10
FEATURE                 Location/Qualifiers
REGION                  1..10
                        note = RECOMBINANT SPIKE PROTEIN
source                  1..10
                        mol_type = protein
                        organism = synthetic construct
SEQUENCE: 104
EDLLFNKVTL                                                        10

SEQ ID NO: 105          moltype = AA  length = 1263
FEATURE                 Location/Qualifiers
REGION                  1..1263
                        note = RECOMBINANT SPIKE PROTEIN
source                  1..1263
                        mol_type = protein
                        organism = synthetic construct
SEQUENCE: 105
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PQQAQSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIAD AGFIKQYGDC LGDIAARDLI  840
CAQKFNGLTV LPPLLTDEMI AQYTSALLAG TITSGWTFGA GAALQIPFAM QMAYRFNGIG  900
VTQNVLYENQ KLIANQFNSA IGKIQDSLSS TASALGKLQD VVNQNAQALN TLVKQLSSNF  960
GAISSVLNDI LSRLDPPEAE VQIDRLITGR LQSLQTYVTQ QLIRAAEIRA SANLAATKMS  1020
ECVLGQSKRV DFCGKGYHLM SFPQSAPHGV VFLHVTYVPA QEKNFTTAPA ICHDGKAHFP  1080
REGVFVSNGT HWFVTQRNFY EPQIITTDNT FVSGNCDVVI GIVNNTVYDP LQPELDSFKE  1140
ELDKYFKNHT SPDVDLGDIS GINASVVNIQ KEIDRLNEVA KNLNESLIDL QELGKYEQYI  1200
KWPWYIWLGF IAGLIAIVMV TIMLCCMTSC CSCLKGCCSC GSCCKFDEDD SEPVLKGVKL  1260
HYT                                                               1263

SEQ ID NO: 106          moltype = AA  length = 1250
FEATURE                 Location/Qualifiers
REGION                  1..1250
                        note = RECOMBINANT SPIKE PROTEIN
source                  1..1250
                        mol_type = protein
                        organism = synthetic construct
SEQUENCE: 106
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
```

```
YQTQTNSPQQ AQSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIADAGF IKQYGDCLGD IAARDLICAQ KFNGLTVLPP  840
LLTDEMIAQY TSALLAGTIT SGWTFGAGAA LQIPFAMQMA YRFNGIGVTQ NVLYENQKLI  900
ANQFNSAIGK IQDSLSSTAS ALGKLQDVVN QNAQALNTLV KQLSSNFGAI SSVLNDILSR  960
LDPPEAEVQI DRLITGRLQS LQTYVTQQLI RAAEIRASAN LAATKMSECV LGQSKRVDFC  1020
GKGYHLMSFP QSAPHGVVFL HVTYVPAQEK NFTTAPAICH DGKAHFPREG VFVSNGTHWF  1080
VTQRNFYEPQ IITTDNTFVS GNCDVVIGIV NNTVYDPLQP ELDSFKEELD KYFKNHTSPD  1140
VDLGDISGIN ASVVNIQKEI DRLNEVAKNL NESLIDLQEL GKYEQYIKWP WYIWLGFIAG  1200
LIAIVMVTIM LCCMTSCCSC LKGCCSCGSC CKFDEDDSEP VLKGVKLHYT             1250

SEQ ID NO: 107         moltype = AA  length = 1263
FEATURE                Location/Qualifiers
REGION                 1..1263
                       note = RECOMBINANT SPIKE PROTEIN
source                 1..1263
                       mol_type = protein
                       organism = synthetic construct
SEQUENCE: 107
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIAD AGFIKQYGDC LGDIAARDLI  840
CAQKFNGLTV LPPLLTDEMI AQYTSALLAG TITSGWTFGA GAALQIPFAM QMAYRFNGIG  900
VTQNVLYENQ KLIANQFNSA IGKIQDSLSS TASALGKLQD VVNQNAQALN TLVKQLSSNF  960
GAISSVLNDI LSRLDKVEAE VQIDRLITGR LQSLQTYVTQ QLIRAAEIRA SANLAATKMS  1020
ECVLGQSKRV DFCGKGYHLM SFPQSAPHGV VFLHVTYVPA QEKNFTTAPA ICHDGKAHFP  1080
REGVFVSNGT HWFVTQRNFY EPQIITTDNT FVSGNCDVVI GIVNNTVYDP LQPELDSFKE  1140
ELDKYFKNHT SPDVDLGDIS GINASVVNIQ KEIDRLNEVA KNLNESLIDL QELGKYEQYI  1200
KWPWYIWLGF IAGLIAIVMV TIMLCCMTSC CSCLKGCCSC GSCCKFDEDD SEPVLKGVKL  1260
HYT                                                                1263

SEQ ID NO: 108         moltype = AA  length = 1250
FEATURE                Location/Qualifiers
REGION                 1..1250
                       note = RECOMBINANT SPIKE PROTEIN
source                 1..1250
                       mol_type = protein
                       organism = synthetic construct
SEQUENCE: 108
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPRR ARSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIADAGF IKQYGDCLGD IAARDLICAQ KFNGLTVLPP  840
LLTDEMIAQY TSALLAGTIT SGWTFGAGAA LQIPFAMQMA YRFNGIGVTQ NVLYENQKLI  900
ANQFNSAIGK IQDSLSSTAS ALGKLQDVVN QNAQALNTLV KQLSSNFGAI SSVLNDILSR  960
LDKVEAEVQI DRLITGRLQS LQTYVTQQLI RAAEIRASAN LAATKMSECV LGQSKRVDFC  1020
GKGYHLMSFP QSAPHGVVFL HVTYVPAQEK NFTTAPAICH DGKAHFPREG VFVSNGTHWF  1080
VTQRNFYEPQ IITTDNTFVS GNCDVVIGIV NNTVYDPLQP ELDSFKEELD KYFKNHTSPD  1140
VDLGDISGIN ASVVNIQKEI DRLNEVAKNL NESLIDLQEL GKYEQYIKWP WYIWLGFIAG  1200
LIAIVMVTIM LCCMTSCCSC LKGCCSCGSC CKFDEDDSEP VLKGVKLHYT             1250

SEQ ID NO: 109         moltype = AA  length = 1273
FEATURE                Location/Qualifiers
REGION                 1..1273
                       note = Recombinant CoV S polypeptide
source                 1..1273
                       mol_type = protein
                       organism = synthetic construct
```

```
SEQUENCE: 109
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PGSASSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 110          moltype = AA  length = 1260
FEATURE                 Location/Qualifiers
REGION                  1..1260
                        note = Recombinant CoV S polypeptide
source                  1..1260
                        mol_type = protein
                        organism = synthetic construct
SEQUENCE: 110
QCVNLTTRTQ LPPAYTNSFT RGVYYPDKVF RSSVLHSTQD LFLPFFSNVT WFHAIHVSGT  60
NGTKRFDNPV LPFNDGVYFA STEKSNIIRG WIFGTTLDSK TQSLLIVNNA TNVVIKVCEF  120
QFCNDPFLGV YYHKNNKSWM ESEFRVYSSA NNCTFEYVSQ PFLMDLEGKQ GNFKNLREFV  180
FKNIDGYFKI YSKHTPINLV RDLPQGFSAL EPLVDLPIGI NITRFQTLLA LHRSYLTPGD  240
SSSGWTAGAA AYYVGYLQPR TFLLKYNENG TITDAVDCAL DPLSETKCTL KSFTVEKGIY  300
QTSNFRVQPT ESIVRFPNIT NLCPFGEVFN ATRFASVYAW NRKRISNCVA DYSVLYNSAS  360
FSTFKCYGVS PTKLNDLCFT NVYADSFVIR GDEVRQIAPG QTGKIADYNY KLPDDFTGCV  420
IAWNSNNLDS KVGGNYNYLY RLFRKSNLKP FERDISTEIY QAGSTPCNGV EGFNCYFPLQ  480
SYGFQPTNGV GYQPYRVVVL SFELLHAPAT VCGPKKSTNL VKNKCVNFNF NGLTGTGVLT  540
ESNKKFLPFQ QFGRDIADTT DAVRDPQTLE ILDITPCSFG GVSVITPGTN TSNQVAVLYQ  600
DVNCTEVPVA IHADQLTPTW RVYSTGSNVF QTRAGCLIGA EHVNNSYECD IPIGAGICAS  660
YQTQTNSPGS ASSVASQSII AYTMSLGAEN SVAYSNNSIA IPTNFTISVT TEILPVSMTK  720
TSVDCTMYIC GDSTECSNLL LQYGSFCTQL NRALTGIAVE QDKNTQEVFA QVKQIYKTPP  780
IKDFGGFNFS QILPDPSKPS KRSFIEDLLF NKVTLADAGF IKQYGDCLGD IAARDLICAQ  840
KFNGLTVLPP LLTDEMIAQY TSALLAGTIT SGWTFGAGAA LQIPFAMQMA YRFNGIGVTQ  900
NVLYENQKLI ANQFNSAIGK IQDSLSSTAS ALGKLQDVVN QNAQALNTLV KQLSSNFGAI  960
SSVLNDILSR LDPPEAEVQI DRLITGRLQS LQTYVTQQLI RAAEIRASAN LAATKMSECV  1020
LGQSKRVDFC GKGYHLMSFP QSAPHGVVFL HVTYVPAQEK NFTTAPAICH DGKAHFPREG  1080
VFVSNGTHWF VTQRNFYEPQ IITTDNTFVS GNCDVVIGIV NNTVYDPLQP ELDSFKEELD  1140
KYFKNHTSPD VDLGDISGIN ASVVNIQKEI DRLNEVAKNL NESLIDLQEL GKYEQYIKWP  1200
WYIWLGFIAG LIAIVMVTIM LCCMTSCCSC LKGCCSCGSC CKFDEDDSEP VLKGVKLHYT  1260

SEQ ID NO: 111          moltype = AA  length = 4
FEATURE                 Location/Qualifiers
REGION                  1..4
                        note = Recombinant Furin Cleavage Site
source                  1..4
                        mol_type = protein
                        organism = synthetic construct
SEQUENCE: 111
GSGA                                                               4
```

The invention claimed is:

1. A method of manufacturing a nanoparticle comprising a coronavirus (CoV) S glycoprotein and a non-ionic detergent core, comprising:

(i) binding a protein extract comprising a first detergent and a CoV S glycoprotein to a protein purification column, wherein the CoV S glycoprotein comprises two modifications compared to a wild type CoV S glycoprotein wherein (a) the first modification is an inactivated furin cleavage site consisting of mutation of amino acids 669-672 to QQAQ (SEQ ID NO: 7); and (b) the second modification is mutation of amino acids 973 and 974 to proline;

(ii) performing a detergent exchange by substantially replacing the first detergent with a second detergent; and (iii) eluting the bound CoV S glycoprotein from the column in the presence of the second detergent to provide the nanoparticle, the non-ionic detergent core of the nanoparticle comprising the second detergent;

wherein the CoV S glycoprotein is numbered according to the polypeptide of SEQ ID NO: 2; and wherein the second detergent is selected from the group consisting of PS20, PS40, PS60, PS65, and PS80.

2. The method of claim 1, wherein the CoV S glycoprotein has at least 95% identity to the CoV S glycoprotein of SEQ ID NO: 2.

3. The method of claim 1, wherein the first detergent is NP-9.

4. The method of claim 1, wherein the second detergent is PS80.

5. The method of claim 1, comprising suspending the CoV S glycoprotein in a pharmaceutically acceptable buffer.

6. The method of claim 5, wherein the pharmaceutically acceptable buffer comprises sodium chloride.

7. The method of claim 5, wherein the pharmaceutically acceptable buffer comprises sodium phosphate.

8. The method of claim 1, wherein the nanoparticle comprises CoV S glycoprotein trimers.

9. The method of claim 1, wherein the protein purification column is an affinity chromatography column.

10. The method of claim 1, wherein the protein purification column is a lentil lectin column.

11. The method of claim 1, comprising eluting the CoV S glycoprotein with methyl alpha-D-mannopyranoside (MMP).

* * * * *